US012534724B2

(12) United States Patent
Khvorova et al.

(10) Patent No.: US 12,534,724 B2
(45) Date of Patent: Jan. 27, 2026

(54) SYNTHETIC OLIGONUCLEOTIDES HAVING REGIONS OF BLOCK AND CLUSTER MODIFICATIONS

(71) Applicant: UNIVERSITY OF MASSACHUSETTS, Boston, MA (US)

(72) Inventors: Anastasia Khvorova, Westborough, MA (US); Loïc Maurice René Jean Roux, Worcester, MA (US); Ken Yamada, Boston, MA (US)

(73) Assignee: UNIVERSITY OF MASSACHUSETTS, Westborough, MA (US)

(*) Notice: Subject to any disclaimer, the term of this patent is extended or adjusted under 35 U.S.C. 154(b) by 343 days.

(21) Appl. No.: 17/331,146

(22) Filed: May 26, 2021

(65) Prior Publication Data

US 2021/0395739 A1 Dec. 23, 2021

Related U.S. Application Data

(60) Provisional application No. 63/166,459, filed on Mar. 26, 2021, provisional application No. 63/029,880, filed on May 26, 2020.

(51) Int. Cl.
*C12N 15/113* (2010.01)
*C07H 21/04* (2006.01)
*C12Q 1/68* (2018.01)

(52) U.S. Cl.
CPC ........... *C12N 15/113* (2013.01); *C07H 21/04* (2013.01); *C12N 2310/11* (2013.01); *C12N 2310/141* (2013.01)

(58) Field of Classification Search
CPC .... C12N 15/113; C12N 2310/11; C07H 21/04
See application file for complete search history.

(56) References Cited

U.S. PATENT DOCUMENTS

| | | | |
|---|---|---|---|
| 4,522,811 | A | 6/1985 | Khvorova et al. |
| 5,194,596 | A | 3/1993 | Tischer et al. |
| 5,219,739 | A | 6/1993 | Tischer et al. |
| 5,240,848 | A | 8/1993 | Keck et al. |
| 5,328,470 | A | 7/1994 | Nabel et al. |
| 5,332,671 | A | 7/1994 | Ferrara et al. |
| 5,684,143 | A | 11/1997 | Grayaznov et al. |
| 5,814,014 | A | 9/1998 | Elsberry et al. |
| 5,858,988 | A | 1/1999 | Wang |
| 5,939,402 | A | 8/1999 | Weis et al. |
| 6,025,335 | A | 2/2000 | Weis et al. |
| 6,093,180 | A | 7/2000 | Elsberry et al. |
| 6,107,094 | A | 8/2000 | Crooke |
| 6,168,587 | B1 | 1/2001 | Bellhouse et al. |
| 6,177,403 | B1 | 1/2001 | Stedman |
| 6,194,389 | B1 | 2/2001 | Johnston et al. |
| 6,291,438 | B1 | 9/2001 | Wang |
| 6,312,900 | B1 | 11/2001 | Dean et al. |
| 6,383,814 | B1 | 5/2002 | Lee et al. |
| 6,447,768 | B1 | 9/2002 | Van Zonneveld et al. |
| 6,471,996 | B1 | 10/2002 | Sokoll et al. |
| 6,472,375 | B1 | 10/2002 | Hoon et al. |
| 6,489,464 | B1 | 12/2002 | Agrawal et al. |
| 7,250,496 | B2 | 7/2007 | Bentwich |
| 7,459,547 | B2 | 12/2008 | Zamore et al. |
| 7,691,997 | B2 | 4/2010 | Khvorova et al. |
| 7,723,512 | B2 | 5/2010 | Manoharan et al. |
| 7,732,593 | B2 | 6/2010 | Zamore et al. |
| 7,750,144 | B2 | 7/2010 | Zamore et al. |
| 7,772,203 | B2 | 8/2010 | Zamore et al. |
| 7,790,867 | B2 | 9/2010 | Bentwich |
| 7,820,809 | B2 | 10/2010 | Khvorova et al. |
| 7,834,171 | B2 | 11/2010 | Leake et al. |
| 8,013,136 | B2 | 9/2011 | Manoharan et al. |
| 8,097,752 | B2 | 1/2012 | Calogeropolou et al. |
| 8,304,530 | B2 | 11/2012 | Zamore et al. |
| 8,309,704 | B2 | 11/2012 | Zamore et al. |
| 8,309,705 | B2 | 11/2012 | Zamore et al. |
| 8,329,892 | B2 | 12/2012 | Zamore et al. |
| 8,431,544 | B1 | 4/2013 | Agrawal et al. |
| 8,501,706 | B2 | 8/2013 | Yamada et al. |
| 8,507,661 | B2 | 8/2013 | Manoharan et al. |
| 8,664,189 | B2 | 3/2014 | Khvorova et al. |
| 8,703,731 | B2 | 4/2014 | Jimenez et al. |
| 8,796,443 | B2 | 8/2014 | Khvorova et al. |
| 8,815,818 | B2 | 8/2014 | Samarsky et al. |
| 8,871,774 | B2 | 10/2014 | Charifson et al. |
| 8,877,439 | B2 | 11/2014 | Butora et al. |
| 8,906,874 | B2 | 12/2014 | Rao et al. |

(Continued)

FOREIGN PATENT DOCUMENTS

| | | |
|---|---|---|
| CN | 101199858 A | 6/2008 |
| CN | 101365801 A | 2/2009 |

(Continued)

OTHER PUBLICATIONS

Kent et al (RNA 15:14-20, 2009) (Year: 2009).*
NCBI page for EXOSC10 downloaded from (https://www.ncbi.nlm.nih.gov/gene?Db=gene&Cmd=DetailsSearch&Term=5394) (Year: 2024).*
GenBank NM_015532, 2024 retrieved from https://www.ncbi.nlm.nih.gov/nucleotide/NM_015532.5?report=genbank&log$=nuclalign&blast_rank=1&RID=PE9B83R4013 (Year: 2024).*
Akinc et al., A Combinatorial Library of Lipid-like Materials for Delivery of RNAi Therapeutics, Nature Biotechnology, vol. 26, No. 5, 20 Pages, May 2008.
Alagia, et al., Exploring PAZ/3'-overhang Interaction to Improve siRNA Specificity. A Combined Experimental and Modeling Study, Chemical Science, vol. 9, No. 8, pp. 2074-2086, 2018.
Alexopoulou, et al., Recognition of Double-Stranded RNA and Activation of NF-κB by Toll-like receptor 3, Nature, vol. 413, No. 6857, pp. 732-738, Oct. 18, 2001.

(Continued)

*Primary Examiner* — Sean McGarry
(74) *Attorney, Agent, or Firm* — LATHROP GPM LLP; James H. Velema, Esq.

(57) ABSTRACT

This disclosure relates to novel modified oligonucleotides with increased stability. The universal modified nucleotide sequences to increase the stability of an oligonucleotide are also provided.

21 Claims, 24 Drawing Sheets

Specification includes a Sequence Listing.

(56) References Cited

U.S. PATENT DOCUMENTS 8,993,738 B2 3/2015 Prakash et al.
9,029,389 B2 5/2015 No et al.
9,074,211 B2 7/2015 Woolf et al.
9,080,171 B2 7/2015 Khvorova et al.
9,095,504 B2 8/2015 Libertine et al.
9,175,289 B2 11/2015 Khvorova et al.
9,198,981 B2 12/2015 Ambati et al.
9,303,259 B2 4/2016 Khvorova et al.
9,340,786 B2 5/2016 Khvorova et al.
9,493,774 B2 11/2016 Kamens et al.
9,695,206 B2 7/2017 Minomi et al.
9,745,574 B2 8/2017 Woolf et al.
9,796,756 B2 10/2017 Hadwiger et al.
9,809,817 B2 11/2017 Khvorova et al.
9,862,350 B2 1/2018 Guerrero et al.
9,862,952 B2 1/2018 Khvorova et al.
9,867,882 B2 1/2018 Manoharan et al.
10,087,210 B2 10/2018 Prakash et al.
10,435,688 B2 10/2019 Khvorova et al.
10,478,503 B2 11/2019 Khvorova et al.
10,479,992 B2 11/2019 Woolf et al.
10,519,451 B2 12/2019 Khvorova et al.
10,633,653 B2 4/2020 Khvorova et al.
10,774,327 B2 9/2020 Khvorova et al.
10,799,591 B2 10/2020 Khvorova et al.
10,844,377 B2 11/2020 Khvorova et al.
11,230,713 B2 1/2022 Khvorova et al.
11,279,930 B2 3/2022 Khvorova et al.
11,345,917 B2 5/2022 Khvorova et al.
11,492,619 B2 11/2022 Khvorova et al.
11,667,915 B2 6/2023 Woolf et al.
11,702,659 B2 7/2023 Khvorova et al.
11,753,638 B2 9/2023 Khvorova et al.
11,827,882 B2 11/2023 Khvorova et al.
11,896,669 B2 2/2024 Khvorova et al.
12,024,706 B2 7/2024 Khvorova et al.
12,173,286 B2 12/2024 Khvorova et al.
12,180,477 B2 12/2024 Khvorova et al.
12,297,430 B2 5/2025 Khvorova et al.
2001/0027251 A1 10/2001 Cook et al.
2003/0045705 A1 3/2003 Cook
2003/0143732 A1 7/2003 Fosnaugh et al.
2004/0121426 A1 6/2004 Hsieh
2004/0198640 A1 10/2004 Leake et al.
2004/0205839 A1 10/2004 Doutriaux et al.
2005/0096284 A1 5/2005 McSwiggen
2005/0220766 A1 10/2005 Amalfitano et al.
2005/0255487 A1 11/2005 Khvorova et al.
2006/0003322 A1 1/2006 Bentwich et al.
2006/0009409 A1 1/2006 Woolf
2006/0024715 A1 2/2006 Liu et al.
2006/0078542 A1 4/2006 Mah et al.
2006/0094032 A1 5/2006 Fougerolles et al.
2006/0105998 A1 5/2006 Calogeropoulou et al.
2007/0004664 A1 1/2007 Mcswiggen et al.
2007/0004665 A1 1/2007 Mcswiggen et al.
2007/0015722 A1* 1/2007 Kraynack ............ C12N 15/113
514/81
2007/0099860 A1 5/2007 Sah et al.
2007/0135372 A1 6/2007 Maclachlan et al.
2007/0160534 A1 7/2007 Dennis et al.
2007/0191273 A1 8/2007 Ambat et al.
2007/0259827 A1 11/2007 Aronin et al.
2008/0039415 A1 2/2008 Stewart et al.
2008/0108583 A1 5/2008 Feinstein
2008/0108801 A1 5/2008 Manoharan
2008/0113369 A1 5/2008 Khvorova et al.
2008/0119427 A1 5/2008 Bhat et al.
2008/0188429 A1 8/2008 Iyer
2008/0269149 A1 10/2008 Bowles et al.
2009/0143322 A1 6/2009 Burkoth et al.
2009/0234109 A1 9/2009 Han et al.
2009/0269332 A1 10/2009 Gimeno et al.
2009/0281299 A1 11/2009 Manorahan et al.
2009/0306178 A1 12/2009 Bhat et al.
2009/0318676 A1 12/2009 Manoharan et al.
2010/0003258 A1 1/2010 Weng et al.
2010/0015706 A1 1/2010 Quay et al.
2010/0093085 A1 4/2010 Yamada et al.
2010/0184209 A1 7/2010 Vermeulen et al.
2010/0186103 A1 7/2010 Gao et al.
2010/0209487 A1 8/2010 Quay et al.
2010/0240730 A1 9/2010 Beigelman et al.
2011/0039914 A1 2/2011 Pavco et al.
2011/0046206 A1 2/2011 Bhat et al.
2011/0086905 A1 4/2011 Glazer
2011/0097716 A1 4/2011 Natt et al.
2011/0201006 A1 8/2011 Roehl et al.
2011/0237522 A1 9/2011 Khvorova et al.
2011/0237648 A1 9/2011 Khvorova et al.
2011/0251258 A1 10/2011 Samarsky et al.
2011/0263680 A1 10/2011 Khvorova et al.
2012/0016005 A1 1/2012 Samarsky et al.
2012/0040459 A1 2/2012 Khvorova et al.
2012/0052487 A9 3/2012 Khvorova et al.
2012/0059046 A1 3/2012 Woolf et al.
2012/0065243 A1 3/2012 Woolf et al.
2012/0136039 A1 5/2012 Aronin et al.
2013/0065298 A1 3/2013 Davidson et al.
2013/0131141 A1 5/2013 Khvorova et al.
2013/0131142 A1 5/2013 Libertine et al.
2013/0178513 A1 7/2013 Dobie et al.
2013/0196434 A1 8/2013 Maier et al.
2013/0197055 A1 8/2013 Kamens et al.
2013/0345218 A1 12/2013 Charifson et al.
2014/0005192 A1 1/2014 Charifson et al.
2014/0005197 A1 1/2014 Charifson et al.
2014/0113950 A1 4/2014 Khvorova et al.
2014/0155387 A1 6/2014 No et al.
2014/0288148 A1 9/2014 Biegelman et al.
2014/0296486 A1 10/2014 Gao et al.
2014/0315974 A1 10/2014 Khvorova et al.
2014/0364482 A1 12/2014 Khvorova et al.
2015/0025122 A1 1/2015 Smith
2015/0190525 A1 7/2015 Tatro
2015/0209441 A1 7/2015 Carell
2015/0232840 A1 8/2015 Aronin et al.
2015/0247142 A1 9/2015 Esau et al.
2015/0267200 A1 9/2015 Mcswiggen et al.
2015/0307542 A1* 10/2015 Roy ........................ C12P 19/34
536/26.3
2015/0315584 A1 11/2015 Macdonald et al.
2016/0017323 A1 1/2016 Prakash et al.
2016/0115482 A1 4/2016 Libertine et al.
2016/0115484 A1 4/2016 Woolf et al.
2016/0130578 A1 5/2016 Khvorova et al.
2016/0130583 A1 5/2016 Yokota et al.
2016/0244765 A1 8/2016 Khvorova et al.
2016/0281148 A1 9/2016 Greenlee et al.
2016/0319278 A1 11/2016 Khvorova et al.
2016/0348103 A1 12/2016 Wheeler et al.
2016/0355808 A1 12/2016 Khvorova et al.
2016/0355826 A1 12/2016 Khvorova et al.
2016/0376598 A1 12/2016 Lee et al.
2017/0009239 A1 1/2017 Khvorova et al.
2017/0009304 A1 1/2017 Zhou
2017/0037456 A1 2/2017 Kokoris et al.
2017/0043024 A1 2/2017 Khvorova et al.
2017/0043204 A1 2/2017 James
2017/0051283 A1 2/2017 Khvorova
2017/0051286 A1 2/2017 Smith
2017/0067056 A1 3/2017 Khvorova et al.
2017/0183655 A1 6/2017 Grabcysk et al.
2017/0189541 A1 7/2017 Foster
2017/0281795 A1 10/2017 Geall
2017/0312367 A1 11/2017 Khvorova et al.
2017/0327524 A1 11/2017 Nanna et al.
2017/0349903 A1 12/2017 Wanqing et al.
2017/0369882 A1 12/2017 Khvorova et al.
2018/0023082 A1 1/2018 Stanek et al.
2018/0087052 A1 3/2018 Hung et al.
2018/0094263 A1 4/2018 Khvorova et al.
2018/0179546 A1 6/2018 Khvorova et al.
2018/0251764 A1 9/2018 Albaek et al.

(56) References Cited

U.S. PATENT DOCUMENTS

2019/0002880 A1 1/2019 Woolf et al.
2019/0024082 A1 1/2019 Khvorova et al.
2019/0144860 A1 5/2019 Konstantinova et al.
2019/0185855 A1 6/2019 Khvorova et al.
2019/0211341 A1 7/2019 Butler et al.
2019/0225965 A1 7/2019 Khvorova et al.
2019/0247414 A1 8/2019 Yokota et al.
2019/0247507 A1 8/2019 Khvorova et al.
2020/0087663 A1 3/2020 Aronin
2020/0095580 A1 3/2020 Hauptmann et al.
2020/0123543 A1 4/2020 Khvorova et al.
2020/0165618 A1 5/2020 Khvorova et al.
2020/0270605 A1 8/2020 Khvorova et al.
2020/0308578 A1 10/2020 Woolf et al.
2020/0308584 A1 10/2020 Khvorova et al.
2020/0339983 A1 10/2020 Khvorova et al.
2020/0362341 A1 11/2020 Khvorova
2020/0385737 A1 12/2020 Khvorova
2020/0385740 A1 12/2020 Khvorova et al.
2021/0024926 A1 1/2021 Khvorova et al.
2021/0071117 A9 3/2021 Khvorova et al.
2021/0071177 A1 3/2021 Khvorova
2021/0085793 A1 3/2021 Khvorova et al.
2021/0115442 A1 4/2021 Khvorova et al.
2021/0139901 A1 5/2021 Khvorova et al.
2021/0317460 A1 10/2021 Khvorova et al.
2021/0340535 A1 11/2021 Khvorova
2021/0355491 A1 11/2021 Khvorova et al.
2021/0363523 A1 11/2021 Khvorova et al.
2022/0010309 A1 1/2022 Khvorova et al.
2022/0042015 A1 2/2022 Khvorova et al.
2022/0090069 A1 3/2022 Khvorova et al.
2022/0228141 A1 7/2022 Khvorova et al.
2022/0251554 A1 8/2022 Khvorova et al.
2022/0251555 A1 8/2022 Khvorova et al.
2022/0364100 A1 11/2022 Khvorova et al.
2023/0021431 A1 1/2023 Khvorova
2023/0061751 A1 3/2023 Khvorova et al.
2023/0078622 A1 3/2023 Khvorova et al.
2023/0193281 A1 6/2023 Khvorova et al.
2023/0313198 A1 10/2023 Khvorova et al.
2023/0340475 A1 10/2023 Khvorova et al.
2023/0348907 A1 11/2023 Khvorova et al.
2023/0392146 A1 12/2023 Khvorova et al.
2023/0416735 A1 12/2023 Khvorova et al.
2024/0067967 A1 2/2024 Khvorova et al.
2024/0084297 A1 3/2024 Khvorova et al.
2024/0132888 A1 4/2024 Khvorova et al.
2024/0132892 A1 4/2024 Khvorova et al.
2024/0173420 A1 5/2024 Khvorova et al.
2024/0287514 A1 8/2024 Khvorova et al.
2024/0293550 A1 9/2024 Khvorova et al.
2024/0301410 A1 9/2024 Khvorova et al.
2024/0325546 A1 10/2024 Fakih et al.
2024/0327836 A1 10/2024 Khvorova et al.
2025/0188458 A1 6/2025 Khvorova et al.

FOREIGN PATENT DOCUMENTS

CN 104884618 A 11/2015
CN 105194689 A 12/2015
EP 1423428 A2 6/2004
EP 1752536 A1 2/2007
EP 2407539 A1 1/2012
EP 2601204 A2 6/2013
EP 2679600 A1 1/2014
EP 2853597 A1 4/2015
EP 3277811 A1 2/2018
EP 3277814 A1 2/2018
EP 3277815 A1 2/2018
EP 3408391 A1 12/2018
EP 3550021 A1 10/2019
EP 3642341 A1 4/2020
EP 3929293 A2 12/2021
EP 3946369 A2 2/2022
EP 4126040 A2 2/2023
JP H06-41183 A 2/1994
JP H6-504680 A 6/1994
JP 2001-501614 A 2/2001
JP 2009-504782 A 2/2009
JP 2010-506598 A 3/2010
JP 2012-502657 A 2/2012
JP 2013-049714 A 3/2013
JP 2015-061534 A 4/2015
JP 2016-103986 A 6/2016
JP 2016-171815 A 9/2016
JP 2016-526529 A 9/2016
JP 2018-516091 A 6/2018
RU 2568066 C2 11/2015
TW 201038283 A 11/2010
WO WO 1992/013869 A1 8/1992
WO WO 1993/009239 A1 5/1993
WO WO 1993/024641 A2 12/1993
WO WO 1994/022890 A1 10/1994
WO WO 1996/003500 A1 2/1996
WO WO 1998/013526 A1 4/1998
WO WO 2003/029459 A2 4/2003
WO WO 2004/008946 A2 1/2004
WO WO 2004/013280 A2 2/2004
WO WO 2004/044136 A2 5/2004
WO WO 2004/061081 A2 7/2004
WO WO 2004/108956 A1 12/2004
WO WO 2005/078095 A1 8/2005
WO WO 2006/019430 A2 2/2006
WO WO 2007/022470 A2 2/2007
WO WO 2007/022506 A2 2/2007
WO WO 2007/051045 A2 5/2007
WO WO 2007/056153 A2 5/2007
WO WO 2007/091269 A2 8/2007
WO WO 2007/094218 A1 8/2007
WO WO 2007/112414 A2 10/2007
WO WO 2008/005562 A2 1/2008
WO WO 2008/036841 A2 3/2008
WO WO 2008/049078 A1 4/2008
WO WO 2008/070477 A2 6/2008
WO WO 2008/154482 A2 12/2008
WO WO 2008/154482 A3 12/2008
WO WO 2009/002944 A1 12/2008
WO WO 2009/054551 A2 4/2009
WO WO 2009/099991 A2 8/2009
WO WO 2009/102427 A2 8/2009
WO WO 2010/008582 A2 1/2010
WO WO 2010/011346 A1 1/2010
WO WO 2010/033246 A1 3/2010
WO WO 2010/033247 A2 3/2010
WO WO 2010/033248 A2 3/2010
WO WO 2010/048352 A2 4/2010
WO WO 2010/048585 A2 4/2010
WO WO 2010/059226 A2 5/2010
WO WO 2010/078536 A1 7/2010
WO WO 2010/090762 A1 8/2010
WO WO 2010/111367 A1 9/2010
WO WO 2010/111503 A2 9/2010
WO WO 2010/118263 A1 10/2010
WO WO 2011/097643 A1 8/2011
WO WO 2011/109698 A1 9/2011
WO WO 2011/119852 A1 9/2011
WO WO 2011/119871 A1 9/2011
WO WO 2011/119887 A1 9/2011
WO WO 2011/125943 A1 10/2011
WO WO 2011/139702 A2 11/2011
WO WO 2011/158924 A1 12/2011
WO WO 2012/005898 A2 1/2012
WO WO 2012/037254 A1 3/2012
WO WO 2012/058210 A1 5/2012
WO WO 2012/078637 A2 6/2012
WO WO 2012/118911 A1 9/2012
WO WO 2012/131365 A1 10/2012
WO WO 2012/177906 A1 12/2012
WO WO 2013/089283 A1 6/2013
WO WO 2013/165816 A2 11/2013
WO WO 2014/009429 A1 1/2014
WO WO 2014/043544 A1 3/2014
WO WO 2014/076195 A1 5/2014

(56) References Cited

FOREIGN PATENT DOCUMENTS

| | | | |
|---|---|---|---|
| WO | WO 2014/089313 | A1 | 6/2014 |
| WO | WO 2014/201306 | A1 | 12/2014 |
| WO | WO 2014/203518 | A1 | 12/2014 |
| WO | WO 2015/025122 | A1 | 2/2015 |
| WO | WO 2015/057847 | A1 | 4/2015 |
| WO | WO 2015/113004 | A2 | 7/2015 |
| WO | WO 2015/161184 | A1 | 10/2015 |
| WO | WO 2015/200078 | A1 | 12/2015 |
| WO | WO 2016/028649 | A1 | 2/2016 |
| WO | WO 2016/077321 | A1 | 5/2016 |
| WO | WO 2016/077349 | A1 | 5/2016 |
| WO | WO 2016/083623 | A1 | 6/2016 |
| WO | WO 2016/149331 | A2 | 9/2016 |
| WO | WO 2016/161374 | A1 | 10/2016 |
| WO | WO 2016/161378 | A1 | 10/2016 |
| WO | WO 2016/161388 | A1 | 10/2016 |
| WO | WO 2016/164866 | A1 | 10/2016 |
| WO | WO 2016/205410 | A2 | 12/2016 |
| WO | WO 2017/015555 | A1 | 1/2017 |
| WO | WO 2017/024239 | A1 | 2/2017 |
| WO | WO 2017/030973 | A1 | 2/2017 |
| WO | WO 2017/062862 | A2 | 4/2017 |
| WO | WO 2017/132669 | A1 | 8/2017 |
| WO | WO 2017/174572 | A1 | 10/2017 |
| WO | WO 2018/031933 | A2 | 2/2018 |
| WO | WO 2018/041973 | A1 | 3/2018 |
| WO | WO 2018/185241 | A1 | 10/2018 |
| WO | WO 2018/223056 | A1 | 12/2018 |
| WO | WO 2018/237245 | A1 | 12/2018 |
| WO | WO 2019/075418 | A1 | 4/2019 |
| WO | WO 2019/075419 | A1 | 4/2019 |
| WO | WO 2019/099949 | A1 | 5/2019 |
| WO | WO 2019/217459 | A1 | 11/2019 |
| WO | WO 2019/232255 | A1 | 12/2019 |
| WO | WO 2020/033899 | A1 | 2/2020 |
| WO | WO 2020/041769 | A1 | 2/2020 |
| WO | WO 2020/150636 | A1 | 7/2020 |
| WO | WO 2020/198509 | A2 | 10/2020 |
| WO | WO 2021/216556 | A2 | 10/2021 |
| WO | WO 2021/195533 | A2 | 11/2021 |
| WO | WO 2021/242883 | A1 | 12/2021 |

OTHER PUBLICATIONS

Alisky, et al., "Gene Therapy for Amyotrophic Lateral Sclerosis and Other Motor Neuron Diseases", Human Gene Therapy, vol. 11, Issue 17, pp. 2315-2329, Nov. 20, 2000.

Allerson et al., "Fully 2'-modified oligonucleotide duplexes with improved in vitro potency and stability compared to unmodified small interfering RNA", J Med Chem., Feb. 24, 2005, 48(4): 901-904.

Alterman et al., "A divalent siRNA chemical scaffold for potent and sustained modulation of gene expression throughout the central nervous system", Nat Biotechnol., Aug. 2019, 37(8): 884-894.

Alterman, et al., Hydrophobically Modified siRNAs Silence Huntingtin mRNA in Primary Neurons and Mouse Brain, Molecular Therapy-Nucleic Acids, vol. 4, pp. e266, Dec. 1, 2015.

Alvarez-Erviti, et al., "Delivery of siRNA To The Mouse Brain By Systemic Injection Of Targeted Exosomes", Nature Biotechnology, vol. 29, No. 4, pp. 341-345, Apr. 2011.

Alves, et al., Selectivity, Cooperativity, and Reciprocity in the Interactions between the δ-Opioid Receptor, Its Ligands, and G-proteins, Journal of Biological Chemistry, vol. 279 No. 43, pp. 4673-44682, Aug. 17, 2004.

Amarzguioui, et al., "Tolerance for Mutations And Chemical Modifications in a siRNA", Nucleic Acids Research, Jan. 15, 2003, 31(2): 589-595.

Ambardekar et al., "The modification of siRNA with 3' cholesterol to increase nuclease protection and suppression of native mRNA by select siRNA polyplexes", Biomaterials, Elsevier, Amsterdam, NL, vol. 32, No. 5, pp. 1404-1411. (Nov. 2, 2010).

Ambros, et al., MicroRNAs and Other Tiny Endogenous RNAs in C. elegans, Current Biology, vol. 13, Issue 10, pp. 807-818, May 13, 2003.

Ameres, et al., Molecular Basis for Target RNA Recognition and Cleavage by Human RISC, Cell, vol. 130, Issue 1, pp. 101-112, Jul. 13, 2007.

Ämmälä, et al., Targeted Delivery of Antisense Oligonucleotides to Pancreatic β-cells, Science Advances, vol. 4, No. 10, eaat3386, pp. 1-11, Oct. 17, 2018.

Anderson, et al., Experimental Validation Of The Importance Of Seed Complement Frequency To siRNA Specificity, RNA, vol. 14, No. 5, pp. 853-861, Mar. 26, 2008.

Anderson, et al., Identifying siRNA-Induced Off-Targets by Microarray Analysis, Methods in Molecular Biology, vol. 442, pp. 45-63, 2008.

Atwell, et al., Stable Heterodimers From Remodeling The Domain Interface Of A Homodimer Using A Phage Display Library, Journal Of Molecular Biology, vol. 270, Issue 1, pp. 26-35, Jul. 4, 1997.

Aubuchon, et al., "Preeclampsia: Animal Models for a Human Cure", Proceedings of the National Academy of Sciences, vol. 108, No. 4, pp. 1197-1198, Jan. 25, 2011.

Aureli, et al., GM1 Ganglioside: Past Studies and Future Potential, Molecular Neurobiology, vol. 53, Issue 3, pp. 1824-1842, Apr. 2016.

Avino, et al., Branched RNA: A New Architecture for RNA Interference, Journal of Nucleic Acids, Article ID 586935, 7 pages, Mar. 6, 2011.

Bagella, et al., Cloning Of Murine CDK9/PITALRE And Its Tissue-Specific Expression In Development, Journal of cellular physiology, vol. 177, No. 2, pp. 206-213, Dec. 7, 1998.

Bartlett, et al., Can Metastatic Colorectal Cancer Be Cured?, Journal Oncology, Cancer Network, vol. 26, No. 3, pp. 266-275, Mar. 15, 2012.

Bartlett, et al., Insights Into The Kinetics of siRNA-Mediated Gene Silencing From Live-Cell And Live-Animal Bioluminescent Imaging, Nucleic Acids Research, vol. 34, Issue 1, pp. 322-333, Jan. 1, 2006.

Behlke, et al., Chemical Modification of siRNAs for In Vivo Use, Oligonucleotides, vol. 18, No. 4, pp. 305-320, Nov. 29, 2008.

Bell, et al., Liposomal Transfection Efficiency And Toxicity On Glioma Cell Lines: In Vitro And In Vitro Studies, Neuroreport, vol. 9, Issue 5, pp. 793-798, Mar. 30, 1998.

Bertram et al., "Vinylphosphonate Internucleotide Linkages Inhibit the Activity of PcrA DNA Helicase", Biochemistry, Jun. 18, 2002, 41(24): 7725-7731.

Betkekar, et al., A Tandem Enyne/Ring Closing Metathesis Approach to 4-Methylene-2-cyclohexenols: An Efficient Entry to Otteliones and Loloanolides, Organic Letters, Dec. 6, 2011, vol. 14, No. 1, pp. 198-201.

Billy, et al., Specific Interference With Gene Expression Induced By Long, Double-Stranded RNA In Mouse Embryonal Teratocarcinoma Cell Lines, Proceedings of the National Academy of Sciences, vol. 98, No. 25, pp. 14428-14433, Dec. 4, 2001.

Birmingham, et al., 3' UTR Seed Matches, But Not Overall Identity, Are Associated With RNAi Off-Targets, Nature Methods, vol. 3, No. 3, pp. 199-204, Feb. 17, 2006.

Birmingham, et al., A Protocol For Designing siRNAs With High Functionality And Specificity, Nature Protocols, vol. 2, No. 9, pp. 2068-2078, Aug. 23, 2007.

Biscans et al., "Docosanoic acid conjugation to siRNA enables functional and safe delivery to skeletal and cardiac muscles", Molecular Therapy, Apr. 2021, vol. 29, No. 4, pp. 1382-1394.

Biscans et al., "Hydrophobicity of Lipid-Conjugated siRNAs Predicts Productive Loading to Small Extracellular Vesicles", Molecular Therapy, Jun. 2018, vol. 26, No. 6, pp. 1520-1528.

Biscans et al., "The Chemical Structure and Phosphorothioate content of hydrophobically modified siRNAs impact extrahepatic distribution and efficacy", Nucleic Acids Research, 2020, vol. 48, No. 14, pp. 7665-7680.

Biscans et al., Diverse Lipid Conjugates for Functional Extra-Hepatic siRNA Delivery in Vivo, Nucleic Acids Research, vol. 47, No. 3, pp. 1082-1096, Dec. 14, 2018.

(56) References Cited

OTHER PUBLICATIONS

Biscans, et al., The Valency of Fatty Acid Conjugates Impacts siRNA Pharmacokinetics, Distribution, and Efficacy in Vivo, Journal of Controlled Release, vol. 302, pp. 116-125, Mar. 2019.

Boutla et al., "Short 5'-phosphorylated double-stranded RNAs induce RNA interference in *Drosophila*", Biology, 2001, 11: 1776-1780.

Braasch, et al., "RNA Interference in Mammalian Cells by Chemically-Modified RNA", Biochemistry, vol. 42, No. 26, pp. 7967-7975, Jun. 11, 2003.

Brennecke, et al., Towards A Complete Description Of The microRNA Complement Of Animal Genomes, Genome Biology, vol. 4, No. 9, 3 Pages, Aug. 21, 2003.

Brown, et al., Effect of Phosphorothioate Modification of Oligodeoxynucleotides on Specific Protein Binding, Journal of Biological Chemistry, vol. 269, No. 43, pp. 26801-26805, 1994.

Brummelkamp, et al., A System for Stable Expression of Short Interfering RNAs in Mammalian Cells, Science, vol. 296, Issue 5567, pp. 550-553, Apr. 19, 2002.

Burchard, et al., MicroRNA-Like Off-Target Transcript Regulation By siRNAs is Species Specific, RNA, vol. 15, No. 2, pp. 308-315, 2009.

Burke, et al., "Spiral Arterial Remodeling Is Not Essential for Normal Blood Pressure Regulation in Pregnant Mice", Hypertension, vol. 55, No. 3, pp. 729-737, Jan. 25, 2010.

Byrne, et al., Novel Hydrophobically Modified Asymmetric RNAi Compounds (sd-rxRNA) Demonstrate Robust Efficacy in the Eye, Journal of Ocular Pharmacology and Therapeutics, vol. 29, Issue 10, pp. 855-864, Dec. 3, 2013.

Calegari, et al., Tissue-Specific RNA Interference In Postimplantation Mouse Embryos With Endoribonuclease-Prepared Short Interfering RNA, Proceedings of the National Academy of Sciences, vol. 99, No. 22, pp. 14236-14240, Oct. 29, 2002.

Carter, "Handbook of Parvoviruses", ed., P. Tijsser, CRC Press, pp. 155-168, 1990.

Chang, et al., Asymmetric Shorter-duplex siRNA Structures Trigger Efficient Gene Silencing With Reduced Nonspecific Effects, Molecular Therapy, vol. 17, Issue 4, pp. 725-732, Apr. 2009.

Chang, et al., Enhanced intracellular delivery and multi-target gene silencing triggered by tripodal RNA Structure, The journal of gene Medicine, vol. 14, No. 2, pp. 138-146, Feb. 2012.

Chang, et al., Transgenic Animal Models For Study of The Pathogenesis Of Huntington's Disease And Therapy, Drug design, development and therapy, vol. 9, pp. 2179-2188, Apr. 2015.

Chappell, et al., Mechanisms of Palmitic Acid-conjugated Antisense Oligonucleotide Distribution in Mice, Nucleic Acids Research, vol. 48, Issue 8, ,, pp. 4382-4395, May 7, 2020.

Charnock-Jones, et al., "Identification and Localization of Alternately Spliced mRNAs for Vascular Endothelial Growth Factor in Human Uterus and Estrogen Regulation in Endometrial Carcinoma Cell Lines", Biology of Reproduction, vol. 48, pp. 1120-1128, 1993.

Charrier, et al., Inhibition of SRGAP2 Function by Its Human-Specific Paralogs Induces Neoteny during Spine Maturation, Cell, vol. 149, Issue 4, pp. 923-935, May 11, 2012.

Chen et al., "Lipophilic siRNAs mediate efficient gene silencing in oligodendrocytes with direct CNC delivery", Journal Of Controlled Release, Elsevier, vol. 144, pp. 227-232. (Feb. 17, 2010).

Chen et al., "Thermoresponsive polypeptides from pegylated poly-L-glutamates", Biomacromolecules Dec. 2011: 2859-2863.

Chen et al., Influence of Particle Size on the in Vivo Potency of Lipid Nanoparticle Formulations of siRNA, Journal of Controlled Release, vol. 235, pp. 236-244, Aug. 10, 2016.

Chen, et al., "Gene Therapy For Brain Tumors: Regression Of Experimental Gliomas By Adenovirus-Mediated Gene Transfer In Vivo", Proceedings of the National Academy of Sciences, vol. 91, No. 8, pp. 3054-3057, 1994.

Cheng, et al., Enhanced Hepatic Uptake and Bioactivity of Type α1(I) Collagen Gene Promoter-Specific Triplex-Forming Oligonucleotides after Conjugation with Cholesterol, Journal of Pharmacology and Experimental Therapeutics, vol. 370, Issue 2, pp. 797-805, Aug. 1, 2019.

Cheung, et al., Effects of All-Trans-Retinoic Acid on Human SH-SYSY Neuroblastoma as in Vitro Model in Neurotoxicity Research, Neurotoxicology, vol. 30, No. 1, pp. 127-135, Jan. 1, 2009.

Cho, et al., Vascular Endothelial Growth Factor Receptor 1 Morpholino Decreases Angiogenesis in a Murine Corneal Suture Model, Investigative ophthalmology & visual science, vol. 53, Issue 2, pp. 685-692, Feb. 2012.

Choe, et al., Crystal Structure of Human Toll-Like Receptor 3 (TLR3) Ectodomain, Science, vol. 309, Issue 5734, pp. 581-585, Jun. 16, 2005.

Choi et al., Suppression of diacylglycerol acyltransferase-2 (DGAT2), but not DGAT1, with antisense oligonucleotides reverses diet-induced hepatic steatosis and insulin resistance, J Biol Chem., Aug. 3, 2007, 282(31): 22678-22688.

Chu, et al., Potent RNAi by Short RNA Triggers, RNA, vol. 14, pp. 1714-1719, 2008.

Chung et al., "Reducible siRNA Dimeric Conjugates for Efficient Cellular Uptake and Gene Silencing", Bioconjugate Chem., 2011, 22(2): 299-306.

Coelho, et al., Safety and Efficacy of RNAi Therapy for Transthyretin Amyloidosis, New England Journal of Medicine, vol. 369, No. 9, pp. 819-829, Aug. 29, 2013.

Coles, et al., A High-Throughput Method for Direct Detection of Therapeutic Oligonucleotide-Induced Gene Silencing In Vivo, Nucleic Acid Therapeutics, vol. 26, Issue 2, pp. 86-92, Apr. 11, 2016.

Collis, "The synthesis of vinylphosphonate-linked RNA", Ph.D. Thesis, University of Nottingham, Feb. 2008.

Crooke, et al., Cellular Uptake and Trafficking of Antisense Oligonucleotides, Nature Biotechnology, vol. 35, No. 3, pp. 230-237, Mar. 2017.

Crooke, et al., Phosphorothioate Modified Oligonucleotide—Protein Interactions, Nucleic Acids Research, May 1, 2020, 48(10): 5235-5253.

Cui, et al., "Role of Corin in Trophoblast Invasion and Uterine Spiral Artery Remodelling in Pregnancy", Nature, vol. 484, No. 7393, pp. 246-250, Mar. 21, 2012.

Czauderna, et al., Structural Variations and Stabilising Modifications of Synthetic siRNAs in Mammalian Cells, Nucleic Acids Research, vol. 31, Issue 11, pp. 2705-2716, Jun. 2003.

Dahlman et al., In Vivo Endothelial siRNA Delivery using Polymeric Nanoparticles with Low Molecular Weight, Nature Nanotechnology, vol. 9, No. 8, 17 Pages, Aug. 2014.

Damha et al. (1990) "An improved procedure for derivatization of controlled-pore glass beads for solid-phase oligonucleotide synthesis," Nucleic Acids Research, 18(13):3813-3821.

Dass, Crispin R., Cytotoxicity Issues Pertinent To Lipoplex-Mediated Gene Therapy In-Vivo, Journal of Pharmacy and Pharmacology, vol. 54, Issue 5, pp. 593-601, Feb. 18, 2010.

Davidson, et al., A Model System For In Vivo Gene Transfer Into The Central Nervous System Using An Adenoviral Vector, Nature Genetics, vol. 3, No. 3, pp. 219-223, Mar. 1, 1993.

Davidson, et al., Recombinant Adeno-Associated Virus Type 2, 4, and 5 Vectors: Transduction of Variant Cell Types And Regions In The Mammalian Central Nervous System, Proceedings of the National Academy of Sciences, vol. 97, No. 7, pp. 3428-3432, Mar. 28, 2000.

De Fougerolles, et al., "Interfering With Disease: a Progress Report on siRNA-based Therapeutics", Nature Reviews Drug Discovery, vol. 6, pp. 443-453, Jun. 2007.

De Marre et al., "Synthesis, characterization, and in vitro biodegradation of poly(ethylene glycol) modified poly[5N-(2-hydroxyethyl-L-glutamine]", J Bioact Compat Polym, Nov. 1996: 85-99.

De Paula et al., "Hydrophobization and bioconjugation for enhanced siRNA delivery and targeting", RNA, Feb. 28, 2007, vol. 13, No. 4, pp. 431-456.

Deleavey, et al., The 5' Binding MID Domain of Human Argonaute2 Tolerates Chemically Modified Nucleotide Analogues, Nucleic acid therapeutics, vol. 23, No. 1, pp. 81-87, Feb. 7, 2013.

Difiglia, et al., Therapeutic Silencing Of Mutant Huntingtin With siRNA Attenuates Striatal And Cortical Neuropathology And Behavioral Deficits, Proceedings of the National Academy of Sciences, vol. 104, No. 43, pp. 17204-17209, Oct. 23, 2007.

(56) References Cited

OTHER PUBLICATIONS

Dinusha, Differnce Between Sterol and Steroid, Home / Health / Medicine / Nutrients & Drugs, Aug. 4, 2011.
Doddridge et al., Effects of Vinylphosphonate Internucleotide Linkages on the Cleavage Specificity of Exonuclease III and on the Activity of DNA Polymerase I, Biochemistry, Mar. 25, 2003, 42(11): 3239-3246.
Doench, et al., siRNAs Can Function As miRNAs, Genes & Development, vol. 17, pp. 438-442, 2003.
Dohmen et al., "Defined Folate-PEG-siRNA Conjugates for Receptor-specific Gene Slicing", Molecular Therapy-Nucleic Acids, 2012, 1(1): e7.
Dowdy, Overcoming Cellular Barriers for RNA Therapeutics, Nature Biotechnology, vol. 35, pp. 222-229, Feb. 27, 2017.
Dua et al., "Modified siRNA Structure With a Single Nucleotide Bulge Overcomes Conventional siRNA-mediated Off-target Silencing", Molecular Therapy, Jun. 2011, 16(9): 1676-1687.
Ducruix, et al., Crystallization of Nucleic Acids and Proteins: A Practical Approach, Second Edition, 1999, pp. 201-216.
Dufour, et al., Intrajugular Vein Delivery of AAV9-RNAi Prevents Neuropathological Changes and Weight Loss in Huntington's Disease Mice, Molecular Therapy, vol. 22, No. 4, pp. 797-810, Jan. 6, 2014.
Dyall, et al., Long-chain omega-3 fatty acids and the brain: a review of the independent and shared effects of EPA, DPA and DHA, Frontiers in Aging Neuroscience, vol. 7, p. 52, Apr. 21, 2015.
Echevarría, et al., Evaluating the Impact of Variable Phosphorothioate Content in Tricyclo-DNA Antisense Oligonucleotides in a Duchenne Muscular Dystrophy Mouse Model, Nucleic Acid Therapeutics, vol. 29, No. 3, pp. 148-160, May 30, 2019.
Eckstein, Developments in RNA Chemistry, A Personal View, Biochimie, vol. 84, No. 9, pp. 841-848, Sep. 2002.
Eckstein, Phosphorothioate Oligodeoxynucleotides: What Is Their Origin and What Is Unique About Them?, Antisense and Nucleic Acid Drug Development, vol. 10, Issue 2, pp. 117-121, Jan. 30, 2009.
Egli, et al., Re-engineering RNA Molecules Into Therapeutic Agents, Accounts of Chemical Research, vol. 52, pp. 1036-1047, 2019.
Egusquiaguirre, et al., "Nanoparticle Delivery Systems For Cancer Therapy: Advances In Clinical And Preclinical Research", Clinical and Translational Oncology, vol. 14, pp. 83-93, 2012.
El Andaloussi, et al., "Exosome-Mediated Delivery of siRNA In Vitro And In Vivo", Nature Protocols, vol. 7, No. 12, pp. 2112-2126, Nov. 15, 2012.
El Andaloussi, et al., "Exosomes For Targeted siRNA Delivery Across Biological Barriers", Advanced Drug Delivery Reviews, vol. 65, pp. 391-397, 2013.
El Andaloussi, et al., "Extracellular Vesicles: Biology And Emerging Therapeutic Opportunities", Nature Reviews Drug Discovery, vol. 12, pp. 347-357, May 2013.
Elbashir, et al., RNA Interference Is Mediated By 21- and 22-Nucleotide RNAs, Genes & Development, vol. 15, No. 2, pp. 188-200, 2001.
Elmen, et al., Locked Nucleic Acid (LNA) Mediated Improvements in siRNA Stability And Functionality, Nucleic Acids Research, vol. 33, Issue 1, pp. 439-447, Jan. 14, 2005.
EMBL Database, WO 2005116204-A/113070: Double Strand Polynucleotides Generating RNA Interference, EBI Accession No. EM PAT:FW706544, XP055753619, , Apr. 18, 2011.
Eremina, et al., "Glomerular-Specific Alterations of VEGF-A Expression Lead to Distinct Congenital and Acquired Renal Diseases", Journal of Clinical Investigation, vol. 111, No. 5, pp. 707-716, Mar. 2003.
Eremina, et al., "VEGF Inhibition and Renal Thrombotic Microangiopathy", New England Journal of Medicine, vol. 358, No. 11, pp. 1129-1136, Mar. 13, 2008.
Etzold et al., "The extension of the sugar chain of thymidine: a new route to 5'-deoxyhexose nucleosides", Chemical Communications (London), 1968, Issue 7.
Evers, et al., Antisense Oligonucleotides In Therapy For Neurodegenerative Disorders, Advanced Drug Delivery Reviews, vol. 87, pp. 90-103, Jun. 29, 2015.
Extended European Search Report for European Patent Application No. 16837593.9, dated Mar. 20, 2019.
Extended European Search Report for European Patent Application No. 17745083.0, dated on Jul. 31, 2019.
Extended European Search Report for European Patent Application No. 17840367.1, dated Oct. 14, 2020.
Extended European Search Report for European Patent Application No. 18819571.3, dated May 14, 2021.
Extended European Search Report for European Patent Application No. 19847586.5, dated Jun. 21, 2023.
Extended European Search Report for European Patent Application No. 19852320.1, dated May 2, 2022.
Extended European Search Report for European Patent Application No. 20164108.1, dated on Dec. 3, 2020.
Extended European Search Report for European Patent Application No. 20216265.7, dated Feb. 10, 2022.
Extended European Search Report for European Patent Application No. 20741865.8, dated Apr. 26, 2023.
Extended European Search Report for European Patent Application No. 20856904.6, mailed Jan. 2, 2024.
Extended European Search Report for European Patent Application No. 21197881.2, dated Oct. 31, 2022.
Extended European Search Report for European Patent Application No. 21741867.2, mailed Mar. 12, 2024.
Extended Supplementary European Search Report for European Patent Application No. 20777915.8, mailed Sep. 15, 2023.
Fan, et al., Endometrial VEGF Induces Placental sFLT1 And Leads To Pregnancy Complications, The Journal of clinical investigation, vol. 124, No. 11, pp. 4941-4952, Oct. 20, 2014.
Fattal, et al., Biodegradable Polyalkylcyanoacrylate Nanoparticles For The Delivery Of Oligonucleotides, Journal of Controlled Release, vol. 53, pp. 137-143, May 1998.
Fedorov, et al., Off-Target Effects By siRNA Can Induce Toxic Phenotype, RNA, vol. 12, No. 7, pp. 1188-1196, May 2006.
Felber, et al., The Interactions of Amphiphilic Antisense Oligonucleotides With Serum Proteins And Their Effects on In Vitro Silencing Activity, Biomaterials, vol. 33, Issue 25, pp. 5955-5965, Sep. 2012.
Figueroa, et al., Neurorestorative Targets of Dietary Long-Chain Omega-3 Fatty Acids in Neurological Injury, Molecular Neurobiology, vol. 50, Issue 1, pp. 197-213, Aug. 2014.
Fisher, et al., Transduction With Recombinant Adeno-Associated Virus For Gene Therapy Is Limited By Leading-Strand Synthesis, Journal of virology, vol. 70, No. 1, pp. 520-532, Jan. 1996.
Fitzgerald, et al., A Highly Durable RNAi Therapeutic Inhibitor of PCSK9, New England Journal of Medicine, vol. 376, No. 1, pp. 41-51, Jan. 5, 2017.
Flower et al., MSH3 Modifies Somatic instability and Disease Severity in Huntington's and Myotonic Dystrophy Type 1, Brain, A Journal of Neurology, Jul. 2019, 142(7): 1876-1886.
Foster et al., "Advanced siRNA Designs Further Improve In Vivo Performance of GalNAc-siRNA Conjugates", Molecular Therapy, vol. 26, No. 3, pp. 709-717, Mar. 2018.
Franich, et al., AAV Vector—Mediated RNAi of Mutant Huntingtin Expression is Neuroprotective in a Novel Genetic Rat Model of Huntington's Disease, Molecular Therapy, vol. 16, Issue 5, pp. 947-956, Mar. 25, 2008.
Frank et al., Structural Basis for 5'-Nucleotide Base-specific Recognition of Guide RNA by Human AGO2, Nature, vol. 465, pp. 818-822, Jun. 2010.
Frazier, Antisense Oligonucleotide Therapies: The Promise and the Challenges from a Toxicologic Pathologist's Perspective, Toxicologic pathology, vol. 43, Issue 1, pp. 78-89, Nov. 9, 2014.
Frigg et al., Relationships between vitamin A and vitamin E in the chick, Int J Vitam Nutr Res., 1984, 54(2-3): 125-133.
Furuhashi et al., Expression of Low Density Lipoprotein Receptor Gene in Hjuman Placenta during Pregnancy, Molecular Endocrinology, 1989, 3: 1252-1256.

(56) References Cited

OTHER PUBLICATIONS

Gaglione, et al., Recent Progress in Chemically Modified siRNAs, Mini Reviews in Medicinal Chemistry, vol. 10, No. 7, pp. 578-595, 2010.
Gaus, et al., Characterization of the Interactions of Chemically-modified Therapeutic Nucleic Acids With Plasma Proteins Using a Fluorescence Polarization Assay, Nucleic Acids Research, vol. 47, No. 3, pp. 1110-1122, 2019.
Gavrilov et al. (Jun. 2012) "Therapeutic siRNA: principles, challenges, and strategies", Yale Journal of Biology and Medicine, 85:187-200.
Geary, Antisense Oligonucleotide Pharmacokinetics and Metabolism, Expert Opinion on Drug Metabolism & Toxicology, vol. 5, pp. 381-391, Apr. 1, 2009.
Geary, et al., Pharmacokinetics, Biodistribution And Cell Uptake of Antisense Oligonucleotides, Advanced Drug Delivery Reviews, vol. 87, pp. 46-51, Jun. 29, 2015.
GenBank, Mus Musculus Non-Coding RNA, Oocyte_Clustered_Small_RNA6599, Complete Sequence, GenBank Accession No. AB341398.1, May 24, 2008, 1 page.
GenBank, Rattus Norvegicus piRNA piR-182271, Complete Sequence, GenBank Accession No. DQ766949.1, Jul. 12, 2006, 1 Page.
GenBank, Signal Recognition Particle 54 kDa protein 2 [Perkinsus marinus ATCC 50983], NCBI Reference Sequence: XP_002784438.1, Apr. 30, 2010.
Ghidini et al., "An RNA modification with remarkable resistance to RNase A", Chemical Communications, Aug. 8, 2013, 49(79): 9036-9038.
Ghosh et al., "Comparing 2-nt 3' overhangs against blunt-ended siRNAs: a systems biology based study", BMC Genomics, 2009, 10(Suppl. 1):S17.
Gilany, et al., The Proteome of The Human Neuroblastoma Cell Line SH-SY5Y: An Enlarged Proteome, Biochimica et Biophysica Acta (BBA)—Proteins and Proteomics, vol. 1784, Issues 7-8, pp. 983-985, Jul.-Aug. 2008.
Gilbert, et al., "Hypertension Produced by Reduced Uterine Perfusion in Pregnant Rats Is Associated With Increased Soluble fms-like Tyrosine Kinase-1 Expression", Hypertension, vol. 50, No. 6, pp. 1142-1147, Oct. 8, 2007.
Gille, et al., "Analysis of Biological Effects and Signaling Properties of Flt-1 (VEGFR-1) and KDR (VEGFR-2)", Mechanisms of Signal Transduction, vol. 276, Issue 5, pp. 3222-3230, Feb. 2001.
Godard, et al., "Antisense Effects of Cholesterol-Oligodeoxynucleotide Conjugates Associated with Poly(alkylcyanoacrylate) Nanoparticles", European Journal of Biochemistry banner, vol. 232, pp. 404-410, 1995.
Godinho et al., "PK-modifying anchors significantly alter clearance kinetics, tissue distribution, and efficacy of therapeutics siRNAs", Mol Ther Nucleic Acids, Jun. 13, 2022,29: 116-132, ePublished Sep. 13, 2022.
Godinho et al., Pharmacokinetic Profiling of Conjugated Therapeutic Oligonucleotides: A High-Throughput Method based upon Serial Blood Microsampling Coupled to Peptide Nucleic Acid Hybridization Assay, Nucleic Acid Therapeutics, vol. 27, pp. 323-334, Dec. 1, 2017.
Goodson et al., Dental Applications, Medical Applications of Controlled Release, vol. 2, pp. 115-138, 1984.
Grad, et al., Computational and Experimental Identification of C. elegans microRNAs, Molecular Cell, vol. 11, Issue 5, pp. 1253-1263, May 2003.
Gray, et al., Human Mutant Huntingtin with a Stable Polyglutamine Repeat Can Elicit Progressive and Selective Neuropathogenesis in BACHD Mice, Journal of Neuroscience, vol. 28, Issue 24, pp. 6182-6195, Jun. 11, 2008.
Griffiths-Jones, SAN, The microRNA Registry, Nucleic Acids Research, vol. 32, Issue Supplement 1, pp. D109-D111, Jan. 1, 2004.
Grimm, D, Asymmetry in siRNA Design, Gene Therapy, vol. 16, No. 7, pp. 827-829, Apr. 30, 2009.
Grimm, et al., Fatality In Mice Due To Oversaturation Of Cellular MicroRNA/short Hairpin RNA Pathways, Nature, vol. 441, No. 7092, pp. 537-541, May 25, 2006.
Gvozdeva et al., "Noncanonical Synthetic RNAi Inducers InL RNA Interference", InTech, Apr. 6, 2016.
Haly et al., "An extended phosphate linkage: Synthesis, hybridization and modeling studies of modified oligonucleotides", Nucleosides and Nucleotides, 1996, 15(7-8): 1383-1395.
Hamajima, et al., Intranasal Administration of HIV-DNA Vaccine Formulated with a Polymer, Carboxymethylcellulose, Augments Mucosal Antibody Production and Cell-Mediated Immune Response, Clinical Immunology and Immunopathology, vol. 88, Issue 2, pp. 205-210, Aug. 1998.
Hammerling et al., Monoclonal Antibodies and T-Cell Hybridomas, Research Monographs in Immunology, vol. 3, pp. 563-681, 1981.
Hanuš et al., "-CH2—lengthening of the internucleotide linkage in the ApA dimer can improve its conformational compatibility with its natural polynucleotide counterpart", Nucleic Acids Research, Dec. 15, 2001, 29(24): 5182-5194.
Haraszti, et al., "5'-Vinylphosphonate improves tissue accumulation and efficacy of conjugated siRNAs in vivo", Nucleic Acids Research, Jul. 27, 2017, 45(13): 7581-7592.
Harborth et al., Sequence, Chemical, and Structural Variation of Small Interfering RNAs and Short Hairpin RNAs and the Effect on Mammalian Gene Silencing, Antisense and Nucleic Acid Drug Development, vol. 13, pp. 83-105, Apr. 1, 2003.
Harlow et al., "Antibodies: A Laboratory Manual", Cold Spring Harbor Laboratory Chapter 14, Second Edition, 2013.
Hassler et al., Comparison of Partially and Fully Chemically-Modified siRNA in Conjugate-Mediated Delivery in Vivo, Nucleic Acids Research, vol. 46, No. 5, pp. 2185-2196, Mar. 16, 2018.
Herdewijn, Piet, Heterocyclic Modifications of Oligonucleotides and Antisense Technology, Antisense and Nucleic Acid Drug Development, vol. 10, Issue 4, pp. 297-310, Jul. 8, 2004.
Heydarian, et al., Novel Splice Variants of sFlt1 are Upregulated in Preeclampsia, Placenta, vol. 30, Issue 3, pp. 250-255, Mar. 2009.
Heyer, et al., An Optimized Kit-Free Method For Making Strand-Specific Deep Sequencing Libraries From RNA Fragments, Nucleic Acids Research, vol. 43, Issue 1, pp. 1-14, Jan. 9, 2015.
Hillier et al., yw97a12.r1 Soares_placenta_8to9weeks_2NbHP8to9W *Homo sapiens* cDNA clone Image:260158 5' similar to GB:X51602_cds1 Vascular Endothelial Growth Factor Receptor 1 (Human); contains element OFR repetitive element, mRNA sequence, NIH, Genbank Accession No. N47911.1, Feb. 14, 1996.
Hirashima, et al., "Trophoblast Expression of Fms-like Tyrosine Kinase 1 Is Not Required for the Establishment of the Maternal-fetal Interface in the Mouse Placenta", Proceedings of the National Academy of Sciences of the United States of America, vol. 100, No. 26, pp. 15637-15642, Dec. 23, 2003.
Hodgson, et al., A YAC Mouse Model for Huntington's Disease with Full-Length Mutant Huntingtin, Cytoplasmic Toxicity, and Selective Striatal Neurodegeneration, Neuron, vol. 23, Issue 1, pp. 181-192, May 1999.
Hong et al., "Reducible Dimeric Conjugates of Small Internally Segment Interfering RNA for Efficient Gene Silencing", Macromolecular Bioscience, Jun. 2016, vol. 16, No. 10, pp. 1442-1449.
Huang, Preclinical and Clinical Advances of GalNAc-Decorated Nucleic Acid Therapeutics, Molecular Therapy—Nucleic Acids, vol. 6,, pp. 116-132, Mar. 17, 2017.
Hult, et al., Mutant Huntingtin Causes Metabolic Imbalance by Disruption of Hypothalamic Neurocircuits, Cell Metabolism, vol. 13, Issue 4, pp. 428-439, Apr. 6, 2011.
Hutvagner, et al., A microRNA in a Multiple-Turnover RNAi Enzyme Complex, Science, vol. 297, Issue 5589, pp. 2056-2060, Sep. 20, 2002.
Intapad, et al., "Reduced Uterine Perfusion Pressure Induces Hypertension in the Pregnant Mouse", American Journal of Physiology-Regulatory, Integrative and Comparative Physiology, vol. 307, Issue 11, pp. R1353-R1357, Dec. 2014.
International Search Report & Written Opinion Received for PCT Application No. PCT/US2019/046013, mailed on Jan. 9, 2020.
International Search Report & Written Opinion Received for PCT Application No. PCT/US2020/014181, mailed on Jun. 2, 2020.

(56) References Cited

OTHER PUBLICATIONS

International Search Report & Written Opinion Received for PCT Application No. PCT/US2021/028166, mailed on Nov. 26, 2021.
International Search Report & Written Opinion Received for PCT Application No. PCT/US2021/044158, dated Jan. 31, 2022.
International Search Report & Written Opinion Received for PCT Application No. PCT/US2022/039047, dated Mar. 3, 2023.
International Search Report and Written Opinion for PCT International Patent Application No. PCT/US2019/048027 mailed Nov. 15, 2019.
International Search Report and Written Opinion for PCT International Patent Application No. PCT/US2020/025017, mailed Sep. 18, 2020.
International Search Report and Written Opinion for PCT International Patent Application No. PCT/US2020/047492, mailed Feb. 17, 2022.
International Search Report and Written Opinion in related PCT Application No. PCT/US2020/014146, mailed May 22, 2020.
International Search Report and Written Opinion in related PCT Application No. PCT/US2021/024425, mailed Oct. 15, 2021.
International Search Report and Written Opinion received for PCT Patent Application No. PCT/US2016/025722, mailed on Aug. 12, 2016.
International Search Report and Written Opinion received for PCT Patent Application No. PCT/US2016/025731, mailed on Sep. 9, 2016.
International Search Report and Written Opinion received for PCT Patent Application No. PCT/US2016/025753, mailed on Sep. 14, 2016.
International Search Report and Written Opinion received for PCT Patent Application No. PCT/US2016/046810, mailed on Nov. 29, 2016.
International Search Report and Written Opinion received for PCT Patent Application No. PCT/US2017/015633, mailed on May 11, 2017.
International Search Report and Written Opinion received for PCT Patent Application No. PCT/US2018/038952, mailed on Sep. 24, 2018.
International Search Report and Written Opinion received for PCT Patent Application No. PCT/US2020/045487, mailed on Dec. 31, 2020.
International Search Report and Written Opinion received for PCT Patent Application No. PCT/US2021/013620, mailed on Apr. 26, 2021.
International Search Report and Written Opinion received for PCT Patent Application No. PCT/US2021/034290, mailed on Nov. 4, 2021.
International Search Report and Written Opinion received for PCT Patent Application No. PCT/US2021/041946, mailed on Oct. 29, 2021.
International Search Report and Written Opinion received for PCT Patent Application No. PCT/US2021/060356, mailed on Apr. 13, 2022.
Iriyama et al., Hypoxia-independent up-regulation of placental HIF-1α gene expression contributes to the pathogenesis of preeclampsia, Hypertension, Jun. 2015, 65(6): 1307-1315, Supplemental Data.
Iversen et al., "Optimized siRNA-PEG Conjugates for Extended Blood Circulation and Reduced Urine Excretion in Mice", Feb. 25, 2013, Theranostics 2013, vol. 3, Issue 3, pp. 201-209.
Jackson et al., Position-Specific Chemical Modification Of siRNAs Reduces "Off-Target" Transcript Silencing, RNA, vol. 12, No. 7, pp. 1197-1205, May 8, 2006.
Jackson, et al., Recognizing And Avoiding siRNA Off-Target Effects For Target Identification And Therapeutic Application, Nature Reviews Drug Discovery, vol. 9, No. 1, pp. 57-67, Jan. 1, 2010.
Jacque, et al., Modulation of HIV-1 replication by RNA interference, Nature, vol. 418, No. 6896, pp. 435-438, Jun. 26, 2002.
Janssen, et al., Long-Chain Polyunsaturated Fatty Acids (LCPUFA) From Genesis To Senescence: The Influence of LCPUFA On Neural Development, Aging, And Neurodegeneration, Progress in Lipid Research, vol. 53, pp. 1-17, Jan. 2014.
Jebbink et al., "Expression of Placental FLT1 Transcript Variants Relates to Both Gestational Hypertensive Disease and Fetal Growth", Hypertension, Apr. 25, 2011, 58(1): 70-76.
Jin, et al., DARPP-32 to Quantify Intracerebral Hemorrhage-induced Neuronal Death in Basal Ganglia, Translational Stroke Research, vol. 4, No. 1, pp. 130-134, Feb. 1, 2013.
Jo et al., "Small Interfering RNA Nunchucks with a Hydrophobic Linker for Efficient Intracellular Delivery", Macromol Biosci., 2014, 14: 195-201.
Jo, et al., Selection and Optimization of Asymmetric siRNA Targeting the Human c-MET Gene, Molecules and cells, vol. 32, No. 6, pp. 543-548, Dec. 31, 2011.
Judge, et al., Design of Noninflammatory Synthetic siRNA Mediating Potent Gene Silencing in Vivo, Molecular Therapy, vol. 13, Issue 3, pp. 494-505, Mar. 2006.
Jung et al., "Gene silencing efficiency of siRNA-PEG conjugates: Effect of PEGylation site and PEG molecular weight", Journal of Controlled Release, Mar. 4, 2010, vol. 144, No. 3, pp. 306-313.
Kachare et al., "Phospho-carboxylic anhydride of a homologated nucleoside leads to primer degradation in the presence of a polymerase", Bioorg Med Chem Letters, Jun. 15, 2014, 24(12): 2720-2723.
Kamba, et al., "VEGF-dependent Plasticity of Fenestrated Capillaries in the Normal Adult Microvasculature", American Journal of Physiology—Heart and Circulatory Physiology, vol. 29, pp. H560-H576, Feb. 1, 2006.
Karaki et al., Lipid-Oligonucleotide Conjugates Improve Cellular Uptake and Efficiency of TCTP-Antisense in Castration-Resistant Prostate Cancer, Journal of Controlled Release, vol. 258, pp. 1-9, Jul. 28, 2017.
Karlin, et al., Applications And Statistics For Multiple High-Scoring Segments In Molecular Sequences, Proceedings of the National Academy of Sciences of the USA, vol. 90, pp. 5873-5877, Jun. 1993.
Karlin, et al., Methods For Assessing The Statistical Significance Of Molecular Sequence Features By Using General Scoring Schemes, Proceedings of the National Academy of science of the USA, vol. 87, No. 6, pp. 2264-2268, Mar. 1990.
Karra, et al., Transfection Techniques for Neuronal Cells, Journal of Neuroscience, vol. 30, No. 18, pp. 6171-6177, May 5, 2010.
Kaura, et al., Synthesis, Hybridization Characteristics, and Fluorescence Properties of Oligonucleotides Modified with Nucleobase-Functionalized Locked Nucleic Acid Adenosine and Cytidine Monomers, The Journal of Organic Chemistry, Jun. 16, 2014, 79: 6256-6268.
Kenski et al. (2012) "siRNA-optimized Modifications for Enhanced In Vivo Activity," Mol. Ther. Nucleic Acids. 1:e5. pp. 1-8.
Khan et al., Silencing Myostatin using Cholesterol-Conjugated siRNAs Induces Muscle Growth, Molecular Therapy, Nucleic Acids, vol. 5, 9 Pages, Jan. 1, 2016.
Khankin, et al., "Intravital High-frequency Ultrasonography to Evaluate Cardiovascular and Uteroplacental Blood Flow in Mouse Pregnancy", Pregnancy Hypertension: An International Journal of Women's Cardiovascular Health, vol. 2, pp. 84-92, 2012.
Khorev et al., Trivalent, Gal//GalNAc-containing ligands designed for the asialoglycoprotein receptor, Bioorgan. & Medicin. Chem., 2008, 16: 5216-5231.
Khvorova, et al., Abstract IA27: Advances In Oligonucleotide Chemistry For The Treatment Of Neurodegenerative Disorders And Brain Tumors, Cancer Research, vol. 76, Issue 6, Abstract IA27, Mar. 2016.
Khvorova, et al., Functional siRNAs and miRNAs Exhibit Strand Bias, Cell, vol. 115, Issue 2, pp. 209-216, Oct. 17, 2003.
Khvorova, Oligonucleotide Therapeutics—A New Class of Cholesterol-Lowering Drugs, The New England Journal of Medicine, vol. 376, No. 1, pp. 4-7, Jan. 5, 2017.
Kim et al., "LHRH Receptor-Mediated Delivery of siRNA Using Polyelectrolyte Complex Micelles Self-Assembled from siRNA-PEG-LHRH Conjugate and PEI", Bioconjugate Chemistry, Oct. 14, 2008, vol. 19, No. 11, pp. 2156-2162.

(56) References Cited

OTHER PUBLICATIONS

Kim et al., "PEG conjugated VEGF siRNA for anti-angiogenic gene therapy", Journal of Controlled Release, Jun. 3, 2006, vol. 116, No. 2, pp. 123-129.
Kofoed et al., "Oligodeoxynucleotides with Extended 3'- and 5'-Homologous Internucleotide Linkages", Acta Chemica Scandanavia, 1997, 51: 318-324.
Kordasiewicz, et al., Sustained Therapeutic Reversal of Huntington's Disease by Transient Repression of Huntingtin Synthesis, Neuron, vol. 74, Issue 6, pp. 1031-1044, Jun. 21, 2012.
Kubo et al., "Lipid-Conjugated 27-Nucleotide Double-Stranded RNAs with Dicer-Substrate Potency enhance RNAi-Mediated Gene Silencing", Molecular Pharmaceutics, American Chemical Society, US, vol. 9, No. 5, pp. 1374-1382, DOI: 10.1021/MP2006278. (Apr. 11, 2012).
Kubo et al., "Palmitic Acid-Conjugated 21-Nucleotide siRNA Enhances Gene-Silencing Activity", Molecular Pharmaceutics, vol. 8, No. 6, pp. 2193-2203, DOI: 10.1021/mp200250f. (Oct. 10, 2011).
Kubo, et al., Modified 27-nt dsRNAs With Dramatically Enhanced Stability in Serum and Long-term RNAi Activity, Oligonucleotides, vol. 17, No. 4, pp. 445-464, 2007.
Kumar, et al., "Shielding of Lipid Nanoparticles for siRNA Delivery: Impact on Physicochemical Properties", Cytokine Induction, and Efficacy, Molecular Therapy—Nucleic Acids, vol. 3, e210, pp. 1-7, Nov. 18, 2014.
Lagos-Quintana, et al., Identification of Novel Genes Coding for Small Expressed RNAs, Science, vol. 294, Issue 5543, pp. 853-858, Oct. 26, 2001.
Lagos-Quintana, et al., Identification of Tissue-Specific MicroRNAs from Mouse, Current Biology, vol. 12, Issue 9, pp. 735-739, Apr. 30, 2002.
Lagos-Quintana, et al., New microRNAs From Mouse And Human, RNA, vol. 9, No. 2, pp. 175-179, 2003.
Lai, et al., Computational Identification of Drosophila microRNA Genes, Genome Biology, vol. 4, No. 7, pp. 1-20, Jun. 30, 2003.
Lam, et al., "A New Type of Synthetic Peptide Library For Identifying Ligand-Binding Activity", Nature, vol. 354, pp. 82-84, Nov. 7, 1991.
Lambert, et al., "Nanoparticulate Systems For The Delivery Of Antisense Oligonucleotides", Advanced Drug Delivery Reviews, vol. 47, pp. 99-112, 2001.
Lan, et al., Neuroactive Steroid Actions at the GABAA Receptor, Hormones and Behavior, vol. 28, Issue 4, pp. 537-544, Dec. 1994.
Landis, et al., "A Call for Transparent Reporting to Optimize the Predictive Value of Preclinical Research", Nature, vol. 490, pp. 187-191, Oct. 10, 2012.
Lau, et al., An Abundant Class of Tiny RNAs with Probable Regulatory Roles in Caenorhabditis elegans, Science, vol. 294, Issue 5543, pp. 858-862, Oct. 26, 2001.
Lau, et al., Characterization of the piRNA Complex from Rat Testes, Science, vol. 313, Issue 5785, pp. 363-367, Jul. 21, 2006.
Laufer, et al., "Selected Strategies for the Delivery of siRNA In Vitro and In Vivo", RNA Technologies and Their Applications, 2010, pp. 29-58.
Lebedeva et al., "Phosphorothioate oligodeoxynucleotides as inhibitors of gene expression: antisense and non-antisense effects", Applications of Antisense therapies to restenosis, 1999, p. 101.
Lee et al., A Novel Approach to Investigate Tissue-specific Trinucleotide Repeat Instability, BMC Systems Biology, Mar. 19, 2010, 4(29): 1-16.
Lee et al., Adeno-associated virus (AAV) vectors: Rational design strategies for capsid engineering, Current Opinion in Biomed. Eng., 2018, 58-63.
Lee et al., "Current preclinical small interfering RNA (siRNA)-based conjugate systems for RNA therapeutics", Advanced Drug Delivery Reviews, Oct. 27, 2015, vol. 104, pp. 78-92.
Lee, et al., "Recent Developments In Nanoparticle-Based siRNA Delivery For Cancer Therapy", BioMed Research International, vol. 2013, Article ID 782041, 10 Pages, Jun. 2013.
Lee, et al., An Extensive Class of Small RNAs in Caenorhabditis elegans, Science, vol. 294, Issue 5543, pp. 862-864, Oct. 26, 2001.
Lee, et al., Expression of Small Interfering RNAs Targeted Against HIV-1 rev Transcripts in Human Cells, Nature Biotechnology, vol. 20, No. 5, pp. 500-505, May 1, 2002.
Lee, et al., RNA Interference-Mediated Simultaneous Silencing of Four Genes Using Cross-Shaped RNA, Molecules and Cells, vol. 35, No. 4, pp. 320-326, Apr. 4, 2013.
Lee, et al., Small-interfering RNA (siRNA)-based functional micro-and nanostructures for efficient and selective gene silencing, Accounts of Chemical Research, vol. 45, No. 7, pp. 1014-1025, Jul. 17, 2012.
Levine, et al., "Circulating Angiogenic Factors and the Risk of Preeclampsia", The New England Journal of Medicine, vol. 350, pp. 672-683, 2004.
Li, et al., "Recombinant Vascular Endothelial Growth Factor 121 Attenuates Hypertension and Improves Kidney Damage in a Rat Model of Preeclampsia", Hypertension, vol. 50, pp. 686-692, 2007.
Li, et al., Distribution of 5-Hydroxymethylcytosine in Different Human Tissues, "SAGE—Hindawi Access to Research, Journal of Nucleic Acids, vol. 2011", pp. 1-7, 2011.
Li, et al., Huntington's Disease Gene (IT15) Is Widely Expressed In Human And Rat Tissues, Neuron, vol. 11, No. 5, pp. 985-993, Nov. 1993.
Liang, et al., Identification and Characterization of Intracellular Proteins That Bind Oligonucleotides With Phosphorothioate Linkages, Nucleic Acids Research, vol. 43, Issue 5, pp. 2927-2945, Mar. 11, 2015.
Lim, et al., The microRNAs of Caenorhabditis elegans, Genes & Development, vol. 17, No. 8, pp. 991-1008, 2003.
Lim, et al., Vertebrate MicroRNA Genes, Science, vol. 299, Issue 5612, p. 1540, Mar. 7, 2003.
Lima, et al., Single-Stranded siRNAs Activate RNAi in Animals, Cell, vol. 150, Issue 5, pp. 883-894, Aug. 31, 2012.
Liu et al., Snapshot PK: A Rapid Rodent in Vivo Preclinical Screening Approach, Drug Discovery Today, vol. 13, No. 7-8, pp. 360-367, Apr. 1, 2008.
Lopes, et al., Comparison Between Proliferative And Neuron-Like SH-SY5Y Cells As An In Vitro Model For Parkinson Disease Studies, Brain Research, vol. 1337, pp. 85-94, Jun. 14, 2010.
Lorenz, et al., Steroid And Lipid Conjugates of siRNAs To Enhance Cellular Uptake And Gene Silencing In Liver Cells, Bioorganic & Medicinal Chemistry Letters, vol. 14, Issue 19, pp. 4975-4977, Oct. 4, 2004.
Loy et al., "Allele-Specific Gene Silencing in Two Mouse Models of Autosomal Dominant Skeletal Myopathy", PLoS One, Nov. 2012, 7(11): e49757, 11 pages.
Lundh, et al., Hypothalamic Expression Of Mutant Huntingtin Contributes To The Development Of Depressive-Like Behavior In The Bac Transgenic Mouse Model Of Huntington's Disease, Human Molecular Genetics, vol. 22, Issue 17, pp. 3485-3497, Sep. 1, 2013.
Luo, et al., Photoreceptor Avascular Privilege Is Shielded By Soluble VEGF Receptor-1, Elife, vol. 2, pp. 1-22, Jun. 18, 2013.
Ly et al., Visualization of Self-Delivering Hydrophobically Modified siRNA Cellular Internalization, Nucleic Acids Research, vol. 45, pp. 15-25, Nov. 29, 2016.
Ma et al., Structural Basis For 5'-End-Specific Recognition Of Guide RNA By The A. Fulgidus Piwi Protein, Nature, vol. 434, No. 7033, pp. 666-670, Mar. 31, 2005.
Ma, et al., Structural Basis For Overhang-Specific Small Interfering RNA Recognition By The PAZ Domain, Nature, vol. 429, No. 6989, pp. 318-322, May 20, 2004.
Magner et al., "Influence of mismatched and bulged nucleotides on SNP-preferential RNase H cleavage of RNA-antisense gapmer heteroduplexes", Scientific Reports, Oct. 2017, 7(12532), 16 pages.
Makris, et al., "Uteroplacental Ischemia Results in Proteinuric Hypertension and Elevated sFLT-1", Kidney International, vol. 71, Issue 1, pp. 977-984, May 2, 2007.
Maltepe, et al., "The Placenta: Transcriptional, Epigenetic, and Physiological Integration During Development", The Journal of Clinical Investigation, vol. 120, No. 4, pp. 1016-1025, Apr. 1, 2010.

(56) References Cited

OTHER PUBLICATIONS

Mangiarini, et al., Exon 1 of the HD Gene with an Expanded CAG Repeat Is Sufficient to Cause a Progressive Neurological Phenotype in Transgenic Mice, Cell, vol. 87, Issue 3, pp. 493-506, Nov. 1, 1996.
Mantha, et al., Rnai-Based Therapies For Huntington's Disease: Delivery Challenges And Opportunities, Therapeutic Delivery, vol. 3, No. 9, pp. 1061-1076, Aug. 29, 2012.
Marcus, et al., FedExosomes: Engineering Therapeutic Biological Nanoparticles that Truly Deliver, Pharmaceuticals, vol. 6, No. 5, pp. 659-680, Apr. 29, 2013.
Marques, et al., A Structural Basis For Discriminating Between Self And Nonself Double-Stranded Rnas In Mammalian Cells, Nature biotechnology, vol. 23, No. 11, pp. 1399-1405, 2005.
Masotti, et al., Comparison of Different Commercially Available Cationic Liposome-DNA Lipoplexes: Parameters Influencing Toxicity And Transfection Efficiency, Colloids and Surfaces B: Biointerfaces, vol. 68, Issue 2, pp. 136-144, Feb. 1, 2009.
Matsuda et al., siRNA Conjugates Carrying Sequentially Assembled Trivalent N-Acetylgalactosamine Linked Through Nucleosides Elicit Robust Gene Silencing In Vivo in Hepatocytes, ACS Chemical Biology, vol. 10, No. 5, pp. 1181-1187, Mar. 2, 2015.
Maynard, et al., "Excess Placental Soluble fms-like Tyrosine Kinase 1 (sFltI) may Contribute to Endothelial Dysfunction", Hypertension, and Proteinuria in Preeclampsia, The Journal of Clinical Investigation, vol. 111, pp. 649-658, 2003.
Mazur et al., "Isosteres of natural phosphates. 11. Synthesis of a phosphonic acid analogue of an oligonucleotide", Tetrahedron, 1984, 40(20): 3949-3956.
McCaffrey, et al., Gene Expression: RNA Interference in Adult Mice, Nature, vol. 418, No. 6893, pp. 38-39, Jul. 4, 2002.
McManus, et al., Gene Silencing Using Micro-RNA Designed Hairpins, RNA, vol. 8, Issue 6, pp. 842-850, Aug. 20, 2002.
Mikhailov et al., "Use of 5-deoxy-ribo-hexofuranose derivatives for the preparation of 5'-nucleotide phosphonates and homoribonucleosides", Collect Czech Chem Commun., 1989, 54(4): 1055-1066.
Miller et al., Adaptable Synthesis of C-Glycosidic Multivalent Carbohydrates and Succinamide-Linked Derivization, Org. Letter., 2010, 12(22): 5262-5265.
Miller, et al., Receptor-mediated Uptake of Phosphorothioate Antisense Oligonucleotides in Different Cell Types of the Liver, Nucleic Acid Therapeutics, vol. 28, No. 3, pp. 119-127, 2018.
Miyagishi, et al., U6 promoter-driven siRNAs With Four Uridine 3' Overhangs Efficiently Suppress Targeted Gene Expression In Mammalian Cells, Nature Biotechnology, vol. 20, No. 5, pp. 497-500, May 1, 2002.
Mok, et al., Multimeric small interfering ribonucleic acid for highly efficient sequence-specific gene silencing~, Nature Materials, vol. 9, pp. 272-278, Jan. 24, 2010.
Molitoris, et al., siRNA Targeted to p53 Attenuates Ischemic and Cisplatin-Induced Acute Kidney Injury, Journal of the American Society of Nephrology, vol. 20, Issue 8, pp. 1754-1764, Aug. 1, 2009.
Monteys et al., "Artificial miRNAs Targeting Mutant Huntingtin Show Preferential Silencing In Vitro and In Vivo", Molecular Therapy, Nucleic Acids, Apr. 2015: E234, 11 pages.
Morrissey et al., "Activity of stabilized short interfering RNA in a mouse model of hepatitis B virus replication", Hepatology, 2005, 41: 1349-1356.
Moss et al., Identification of Genetic Variants Associated with Huntington's Disease Progression: A Genome-wide Association Study, The Lancet, Neurology, Sep. 2017, 16(9): 701-711.
Mourelatos, et al., miRNPs: A Novel Class Of Ribonucleoproteins Containing Numerous microRNAs, Genes & Development, vol. 16, No. 6, pp. 720-728, 2002.
Mullen, et al., NeuN, A Neuronal Specific Nuclear Protein In Vertebrates, Development, vol. 116, No. 1, pp. 201-211, 1992.
Myers, et al., Optimal Alignments In Linear Space, Computer Applications in the Biosciences, vol. 4, No. 1, pp. 11-17, Mar. 1988.
Nagamatsu, et al., "Cytotrophoblasts Up-Regulate Soluble Fms-Like Tyrosine Kinase-1 Expression under Reduced Oxygen: An Implication for the Placental Vascular Development and the Pathophysiology of Preeclampsia", Endocrinology, vol. 145, Issue 11, pp. 4838-484, Nov. 1, 2004.
Nair, et al., Impact of Enhanced Metabolic Stability on Pharmacokinetics and Pharmacodynamics of GalNAc-siRNA Conjugates, Nucleic Acids Research, vol. 45, Issue 19, pp. 10969-10977, Nov. 2, 2017.
Nair, et al., Multivalent N-Acetylgalactosamine-Conjugated siRNA Localizes in Hepatocytes and Elicits Robust RNAi-Mediated Gene Silencing, Journal of the American Chemical Society, vol. 136, No. 49, pp. 16958-16961, Dec. 10, 2014.
Nallagatla et al., Nucleoside Modifications Modulate Activation of the Protein Kinase PKR in an RNA Structure-Specific Manner, RNA, vol. 14, pp. 1201-1213, Jun. 1, 2008.
Namjou et al., "GWAS and enrichment analyses of non-alcoholic fatty liver disease identify new trait-associated genes and pathways across eMERGE Network", BMC Medicine, Jul. 2019, 17: 135, 19 pages.
Nelson et al. (1992) "Oligonucleotide labeling methods 3. Direct labeling of oligonucleotides employing a novel, non-nucleosidic, 2-aminobutyl-1 ,3-propanediol backbone," 20(23):6253-6259.
Neufeld, et al., "Similarities and Differences Between the Vascular Endothelial Growth Factor (VEGF) Splice Variants", Cancer and Metastasis Reviews, vol. 15, pp. 153-158, Jun. 1996.
Nielsen, et al., Sequence-Selective Recognition of DNA by Strand Displacement With A Thymine-Substituted Polyamide, Science, vol. 254, Issue 5037, pp. 1497-1500, Dec. 6, 1991.
Nikan et al., Synthesis and Evaluation of Parenchymal Retention and Efficacy of a Metabolically Stable, O-Phosphocholine-N-Docosahexaenoyl-L-serine siRNA Conjugate in Mouse Brain, Bioconjugate Chemistry, vol. 28, No. 6, 21 Pages, Jun. 21, 2017.
Nikan, et al., Docosahexaenoic Acid Conjugation Enhances Distribution and Safety of siRNA upon Local Administration in Mouse Brain, Molecular Therapy—Nucleic Acids, vol. 5, No. 8, pp. 1-11, Aug. 9, 2016, with Supplement.
Nishina et al., "Efficient In Vivo Delivery of siRNA to the Liver by Conjugation of α-Tocopherol", Mol Ther., Apr. 2008, 16(4): 734-740.
Noguchi et al., "Allele-specific Gene Silencing of Mutant mRNA Restores Cellular Function in Ullrich Congenital Muscular Dystrophy Fibroblasts", Molecular Therapy—Nucleic Acids, Jun. 2014, 3: e171.
Oberbauer et al., Renal Uptake of an 18-mer Phosphorothioate Oligonucleotide, Kidney International, vol. 48, pp. 1226-1232, 1995.
Ohnishi, et al., "Enhancement of Allele Discrimination by Introduction of Nucleotide Mismatches into siRNA in Allele-Specific Gene Silencing by RNAi", Plos One, vol. 3, Issue 5, e2248, 9 Pages, May 2008.
Ohtsuka et al., "Joining of synthetic ribotrinucleotides with defined catalyzed by T4 RNA ligase", European Journal of Biochemistry, 1977, 81(2): 285-291.
Oishi et al., "Lactosylated Poly(ethylene glycol)-siRNA Conjugate through Acid-Labile B-Thiopropionate Linkage to Construct pH-Sensitive Polyion Complex Micelles Achieving Enhanced Gene Silencing in Hepatoma Cells", J. Am. Chem. Soc., 2005, 127: 1624-1625.
Old et al., "Cloning in Yeast and Microbial Eukaryotes", Principles of Gene Manipulation: An Introduction to Genetic Engineering, Studies in Microbiology, 1989, 2(11): 199-221.
Osborn et al., Hydrophobicity Drives the Systemic Distribution of Lipid-Conjugated siRNAs Via Lipid Transport Pathways, Nucleic Acids Research, vol. 47, No. 3, pp. 1070-1081, Dec. 8, 2018.
Osborn, et al., "Improving siRNA Delivery In Vivo Through Lipid Conjugation", Nucleic Acid Therapeutics, vol. 28, No. 3, pp. 128-136, May 10, 2018.
Østergaard et al., "Conjugation of hydrophobic moieties enhances potency of antisense oligonucleotides in the muscle of rodents and non-human primates", Nucleic Acids Research, 2019, 47(12): 6045-6058.

(56) References Cited

OTHER PUBLICATIONS

Østergaard, et al., "Fluorinated Nucleotide Modifications Modulate Allele Selectivity of SNP-Targeting Antisense Oligonucleotides", Molecular Therapy Nucleic Acids, vol. 7, pp. 20-30, Jun. 2017.

Ouimet, et al., DARPP-32, A Dopamine- And Adenosine 3':5'-Monophosphate-Regulated Phosphoprotein Enriched In Dopamine-Innervated Brain Regions. III. Immunocytochemical Localization, Journal of Neuroscience, vol. 4, No. 1, pp. 111-124, Jan. 1, 1984.

Overhoff, et al., "Quantitative Detection of siRNA and Single-stranded Oligonucleotides: Relationship Between Uptake and Biological Activity of siRNA", Nucleic Acids Research, vol. 32, Issue 21, pp. 1-5, Dec. 2, 2004.

Owen, Morpholino-Mediated Increase in Soluble Flt-1 Expression Results in Decreased Ocular and Tumor Neovascularization, PLoS One, vol. 7, No. 3, pp. e33576, Mar. 15, 2012.

Paddison, et al., Short Hairpin RNAs (shRNAs) Induce Sequence-Specific Silencing In Mammalian Cells, Genes & Development, vol. 16, No. 8, pp. 948-958, 2002.

Padiukova et al., "Synthesis of 5'-derivatives of thymidine", Bioorg Khim., 1990, 16(5): 668-673 [Article in Russian—no abstract available].

Parmar, et al., 5'-(E)-Vinylphosphonate: A Stable Phosphate Mimic can Improve the RNAi Activity of siRNA-GalNAc Conjugates, ChemBioChem, vol. 17, pp. 985-989, Jun. 2, 2016.

Partial European Search Report for European Patent Application No. 20216265.7, dated Nov. 10, 2021.

Partial European Search Report for European Patent Application No. 21197881.2, mailed Mar. 14, 2022.

Partial Supplementary European Search Report for European Patent Application No. 20741865.8, mailed Dec. 20, 2022.

Partial Supplementary European Search Report for European Patent Application No. 20777915.8, mailed Apr. 5, 2023.

Partial Supplementary European Search Report for European Patent Application No. 20852443.9, mailed Aug. 25, 2023.

Partial Supplementary European Search Report for European Patent Application No. 20856904.6, mailed Sep. 13, 2023.

Pasquinelli, et al., Conservation of The Sequence And Temporal Expression of let-7 Heterochronic Regulatory RNA, Nature, vol. 408, No. 6808, pp. 86-89., Nov. 2, 2000.

Paul, et al., Effective Expression of Small Interfering RNA In Human Cells, Nature Biotechnology, vol. 20, No. 5, pp. 505-508, May 1, 2002.

Peel, et al., Conjugation and Evaluation of Small Hydrophobic Molecules to Triazole-Linked siRNAs, ACS medicinal chemistry letters, vol. 6, No. 2, pp. 117-122, Dec. 4, 2014.

Pei, et al., Quantitative Evaluation of siRNA Delivery in Vivo, RNA, vol. 16, No. 12, pp. 2553-2563, Oct. 12, 2010.

Petersen, et al., LNA: A Versatile Tool for Therapeutics and Genomics, Trends in Biotechnology, vol. 21, Issue 2, pp. 74-81, Feb. 2003.

Pfister, et al., "Five siRNAs Targeting Three SNPs in Huntingtin May Provide Therapy for Three-Quarters of Huntington's Disease Patients", Current Biology, vol. 19, No. 9, pp. 774-778., May 12, 2009.

Podbevsek et al., "Solution-state structure of a fully alternately 2'-F/2'-OMe modified 42-nt dimeric siRNA construct", Nucleic Acids Research, vol. 38, No. 20, pp. 7298-7307, DOI: 10.1093/nar/gkq621. (Jul. 12, 2010).

Pokholenko et al., Lipid Oligonucleotide Conjugates as Responsive Nanomaterials for Drug Delivery, Journal of Materials Chemistry B, vol. 1, 6 Pages, 2013.

Posocco, et al., "Impact of siRNA Overhangs for Dendrimer-mediated siRNA Delivery and Gene Silencing", Molecular Pharmaceutics, Aug. 5, 2013, 10(8): 3262-3273.

Powe, et al., "Preeclampsia, a Disease of the Maternal Endothelium: the Role of Antiangiogenic Factors and Implications for Later Cardiovascular Disease", Circulation, vol. 123, No. 24, pp. 2856-2869, Jun. 11, 2011.

Prakash et al., Targeted Delivery Of Antisense Oligonucleotides To Hepatocytes Using Triantennary N-Acetyl Galactosamine Improves Potency 10-Fold In Mice, Nucleic Acids Research, vol. 42, Issue 13, pp. 8796-8807, Jul. 29, 2014.

Prakash, et al., Identification of Metabolically Stable 5'-Phosphate Analogs That Support Single-Stranded siRNA Activity, Nucleic Acids Research, Mar. 9, 2015, 43(6): 2993-3011.

PubChem Database, AMINO-TEG-DIOL, National Institute or Biotechnology Information, PubChem Accession No. 22136768, 2003.

PubChem Database, SCHEMBL867745, National Institute for Biotechnology Information, PubChem Accession No. 12454428, 12 pages, 2005.

PubChem Detabase, CID-16131506, Compund Summary: dGTGGGTGGGT, Jul. 3, 2007, Retrieved from url: https://pubchem.ncbi.nlm.nih.gov/compound/16131506.

Putnam, David A., Antisense Strategies and Therapeutic Applications, American Journal of Health System Pharmacy, vol. 53, No. 2, pp. 151-160, Jan. 15, 1996.

Raal, et al., Inclisiran for the Treatment of Heterozygous Familial Hypercholesterolemia, New England Journal of Medicine, vol. 382, No. 16, pp. 1520-1530, Apr. 16, 2020.

Rajeev et al., Hepatocyte-Specific Delivery of Sirnas Conjugated to Novel Non-Nucleosidic Trivalent N-Acetylgalactosamine Elicits Robust Gene Silencing in Vivo, ChemBioChem, vol. 16, pp. 903-908, Apr. 13, 2015.

Raouane et al., "Lipid Conjugated Oligonucleotides: A Useful Strategy for Delivery", Chem., 2012, 23: 1091-1104.

Reed et al., Forty Mouse Strain Survey of Body Composition, Physiology & Behavior, vol. 91, No. 5, 15 Pages, Aug. 15, 2007.

Reinhart, et al., Small RNAs Correspond to Centromere Heterochromatic Repeats, Science, vol. 297, No. 5588, 1 Page, Sep. 13, 2002.

Reynolds, A, et al., Rational siRNA Design for RNA Interference, Nature Biotechnology, vol. 22, No. 3, pp. 326-330, Apr. 2004.

Rigo, et al., Pharmacology of a Central Nervous System Delivered 2'-O-Methoxyethyl-Modified Survival of Motor Neuron Splicing Oligonucleotide in Mice and Nonhuman Primates, Journal of Pharmacology and Experimental Therapeutics, vol. 350, Issue 1, pp. 46-55, Jul. 1, 2014.

Rodriguez-Lebron, et al., Intrastriatal rAAV-Mediated Delivery of Anti-Huntingtin shRNAs Induces Partial Reversal Of Disease Progression In R6/1 Huntington's Disease Transgenic Mice, Molecular Therapy, vol. 12, Issue 4, pp. 618-633, Oct. 2005.

Roy et al., "Synthesis of DNA/RNA and Their Analogs via Phosphoramidite and H-Phosphonate Chemistries", Molecules, 2013, 18(11): 14268-14284.

Rozners et al., "Synthesis and Properties of RNA Analogues Having Amides as Interuridine Linkages at Selected Positions", JACS Articles, Sep. 6, 2003, 125: 12125-12136.

Rupprecht, et al., Neuroactive Steroids: Mechanisms Of Action And Neuropsychopharmacological Properties, Psychoneuroendocrinology, vol. 28, Issue 2, pp. 139-168, Feb. 2003.

Rusckowski, et al., Biodistribution and Metabolism of a Mixed Backbone Oligonucleotide (GEM 231) Following Single and Multiple Dose Administration in Mice, Antisense and Nucleic Acid Drug Development, vol. 10, Issue 5, pp. 333-345, Jan. 30, 2009.

Sah, et al., Oligonucleotide Therapeutic Approaches for Huntington disease, The Journal of Clinical Investigation, vol. 121, No. 2, pp. 500-507, Feb. 1, 2011.

Samuelson, Kristin W., Post-Traumatic Stress Disorder And Declarative Memory Functioning: A Review, Dialogues In Clinical Neuroscience, vol. 13, No. 3, pp. 346-351, Sep. 2011.

Sarett et al., Lipophilic siRNA Targets Albumin in Situ and Promotes Bioavailability, tumor Penetration, and Carrier-Free Gene Silencing, Proceedings of the National Academy of Sciences, vol. 114, pp. E6490-E6497, Jul. 24, 2017.

Scherman et al., Genetic Pharmacology: Progresses in siRNA Delivery and Therapeutic Applications, Gene Therapy, vol. 24, pp. 151-156, Mar. 2017.

Schirle, et al., Structural Basis for MicroRNA Targeting, Science, vol. 346, Issue 6209, pp. 608-613, Oct. 31, 2014.

Schlegal et al., "Chirality Dependent Potency Enhancement and Structural Impact of Glycol Nucleic Acid Modification on siRNA", JACS, Jun. 1, 2017, pp. 1-28.

(56) References Cited

OTHER PUBLICATIONS

Schoch, et al., Antisense Oligonucleotides: Translation From Mouse Models to Human Neurodegenerative Diseases, Neuron, vol. 94, Issue 6, pp. 1056-1070, Jun. 21, 2017.
Schwab, et al., An Approach For New Anticancer Drugs:Oncogene-Targeted Antisense DNA, Annals of Oncology, vol. 5, Issue 4, pp. 55-58, 1994.
Schwarz et al., "Designing siRNA that distinguish between genes that differ by a single nucleotide", PLOS Genetics, Sep. 2006, 2(9): e140.
Schwarz, et al., Asymmetry in the Assembly of the RNAi Enzyme Complex, Cell, vol. 115, Issue 2, pp. 199-208, Oct. 17, 2003.
SEQ ID No. 1112 from U.S. Pat. No. 7,790,867. [Accessed Nov. 28, 2018].
Setten, et al., The Current State and Future Directions of RNAi-based Therapeutics, Nature Reviews Drug Discovery, vol. 18, pp. 421-446, Mar. 7, 2019.
Shen, et al., 2'-fluoro-modified Phosphorothioate Oligonucleotide Can Cause Rapid Degradation of P54nrb and PSF, Nucleic Acids Research, vol. 43, Issue 9, pp. 4569-4578, May 19, 2015.
Shen, et al., Acute Hepatotoxicity of 2' Fluoro-modified 5-10-5 Gapmer Phosphorothioate Oligonucleotides in Mice Correlates With Intracellular Protein Binding and the Loss of DBHS Proteins, Nucleic Acids Research, vol. 46, Issue 5, pp. 2204-2217, Mar. 16, 2018.
Shen, et al., Chemical Modification of PS-ASO Therapeutics Reduces Cellular Protein-binding and Improves the Therapeutic Index, Nature Biotechnology, vol. 37, pp. 640-650, Apr. 29, 2019.
Shukla et al., "Exploring Chemical Modifications for siRNA Therapeutics: A Structural and Functional Outlook", ChemMedChem, Feb. 19, 2010, 5(3): 328-349.
Sibley et al., "Identification of Allele-Specific RNAi Effectors Targeting Genetic Forms of Parkinson's Disease", PLOS One, Oct. 2011, 6(10): e26194.
Sipova et al., "5'-O-Methylphosphonate nucleic acids—new modified DNAs that increase the *Escherichia coli* RNase H cleavage rate of hybrid duplexes", Nucleic Acids Research, 2014, 42(8): 5378-5389.
Smith et al., "RNA Nanotherapeutics for the Amelioration of Astroglial Reactivity", Mol Ther Nucleic Acids, Mar. 2, 2018, 10: 103-121, ePublished Nov. 24, 2017.
Smith et al., Reversed-Phase High Performance Liquid Chromatography of Phosphatidylcholine: A Simple Method for Determining Relative Hydrophobic Interaction of Various Molecular Species, Journal of Lipid Research, vol. 22, pp. 697-704, May 1, 1981.
Solano et al., Toxicological and Pharmacokinetic Properties of QPI-1007, a Chemically Modified Synthetic siRNA Targeting Caspase 2 mRNA, Following Intravitreal Injection, Nucleic Acid Therapeutics, vol. 24, pp. 258-266, Aug. 1, 2014.
Song, et al., Sustained Small Interfering RNA-Mediated Human Immunodeficiency Virus Type 1 Inhibition in Primary Macrophages, Journal of Virology, vol. 77, No. 13, pp. 7174-7181, 2003.
Soutschek, et al., Therapeutic Silencing of An Endogenous Gene By Systemic Administration Of Modified siRNAs, Nature, vol. 432, No. 7014, pp. 173-178, Nov. 11, 2004.
Stalder, et al., The Rough Endoplasmatic Reticulum Is A Central Nucleation Site of siRNA-Mediated RNA Silencing, The EMBO Journal, vol. 32, Issue 8, pp. 1115-1127, Mar. 19, 2013.
Stein, et al., Inhibition of Vesivirus Infections in Mammalian Tissue Culture with Antisense Morpholino Oligomers, Antisense and Nucleic Acid Drug Development, vol. 11, Issue 5, pp. 317-325, Oct. 2001.
Stein, et al., Physicochemical Properties Of Phosphorothioate Oligodeoxynucleotides, Nucleic Acids Research, vol. 16, No. 8, pp. 3209-3221, Apr. 25, 1988.
Stein, et al., Systemic and Central Nervous System Correction of Lysosomal Storage in Mucopolysaccharidosis Type VII Mice, Journal of Virology, vol. 73, No. 4, pp. 3424-3429, Apr. 1999.
Stokman, et al., Application of siRNA In Targeting Protein Expression In Kidney Disease, Advanced Drug Delivery Reviews, vol. 62, Issue 14, pp. 1378-1389, Nov. 30, 2010.
Sugo et al., "Development of antibody-siRNA conjugate targeted to cardiac and skeletal muscles", Journal of Controlled Release, Jun. 29, 2016, vol. 237, pp. 1-13.
Suhr et al., Efficacy and Safety of Patisiran for Familial Amyloidotic Polyneuropathy: A Phase II Multi-Dose Study, Orphanet Journal of Rare Diseases, vol. 10, pp. 1-9, Dec. 1, 2015.
Sui, et al., A DNA Vector-Based RNAi Technology To Suppress Gene Expression In Mammalian Cells, Proceedings of the National Academy of Sciences, vol. 99, No. 8, pp. 5515-5520, Apr. 16, 2002.
Sun, et al., Asymmetric RNA Duplexes Mediate RNA Interference in Mammalian Cells, Nature Biotechnology, vol. 26, pp. 1379-1382, Dec. 2008.
Tabernero, et al., First-in-Humans Trial of an RNA Interference Therapeutic Targeting VEGF and KSP in Cancer Patients with Liver Involvement, vol. 3, Issue 4, pp. 406-417, Apr. 2013.
Tai et al., "Current Aspects of siRNA Bioconjugate for In Vitro and In Vivo Delivery", Molecules, Jun. 2019, 24(12): 2211, ePublished Jun. 13, 2019.
Tan et al., "Allele-Specific Targeting of microRNAs to HLA-G and Risk of Asthma", American Journal of Human Genetics, Oct. 2007, 81(4): 829-834.
Tang, et al., "Excess Soluble Vascular Endothelial Growth Factor Receptor-1 in Amniotic Fluid Impairs Lung Growth in Rats: Linking Preeclampsia With Bronchopulmonary Dysplasia", American Journal of Physiology-Lung Cellular and Molecular Physiology, vol. 302, No. 1, pp. L36-L46, Jan. 1, 2012.
Taniguchi et al., Plasmodium Berghei ANKA Causes Intestinal Malaria Associated with Dysbiosis, Scientific Reports, vol. 5, pp. 1-12, Oct. 27, 2015.
Tanowitz et al., Asialoglycoprotein Receptor 1 Mediates Productive Uptake of N-Acetylgalactosamine-Conjugated and Unconjugated Phosphorothioate Antisense Oligonucleotides into Liver Hepatocytes, Nucleic Acids Research, vol. 45, No. 21, pp. 12388-12400, Dec. 1, 2017.
Teng et al., "A GDF15 3' UTR variant, rs1054564, results in allele-specific translational repression of GDF15 by hsa-miR-1233-3p", PLoS One, Aug. 2017, 12(8): e0183187, 15 pages.
Thadani, et al., "Pilot Study of Extracorporeal Removal of Soluble fms-like Tyrosine kinase 1 in Preeclampsia", Circulation, vol. 124, No. 8, pp. 940-950, Aug. 1, 2011.
Thomas et al. (2007) "Intronic polyadenylation signal sequences and alternate splicing generate human soluble F1t1 variants and regulate the abundance of soluble F1t1 in the placenta," The FASEB Journal, 21(14):3885-3895.
Thomas, et al., A Recently Evolved Novel Trophoblast-Enriched Secreted Form of fms-Like Tyrosine Kinase-1 Variant Is Up-Regulated in Hypoxia and Preeclampsia, The Journal of Clinical Endocrinology & Metabolism, vol. 94, Issue 7, pp. 2524-2530, Jul. 1, 2009.
Thompson et al., Toxicological and Pharmacokinetic Properties of Chemically Modified siRNAs Targeting p53 RNA Following Intravenous Administration, Nucleic Acid Therapeutics, vol. 22, No. 4, pp. 255-264, Aug. 1, 2012.
Tischer, et al., "The Human Gene for Vascular Endothelial Growth Factor. Multiple Protein Forms are Encoded Through Alternative Exon Splicing", The Journal of Biological Chemistry, vol. 266, pp. 11947-11954, Jun. 25, 1991.
Tome et al., MSH3 Polymorphisms and Protein Levels Affect CAG Repeat Instability in Huntington's Disease Mice, PLOS Genetics, Feb. 28, 2013, 9(2): el003280, 1-16.
Turanov et al., "RNAi Modulation of Placental sFLT1 for the Treatment of Preeclampsia", Nature Biotechnology, Nov. 19, 2018, 36: 1164-1173.
Tuschl et al. (May 6, 2004) "The siRNA User Guide," Accessible on the Internet at URL: http://diyhpl.us/~bryan/irc/protocol-online/protocol-cache/sirna.html. [Last Accessed Aug. 11, 2016].
Tuschl, et al., Expanding small RNA interference, Nature Biotechnology, vol. 20, No. 5, pp. 446-448, 2002.
Uchida, et al., "An Integrated Approach for the Systematic Identification and Characterization of Heart-enriched Genes With Unknown Functions", BMC Genomics, vol. 10, No. 100, pp. 1-12, Mar. 2009.

(56) References Cited

OTHER PUBLICATIONS

Ueno et al., "Synthesis and silencing properties of siRNAs possessing lipophilic groups at their 3'-termini", Nucleic Acids Symposium Series, vol. 52, Issue 1, pp. 503-504, https://doi.org/10.1093/nass/nrn255. (Sep. 2008).
Vaught, et al., T7 RNA Polymerase Transcription with 5-Position Modified UTP Derivatives, Journal of the American Chemical Society, vol. 126, No. 36, pp. 11231-11237, Aug. 19, 2004.
Vickers, et al., Development of a Quantitative BRET Affinity Assay for Nucleic Acid-protein Interactions, PloS One, vol. 11, No. 8, p. e0161930, pp. 1-17, Aug. 29, 2016.
Videira, et al., "Preclinical Development of siRNA Therapeutics: Towards the Match Between Fundamental Science and Engineered Systems", Nanomedicine: Nanotechnology, Biology and Medicine, vol. 10, No. 4, pp. 689-702, 2014.
Vorlová, et al., "Induction of Antagonistic Soluble Decoy Receptor Tyrosine Kinases by Intronic polyA Activation", Molecular Cell, vol. 43, Issue 6, pp. 927-939, Sep. 16, 2011.
Vorobjev, et al., Nuclease Resistance and RNase H Sensitivity of Oligonucleotides Bridged by Oligomethylenediol and Oligoethylene Glycol Linkers, Antisense and Nucleic Acid Drug Development, vol. 11, No. 2, pp. 77-85, Apr. 2011.
Wada et al., "Evaluation of the effects of chemically different linkers on hepatic accumulations, cell tropism and gene silencing ability of cholesterol-conjugated antisense oligonucleotides", Journal Of Controlled Release, Elsevier, vol. 226, pp. 57-65, DOI: 10.1016/J.JCONREL.2016.02.007. (Feb. 5, 2016).
Wang, et al., Nanoparticle-Based Delivery System for Application of siRNA In Vivo, Current Drug Metabolism, vol. 11, No. 2, pp. 182-196, 2010.
Wanke et al., Overgrowth of Skin in Growth Hormone Transgenic Mice Depends on the Presence of Male Gonads, Journal of Investigative Dermatology, vol. 113, pp. 967-971, Dec. 1, 1999.
Watanabe, et al., Endogenous siRNAs From Naturally Formed dsRNAs Regulate Transcripts In Mouse Oocytes, Nature, vol. 453, No. 7194, pp. 539-543, Apr. 10, 2008.
Weyer, et al., Developmental And Cell Type-Specific Expression Of The Neuronal Marker NeuN In The Murine Cerebellum, Journal of Neuroscience Research, vol. 73, Issue 3, pp. 400-409, May 23, 2003.
Whitehead et al., Degradable Lipid Nanoparticles with Predictable in Vivo siRNA Delivery Activity, Nature Communications, vol. 5, pp. 1-10, Jun. 27, 2014.
Whitehead, et al., "Knocking Down Barriers: Advances in siRNA Delivery", Nature Reviews Drug Discovery, vol. 8, No. 2, pp. 129-138, Feb. 2009.
Wickstrom, Oligodeoxynucleotide Stability in Subcellular Extracts and Culture Media, Journal of Biochemical and Biophysical Methods, vol. 13, Issue 2, pp. 97-102, Sep. 1986.
Wolfrum et al., "Mechanisms and optimization of in vivo delivery of lipophilic siRNAs", Nature Biotechnology, Oct. 2007, 25(10): 1149-1157.
Wong, et al., Co-Injection of a Targeted, Reversibly Masked Endosomolytic Polymer Dramatically Improves the Efficacy of Cholesterol-Conjugated Small Interfering RNAs In Vivo, Nucleic Acid Therapeutics, vol. 22, No. 6, pp. 380-390, Nov. 26, 2012.
Wooddell, et al., Hepatocyte-targeted RNAi Therapeutics for the Treatment of Chronic Hepatitis B Virus Infection, Molecular Therapy, vol. 21, Issue 5, pp. 973-985, May 2013.
Wright, et al., Identification Of Factors That Contribute To Recombinant AAV2 Particle Aggregation And Methods To Prevent Its Occurrence During Vector Purification And Formulation, Molecular Therapy, vol. 12, Issue 1,, pp. 171-178, Jul. 2005.
Xia, et al., siRNA-Mediated Gene Silencing in Vitroand In Vivo, Nature Biotechnology, vol. 20, No. 10, pp. 1006-1010, Sep. 16, 2002.
Yamana, et al., 2'-Pyrene Modified Oligonucleotide Provides a Highly Sensitive Fluorescent Probe of RNA, Nucleic Acids Research, 1999, 27(11): 2387-2392.
Yekta, et al., MicroRNA-Directed Cleavage of HOXB8 mRNA, Science, Apr. 23, 2004, 304(5670): 594-596.
You et al., "Design of LNA probes that improve mismatch discrimination", Nucleic Acids Research, May 2006, 34(8): e60, 11 pages.
Young, et al., Pathogenesis of Preeclampsia, Annual Review of Pathology: Mechanisms of Disease, vol. 5, pp. 173-192, Feb. 2, 2010.
Younis, et al., Overview of the Nonclinical Development Strategies and Class-Effects of Oligonucleotide-Based Therapeutics, A Comprehensive Guide to Toxicology in Preclinical Drug Development, Chapter 26, pp. 647-664, 2013.
Yu, et al., RNA Interference by Expression Of Short-Interfering RNAs And Hairpin Rnas In Mammalian Cells, Proceedings of the National Academy of Sciences, vol. 99, No. 9, pp. 6047-6052., Apr. 30, 2002.
Yu, et al., Single-Stranded RNAs Use RNAi to Potently and Allele-Selectively Inhibit Mutant Huntingtin Expression, Cell, vol. 150, Issue 5, pp. 895-908, Aug. 31, 2012.
Yuan, et al., Recent Advances of siRNA Delivery By Nanoparticles, Expert Opinion on Drug Delivery vol. 8, Issue 4, pp. 521-536, 2011.
Zamore, et al., Ancient Pathways Programmed by Small RNAs, Science, May 17, 2002, 296(5571): 1265-1269.
Zeng et al., "RNA Interference in human cells is restricted to the cytoplasm", RNA, Jul. 1, 2002, 8(7): 855-860.
Zeng, et al., Both Natural and Designed Micro RNAs Can Inhibit the Expression of Cognate mRNAs When Expressed in Human Cells, Molecular Cell, vol. 9, pp. 1327-1333, Jun. 2002.
Zeng, et al., Sequence Requirements for Micro RNA Processing and Function in Human Cells, RNA, vol. 9, pp. 112-123, 2003.
Zhang, et al., "Birth-weight-for-gestational-age Patterns by Race, Sex, and Parity in the United States Population", Obstetrics & Gynecology, vol. 86, No. 2, pp. 200-208, 1995.
Zhang, et al., "Several rAAV Vectors Efficiently Cross the Blood-brain Barrier and Transduce Neurons and Astrocytes in the Neonatal Mouse Central Nervous System", Molecular Therapy, vol. 19, Issue 8, pp. 1440-1448, Aug. 1, 2011.
Zhang, et al., Cyclohexane 1,3-Diones And Their Inhibition Of Mutant SOD1-Dependent Protein Aggregation And Toxicity In PC12 Cells, Bioorganic & Medicinal Chemistry, vol. 20, Issue 2, pp. 1029-1045, Jan. 15, 2012.
Zhou et al., "Functional In Vivo Delivery of Multiplexed Anti-HIV-1 siRNAs via a Chemically Synthesized Aptamer With a Sticky Bridge", Mol Ther., Jan. 2013, 21(1): 192-200.
Zhou et al., Nanoparticle-based Delivery of RNAi Therapeutics: Progress and Challenges, Pharmaceuticals, vol. 6, pp. 85-107, Jan. 2013.
Zimmermann et al., Clinical Proof of Concept for a Novel Hepatocyte-Targeting GalNAc-siRNA Conjugate, Molecular Therapy, vol. 25, Issue 1, pp. 71-78, Jan. 4, 2017.
Zlatev, et al., Reversal of siRNA-mediated Gene Silencing in Vivo, Nature Biotechnology, vol. 36, No. 6, pp. 509-511, 2018.
Zou, et al., Liposome-Mediated NGF Gene Transfection Following Neuronal Injury: Potential Therapeutic Applications, Gene Therapy, vol. 6, No. 6, pp. 994-1005, Jun. 25, 1999.
Zuccato, et al., Molecular Mechanisms and Potential Therapeutical Targets in Huntington's Disease, Physiological Reviews, vol. 90, No. 3, pp. 905-981, Jul. 1, 2010.
Chatterjee et al., "Mechanisms of DNA damage, repair, and mutagenesis", DNA Repair, Apr. 16, 2016, 42: 26-32.
Extended European Search Report for European Patent Application No. 21792058.6, dated Jul. 8, 2024.
Extended Supplementary European Search Report for European Patent Application No. 21814030.9, mailed May 24, 2024.
Hong et al., "Effect of the guide strand 3'-end structure on the gene-silencing potency of asymmetric siRNA", Biochem J., Aug. 1, 2014, 461(3): 427-434.
Huang et al., "Effects of Conformational Alteration Induced by d-/I-Isonucleoside Incorporation in siRNA on Their Stability in Serum and Silencing Activity" Effects of Conformational Alteration Induced by d-/I-Isonucleoside Incorporation in siRNA on Their Stability in Serum and Silencing Activity, Bioconjugate Chemistry, May 17, 2013, 24(6): 951-959.

(56) References Cited

OTHER PUBLICATIONS

Jeong et al., "Synthesis and Hybridization Property of Sugar and Phosphate Linkage Modified Oligonucleotides", Bioorganic & Medicinal Chemistry, Jul. 1999: 1467-1473.
Lorenzer et al., Going beyond the liver: Progress and challenges of targeted delivery of siRNA therapeutics, Journ Controlled Release, Apr. 10, 2015, 203: 1-15.
Partial European Search Report for European Patent Application No. 21792058.6, dated Apr. 17, 2024.
Svendsen et al., "Oligodeoxynucleotide analogues containing 3'-deoxy-3'-C-threo-hydroxymethylthymidine: Synthesis, hybridization properties and enzymatic stability", Tetrahedron, 1993, 49(48): 11341-11352.
U.S. Appl. No. 15/089,319 2016/0355808 now U.S. Pat. No. 9,809,817, filed Apr. 1, 2016 Dec. 8, 2016 Nov. 7, 2017, Anastasia Khvorova, Oligonucleotide Compounds for Targeting Huntingtin mRNA.
U.S. Appl. No. 15/697,120 2018/0094263 now U.S. Pat. No. 10,435,688, filed Sep. 6, 2017 Apr. 5, 2018 Oct. 8, 2019, Anastasia Khvorova, Oligonucleotide Compounds for Targeting Huntingtin mRNA.
U.S. Appl. No. 16/263,200 2019/0225965 now U.S. Pat. No. 10,744,327, filed Jan. 31, 2019 Jul. 25, 2019 Sep. 15, 2020, Anastasia Khvorova, Oligonucleotide Compounds for Targeting Huntingtin mRNA.
U.S. Appl. No. 16/811,580 2020/0308584 now U.S. Pat. No. 11,230,713, filed Mar. 6, 2020 Oct. 1, 2020 Jan. 5, 2022, Anastasia Khvorova, Oligonucleotide Compounds for Targeting Huntingtin mRNA.
U.S. Appl. No. 17/536,647 2022/0251554, filed Nov. 29, 2021 Aug. 11, 2022, Anastasia Khvorova, Oligonucleotide Compounds for Targeting Huntingtin mRNA.
U.S. Appl. No. 15/089,437 2016/0355826 now U.S. Pat. No. 9,862,952, filed Apr. 1, 2016 Dec. 8, 2016 Jan. 9, 2018, Anastasia Khvorova, Oligonucleotide Compounds For Treatment of Preeclampsia And Other Angiogenic Disorders.
U.S. Appl. No. 15/814,350 2018/0179546 now U.S. Pat. No. 10,519,451, filed Nov. 15, 2017 Jun. 28, 2018 Dec. 31, 2019, Anastasia Khvorova, Oligonucleotide Compounds For Treatment of Preeclampsia And Other Angiogenic Disorders.
U.S. Appl. No. 16/675,369 2020/0165618 now U.S. Pat. No. 11,345,917, filed Nov. 6, 2019 May 28, 2020 May 11, 2022, Anastasia Khvorova, Oligonucleotide Compounds For Treatment of Preeclampsia And Other Angiogenic Disorders.
U.S. Appl. No. 17/718,918 2022/0364100, filed Apr. 12, 2022 Nov. 17, 2022, Anastasia Khvorova, Oligonucleotide Compounds For Treatment of Preeclampsia And Other Angiogenic Disorders.
U.S. Appl. No. 15/089,423 2016/0319278, filed Apr. 1, 2016 Nov. 3, 2016, Anastasia Khvorova, Fully Stabilized Asymmetric siRNA.
U.S. Appl. No. 15/691,120 2017/0369882, filed Aug. 30, 2017 Dec. 28, 2017, Anastasia Khvorova, Fully Stabilized Asymmetric siRNA.
U.S. Appl. No. 16/927,543 2021/0024926, filed Jul. 13, 2020 Jan. 28, 2021, Anastasia Khvorova, Fully Stabilized Asymmetric siRNA.
U.S. Appl. No. 15/236,051 2017/0043024 now U.S. Pat. No. 10,633,653,, filed Aug. 12, 2016 Feb. 16, 2017 Apr. 28, 2020, Anastasia Khvorova, Bioactive Conjugates For Oligonucleotide Delivery.
U.S. Appl. No. 16/812,714 2020/0339983, filed Mar. 9, 2020 Oct. 29, 2020, Anastasia Khvorova, Bioactive Conjugates For Oligonucleotide Delivery.
U.S. Appl. No. 18/769,546, filed Jul. 11, 2024, Anastasia Khvorova Bioactive Conjugates For Oligonucleotide Delivery.
U.S. Appl. No. 15/419,593 2017/0312367 now U.S. Pat. No. 10,478,503, filed Jan. 30, 2017 Nov. 2, 2017 Nov. 19, 2019, Anastasia Khvorova, Branched Oligonucleotides.
U.S. Appl. No. 16/390,712 2019/0247507 now U.S. Pat. No. 10,799,591, filed Apr. 22, 2019 Aug. 15, 2019 Oct. 13, 2020, Anastasia Khvorova, Branched Oligonucleotides.
U.S. Appl. No. 17/012,787 2021/0085793 now U.S. Pat. No. 11,896,669, filed Sep. 4, 2020 Mar. 25, 2021 Feb. 13, 2024, Anastasia Khvorova, Branched Oligonucleotides.
U.S. Appl. No. 18/396,613 2024/0293550, filed Dec. 26, 2023 Sep. 5, 2024, Anastasia Khvorova, Branched Oligonucleotides.
U.S. Appl. No. 16/322,212 2019/0185855 now U.S. Pat. No. 11,753,638, filed Jan. 31, 2019 Jun. 20, 2019 Sep. 12, 2023, Anastasia Khvorova, Conjugated Oligonucleotides.
U.S. Appl. No. 18/170,167 2024/0084297, filed Feb. 16, 2023 Mar. 14, 2024, Anastasia Khvorova, Conjugated Oligonucleotides.
U.S. Appl. No. 16/015,440 2019/0024082 now U.S. Pat. No. 10,844,377, filed Jun. 22, 2018 Jan. 24, 2019 Nov. 24, 2020, Anastasia Khvorova, Two-Tailed Self-Delivering siRNA.
U.S. Appl. No. 17/071,473 2021/0139901, filed Oct. 15, 2020 May 13, 2021, Anastasia Khvorova, Two-Tailed Self-Delivering siRNA.
U.S. Appl. No. 16/537,374 2020/0123543 now U.S. Pat. No. 11,827,882, filed Aug. 9, 2019 Apr. 23, 2020 Nov. 28, 2023, Anastasia Khvorova, Modified Oligonucleotides Targeting SNPs.
U.S. Appl. No. 16/988,391 2021/0071177, filed Aug. 7, 2020 Mar. 11, 2021, Anastasia Khvorova, Modified Oligonucleotides Targeting SNPs.
U.S. Appl. No. 18/446,929 2024/0132888, filed Aug. 9, 2023 Apr. 25, 2024, Anastasia Khvorova, Modified Oligonucleotides Targeting SNPs.
U.S. Appl. No. 18/421,647, filed Jan. 24, 2024, Anastasia Khvorova, Modified Oligonucleotides Targeting SNPs.
U.S. Appl. No. 16/746,555 2020/0270605 now U.S. Pat. No. 11,492,619, filed Jan. 17, 2020 Aug. 27, 2020 Nov. 8, 2022, Anastasia Khvorova, Dynamic Pharmacokinetic-Modifying Anchors.
U.S. Appl. No. 17/725,102 2022/0372476, filed Apr. 20, 2022 Nov. 24, 2022, Anastasia Khvorova, Dynamic Pharmacokinetic-Modifying Anchors.
U.S. Appl. No. 17/792,705 2023/0061751, filed Jul. 13, 2022 Mar. 2, 2023, Anastasia Khvorova, Universal Dynamic Pharmacokinetic-Modifying Anchors.
U.S. Appl. No. 16/550,076 2020/0087663 now U.S. Pat. No. 11,279,930, filed Aug. 23, 2019 / Mar. 19, 2020 / Mar. 22, 2022, Anastasia Khvorova, O-Methyl Rich Fully Stabilized Oligonucleotides.
U.S. Appl. No. 16/999,759 2021/0115442, filed Aug. 21, 2020 / Apr. 22, 2021, Anastasia Khvorova, O-Methyl Rich Fully Stabilized Oligonucleotides.
U.S. Appl. No. 17/580,269 2022/0251555, filed Jan. 20, 2022 / Aug. 11, 2022, Anastasia Khvorova, O-Methyl Rich Fully Stabilized Oligonucleotides.
U.S. Appl. No. 17/022,678 2021/0108200, filed Sep. 16, 2020 Apr. 15, 2021, Anastasia Khvorova, Branched Lipid Conjugates Of siRNA For Specific Tissue Delivery.
U.S. Appl. No. 17/235,153 2021/0355491, filed Apr. 20, 2021 Nov. 18, 2021, Anastasia Khvorova, Oligonucleotides For MSH3 Modulation.
U.S. Appl. No. 17/391,475 2022/0090069, filed Aug. 2, 2021 Mar. 24, 2022, Anastasia Khvorova, Oligonucleotides For HTT-1A Modulation.
U.S. Appl. No. 18/430,581 2024/0301410, filed Feb. 1, 2024 Sep. 12, 2024, Anastasia Khvorova, Oligonucleotides For HTT-1A Modulation.
U.S. Appl. No. 17/377,632 2022/0042015, filed Jul. 16, 2021 Feb. 10, 2022, Anastasia Khvorova, Conjugated Oligonucleotides for Tissue Specific Delivery.
U.S. Appl. No. 17/846,526, filed Jun. 22, 2022 Mar. 16, 2023 Jul. 18, 2023, Anastasia Khvorova, Optimized ANTI-FLT1 Oligonucleotide Compounds for Treatment of Preeclampsia and Other Angiogenic Disorders.
U.S. Appl. No. 18/321,971 2024/0067967, filed May 23, 2023 Feb. 29, 2024, Anastasia Khvorova, Oligonucleotide Compounds for Treatment of Preeclampsia and Other Angiogenic Disorders.
Aguiar et al., "RNAi mechanisms in Huntington's disease therapy: siRNA versus shRNA", Transl Neurodegener., Nov. 27, 2017, 6:30, eCollection 2017.

(56) References Cited

OTHER PUBLICATIONS

Bioinformatics.org (Oct. 1, 2023) DNA Molecular Weight Calculator, Available online at: bioinformatics.org/sms2/dna_mw.html.
Biosyn, (2006) Oligonucleotide Properties Calculator., Available online at: biosyn.com/gizmo/tools/oligo/oligonucleotide%20properties %20calculator.htm.
Charoenphol et al. (Apr. 16, 2014), "Aptamer-Targeted DNA Nanostructures for Therapeutic Delivery", Molec. Pharmaceut., 11(5): 1721-1725.
Cleveland Clinic (2022) "Peripheral Neuropathy" and "Personality disorders", Available online at: my.clevelandclinic.org.
Espe et al. (Jan. 2018) "Malacards", J. Med. Libr. Assoc., 106(1): 140-141.
Extended European Search Report for European Application No. 21843183.1, mailed Jun. 17, 2025.
Gannon et al., "MutSβ and histone deacetylase complexes promote expansions of trinucleotide repeats in human cells", Nucleic Acids Research, Nov. 1, 2012, 40(20): 10324-10333. Epub Aug. 31, 2012.
Greco et al., "Soluble Fms-Like Tyrosine Kinase-1 Is A Marker of Endothelial Dysfunction During Sepsis", J. Clin. Med. Res., Sep. 2018, 10(9): 700-706. Epub Jul. 31, 2018.
Hastie et al., "EGFR (Epidermal Growth Factor Receptor) Signaling and the Mitochondria Regulate sFlt-1 (Soluble FMS-Like Tyrosine Kinase-1) Secretion", Hypertension, Mar. 2019, 73(3): 659-670.
Hu et al. (Jan. 22, 2018) "DNA Nanostructure-Based Systems for Intelligent Delivery of Therapeutic Oligonucleotides", Adv. Healthcare Mater., 7: 1701153.
Hu et al., "Therapeutic siRNA: State of the Art", Signal Transduct. Target Ther., Jun. 19, 2020, 5(1):101.
International Preliminary Report on Patentability (Chapter II) for PCT International Patent Application No. PCT/US2019/046013, mailed Apr. 10, 2020.
Lee et al. (Jun. 3, 2012) "Molecularly self-assembled nucleic acid nanoparticles for targeted in vivo siRNA delivery", Nat. Nanotechnol., 7: 389-393.
Maric-Bilkan et al., "Research Recommendations From the National Institutes of Health Workshop on Predicting, Preventing, and Treating Preeclampsia", Hypertension, Apr. 2019, 73(4): 757-766.
Nishina et al., "DNA/RNA heteroduplex oligonucleotide for highly efficient gene silencing", Nat. Commun., Aug. 10, 2015, 6: 7969.
Peptide2.0 (2025) Peptide Molecular Weight Calculator, Available online at: peptide2.com/peptide_molecular_weight_calculator.php.
Watts et al., "Chemically modified siRNA: tools and applications", Drug Discov. Today, Oct. 2008, 13(19-20): 842-855.

* cited by examiner

Canonical Phosphodiester

5'-Extended Nucleic Acid (5'-exNA)

3'-Extended Nucleic Acid (3'-exNA)

3'-Ara-extended Nucleic Acid (3'-ara-exNA)

5'-3'-Extended Nucleic Acid (5'-3'-bis-exNA)

5'-(3'-Ara)-extended Nucleic Acid ( 5'-(3'-ara)-bis-exNA )

Examples of exNA-modified RNA oligonucleotides

| Name | Sequence (5' -> 3') |
| --- | --- |
| Themo-ex1a | (rC)(rG)(rC)(rA)(rU)(**ex-rU**)(rA)(rG)(rC)(rC)(rG) |
| Themo-ex1b | (rC)(rG)(rC)(rA)(rU)(**ex-rU**)(rA)(rG)(rC)(rC)(rG) |
| Themo-ex2 | (rC)(rG)(rC)(rA)(rG)(**ex-rU**)(rA)(rG)(rC)(rC)(rG) |
| Themo-ex3 | (rC)(rG)(rC)(rA)(rA)(**ex-rU**)(rA)(rG)(rC)(rC)(rG) |
| Themo-ex4 | (rC)(rG)(rC)(rA)(rC)(**ex-rU**)(rA)(rG)(rC)(rC)(rG) |
| UC-seq-ex1 | (rU)(rC)(rU)(rC)(rU)(**ex-rU**)(rU)(rC)(rU)(rC)(rU) |
| UC-seq-ex2 | (rU)(rC)(rU)(rC)(**ex-rU**)(**ex-rU**)(**ex-rU**)(rC)(rU)(rC)(rU) |
| UC-seq-ex3 | (**ex-rU**)(rC)(**ex-rU**)(rC)(**ex-rU**)(rU)(**ex-rU**)(rC)(**ex-rU**)(rC)(**ex-rU**) |

(rN): 2'-OH ribonucleoside, (ex-rU):exNA ribo-uridine

FIG. 13

SEQUENCE LISTING

<160> NUMBER OF SEQ ID NOS: 92

<210> SEQ ID NO 1
<211> LENGTH: 20
<212> TYPE: RNA
<213> ORGANISM: Artificial Sequence
<220> FEATURE:
<223> OTHER INFORMATION: ex-1
<220> FEATURE:
<221> NAME/KEY: modified_base
<222> LOCATION: (1)..(1)
<223> OTHER INFORMATION: 5-methylene-exNA-uridine with 2'-OMe uridine
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-uridine
<220> FEATURE:
<221> NAME/KEY: modified_base
<222> LOCATION: (3)..(3)

<223> OTHER INFORMATION: 2'-OMe adenosine
<220> FEATURE:
<221> NAME/KEY: modified_base
<222> LOCATION: (4)..(4)
<223> OTHER INFORMATION: 2'-fluoro-adenosine
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: 2'-fluoro-cytidine
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (8)..(8)
<223> OTHER INFORMATION: 2'-fluoro-cytidine
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(10)
<223> OTHER INFORMATION: 2'-fluoro-uridine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-fluoro-adenosine
<220> FEATURE:
<221> NAME/KEY: misc_feature
<222> LOCATION: (13)..(20)
<223> OTHER INFORMATION: Phosphorothioate Linkage
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (14)..(14)
<223> OTHER INFORMATION: 2'-fluoro-uridine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: 2'-fluoro-adenosine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: 2'-fluoro-adenosine
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(20)
<223> OTHER INFORMATION: 2'-fluoro-adenosine

<400> SEQUENCE: 1
uuaaucucuu uacugauaua 20

-continued

<210> SEQ ID NO 2
<211> LENGTH: 20
<212> TYPE: RNA
<213> ORGANISM: Artificial Sequence
<220> FEATURE:
<223> OTHER INFORMATION: ex-2
<220> FEATURE:
<221> NAME/KEY: modified_base
<222> LOCATION: (1)..(1)
<223> OTHER INFORMATION: um
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 5-methylene-exNA-uridine with 2'-fluoro-ex-uridine
<220> FEATURE:
<221> NAME/KEY: modified_base
<222> LOCATION: (3)..(3)
<223> OTHER INFORMATION: 2'-OMe adenosine
<220> FEATURE:
<221> NAME/KEY: modified_base
<222> LOCATION: (4)..(4)
<223> OTHER INFORMATION: 2'-fluoro-adenosine
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: 2'-fluoro-cytidine
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (8)..(8)
<223> OTHER INFORMATION: 2'-fluoro-cytidine
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(10)
<223> OTHER INFORMATION: 2'-fluoro-uridine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-fluoro-adenosine
<220> FEATURE:
<221> NAME/KEY: modified_base
<222> LOCATION: (13)..(13)
<223> OTHER INFORMATION: cm
<220> FEATURE:
<221> NAME/KEY: misc_feature
<222> LOCATION: (13)..(20)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-fluoro-uridine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: 2'-fluoro-adenosine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: 2'-fluoro-adenosine
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(20)
<223> OTHER INFORMATION: 2'-fluoro-adenosine

<400> SEQUENCE: 2
uuaaucucuu uacugauaua 20

<210> SEQ ID NO 3
<211> LENGTH: 20
<212> TYPE: RNA
<213> ORGANISM: Artificial Sequence
<220> FEATURE:
<223> OTHER INFORMATION: ex-3
<220> FEATURE:
<221> NAME/KEY: modified_base
<222> LOCATION: (1)..(1)
<223> OTHER INFORMATION: um
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-uridine
<220> FEATURE:
<221> NAME/KEY: modified_base
<222> LOCATION: (3)..(3)
<223> OTHER INFORMATION: 5-methylene-exNA-uridine with 2'-OMe uridine
<220> FEATURE:
<221> NAME/KEY: modified_base
<222> LOCATION: (4)..(4)
<223> OTHER INFORMATION: 2'-fluoro-uridine
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: 2'-fluoro-adenosine
<220> FEATURE:
<221> NAME/KEY: modified_base
<222> LOCATION: (7)..(7)
<223> OTHER INFORMATION: 2'-OMe adenosine
<220> FEATURE:
<221> NAME/KEY: modified_base
<222> LOCATION: (8)..(8)
<223> OTHER INFORMATION: 2'-fluoro-adenosine
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(10)
<223> OTHER INFORMATION: 2'-fluoro-cytidine
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(12)

<223> OTHER INFORMATION: 2'-fluoro-uridine
<220> FEATURE:
<221> NAME/KEY: modified_base
<222> LOCATION: (13)..(13)
<223> OTHER INFORMATION: gm
<220> FEATURE:
<221> NAME/KEY: misc_feature
<222> LOCATION: (13)..(20)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-fluoro-adenosine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: 2'-fluoro-adenosine
<220> FEATURE:
<221> NAME/KEY: modified_base
<222> LOCATION: (17)..(17)
<223> OTHER INFORMATION: 2'-OMe adenosine
<220> FEATURE:
<221> NAME/KEY: modified_base
<222> LOCATION: (18)..(18)
<223> OTHER INFORMATION: 2'-fluoro-guanosine
<220> FEATURE:
<221> NAME/KEY: modified_base
<222> LOCATION: (19)..(19)
<223> OTHER INFORMATION: 2'-OMe adenosine
<220> FEATURE:
<221> NAME/KEY: modified_base
<222> LOCATION: (20)..(20)
<223> OTHER INFORMATION: 2'-fluoro-adenosine

<400> SEQUENCE: 3
uuuuuaaauc cugagaagaa 20

<210> SEQ ID NO 4
<211> LENGTH: 20
<212> TYPE: RNA
<213> ORGANISM: Artificial Sequence
<220> FEATURE:
<223> OTHER INFORMATION: ex-4
<220> FEATURE:
<221> NAME/KEY: modified_base
<222> LOCATION: (1)..(1)
<223> OTHER INFORMATION: um
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-uridine
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (4)..(4)
<223> OTHER INFORMATION: 5-methylene-exNA-uridine with 2'-fluoro-ex-
uridine
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: 2'-fluoro-adenosine
<220> FEATURE:

-continued

<221> NAME/KEY: modified_base
<222> LOCATION: (7)..(7)
<223> OTHER INFORMATION: 2'-OMe adenosine
<220> FEATURE:
<221> NAME/KEY: modified_base
<222> LOCATION: (8)..(8)
<223> OTHER INFORMATION: 2'-fluoro-adenosine
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(10)
<223> OTHER INFORMATION: 2'-fluoro-cytidine
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(12)
<223> OTHER INFORMATION: 2'-fluoro-uridine
<220> FEATURE:
<221> NAME/KEY: modified_base
<222> LOCATION: (13)..(13)
<223> OTHER INFORMATION: gm
<220> FEATURE:
<221> NAME/KEY: misc_feature
<222> LOCATION: (13)..(20)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-fluoro-adenosine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: 2'-fluoro-adenosine
<220> FEATURE:
<221> NAME/KEY: modified_base
<222> LOCATION: (17)..(17)
<223> OTHER INFORMATION: 2'-OMe adenosine
<220> FEATURE:
<221> NAME/KEY: modified_base
<222> LOCATION: (18)..(18)
<223> OTHER INFORMATION: 2'-fluoro-guanosine
<220> FEATURE:
<221> NAME/KEY: modified_base
<222> LOCATION: (19)..(19)
<223> OTHER INFORMATION: 2'-OMe adenosine
<220> FEATURE:
<221> NAME/KEY: modified_base
<222> LOCATION: (20)..(20)
<223> OTHER INFORMATION: 2'-fluoro-adenosine

<400> SEQUENCE: 4
uuuuuaaauc cugagaagaa 20

<210> SEQ ID NO 5
<211> LENGTH: 20
<212> TYPE: RNA
<213> ORGANISM: Artificial Sequence
<220> FEATURE:
<223> OTHER INFORMATION: ex-5
<220> FEATURE:
<221> NAME/KEY: modified_base
<222> LOCATION: (1)..(1)
<223> OTHER INFORMATION: um
<220> FEATURE:
<221> NAME/KEY: misc_feature
<222> LOCATION: (1)..(3)
<223> OTHER INFORMATION: Phosphorothioate Linkage -continued
<220> FEATURE:
<221> NAME/KEY: modified_base
<222> LOCATION: (2)..(2)
<223> OTHER INFORMATION: 2'-fluoro-uridine
<220> FEATURE:
<221> NAME/KEY: modified_base
<222> LOCATION: (3)..(3)
<223> OTHER INFORMATION: 2'-OMe adenosine
<220> FEATURE:
<221> NAME/KEY: modified_base
<222> LOCATION: (4)..(4)
<223> OTHER INFORMATION: 2'-fluoro-adenosine
<220> FEATURE:
<221> NAME/KEY: modified_base
<222> LOCATION: (5)..(5)
<223> OTHER INFORMATION: 5-methylene-exNA-uridine with 2'-OMe uridine
<220> FEATURE:
<221> NAME/KEY: modified_base
<222> LOCATION: (6)..(6)
<223> OTHER INFORMATION: 2'-fluoro-cytidine
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (8)..(8)
<223> OTHER INFORMATION: 2'-fluoro-cytidine
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(10)
<223> OTHER INFORMATION: 2'-fluoro-uridine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-fluoro-adenosine
<220> FEATURE:
<221> NAME/KEY: modified_base
<222> LOCATION: (13)..(13)
<223> OTHER INFORMATION: cm
<220> FEATURE:
<221> NAME/KEY: misc_feature
<222> LOCATION: (13)..(20)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-fluoro-uridine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: 2'-fluoro-adenosine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: 2'-fluoro-adenosine
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(20)

-continued

<223> OTHER INFORMATION: 2'-fluoro-adenosine

<400> SEQUENCE: 5
uuaaucucuu uacugauaua 20

<210> SEQ ID NO 6
<211> LENGTH: 20
<212> TYPE: RNA
<213> ORGANISM: Artificial Sequence
<220> FEATURE:
<223> OTHER INFORMATION: ex-6
<220> FEATURE:
<221> NAME/KEY: modified_base
<222> LOCATION: (1)..(1)
<223> OTHER INFORMATION: um
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-cytidine
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (4)..(4)
<223> OTHER INFORMATION: 2'-fluoro-adenosine
<220> FEATURE:
<221> NAME/KEY: modified_base
<222> LOCATION: (5)..(5)
<223> OTHER INFORMATION: cm
<220> FEATURE:
<221> NAME/KEY: modified_base
<222> LOCATION: (6)..(6)
<223> OTHER INFORMATION: 5-methylene-exNA-uridine with 2'-fluoro-ex-
      uridine
<220> FEATURE:
<221> NAME/KEY: modified_base
<222> LOCATION: (7)..(7)
<223> OTHER INFORMATION: 2'-OMe adenosine
<220> FEATURE:
<221> NAME/KEY: modified_base
<222> LOCATION: (8)..(8)
<223> OTHER INFORMATION: 2'-fluoro-uridine
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (10)..(10)
<223> OTHER INFORMATION: 2'-fluoro-uridine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-fluoro-uridine
<220> FEATURE:
<221> NAME/KEY: modified_base
<222> LOCATION: (13)..(13)
<223> OTHER INFORMATION: um
<220> FEATURE:
<221> NAME/KEY: misc_feature
<222> LOCATION: (13)..(20)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-fluoro-cytidine
<220> FEATURE:

-continued

<221> NAME/KEY: modified_base
<222> LOCATION: (15)..(15)
<223> OTHER INFORMATION: 2'-OMe adenosine
<220> FEATURE:
<221> NAME/KEY: modified_base
<222> LOCATION: (16)..(16)
<223> OTHER INFORMATION: 2'-fluoro-cytidine
<220> FEATURE:
<221> NAME/KEY: modified_base
<222> LOCATION: (17)..(17)
<223> OTHER INFORMATION: 2'-OMe adenosine
<220> FEATURE:
<221> NAME/KEY: modified_base
<222> LOCATION: (18)..(18)
<223> OTHER INFORMATION: 2'-fluoro-uridine
<220> FEATURE:
<221> NAME/KEY: modified_base
<222> LOCATION: (19)..(19)
<223> OTHER INFORMATION: 2'-OMe adenosine
<220> FEATURE:
<221> NAME/KEY: modified_base
<222> LOCATION: (20)..(20)
<223> OTHER INFORMATION: 2'-fluoro-uridine

<400> SEQUENCE: 6
uccacuaugu uuucacauau 20

<210> SEQ ID NO 7
<211> LENGTH: 20
<212> TYPE: RNA
<213> ORGANISM: Artificial Sequence
<220> FEATURE:
<223> OTHER INFORMATION: ex-7
<220> FEATURE:
<221> NAME/KEY: modified_base
<222> LOCATION: (1)..(1)
<223> OTHER INFORMATION: um
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-uridine
<220> FEATURE:
<221> NAME/KEY: modified_base
<222> LOCATION: (3)..(3)
<223> OTHER INFORMATION: 2'-OMe adenosine
<220> FEATURE:
<221> NAME/KEY: modified_base
<222> LOCATION: (4)..(4)
<223> OTHER INFORMATION: 2'-fluoro-adenosine
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: 2'-fluoro-cytidine
<220> FEATURE:
<221> NAME/KEY: modified_base
<222> LOCATION: (7)..(7)
<223> OTHER INFORMATION: 5-methylene-exNA-uridine with 2'-OMe uridine
<220> FEATURE:
<221> NAME/KEY: modified_base
<222> LOCATION: (8)..(8)
<223> OTHER INFORMATION: 2'-fluoro-cytidine
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(10)
<223> OTHER INFORMATION: 2'-fluoro-uridine -continued
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-fluoro-adenosine
<220> FEATURE:
<221> NAME/KEY: modified_base
<222> LOCATION: (13)..(13)
<223> OTHER INFORMATION: cm
<220> FEATURE:
<221> NAME/KEY: misc_feature
<222> LOCATION: (13)..(20)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-fluoro-uridine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: 2'-fluoro-adenosine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: 2'-fluoro-adenosine
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(20)
<223> OTHER INFORMATION: 2'-fluoro-adenosine

<400> SEQUENCE: 7
uuaaucucuu uacugauaua 20

<210> SEQ ID NO 8
<211> LENGTH: 20
<212> TYPE: RNA
<213> ORGANISM: Artificial Sequence
<220> FEATURE:
<223> OTHER INFORMATION: ex-8
<220> FEATURE:
<221> NAME/KEY: modified_base
<222> LOCATION: (1)..(1)
<223> OTHER INFORMATION: um
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-cytidine
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (4)..(4)
<223> OTHER INFORMATION: 2'-fluoro-adenosine
<220> FEATURE:
<221> NAME/KEY: modified_base
<222> LOCATION: (5)..(5)

-continued

<223> OTHER INFORMATION: cm
<220> FEATURE:
<221> NAME/KEY: modified_base
<222> LOCATION: (6)..(6)
<223> OTHER INFORMATION: 2'-fluoro-uridine
<220> FEATURE:
<221> NAME/KEY: modified_base
<222> LOCATION: (7)..(7)
<223> OTHER INFORMATION: 2'-OMe adenosine
<220> FEATURE:
<221> NAME/KEY: modified_base
<222> LOCATION: (8)..(8)
<223> OTHER INFORMATION: 5-methylene-exNA-uridine with 2'-fluoro-ex-
uridine
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (10)..(10)
<223> OTHER INFORMATION: 2'-fluoro-uridine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-fluoro-uridine
<220> FEATURE:
<221> NAME/KEY: modified_base
<222> LOCATION: (13)..(13)
<223> OTHER INFORMATION: um
<220> FEATURE:
<221> NAME/KEY: misc_feature
<222> LOCATION: (13)..(20)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-fluoro-cytidine
<220> FEATURE:
<221> NAME/KEY: modified_base
<222> LOCATION: (15)..(15)
<223> OTHER INFORMATION: 2'-OMe adenosine
<220> FEATURE:
<221> NAME/KEY: modified_base
<222> LOCATION: (16)..(16)
<223> OTHER INFORMATION: 2'-fluoro-cytidine
<220> FEATURE:
<221> NAME/KEY: modified_base
<222> LOCATION: (17)..(17)
<223> OTHER INFORMATION: 2'-OMe adenosine
<220> FEATURE:
<221> NAME/KEY: modified_base
<222> LOCATION: (18)..(18)
<223> OTHER INFORMATION: 2'-fluoro-uridine
<220> FEATURE:
<221> NAME/KEY: modified_base
<222> LOCATION: (19)..(19)
<223> OTHER INFORMATION: 2'-OMe adenosine
<220> FEATURE:
<221> NAME/KEY: modified_base
<222> LOCATION: (20)..(20)
<223> OTHER INFORMATION: 2'-fluoro-uridine

<400> SEQUENCE: 8
uccacuaugu uuucacauau 20

<210> SEQ ID NO 9
<211> LENGTH: 20
<212> TYPE: RNA
<213> ORGANISM: Artificial Sequence
<220> FEATURE:
<223> OTHER INFORMATION: ex-9
<220> FEATURE:

-continued

<221> NAME/KEY: modified_base
<222> LOCATION: (1)..(1)
<223> OTHER INFORMATION: um
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-uridine
<220> FEATURE:
<221> NAME/KEY: modified_base
<222> LOCATION: (3)..(3)
<223> OTHER INFORMATION: 2'-OMe adenosine
<220> FEATURE:
<221> NAME/KEY: modified_base
<222> LOCATION: (4)..(4)
<223> OTHER INFORMATION: 2'-fluoro-adenosine
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: 2'-fluoro-cytidine
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (8)..(8)
<223> OTHER INFORMATION: 2'-fluoro-cytidine
<220> FEATURE:
<221> NAME/KEY: modified_base
<222> LOCATION: (9)..(9)
<223> OTHER INFORMATION: 5-methylene-exNA-uridine with 2'-OMe uridine
<220> FEATURE:
<221> NAME/KEY: modified_base
<222> LOCATION: (10)..(10)
<223> OTHER INFORMATION: 2'-fluoro-uridine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-fluoro-adenosine
<220> FEATURE:
<221> NAME/KEY: misc_feature
<222> LOCATION: (13)..(20)
<223> OTHER INFORMATION: Phosphorothioate Linkage
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (14)..(14)
<223> OTHER INFORMATION: 2'-fluoro-uridine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: 2'-fluoro-adenosine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: 2'-fluoro-adenosine

```
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(20)
<223> OTHER INFORMATION: 2'-fluoro-adenosine

<400> SEQUENCE: 9

uuaaucucuu uacugauaua                                              20


<210> SEQ ID NO 10
<211> LENGTH: 20
<212> TYPE: RNA
<213> ORGANISM: Artificial Sequence
<220> FEATURE:
<223> OTHER INFORMATION: ex-10
<220> FEATURE:
<221> NAME/KEY: modified_base
<222> LOCATION: (1)..(1)
<223> OTHER INFORMATION: um
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-uridine
<220> FEATURE:
<221> NAME/KEY: modified_base
<222> LOCATION: (3)..(3)
<223> OTHER INFORMATION: 2'-OMe adenosine
<220> FEATURE:
<221> NAME/KEY: modified_base
<222> LOCATION: (4)..(4)
<223> OTHER INFORMATION: 2'-fluoro-adenosine
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: 2'-fluoro-cytidine
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (8)..(8)
<223> OTHER INFORMATION: 2'-fluoro-cytidine
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(10)
<223> OTHER INFORMATION: 5-methylene-exNA-uridine with 2'-fluoro-ex-
      uridine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-fluoro-adenosine
<220> FEATURE:
<221> NAME/KEY: modified_base
<222> LOCATION: (13)..(13)
<223> OTHER INFORMATION: cm
<220> FEATURE:
<221> NAME/KEY: misc_feature
```

<222> LOCATION: (13)..(20)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-fluoro-uridine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: 2'-fluoro-adenosine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: 2'-fluoro-adenosine
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(20)
<223> OTHER INFORMATION: 2'-fluoro-adenosine

<400> SEQUENCE: 10
uuaaucucuu uacugauaua 20

<210> SEQ ID NO 11
<211> LENGTH: 20
<212> TYPE: RNA
<213> ORGANISM: Artificial Sequence
<220> FEATURE:
<223> OTHER INFORMATION: ex-11
<220> FEATURE:
<221> NAME/KEY: modified_base
<222> LOCATION: (1)..(1)
<223> OTHER INFORMATION: um
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-uridine
<220> FEATURE:
<221> NAME/KEY: modified_base
<222> LOCATION: (3)..(3)
<223> OTHER INFORMATION: 2'-OMe adenosine
<220> FEATURE:
<221> NAME/KEY: modified_base
<222> LOCATION: (4)..(4)
<223> OTHER INFORMATION: 2'-fluoro-adenosine
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: 2'-fluoro-cytidine
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (8)..(8)
<223> OTHER INFORMATION: 2'-fluoro-cytidine
<220> FEATURE:

<221> NAME/KEY: modified_base
<222> LOCATION: (9)..(9)
<223> OTHER INFORMATION: um
<220> FEATURE:
<221> NAME/KEY: modified_base
<222> LOCATION: (10)..(10)
<223> OTHER INFORMATION: 2'-fluoro-uridine
<220> FEATURE:
<221> NAME/KEY: modified_base
<222> LOCATION: (11)..(11)
<223> OTHER INFORMATION: 5-methylene-exNA-uridine with 2'-OMe uridine
<220> FEATURE:
<221> NAME/KEY: modified_base
<222> LOCATION: (12)..(12)
<223> OTHER INFORMATION: 2'-fluoro-adenosine
<220> FEATURE:
<221> NAME/KEY: modified_base
<222> LOCATION: (13)..(13)
<223> OTHER INFORMATION: cm
<220> FEATURE:
<221> NAME/KEY: misc_feature
<222> LOCATION: (13)..(20)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-fluoro-uridine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: 2'-fluoro-adenosine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: 2'-fluoro-adenosine
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(20)
<223> OTHER INFORMATION: 2'-fluoro-adenosine

<400> SEQUENCE: 11
uuaaucucuu uacugauaua 20

<210> SEQ ID NO 12
<211> LENGTH: 20
<212> TYPE: RNA
<213> ORGANISM: Artificial Sequence
<220> FEATURE:
<223> OTHER INFORMATION: ex-12
<220> FEATURE:
<221> NAME/KEY: modified_base
<222> LOCATION: (1)..(1)
<223> OTHER INFORMATION: um
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-cytidine
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (4)..(4)
<223> OTHER INFORMATION: 2'-fluoro-adenosine
<220> FEATURE:
<221> NAME/KEY: modified_base
<222> LOCATION: (5)..(5)
<223> OTHER INFORMATION: cm
<220> FEATURE:
<221> NAME/KEY: modified_base
<222> LOCATION: (6)..(6)
<223> OTHER INFORMATION: 2'-fluoro-uridine
<220> FEATURE:
<221> NAME/KEY: modified_base
<222> LOCATION: (7)..(7)
<223> OTHER INFORMATION: 2'-OMe adenosine
<220> FEATURE:
<221> NAME/KEY: modified_base
<222> LOCATION: (8)..(8)
<223> OTHER INFORMATION: 2'-fluoro-uridine
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (10)..(10)
<223> OTHER INFORMATION: 2'-fluoro-uridine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 5-methylene-exNA-uridine with 2'-fluoro-ex-
uridine
<220> FEATURE:
<221> NAME/KEY: modified_base
<222> LOCATION: (13)..(13)
<223> OTHER INFORMATION: um
<220> FEATURE:
<221> NAME/KEY: misc_feature
<222> LOCATION: (13)..(20)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-fluoro-cytidine
<220> FEATURE:
<221> NAME/KEY: modified_base
<222> LOCATION: (15)..(15)
<223> OTHER INFORMATION: 2'-OMe adenosine
<220> FEATURE:
<221> NAME/KEY: modified_base
<222> LOCATION: (16)..(16)
<223> OTHER INFORMATION: 2'-fluoro-cytidine
<220> FEATURE:
<221> NAME/KEY: modified_base
<222> LOCATION: (17)..(17)
<223> OTHER INFORMATION: 2'-OMe adenosine
<220> FEATURE:
<221> NAME/KEY: modified_base
<222> LOCATION: (18)..(18)
<223> OTHER INFORMATION: 2'-fluoro-uridine
<220> FEATURE:
<221> NAME/KEY: modified_base
<222> LOCATION: (19)..(19)
<223> OTHER INFORMATION: 2'-OMe adenosine
<220> FEATURE:
<221> NAME/KEY: modified_base
<222> LOCATION: (20)..(20)
<223> OTHER INFORMATION: 2'-fluoro-uridine

<400> SEQUENCE: 12
uccacuaugu uuucacauau 20

-continued

<210> SEQ ID NO 13
<211> LENGTH: 20
<212> TYPE: RNA
<213> ORGANISM: Artificial Sequence
<220> FEATURE:
<223> OTHER INFORMATION: ex-13
<220> FEATURE:
<221> NAME/KEY: modified_base
<222> LOCATION: (1)..(1)
<223> OTHER INFORMATION: um
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-cytidine
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (4)..(4)
<223> OTHER INFORMATION: 2'-fluoro-adenosine
<220> FEATURE:
<221> NAME/KEY: modified_base
<222> LOCATION: (5)..(5)
<223> OTHER INFORMATION: cm
<220> FEATURE:
<221> NAME/KEY: modified_base
<222> LOCATION: (6)..(6)
<223> OTHER INFORMATION: 2'-fluoro-uridine
<220> FEATURE:
<221> NAME/KEY: modified_base
<222> LOCATION: (7)..(7)
<223> OTHER INFORMATION: 2'-OMe adenosine
<220> FEATURE:
<221> NAME/KEY: modified_base
<222> LOCATION: (8)..(8)
<223> OTHER INFORMATION: 2'-fluoro-uridine
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (10)..(10)
<223> OTHER INFORMATION: 2'-fluoro-uridine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-fluoro-uridine
<220> FEATURE:
<221> NAME/KEY: modified_base
<222> LOCATION: (13)..(13)
<223> OTHER INFORMATION: 5-methylene-exNA-uridine with 2'-OMe uridine
<220> FEATURE:
<221> NAME/KEY: misc_feature
<222> LOCATION: (13)..(20)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-fluoro-cytidine
<220> FEATURE:
<221> NAME/KEY: modified_base
<222> LOCATION: (15)..(15)
<223> OTHER INFORMATION: 2'-OMe adenosine
<220> FEATURE:
<221> NAME/KEY: modified_base
<222> LOCATION: (16)..(16)
<223> OTHER INFORMATION: 2'-fluoro-cytidine
<220> FEATURE:

<221> NAME/KEY: modified_base
<222> LOCATION: (17)..(17)
<223> OTHER INFORMATION: 2'-OMe adenosine
<220> FEATURE:
<221> NAME/KEY: modified_base
<222> LOCATION: (18)..(18)
<223> OTHER INFORMATION: 2'-fluoro-uridine
<220> FEATURE:
<221> NAME/KEY: modified_base
<222> LOCATION: (19)..(19)
<223> OTHER INFORMATION: 2'-OMe adenosine
<220> FEATURE:
<221> NAME/KEY: modified_base
<222> LOCATION: (20)..(20)
<223> OTHER INFORMATION: 2'-fluoro-uridine

<400> SEQUENCE: 13
uccacuaugu uuucacauau 20

<210> SEQ ID NO 14
<211> LENGTH: 20
<212> TYPE: RNA
<213> ORGANISM: Artificial Sequence
<220> FEATURE:
<223> OTHER INFORMATION: ex-14
<220> FEATURE:
<221> NAME/KEY: modified_base
<222> LOCATION: (1)..(1)
<223> OTHER INFORMATION: um
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-uridine
<220> FEATURE:
<221> NAME/KEY: modified_base
<222> LOCATION: (3)..(3)
<223> OTHER INFORMATION: 2'-OMe adenosine
<220> FEATURE:
<221> NAME/KEY: modified_base
<222> LOCATION: (4)..(4)
<223> OTHER INFORMATION: 2'-fluoro-adenosine
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: 2'-fluoro-cytidine
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (8)..(8)
<223> OTHER INFORMATION: 2'-fluoro-cytidine
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(10)
<223> OTHER INFORMATION: 2'-fluoro-uridine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-fluoro-adenosine
<220> FEATURE:
<221> NAME/KEY: modified_base
<222> LOCATION: (13)..(13)
<223> OTHER INFORMATION: cm
<220> FEATURE:
<221> NAME/KEY: misc_feature
<222> LOCATION: (13)..(20)
<223> OTHER INFORMATION: Phosphorothioate Linkage
<220> FEATURE:
<221> NAME/KEY: modified_base
<222> LOCATION: (14)..(14)
<223> OTHER INFORMATION: 5-methylene-exNA-uridine with 2'-fluoro-ex-
uridine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: 2'-fluoro-adenosine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: 2'-fluoro-adenosine
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(20)
<223> OTHER INFORMATION: 2'-fluoro-adenosine

<400> SEQUENCE: 14
uuaaucucuu uacugauaua 20

<210> SEQ ID NO 15
<211> LENGTH: 20
<212> TYPE: RNA
<213> ORGANISM: Artificial Sequence
<220> FEATURE:
<223> OTHER INFORMATION: ex-15
<220> FEATURE:
<221> NAME/KEY: modified_base
<222> LOCATION: (1)..(1)
<223> OTHER INFORMATION: um
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-guanosine
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (4)..(4)
<223> OTHER INFORMATION: 2'-fluoro-cytidine
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: 2'-fluoro-adenosine
<220> FEATURE:
<221> NAME/KEY: modified_base
<222> LOCATION: (7)..(7)
<223> OTHER INFORMATION: 2'-OMe adenosine
<220> FEATURE:
<221> NAME/KEY: modified_base
<222> LOCATION: (8)..(8)
<223> OTHER INFORMATION: 2'-fluoro-guanosine
<220> FEATURE:
<221> NAME/KEY: modified_base
<222> LOCATION: (9)..(9)
<223> OTHER INFORMATION: 2'-OMe adenosine
<220> FEATURE:
<221> NAME/KEY: modified_base
<222> LOCATION: (10)..(10)
<223> OTHER INFORMATION: 2'-fluoro-guanosine
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(12)
<223> OTHER INFORMATION: 2'-fluoro-adenosine
<220> FEATURE:
<221> NAME/KEY: modified_base
<222> LOCATION: (13)..(13)
<223> OTHER INFORMATION: cm
<220> FEATURE:
<221> NAME/KEY: misc_feature
<222> LOCATION: (13)..(20)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-fluoro-adenosine
<220> FEATURE:
<221> NAME/KEY: modified_base
<222> LOCATION: (15)..(15)
<223> OTHER INFORMATION: 5-methylene-exNA-uridine with 2'-OMe uridine
<220> FEATURE:
<221> NAME/KEY: modified_base
<222> LOCATION: (16)..(16)
<223> OTHER INFORMATION: 2'-fluoro-uridine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: 2'-fluoro-adenosine
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (20)..(20)
<223> OTHER INFORMATION: 2'-fluoro-uridine

<400> SEQUENCE: 15
ugccuaagag cacauuuagu 20

<210> SEQ ID NO 16
<211> LENGTH: 20
<212> TYPE: RNA
<213> ORGANISM: Artificial Sequence
<220> FEATURE:
<223> OTHER INFORMATION: ex-16
<220> FEATURE:
<221> NAME/KEY: modified_base
<222> LOCATION: (1)..(1)
<223> OTHER INFORMATION: um
<220> FEATURE:
<221> NAME/KEY: misc_feature
<222> LOCATION: (1)..(3)
<223> OTHER INFORMATION: Phosphorothioate Linkage
<220> FEATURE:

-continued

<221> NAME/KEY: modified_base
<222> LOCATION: (2)..(2)
<223> OTHER INFORMATION: 2'-fluoro-guanosine
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (4)..(4)
<223> OTHER INFORMATION: 2'-fluoro-cytidine
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: 2'-fluoro-adenosine
<220> FEATURE:
<221> NAME/KEY: modified_base
<222> LOCATION: (7)..(7)
<223> OTHER INFORMATION: 2'-OMe adenosine
<220> FEATURE:
<221> NAME/KEY: modified_base
<222> LOCATION: (8)..(8)
<223> OTHER INFORMATION: 2'-fluoro-guanosine
<220> FEATURE:
<221> NAME/KEY: modified_base
<222> LOCATION: (9)..(9)
<223> OTHER INFORMATION: 2'-OMe adenosine
<220> FEATURE:
<221> NAME/KEY: modified_base
<222> LOCATION: (10)..(10)
<223> OTHER INFORMATION: 2'-fluoro-guanosine
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(12)
<223> OTHER INFORMATION: 2'-fluoro-adenosine
<220> FEATURE:
<221> NAME/KEY: modified_base
<222> LOCATION: (13)..(13)
<223> OTHER INFORMATION: cm
<220> FEATURE:
<221> NAME/KEY: misc_feature
<222> LOCATION: (13)..(20)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-fluoro-adenosine
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (16)..(16)
<223> OTHER INFORMATION: 5-methylene-exNA-uridine with 2'-fluoro-ex-
uridine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: 2'-fluoro-adenosine
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (20)..(20)

<223> OTHER INFORMATION: 2'-fluoro-uridine

<400> SEQUENCE: 16
ugccuaagag cacauuuagu 20

<210> SEQ ID NO 17
<211> LENGTH: 20
<212> TYPE: RNA
<213> ORGANISM: Artificial Sequence
<220> FEATURE:
<223> OTHER INFORMATION: ex-17
<220> FEATURE:
<221> NAME/KEY: modified_base
<222> LOCATION: (1)..(1)
<223> OTHER INFORMATION: um
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-uridine
<220> FEATURE:
<221> NAME/KEY: modified_base
<222> LOCATION: (3)..(3)
<223> OTHER INFORMATION: 2'-OMe adenosine
<220> FEATURE:
<221> NAME/KEY: modified_base
<222> LOCATION: (4)..(4)
<223> OTHER INFORMATION: 2'-fluoro-adenosine
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: 2'-fluoro-cytidine
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (8)..(8)
<223> OTHER INFORMATION: 2'-fluoro-cytidine
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(10)
<223> OTHER INFORMATION: 2'-fluoro-uridine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-fluoro-adenosine
<220> FEATURE:
<221> NAME/KEY: modified_base
<222> LOCATION: (13)..(13)
<223> OTHER INFORMATION: cm
<220> FEATURE:
<221> NAME/KEY: misc_feature
<222> LOCATION: (13)..(20)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-fluoro-uridine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: 2'-fluoro-adenosine
<220> FEATURE:
<221> NAME/KEY: modified_base
<222> LOCATION: (17)..(17)
<223> OTHER INFORMATION: 5-methylene-exNA-uridine with 2'-OMe uridine
<220> FEATURE:
<221> NAME/KEY: modified_base
<222> LOCATION: (18)..(18)
<223> OTHER INFORMATION: 2'-fluoro-adenosine
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(20)
<223> OTHER INFORMATION: 2'-fluoro-adenosine

<400> SEQUENCE: 17
uuaaucucuu uacugauaua 20

<210> SEQ ID NO 18
<211> LENGTH: 20
<212> TYPE: RNA
<213> ORGANISM: Artificial Sequence
<220> FEATURE:
<223> OTHER INFORMATION: ex-18
<220> FEATURE:
<221> NAME/KEY: modified_base
<222> LOCATION: (1)..(1)
<223> OTHER INFORMATION: um
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-cytidine
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (4)..(4)
<223> OTHER INFORMATION: 2'-fluoro-adenosine
<220> FEATURE:
<221> NAME/KEY: modified_base
<222> LOCATION: (5)..(5)
<223> OTHER INFORMATION: cm
<220> FEATURE:
<221> NAME/KEY: modified_base
<222> LOCATION: (6)..(6)
<223> OTHER INFORMATION: 2'-fluoro-uridine
<220> FEATURE:
<221> NAME/KEY: modified_base
<222> LOCATION: (7)..(7)
<223> OTHER INFORMATION: 2'-OMe adenosine
<220> FEATURE:
<221> NAME/KEY: modified_base
<222> LOCATION: (8)..(8)
<223> OTHER INFORMATION: 2'-fluoro-uridine
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (10)..(10)
<223> OTHER INFORMATION: 2'-fluoro-uridine
<220> FEATURE:

<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-fluoro-uridine
<220> FEATURE:
<221> NAME/KEY: modified_base
<222> LOCATION: (13)..(13)
<223> OTHER INFORMATION: um
<220> FEATURE:
<221> NAME/KEY: misc_feature
<222> LOCATION: (13)..(20)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-fluoro-cytidine
<220> FEATURE:
<221> NAME/KEY: modified_base
<222> LOCATION: (15)..(15)
<223> OTHER INFORMATION: 2'-OMe adenosine
<220> FEATURE:
<221> NAME/KEY: modified_base
<222> LOCATION: (16)..(16)
<223> OTHER INFORMATION: 2'-fluoro-cytidine
<220> FEATURE:
<221> NAME/KEY: modified_base
<222> LOCATION: (17)..(17)
<223> OTHER INFORMATION: 2'-OMe adenosine
<220> FEATURE:
<221> NAME/KEY: modified_base
<222> LOCATION: (18)..(18)
<223> OTHER INFORMATION: 5-methylene-exNA-uridine with 2'-fluoro-ex-
uridine
<220> FEATURE:
<221> NAME/KEY: modified_base
<222> LOCATION: (19)..(19)
<223> OTHER INFORMATION: 2'-OMe adenosine
<220> FEATURE:
<221> NAME/KEY: modified_base
<222> LOCATION: (20)..(20)
<223> OTHER INFORMATION: 2'-fluoro-uridine

<400> SEQUENCE: 18
uccacuaugu uuucacauau 20

<210> SEQ ID NO 19
<211> LENGTH: 20
<212> TYPE: RNA
<213> ORGANISM: Artificial Sequence
<220> FEATURE:
<223> OTHER INFORMATION: ex-19
<220> FEATURE:
<221> NAME/KEY: modified_base
<222> LOCATION: (1)..(1)
<223> OTHER INFORMATION: um
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-uridine
<220> FEATURE:
<221> NAME/KEY: modified_base
<222> LOCATION: (3)..(3)
<223> OTHER INFORMATION: 2'-OMe adenosine
<220> FEATURE:
<221> NAME/KEY: modified_base
<222> LOCATION: (4)..(4)
<223> OTHER INFORMATION: 2'-fluoro-adenosine
<220> FEATURE:
<221> NAME/KEY: modified_base
<222> LOCATION: (5)..(5)

<223> OTHER INFORMATION: um
<220> FEATURE:
<221> NAME/KEY: modified_base
<222> LOCATION: (6)..(6)
<223> OTHER INFORMATION: 2'-fluoro-cytidine
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (8)..(8)
<223> OTHER INFORMATION: 2'-fluoro-cytidine
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(10)
<223> OTHER INFORMATION: 2'-fluoro-uridine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-fluoro-adenosine
<220> FEATURE:
<221> NAME/KEY: modified_base
<222> LOCATION: (13)..(13)
<223> OTHER INFORMATION: cm
<220> FEATURE:
<221> NAME/KEY: misc_feature
<222> LOCATION: (13)..(20)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-fluoro-uridine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: 2'-fluoro-adenosine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: 2'-fluoro-adenosine
<220> FEATURE:
<221> NAME/KEY: modified_base
<222> LOCATION: (19)..(19)
<223> OTHER INFORMATION: 5-methylene-exNA-uridine with 2'-OMe uridine
<220> FEATURE:
<221> NAME/KEY: modified_base
<222> LOCATION: (20)..(20)
<223> OTHER INFORMATION: 2'-fluoro-adenosine

<400> SEQUENCE: 19
uuaaucucuu uacugauaua 20

<210> SEQ ID NO 20
<211> LENGTH: 20
<212> TYPE: RNA
<213> ORGANISM: Artificial Sequence
<220> FEATURE:
<223> OTHER INFORMATION: ex-20
<220> FEATURE:
<221> NAME/KEY: modified_base
<222> LOCATION: (1)..(1)
<223> OTHER INFORMATION: um
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-cytidine
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (4)..(4)
<223> OTHER INFORMATION: 2'-fluoro-adenosine
<220> FEATURE:
<221> NAME/KEY: modified_base
<222> LOCATION: (5)..(5)
<223> OTHER INFORMATION: cm
<220> FEATURE:
<221> NAME/KEY: modified_base
<222> LOCATION: (6)..(6)
<223> OTHER INFORMATION: 2'-fluoro-uridine
<220> FEATURE:
<221> NAME/KEY: modified_base
<222> LOCATION: (7)..(7)
<223> OTHER INFORMATION: 2'-OMe adenosine
<220> FEATURE:
<221> NAME/KEY: modified_base
<222> LOCATION: (8)..(8)
<223> OTHER INFORMATION: 2'-fluoro-uridine
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (10)..(10)
<223> OTHER INFORMATION: 2'-fluoro-uridine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-fluoro-uridine
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (14)..(14)
<223> OTHER INFORMATION: 2'-fluoro-cytidine
<220> FEATURE:
<221> NAME/KEY: modified_base
<222> LOCATION: (15)..(15)
<223> OTHER INFORMATION: 2'-OMe adenosine
<220> FEATURE:
<221> NAME/KEY: modified_base
<222> LOCATION: (16)..(16)
<223> OTHER INFORMATION: 2'-fluoro-cytidine
<220> FEATURE:
<221> NAME/KEY: modified_base
<222> LOCATION: (17)..(17)
<223> OTHER INFORMATION: 2'-OMe adenosine
<220> FEATURE:
<221> NAME/KEY: modified_base
<222> LOCATION: (18)..(18)
<223> OTHER INFORMATION: 2'-fluoro-uridine
<220> FEATURE:
<221> NAME/KEY: modified_base
<222> LOCATION: (19)..(19)
<223> OTHER INFORMATION: 2'-OMe adenosine
<220> FEATURE:

<221> NAME/KEY: modified_base
<222> LOCATION: (20)..(20)
<223> OTHER INFORMATION: 5-methylene-exNA-uridine with 2'-fluoro-ex-
uridine

<400> SEQUENCE: 20
uccacuaugu uuucacauau 20

<210> SEQ ID NO 21
<211> LENGTH: 20
<212> TYPE: RNA
<213> ORGANISM: Artificial Sequence
<220> FEATURE:
<223> OTHER INFORMATION: ex-21
<220> FEATURE:
<221> NAME/KEY: modified_base
<222> LOCATION: (1)..(1)
<223> OTHER INFORMATION: um
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-uridine
<220> FEATURE:
<221> NAME/KEY: modified_base
<222> LOCATION: (3)..(3)
<223> OTHER INFORMATION: 2'-OMe adenosine
<220> FEATURE:
<221> NAME/KEY: modified_base
<222> LOCATION: (4)..(4)
<223> OTHER INFORMATION: 2'-fluoro-adenosine
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: 2'-fluoro-cytidine
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (8)..(8)
<223> OTHER INFORMATION: 2'-fluoro-cytidine
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(10)
<223> OTHER INFORMATION: 2'-fluoro-uridine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-fluoro-adenosine
<220> FEATURE:
<221> NAME/KEY: modified_base
<222> LOCATION: (13)..(13)
<223> OTHER INFORMATION: cm
<220> FEATURE:
<221> NAME/KEY: misc_feature
<222> LOCATION: (13)..(20)
<223> OTHER INFORMATION: Phosphorothioate Linkage
<220> FEATURE:
<221> NAME/KEY: modified_base
<222> LOCATION: (14)..(14)

<223> OTHER INFORMATION: 2'-fluoro-uridine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: 2'-fluoro-adenosine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: 2'-fluoro-uridine
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(20)
<223> OTHER INFORMATION: 5-methylene-exNA-uridine with 2'-fluoro-ex-
uridine

<400> SEQUENCE: 21
uuaaucucuu uacugauuuu 20

<210> SEQ ID NO 22
<211> LENGTH: 20
<212> TYPE: RNA
<213> ORGANISM: Artificial Sequence
<220> FEATURE:
<223> OTHER INFORMATION: ex-22
<220> FEATURE:
<221> NAME/KEY: modified_base
<222> LOCATION: (1)..(1)
<223> OTHER INFORMATION: um
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-uridine
<220> FEATURE:
<221> NAME/KEY: modified_base
<222> LOCATION: (3)..(3)
<223> OTHER INFORMATION: 2'-OMe adenosine
<220> FEATURE:
<221> NAME/KEY: modified_base
<222> LOCATION: (4)..(4)
<223> OTHER INFORMATION: 2'-fluoro-adenosine
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: 2'-fluoro-cytidine
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (8)..(8)
<223> OTHER INFORMATION: 2'-fluoro-cytidine
<220> FEATURE:
<221> NAME/KEY: modified_base
<222> LOCATION: (9)..(9)
<223> OTHER INFORMATION: um
<220> FEATURE:

<221> NAME/KEY: modified_base
<222> LOCATION: (10)..(10)
<223> OTHER INFORMATION: 2'-fluoro-uridine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-fluoro-adenosine
<220> FEATURE:
<221> NAME/KEY: modified_base
<222> LOCATION: (13)..(13)
<223> OTHER INFORMATION: cm
<220> FEATURE:
<221> NAME/KEY: misc_feature
<222> LOCATION: (13)..(20)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-fluoro-uridine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: 2'-fluoro-adenosine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: 2'-fluoro-uridine
<220> FEATURE:
<221> NAME/KEY: modified_base
<222> LOCATION: (19)..(19)
<223> OTHER INFORMATION: 5-methylene-exNA-uridine with 2'-OMe uridine
<220> FEATURE:
<221> NAME/KEY: modified_base
<222> LOCATION: (20)..(20)
<223> OTHER INFORMATION: 5-methylene-exNA-uridine with 2'-fluoro-ex-
uridine

<400> SEQUENCE: 22
uuaaucucuu uacugauuuu 20

<210> SEQ ID NO 23
<211> LENGTH: 20
<212> TYPE: RNA
<213> ORGANISM: Artificial Sequence
<220> FEATURE:
<223> OTHER INFORMATION: ex-23
<220> FEATURE:
<221> NAME/KEY: modified_base
<222> LOCATION: (1)..(1)
<223> OTHER INFORMATION: um
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-uridine
<220> FEATURE:
<221> NAME/KEY: modified_base
<222> LOCATION: (3)..(3)
<223> OTHER INFORMATION: 2'-OMe adenosine
<220> FEATURE:
<221> NAME/KEY: modified_base
<222> LOCATION: (4)..(4)

<223> OTHER INFORMATION: 2'-fluoro-adenosine
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: 2'-fluoro-cytidine
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (8)..(8)
<223> OTHER INFORMATION: 2'-fluoro-cytidine
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(10)
<223> OTHER INFORMATION: 2'-fluoro-uridine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-fluoro-adenosine
<220> FEATURE:
<221> NAME/KEY: modified_base
<222> LOCATION: (13)..(13)
<223> OTHER INFORMATION: cm
<220> FEATURE:
<221> NAME/KEY: misc_feature
<222> LOCATION: (13)..(20)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-fluoro-uridine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: 2'-fluoro-adenosine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: 5-methylene-exNA-uridine with 2'-fluoro-ex-
uridine
<220> FEATURE:
<221> NAME/KEY: modified_base
<222> LOCATION: (19)..(19)
<223> OTHER INFORMATION: 5-methylene-exNA-uridine with 2'-OMe uridine
<220> FEATURE:
<221> NAME/KEY: modified_base
<222> LOCATION: (20)..(20)
<223> OTHER INFORMATION: 5-methylene-exNA-uridine with 2'-fluoro-ex-
uridine

<400> SEQUENCE: 23
uuaaucucuu uacugauuuu 20

<210> SEQ ID NO 24
<211> LENGTH: 20

<212> TYPE: RNA
<213> ORGANISM: Artificial Sequence
<220> FEATURE:
<223> OTHER INFORMATION: ex-24
<220> FEATURE:
<221> NAME/KEY: modified_base
<222> LOCATION: (1)..(1)
<223> OTHER INFORMATION: um
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-uridine
<220> FEATURE:
<221> NAME/KEY: modified_base
<222> LOCATION: (3)..(3)
<223> OTHER INFORMATION: 2'-OMe adenosine
<220> FEATURE:
<221> NAME/KEY: modified_base
<222> LOCATION: (4)..(4)
<223> OTHER INFORMATION: 2'-fluoro-adenosine
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: 2'-fluoro-cytidine
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (8)..(8)
<223> OTHER INFORMATION: 2'-fluoro-cytidine
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(10)
<223> OTHER INFORMATION: 2'-fluoro-uridine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-fluoro-adenosine
<220> FEATURE:
<221> NAME/KEY: modified_base
<222> LOCATION: (13)..(13)
<223> OTHER INFORMATION: cm
<220> FEATURE:
<221> NAME/KEY: misc_feature
<222> LOCATION: (13)..(20)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-fluoro-uridine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: 2'-fluoro-adenosine
<220> FEATURE:
<221> NAME/KEY: modified_base
<222> LOCATION: (17)..(17)

```
<223> OTHER INFORMATION: 5-methylene-exNA-uridine with 2'-OMe nucleotide
<220> FEATURE:
<221> NAME/KEY: modified_base
<222> LOCATION: (18)..(18)
<223> OTHER INFORMATION: 5-methylene-exNA-uridine with 2'-fluoro-ex-
      uridine
<220> FEATURE:
<221> NAME/KEY: modified_base
<222> LOCATION: (19)..(19)
<223> OTHER INFORMATION: 5-methylene-exNA-uridine with 2'-OMe uridine
<220> FEATURE:
<221> NAME/KEY: modified_base
<222> LOCATION: (20)..(20)
<223> OTHER INFORMATION: 5-methylene-exNA-uridine with 2'-fluoro-ex-
      uridine

<400> SEQUENCE: 24

uuaaucucuu uacugauuuu                                                20


<210> SEQ ID NO 25
<211> LENGTH: 15
<212> TYPE: RNA
<213> ORGANISM: Artificial Sequence
<220> FEATURE:
<223> OTHER INFORMATION: ex-SS-1
<220> FEATURE:
<221> NAME/KEY: modified_base
<222> LOCATION: (1)..(1)
<223> OTHER INFORMATION: 2'-fluoro-ex-uridine
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-fluoro-adenosine
<220> FEATURE:
<221> NAME/KEY: modified_base
<222> LOCATION: (4)..(4)
<223> OTHER INFORMATION: 2'-OMe adenosine
<220> FEATURE:
<221> NAME/KEY: modified_base
<222> LOCATION: (5)..(5)
<223> OTHER INFORMATION: 2'-fluoro-adenosine
<220> FEATURE:
<221> NAME/KEY: modified_base
<222> LOCATION: (6)..(6)
<223> OTHER INFORMATION: 2'-OMe adenosine
<220> FEATURE:
<221> NAME/KEY: modified_base
<222> LOCATION: (7)..(7)
<223> OTHER INFORMATION: 2'-fluoro-cytidine
<220> FEATURE:
<221> NAME/KEY: modified_base
<222> LOCATION: (8)..(8)
<223> OTHER INFORMATION: 2'-OMe adenosine
<220> FEATURE:
<221> NAME/KEY: modified_base
<222> LOCATION: (9)..(9)
<223> OTHER INFORMATION: 2'-fluoro-uridine
<220> FEATURE:
<221> NAME/KEY: modified_base
<222> LOCATION: (10)..(10)
<223> OTHER INFORMATION: 2'-OMe adenosine
<220> FEATURE:
<221> NAME/KEY: modified_base
<222> LOCATION: (11)..(11)
<223> OTHER INFORMATION: 2'-fluoro-guanosine
<220> FEATURE:
<221> NAME/KEY: modified_base
<222> LOCATION: (12)..(12)
<223> OTHER INFORMATION: um
```

<220> FEATURE:
<221> NAME/KEY: modified_base
<222> LOCATION: (13)..(13)
<223> OTHER INFORMATION: 2'-fluoro-guanosine
<220> FEATURE:
<221> NAME/KEY: misc_feature
<222> LOCATION: (13)..(15)
<223> OTHER INFORMATION: Phosphorothioate Linkage
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-fluoro-adenosine

<400> SEQUENCE: 25
ugaaaacaua gugga 15

<210> SEQ ID NO 26
<211> LENGTH: 15
<212> TYPE: RNA
<213> ORGANISM: Artificial Sequence
<220> FEATURE:
<223> OTHER INFORMATION: ex-SS-2
<220> FEATURE:
<221> NAME/KEY: modified_base
<222> LOCATION: (1)..(1)
<223> OTHER INFORMATION: 2'-fluoro-cytidine
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-OMe-ex-uridine
<220> FEATURE:
<221> NAME/KEY: modified_base
<222> LOCATION: (3)..(3)
<223> OTHER INFORMATION: 2'-fluoro-cytidine
<220> FEATURE:
<221> NAME/KEY: modified_base
<222> LOCATION: (4)..(4)
<223> OTHER INFORMATION: 2'-OMe adenosine
<220> FEATURE:
<221> NAME/KEY: modified_base
<222> LOCATION: (5)..(5)
<223> OTHER INFORMATION: 2'-fluoro-guanosine
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (7)..(7)
<223> OTHER INFORMATION: 2'-fluoro-adenosine
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(9)
<223> OTHER INFORMATION: 2'-fluoro-uridine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (11)..(11)
<223> OTHER INFORMATION: 2'-fluoro-adenosine
<220> FEATURE:
<221> NAME/KEY: modified_base
<222> LOCATION: (12)..(12)

<223> OTHER INFORMATION: 2'-OMe adenosine
<220> FEATURE:
<221> NAME/KEY: modified_base
<222> LOCATION: (13)..(13)
<223> OTHER INFORMATION: 2'-fluoro-adenosine
<220> FEATURE:
<221> NAME/KEY: misc_feature
<222> LOCATION: (13)..(15)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-OMe adenosine
<220> FEATURE:
<221> NAME/KEY: modified_base
<222> LOCATION: (15)..(15)
<223> OTHER INFORMATION: 2'-fluoro-adenosine

<400> SEQUENCE: 26
cucaggauuu aaaaa 15

<210> SEQ ID NO 27
<211> LENGTH: 15
<212> TYPE: RNA
<213> ORGANISM: Artificial Sequence
<220> FEATURE:
<223> OTHER INFORMATION: ex-SS-3
<220> FEATURE:
<221> NAME/KEY: modified_base
<222> LOCATION: (1)..(1)
<223> OTHER INFORMATION: 2'-fluoro-adenosine
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-OMe adenosine
<220> FEATURE:
<221> NAME/KEY: modified_base
<222> LOCATION: (3)..(3)
<223> OTHER INFORMATION: 2'-fluoro-ex-uridine
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (5)..(5)
<223> OTHER INFORMATION: 2'-fluoro-uridine
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (7)..(7)
<223> OTHER INFORMATION: 2'-fluoro-guanosine
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(9)
<223> OTHER INFORMATION: 2'-fluoro-guanosine
<220> FEATURE:
<221> NAME/KEY: modified_base
<222> LOCATION: (10)..(10)
<223> OTHER INFORMATION: 2'-OMe adenosine
<220> FEATURE:
<221> NAME/KEY: modified_base
<222> LOCATION: (11)..(11)
<223> OTHER INFORMATION: 2'-fluoro-cytidine
<220> FEATURE:
<221> NAME/KEY: modified_base
<222> LOCATION: (12)..(12)
<223> OTHER INFORMATION: cm
<220> FEATURE:
<221> NAME/KEY: modified_base
<222> LOCATION: (13)..(13)
<223> OTHER INFORMATION: 2'-fluoro-guanosine
<220> FEATURE:
<221> NAME/KEY: misc_feature
<222> LOCATION: (13)..(15)
<223> OTHER INFORMATION: Phosphorothioate Linkage
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-fluoro-adenosine

<400> SEQUENCE: 27
aauguuguga ccgga 15

<210> SEQ ID NO 28
<211> LENGTH: 15
<212> TYPE: RNA
<213> ORGANISM: Artificial Sequence
<220> FEATURE:
<223> OTHER INFORMATION: ex-SS-4
<220> FEATURE:
<221> NAME/KEY: modified_base
<222> LOCATION: (1)..(1)
<223> OTHER INFORMATION: 2'-fluoro-cytidine
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-OMe adenosine
<220> FEATURE:
<221> NAME/KEY: modified_base
<222> LOCATION: (3)..(3)
<223> OTHER INFORMATION: 2'-fluoro-guanosine
<220> FEATURE:
<221> NAME/KEY: modified_base
<222> LOCATION: (4)..(4)
<223> OTHER INFORMATION: 2'-OMe-ex-uridine
<220> FEATURE:
<221> NAME/KEY: modified_base
<222> LOCATION: (5)..(5)
<223> OTHER INFORMATION: 2'-fluoro-adenosine
<220> FEATURE:
<221> NAME/KEY: modified_base
<222> LOCATION: (6)..(6)
<223> OTHER INFORMATION: 2'-OMe adenosine
<220> FEATURE:
<221> NAME/KEY: modified_base
<222> LOCATION: (7)..(7)
<223> OTHER INFORMATION: 2'-fluoro-adenosine
<220> FEATURE:
<221> NAME/KEY: modified_base
<222> LOCATION: (8)..(8)
<223> OTHER INFORMATION: gm
<220> FEATURE:
<221> NAME/KEY: modified_base
<222> LOCATION: (9)..(9)
<223> OTHER INFORMATION: 2'-fluoro-adenosine
<220> FEATURE:
<221> NAME/KEY: modified_base
<222> LOCATION: (10)..(10)
<223> OTHER INFORMATION: gm
<220> FEATURE:
<221> NAME/KEY: modified_base
<222> LOCATION: (11)..(11)
<223> OTHER INFORMATION: 2'-fluoro-adenosine
<220> FEATURE:

<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: 2'-fluoro-uridine
<220> FEATURE:
<221> NAME/KEY: misc_feature
<222> LOCATION: (13)..(15)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-OMe adenosine
<220> FEATURE:
<221> NAME/KEY: modified_base
<222> LOCATION: (15)..(15)
<223> OTHER INFORMATION: 2'-fluoro-adenosine

<400> SEQUENCE: 28
caguaaagag auuaa 15

<210> SEQ ID NO 29
<211> LENGTH: 15
<212> TYPE: RNA
<213> ORGANISM: Artificial Sequence
<220> FEATURE:
<223> OTHER INFORMATION: ex-SS-5
<220> FEATURE:
<221> NAME/KEY: modified_base
<222> LOCATION: (1)..(1)
<223> OTHER INFORMATION: 2'-fluoro-adenosine
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-OMe adenosine
<220> FEATURE:
<221> NAME/KEY: modified_base
<222> LOCATION: (3)..(3)
<223> OTHER INFORMATION: 2'-fluoro-uridine
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (5)..(5)
<223> OTHER INFORMATION: 2'-fluoro-ex-uridine
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (7)..(7)
<223> OTHER INFORMATION: 2'-fluoro-guanosine
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(9)
<223> OTHER INFORMATION: 2'-fluoro-guanosine
<220> FEATURE:
<221> NAME/KEY: modified_base
<222> LOCATION: (10)..(10)
<223> OTHER INFORMATION: 2'-OMe adenosine
<220> FEATURE:
<221> NAME/KEY: modified_base
<222> LOCATION: (11)..(11)
<223> OTHER INFORMATION: 2'-fluoro-cytidine
<220> FEATURE:
<221> NAME/KEY: modified_base
<222> LOCATION: (12)..(12)
<223> OTHER INFORMATION: cm
<220> FEATURE:
<221> NAME/KEY: modified_base
<222> LOCATION: (13)..(13)
<223> OTHER INFORMATION: 2'-fluoro-guanosine
<220> FEATURE:
<221> NAME/KEY: misc_feature
<222> LOCATION: (13)..(15)
<223> OTHER INFORMATION: Phosphorothioate Linkage
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-fluoro-adenosine

<400> SEQUENCE: 29
aauguuguga ccgga 15

<210> SEQ ID NO 30
<211> LENGTH: 15
<212> TYPE: RNA
<213> ORGANISM: Artificial Sequence
<220> FEATURE:
<223> OTHER INFORMATION: ex-SS-6
<220> FEATURE:
<221> NAME/KEY: modified_base
<222> LOCATION: (1)..(1)
<223> OTHER INFORMATION: 2'-fluoro-adenosine
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-OMe adenosine
<220> FEATURE:
<221> NAME/KEY: modified_base
<222> LOCATION: (3)..(3)
<223> OTHER INFORMATION: 2'-fluoro-uridine
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (5)..(5)
<223> OTHER INFORMATION: 2'-fluoro-uridine
<220> FEATURE:
<221> NAME/KEY: modified_base
<222> LOCATION: (6)..(6)
<223> OTHER INFORMATION: 2'-OMe-ex-uridine
<220> FEATURE:
<221> NAME/KEY: modified_base
<222> LOCATION: (7)..(7)
<223> OTHER INFORMATION: 2'-fluoro-guanosine
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(9)
<223> OTHER INFORMATION: 2'-fluoro-guanosine
<220> FEATURE:
<221> NAME/KEY: modified_base
<222> LOCATION: (10)..(10)
<223> OTHER INFORMATION: 2'-OMe adenosine
<220> FEATURE:
<221> NAME/KEY: modified_base
<222> LOCATION: (11)..(11)

<223> OTHER INFORMATION: 2'-fluoro-cytidine
<220> FEATURE:
<221> NAME/KEY: modified_base
<222> LOCATION: (12)..(12)
<223> OTHER INFORMATION: cm
<220> FEATURE:
<221> NAME/KEY: modified_base
<222> LOCATION: (13)..(13)
<223> OTHER INFORMATION: 2'-fluoro-guanosine
<220> FEATURE:
<221> NAME/KEY: misc_feature
<222> LOCATION: (13)..(15)
<223> OTHER INFORMATION: Phosphorothioate Linkage
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-fluoro-adenosine

<400> SEQUENCE: 30
aauguuguga ccgga 15

<210> SEQ ID NO 31
<211> LENGTH: 15
<212> TYPE: RNA
<213> ORGANISM: Artificial Sequence
<220> FEATURE:
<223> OTHER INFORMATION: ex-SS-7
<220> FEATURE:
<221> NAME/KEY: modified_base
<222> LOCATION: (1)..(1)
<223> OTHER INFORMATION: 2'-fluoro-adenosine
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: 2'-fluoro-guanosine
<220> FEATURE:
<221> NAME/KEY: modified_base
<222> LOCATION: (4)..(4)
<223> OTHER INFORMATION: um
<220> FEATURE:
<221> NAME/KEY: modified_base
<222> LOCATION: (5)..(5)
<223> OTHER INFORMATION: 2'-fluoro-guanosine
<220> FEATURE:
<221> NAME/KEY: modified_base
<222> LOCATION: (6)..(6)
<223> OTHER INFORMATION: cm
<220> FEATURE:
<221> NAME/KEY: modified_base
<222> LOCATION: (7)..(7)
<223> OTHER INFORMATION: 2'-fluoro-ex-uridine
<220> FEATURE:
<221> NAME/KEY: modified_base
<222> LOCATION: (8)..(8)
<223> OTHER INFORMATION: cm
<220> FEATURE:
<221> NAME/KEY: modified_base
<222> LOCATION: (9)..(9)
<223> OTHER INFORMATION: 2'-fluoro-uridine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (11)..(11)
<223> OTHER INFORMATION: 2'-fluoro-adenosine
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: 2'-fluoro-guanosine
<220> FEATURE:
<221> NAME/KEY: misc_feature
<222> LOCATION: (13)..(15)
<223> OTHER INFORMATION: Phosphorothioate Linkage
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(15)
<223> OTHER INFORMATION: 2'-fluoro-adenosine

<400> SEQUENCE: 31
augugcucuu aggca 15

<210> SEQ ID NO 32
<211> LENGTH: 15
<212> TYPE: RNA
<213> ORGANISM: Artificial Sequence
<220> FEATURE:
<223> OTHER INFORMATION: ex-SS-8
<220> FEATURE:
<221> NAME/KEY: modified_base
<222> LOCATION: (1)..(1)
<223> OTHER INFORMATION: 2'-fluoro-cytidine
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: 2'-fluoro-cytidine
<220> FEATURE:
<221> NAME/KEY: modified_base
<222> LOCATION: (4)..(4)
<223> OTHER INFORMATION: 2'-OMe adenosine
<220> FEATURE:
<221> NAME/KEY: modified_base
<222> LOCATION: (5)..(5)
<223> OTHER INFORMATION: 2'-fluoro-guanosine
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (7)..(7)
<223> OTHER INFORMATION: 2'-fluoro-adenosine
<220> FEATURE:
<221> NAME/KEY: modified_base
<222> LOCATION: (8)..(8)
<223> OTHER INFORMATION: 2'-OMe-ex-uridine
<220> FEATURE:
<221> NAME/KEY: modified_base
<222> LOCATION: (9)..(9)
<223> OTHER INFORMATION: 2'-fluoro-uridine
<220> FEATURE:
<221> NAME/KEY: modified_base
<222> LOCATION: (10)..(10)
<223> OTHER INFORMATION: um
<220> FEATURE:

<221> NAME/KEY: modified_base
<222> LOCATION: (11)..(11)
<223> OTHER INFORMATION: 2'-fluoro-adenosine
<220> FEATURE:
<221> NAME/KEY: modified_base
<222> LOCATION: (12)..(12)
<223> OTHER INFORMATION: 2'-OMe adenosine
<220> FEATURE:
<221> NAME/KEY: modified_base
<222> LOCATION: (13)..(13)
<223> OTHER INFORMATION: 2'-fluoro-adenosine
<220> FEATURE:
<221> NAME/KEY: misc_feature
<222> LOCATION: (13)..(15)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-OMe adenosine
<220> FEATURE:
<221> NAME/KEY: modified_base
<222> LOCATION: (15)..(15)
<223> OTHER INFORMATION: 2'-fluoro-adenosine

<400> SEQUENCE: 32
cucaggauuu aaaaa 15

<210> SEQ ID NO 33
<211> LENGTH: 15
<212> TYPE: RNA
<213> ORGANISM: Artificial Sequence
<220> FEATURE:
<223> OTHER INFORMATION: ex-SS-9
<220> FEATURE:
<221> NAME/KEY: modified_base
<222> LOCATION: (1)..(1)
<223> OTHER INFORMATION: 2'-fluoro-cytidine
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: 2'-fluoro-cytidine
<220> FEATURE:
<221> NAME/KEY: modified_base
<222> LOCATION: (4)..(4)
<223> OTHER INFORMATION: 2'-OMe adenosine
<220> FEATURE:
<221> NAME/KEY: modified_base
<222> LOCATION: (5)..(5)
<223> OTHER INFORMATION: 2'-fluoro-guanosine
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (7)..(7)
<223> OTHER INFORMATION: 2'-fluoro-adenosine
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(9)
<223> OTHER INFORMATION: 2'-fluoro-ex-uridine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (11)..(11)
<223> OTHER INFORMATION: 2'-fluoro-adenosine
<220> FEATURE:
<221> NAME/KEY: modified_base
<222> LOCATION: (12)..(12)
<223> OTHER INFORMATION: 2'-OMe adenosine
<220> FEATURE:
<221> NAME/KEY: modified_base
<222> LOCATION: (13)..(13)
<223> OTHER INFORMATION: 2'-fluoro-adenosine
<220> FEATURE:
<221> NAME/KEY: misc_feature
<222> LOCATION: (13)..(15)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-OMe adenosine
<220> FEATURE:
<221> NAME/KEY: modified_base
<222> LOCATION: (15)..(15)
<223> OTHER INFORMATION: 2'-fluoro-adenosine

<400> SEQUENCE: 33
cucaggauuu aaaaa 15

<210> SEQ ID NO 34
<211> LENGTH: 15
<212> TYPE: RNA
<213> ORGANISM: Artificial Sequence
<220> FEATURE:
<223> OTHER INFORMATION: ex-SS-10
<220> FEATURE:
<221> NAME/KEY: modified_base
<222> LOCATION: (1)..(1)
<223> OTHER INFORMATION: 2'-fluoro-cytidine
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: 2'-fluoro-cytidine
<220> FEATURE:
<221> NAME/KEY: modified_base
<222> LOCATION: (4)..(4)
<223> OTHER INFORMATION: 2'-OMe adenosine
<220> FEATURE:
<221> NAME/KEY: modified_base
<222> LOCATION: (5)..(5)
<223> OTHER INFORMATION: 2'-fluoro-guanosine
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (7)..(7)
<223> OTHER INFORMATION: 2'-fluoro-adenosine
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(9)
<223> OTHER INFORMATION: 2'-fluoro-uridine
<220> FEATURE:
<221> NAME/KEY: modified_base
<222> LOCATION: (10)..(10)

<223> OTHER INFORMATION: 2'-OMe-ex-uridine
<220> FEATURE:
<221> NAME/KEY: modified_base
<222> LOCATION: (11)..(11)
<223> OTHER INFORMATION: 2'-fluoro-adenosine
<220> FEATURE:
<221> NAME/KEY: modified_base
<222> LOCATION: (12)..(12)
<223> OTHER INFORMATION: 2'-OMe adenosine
<220> FEATURE:
<221> NAME/KEY: misc_feature
<222> LOCATION: (13)..(15)
<223> OTHER INFORMATION: Phosphorothioate Linkage
<220> FEATURE:
<221> NAME/KEY: modified_base
<222> LOCATION: (13)..(13)
<223> OTHER INFORMATION: 2'-fluoro-adenosine
<220> FEATURE:
<221> NAME/KEY: modified_base
<222> LOCATION: (14)..(14)
<223> OTHER INFORMATION: 2'-OMe adenosine
<220> FEATURE:
<221> NAME/KEY: modified_base
<222> LOCATION: (15)..(15)
<223> OTHER INFORMATION: 2'-fluoro-adenosine

<400> SEQUENCE: 34
cucaggauuu aaaaa 15

<210> SEQ ID NO 35
<211> LENGTH: 15
<212> TYPE: RNA
<213> ORGANISM: Artificial Sequence
<220> FEATURE:
<223> OTHER INFORMATION: ex-SS-11
<220> FEATURE:
<221> NAME/KEY: modified_base
<222> LOCATION: (1)..(1)
<223> OTHER INFORMATION: 2'-fluoro-cytidine
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: 2'-fluoro-guanosine
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (5)..(5)
<223> OTHER INFORMATION: 2'-fluoro-adenosine
<220> FEATURE:
<221> NAME/KEY: modified_base
<222> LOCATION: (6)..(6)
<223> OTHER INFORMATION: 2'-OMe adenosine
<220> FEATURE:
<221> NAME/KEY: modified_base
<222> LOCATION: (7)..(7)
<223> OTHER INFORMATION: 2'-fluoro-adenosine
<220> FEATURE:
<221> NAME/KEY: modified_base
<222> LOCATION: (8)..(8)
<223> OTHER INFORMATION: 2'-OMe adenosine
<220> FEATURE:
<221> NAME/KEY: modified_base
<222> LOCATION: (9)..(9)
<223> OTHER INFORMATION: 2'-fluoro-guanosine
<220> FEATURE:
<221> NAME/KEY: modified_base
<222> LOCATION: (10)..(10)
<223> OTHER INFORMATION: cm
<220> FEATURE:
<221> NAME/KEY: modified_base
<222> LOCATION: (11)..(11)
<223> OTHER INFORMATION: 2'-fluoro-ex-uridine
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: 2'-fluoro-adenosine
<220> FEATURE:
<221> NAME/KEY: misc_feature
<222> LOCATION: (13)..(15)
<223> OTHER INFORMATION: Phosphorothioate Linkage
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (15)..(15)
<223> OTHER INFORMATION: 2'-fluoro-adenosine

<400> SEQUENCE: 35
cuggaaaagc ugaua 15

<210> SEQ ID NO 36
<211> LENGTH: 15
<212> TYPE: RNA
<213> ORGANISM: Artificial Sequence
<220> FEATURE:
<223> OTHER INFORMATION: ex-SS-12
<220> FEATURE:
<221> NAME/KEY: modified_base
<222> LOCATION: (1)..(1)
<223> OTHER INFORMATION: 2'-fluoro-cytidine
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-OMe adenosine
<220> FEATURE:
<221> NAME/KEY: modified_base
<222> LOCATION: (3)..(3)
<223> OTHER INFORMATION: 2'-fluoro-guanosine
<220> FEATURE:
<221> NAME/KEY: modified_base
<222> LOCATION: (4)..(4)
<223> OTHER INFORMATION: um
<220> FEATURE:
<221> NAME/KEY: modified_base
<222> LOCATION: (5)..(5)
<223> OTHER INFORMATION: 2'-fluoro-adenosine
<220> FEATURE:
<221> NAME/KEY: modified_base
<222> LOCATION: (6)..(6)
<223> OTHER INFORMATION: 2'-OMe adenosine
<220> FEATURE:
<221> NAME/KEY: modified_base
<222> LOCATION: (7)..(7)
<223> OTHER INFORMATION: 2'-fluoro-adenosine
<220> FEATURE:
<221> NAME/KEY: modified_base
<222> LOCATION: (8)..(8)
<223> OTHER INFORMATION: gm
<220> FEATURE:
<221> NAME/KEY: modified_base
<222> LOCATION: (9)..(9)
<223> OTHER INFORMATION: 2'-fluoro-adenosine
<220> FEATURE:

<221> NAME/KEY: modified_base
<222> LOCATION: (10)..(10)
<223> OTHER INFORMATION: gm
<220> FEATURE:
<221> NAME/KEY: modified_base
<222> LOCATION: (11)..(11)
<223> OTHER INFORMATION: 2'-fluoro-adenosine
<220> FEATURE:
<221> NAME/KEY: modified_base
<222> LOCATION: (12)..(12)
<223> OTHER INFORMATION: 2'-OMe-ex-uridine
<220> FEATURE:
<221> NAME/KEY: modified_base
<222> LOCATION: (13)..(13)
<223> OTHER INFORMATION: 2'-fluoro-uridine
<220> FEATURE:
<221> NAME/KEY: misc_feature
<222> LOCATION: (13)..(15)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-OMe adenosine
<220> FEATURE:
<221> NAME/KEY: modified_base
<222> LOCATION: (15)..(15)
<223> OTHER INFORMATION: 2'-fluoro-adenosine

<400> SEQUENCE: 36
caguaaagag auuaa 15

<210> SEQ ID NO 37
<211> LENGTH: 15
<212> TYPE: RNA
<213> ORGANISM: Artificial Sequence
<220> FEATURE:
<223> OTHER INFORMATION: ex-SS-13
<220> FEATURE:
<221> NAME/KEY: modified_base
<222> LOCATION: (1)..(1)
<223> OTHER INFORMATION: 2'-fluoro-cytidine
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-OMe adenosine
<220> FEATURE:
<221> NAME/KEY: modified_base
<222> LOCATION: (3)..(3)
<223> OTHER INFORMATION: 2'-fluoro-guanosine
<220> FEATURE:
<221> NAME/KEY: modified_base
<222> LOCATION: (4)..(4)
<223> OTHER INFORMATION: um
<220> FEATURE:
<221> NAME/KEY: modified_base
<222> LOCATION: (5)..(5)
<223> OTHER INFORMATION: 2'-fluoro-adenosine
<220> FEATURE:
<221> NAME/KEY: modified_base
<222> LOCATION: (6)..(6)
<223> OTHER INFORMATION: 2'-OMe adenosine
<220> FEATURE:
<221> NAME/KEY: modified_base
<222> LOCATION: (7)..(7)
<223> OTHER INFORMATION: 2'-fluoro-adenosine
<220> FEATURE:
<221> NAME/KEY: modified_base
<222> LOCATION: (8)..(8)
<223> OTHER INFORMATION: gm
<220> FEATURE:
<221> NAME/KEY: modified_base
<222> LOCATION: (9)..(9)
<223> OTHER INFORMATION: 2'-fluoro-adenosine
<220> FEATURE:
<221> NAME/KEY: modified_base
<222> LOCATION: (10)..(10)
<223> OTHER INFORMATION: gm
<220> FEATURE:
<221> NAME/KEY: modified_base
<222> LOCATION: (11)..(11)
<223> OTHER INFORMATION: 2'-fluoro-adenosine
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: 2'-fluoro-ex-uridine
<220> FEATURE:
<221> NAME/KEY: misc_feature
<222> LOCATION: (13)..(15)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-OMe adenosine
<220> FEATURE:
<221> NAME/KEY: modified_base
<222> LOCATION: (15)..(15)
<223> OTHER INFORMATION: 2'-fluoro-adenosine

<400> SEQUENCE: 37
caguaaagag auuaa 15

<210> SEQ ID NO 38
<211> LENGTH: 15
<212> TYPE: RNA
<213> ORGANISM: Artificial Sequence
<220> FEATURE:
<223> OTHER INFORMATION: ex-SS-14
<220> FEATURE:
<221> NAME/KEY: modified_base
<222> LOCATION: (1)..(1)
<223> OTHER INFORMATION: 2'-fluoro-cytidine
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: 2'-fluoro-guanosine
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (5)..(5)
<223> OTHER INFORMATION: 2'-fluoro-adenosine
<220> FEATURE:
<221> NAME/KEY: modified_base
<222> LOCATION: (6)..(6)
<223> OTHER INFORMATION: 2'-OMe adenosine
<220> FEATURE:
<221> NAME/KEY: modified_base
<222> LOCATION: (7)..(7)
<223> OTHER INFORMATION: 2'-fluoro-adenosine
<220> FEATURE:
<221> NAME/KEY: modified_base
<222> LOCATION: (8)..(8)
<223> OTHER INFORMATION: 2'-OMe adenosine
<220> FEATURE:
<221> NAME/KEY: modified_base
<222> LOCATION: (9)..(9)

<223> OTHER INFORMATION: 2'-fluoro-guanosine
<220> FEATURE:
<221> NAME/KEY: modified_base
<222> LOCATION: (10)..(10)
<223> OTHER INFORMATION: cm
<220> FEATURE:
<221> NAME/KEY: modified_base
<222> LOCATION: (11)..(11)
<223> OTHER INFORMATION: 2'-fluoro-uridine
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: 2'-fluoro-adenosine
<220> FEATURE:
<221> NAME/KEY: misc_feature
<222> LOCATION: (13)..(15)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-OMe-ex-uridine
<220> FEATURE:
<221> NAME/KEY: modified_base
<222> LOCATION: (15)..(15)
<223> OTHER INFORMATION: 2'-fluoro-adenosine

<400> SEQUENCE: 38
cuggaaaagc ugaua 15

<210> SEQ ID NO 39
<211> LENGTH: 15
<212> TYPE: RNA
<213> ORGANISM: Artificial Sequence
<220> FEATURE:
<223> OTHER INFORMATION: ex-SS-39
<220> FEATURE:
<221> NAME/KEY: modified_base
<222> LOCATION: (1)..(1)
<223> OTHER INFORMATION: 2'-fluoro-cytidine
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-OMe adenosine
<220> FEATURE:
<221> NAME/KEY: modified_base
<222> LOCATION: (3)..(3)
<223> OTHER INFORMATION: 2'-fluoro-guanosine
<220> FEATURE:
<221> NAME/KEY: modified_base
<222> LOCATION: (4)..(4)
<223> OTHER INFORMATION: um
<220> FEATURE:
<221> NAME/KEY: modified_base
<222> LOCATION: (5)..(5)
<223> OTHER INFORMATION: 2'-fluoro-adenosine
<220> FEATURE:
<221> NAME/KEY: modified_base
<222> LOCATION: (6)..(6)
<223> OTHER INFORMATION: 2'-OMe adenosine
<220> FEATURE:
<221> NAME/KEY: modified_base
<222> LOCATION: (7)..(7)
<223> OTHER INFORMATION: 2'-fluoro-adenosine
<220> FEATURE:
<221> NAME/KEY: modified_base
<222> LOCATION: (8)..(8)
<223> OTHER INFORMATION: gm
<220> FEATURE:
<221> NAME/KEY: modified_base
<222> LOCATION: (9)..(9)
<223> OTHER INFORMATION: 2'-fluoro-adenosine
<220> FEATURE:
<221> NAME/KEY: modified_base
<222> LOCATION: (10)..(10)
<223> OTHER INFORMATION: gm
<220> FEATURE:
<221> NAME/KEY: modified_base
<222> LOCATION: (11)..(11)
<223> OTHER INFORMATION: 2'-fluoro-adenosine
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: 2'-fluoro-uridine
<220> FEATURE:
<221> NAME/KEY: misc_feature
<222> LOCATION: (13)..(15)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-OMe adenosine
<220> FEATURE:
<221> NAME/KEY: modified_base
<222> LOCATION: (15)..(15)
<223> OTHER INFORMATION: 2'-fluoro-ex-uridine

<400> SEQUENCE: 39
caguaaagag auuau 15

<210> SEQ ID NO 40
<211> LENGTH: 20
<212> TYPE: RNA
<213> ORGANISM: Artificial Sequence
<220> FEATURE:
<223> OTHER INFORMATION: AS-0
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (2)..(2)
<223> OTHER INFORMATION: 2'-fluoro-uridine
<220> FEATURE:
<221> NAME/KEY: modified_base
<222> LOCATION: (3)..(3)
<223> OTHER INFORMATION: 2'-OMe adenosine
<220> FEATURE:
<221> NAME/KEY: modified_base
<222> LOCATION: (4)..(4)
<223> OTHER INFORMATION: 2'-fluoro-adenosine
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: 2'-fluoro-cytidine
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (8)..(8)
<223> OTHER INFORMATION: 2'-fluoro-cytidine
<220> FEATURE:
<221> NAME/KEY: modified_base
<222> LOCATION: (9)..(9)
<223> OTHER INFORMATION: um
<220> FEATURE:

<221> NAME/KEY: modified_base
<222> LOCATION: (10)..(10)
<223> OTHER INFORMATION: 2'-fluoro-uridine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-fluoro-adenosine
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (14)..(14)
<223> OTHER INFORMATION: 2'-fluoro-uridine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: 2'-fluoro-adenosine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: 2'-fluoro-uridine
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(20)
<223> OTHER INFORMATION: 2'-fluoro-uridine

<400> SEQUENCE: 40
uuaaucucuu uacugauuuu 20

<210> SEQ ID NO 41
<211> LENGTH: 20
<212> TYPE: RNA
<213> ORGANISM: Artificial Sequence
<220> FEATURE:
<223> OTHER INFORMATION: AS-1
<220> FEATURE:
<221> NAME/KEY: modified_base
<222> LOCATION: (1)..(1)
<223> OTHER INFORMATION: um
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-uridine
<220> FEATURE:
<221> NAME/KEY: modified_base
<222> LOCATION: (3)..(3)
<223> OTHER INFORMATION: 2'-OMe adenosine
<220> FEATURE:
<221> NAME/KEY: modified_base
<222> LOCATION: (4)..(4)
<223> OTHER INFORMATION: 2'-fluoro-adenosine
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: 2'-fluoro-cytidine
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (8)..(8)
<223> OTHER INFORMATION: 2'-fluoro-cytidine
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(10)
<223> OTHER INFORMATION: 2'-fluoro-uridine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-fluoro-adenosine
<220> FEATURE:
<221> NAME/KEY: modified_base
<222> LOCATION: (13)..(13)
<223> OTHER INFORMATION: cm
<220> FEATURE:
<221> NAME/KEY: misc_feature
<222> LOCATION: (13)..(20)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-fluoro-uridine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: 2'-fluoro-adenosine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: 2'-fluoro-adenosine
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(20)
<223> OTHER INFORMATION: 2'-fluoro-adenosine

<400> SEQUENCE: 41
uuaaucucuu uacugauaua 20

<210> SEQ ID NO 42
<211> LENGTH: 20
<212> TYPE: RNA
<213> ORGANISM: Artificial Sequence
<220> FEATURE:
<223> OTHER INFORMATION: AS-2
<220> FEATURE:
<221> NAME/KEY: modified_base
<222> LOCATION: (1)..(1)

-continued

<223> OTHER INFORMATION: um
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-uridine
<220> FEATURE:
<221> NAME/KEY: modified_base
<222> LOCATION: (3)..(3)
<223> OTHER INFORMATION: 2'-OMe adenosine
<220> FEATURE:
<221> NAME/KEY: modified_base
<222> LOCATION: (4)..(4)
<223> OTHER INFORMATION: 2'-fluoro-adenosine
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: 2'-fluoro-cytidine
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (8)..(8)
<223> OTHER INFORMATION: 2'-fluoro-cytidine
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(10)
<223> OTHER INFORMATION: 2'-fluoro-uridine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-fluoro-adenosine
<220> FEATURE:
<221> NAME/KEY: modified_base
<222> LOCATION: (13)..(13)
<223> OTHER INFORMATION: cm
<220> FEATURE:
<221> NAME/KEY: misc_feature
<222> LOCATION: (13)..(20)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-fluoro-uridine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: 2'-fluoro-adenosine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: 2'-fluoro-uridine
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(20)
<223> OTHER INFORMATION: 2'-fluoro-uridine

<400> SEQUENCE: 42
uuaaucucuu uacugauuuu 20

<210> SEQ ID NO 43
<211> LENGTH: 20
<212> TYPE: RNA
<213> ORGANISM: Artificial Sequence
<220> FEATURE:
<223> OTHER INFORMATION: AS-3
<220> FEATURE:
<221> NAME/KEY: modified_base
<222> LOCATION: (1)..(1)
<223> OTHER INFORMATION: um
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-uridine
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (4)..(4)
<223> OTHER INFORMATION: 2'-fluoro-uridine
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: 2'-fluoro-adenosine
<220> FEATURE:
<221> NAME/KEY: modified_base
<222> LOCATION: (7)..(7)
<223> OTHER INFORMATION: 2'-OMe adenosine
<220> FEATURE:
<221> NAME/KEY: modified_base
<222> LOCATION: (8)..(8)
<223> OTHER INFORMATION: 2'-fluoro-adenosine
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(10)
<223> OTHER INFORMATION: 2'-fluoro-cytidine
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(12)
<223> OTHER INFORMATION: 2'-fluoro-uridine
<220> FEATURE:
<221> NAME/KEY: modified_base
<222> LOCATION: (13)..(13)
<223> OTHER INFORMATION: gm
<220> FEATURE:
<221> NAME/KEY: misc_feature
<222> LOCATION: (13)..(20)
<223> OTHER INFORMATION: Phosphorothioate Linkage
<220> FEATURE:

<221> NAME/KEY: modified_base
<222> LOCATION: (14)..(14)
<223> OTHER INFORMATION: 2'-fluoro-adenosine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: 2'-fluoro-adenosine
<220> FEATURE:
<221> NAME/KEY: modified_base
<222> LOCATION: (17)..(17)
<223> OTHER INFORMATION: 2'-OMe adenosine
<220> FEATURE:
<221> NAME/KEY: modified_base
<222> LOCATION: (18)..(18)
<223> OTHER INFORMATION: 2'-fluoro-guanosine
<220> FEATURE:
<221> NAME/KEY: modified_base
<222> LOCATION: (19)..(19)
<223> OTHER INFORMATION: 2'-OMe adenosine
<220> FEATURE:
<221> NAME/KEY: modified_base
<222> LOCATION: (20)..(20)
<223> OTHER INFORMATION: 2'-fluoro-adenosine

<400> SEQUENCE: 43
uuuuuaaauc cugagaagaa 20

<210> SEQ ID NO 44
<211> LENGTH: 20
<212> TYPE: RNA
<213> ORGANISM: Artificial Sequence
<220> FEATURE:
<223> OTHER INFORMATION: AS-4
<220> FEATURE:
<221> NAME/KEY: modified_base
<222> LOCATION: (1)..(1)
<223> OTHER INFORMATION: um
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-cytidine
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (4)..(4)
<223> OTHER INFORMATION: 2'-fluoro-adenosine
<220> FEATURE:
<221> NAME/KEY: modified_base
<222> LOCATION: (5)..(5)
<223> OTHER INFORMATION: cm
<220> FEATURE:
<221> NAME/KEY: modified_base
<222> LOCATION: (6)..(6)
<223> OTHER INFORMATION: 2'-fluoro-uridine
<220> FEATURE:
<221> NAME/KEY: modified_base
<222> LOCATION: (7)..(7)
<223> OTHER INFORMATION: 2'-OMe adenosine
<220> FEATURE:
<221> NAME/KEY: modified_base
<222> LOCATION: (8)..(8)
<223> OTHER INFORMATION: 2'-fluoro-uridine
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (10)..(10)
<223> OTHER INFORMATION: 2'-fluoro-uridine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-fluoro-uridine
<220> FEATURE:
<221> NAME/KEY: misc_feature
<222> LOCATION: (13)..(20)
<223> OTHER INFORMATION: Phosphorothioate Linkage
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (14)..(14)
<223> OTHER INFORMATION: 2'-fluoro-cytidine
<220> FEATURE:
<221> NAME/KEY: modified_base
<222> LOCATION: (15)..(15)
<223> OTHER INFORMATION: 2'-OMe adenosine
<220> FEATURE:
<221> NAME/KEY: modified_base
<222> LOCATION: (16)..(16)
<223> OTHER INFORMATION: 2'-fluoro-cytidine
<220> FEATURE:
<221> NAME/KEY: modified_base
<222> LOCATION: (17)..(17)
<223> OTHER INFORMATION: 2'-OMe adenosine
<220> FEATURE:
<221> NAME/KEY: modified_base
<222> LOCATION: (18)..(18)
<223> OTHER INFORMATION: 2'-fluoro-uridine
<220> FEATURE:
<221> NAME/KEY: modified_base
<222> LOCATION: (19)..(19)
<223> OTHER INFORMATION: 2'-OMe adenosine
<220> FEATURE:
<221> NAME/KEY: modified_base
<222> LOCATION: (20)..(20)
<223> OTHER INFORMATION: 2'-fluoro-uridine

<400> SEQUENCE: 44
uccacuaugu uuucacauau 20

<210> SEQ ID NO 45
<211> LENGTH: 20
<212> TYPE: RNA
<213> ORGANISM: Artificial Sequence
<220> FEATURE:
<223> OTHER INFORMATION: AS-5
<220> FEATURE:
<221> NAME/KEY: modified_base
<222> LOCATION: (1)..(1)
<223> OTHER INFORMATION: um
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-guanosine
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (4)..(4)

<223> OTHER INFORMATION: 2'-fluoro-cytidine
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: 2'-fluoro-adenosine
<220> FEATURE:
<221> NAME/KEY: modified_base
<222> LOCATION: (7)..(7)
<223> OTHER INFORMATION: 2'-OMe adenosine
<220> FEATURE:
<221> NAME/KEY: modified_base
<222> LOCATION: (8)..(8)
<223> OTHER INFORMATION: 2'-fluoro-guanosine
<220> FEATURE:
<221> NAME/KEY: modified_base
<222> LOCATION: (9)..(9)
<223> OTHER INFORMATION: 2'-OMe adenosine
<220> FEATURE:
<221> NAME/KEY: modified_base
<222> LOCATION: (10)..(10)
<223> OTHER INFORMATION: 2'-fluoro-guanosine
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(12)
<223> OTHER INFORMATION: 2'-fluoro-adenosine
<220> FEATURE:
<221> NAME/KEY: modified_base
<222> LOCATION: (13)..(13)
<223> OTHER INFORMATION: cm
<220> FEATURE:
<221> NAME/KEY: misc_feature
<222> LOCATION: (13)..(20)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-fluoro-adenosine
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (16)..(16)
<223> OTHER INFORMATION: 2'-fluoro-uridine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: 2'-fluoro-adenosine
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (20)..(20)
<223> OTHER INFORMATION: 2'-fluoro-uridine

<400> SEQUENCE: 45
ugccuaagag cacauuuagu 20

<210> SEQ ID NO 46
<211> LENGTH: 20
<212> TYPE: RNA
<213> ORGANISM: Artificial Sequence -continued
<220> FEATURE:
<223> OTHER INFORMATION: AS-6
<220> FEATURE:
<221> NAME/KEY: modified_base
<222> LOCATION: (1)..(1)
<223> OTHER INFORMATION: um
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-adenosine
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (4)..(4)
<223> OTHER INFORMATION: 2'-fluoro-cytidine
<220> FEATURE:
<221> NAME/KEY: modified_base
<222> LOCATION: (5)..(5)
<223> OTHER INFORMATION: 2'-OMe adenosine
<220> FEATURE:
<221> NAME/KEY: modified_base
<222> LOCATION: (6)..(6)
<223> OTHER INFORMATION: 2'-fluoro-guanosine
<220> FEATURE:
<221> NAME/KEY: modified_base
<222> LOCATION: (7)..(7)
<223> OTHER INFORMATION: cm
<220> FEATURE:
<221> NAME/KEY: modified_base
<222> LOCATION: (8)..(8)
<223> OTHER INFORMATION: 2'-fluoro-uridine
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(10)
<223> OTHER INFORMATION: 2'-fluoro-uridine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-fluoro-cytidine
<220> FEATURE:
<221> NAME/KEY: modified_base
<222> LOCATION: (13)..(13)
<223> OTHER INFORMATION: cm
<220> FEATURE:
<221> NAME/KEY: misc_feature
<222> LOCATION: (13)..(20)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-fluoro-adenosine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: 2'-fluoro-guanosine
<220> FEATURE:
<221> NAME/KEY: modified_base
<222> LOCATION: (17)..(17)
<223> OTHER INFORMATION: gm
<220> FEATURE:

<221> NAME/KEY: modified_base
<222> LOCATION: (18)..(18)
<223> OTHER INFORMATION: 2'-fluoro-uridine
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (20)..(20)
<223> OTHER INFORMATION: 2'-fluoro-guanosine

<400> SEQUENCE: 46
uaucagcuuu uccagggucg 20

<210> SEQ ID NO 47
<211> LENGTH: 20
<212> TYPE: RNA
<213> ORGANISM: Artificial Sequence
<220> FEATURE:
<223> OTHER INFORMATION: AS-7
<220> FEATURE:
<221> NAME/KEY: modified_base
<222> LOCATION: (1)..(1)
<223> OTHER INFORMATION: um
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-cytidine
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (4)..(4)
<223> OTHER INFORMATION: 2'-fluoro-guanosine
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (6)..(6)
<223> OTHER INFORMATION: 2'-fluoro-uridine
<220> FEATURE:
<221> NAME/KEY: modified_base
<222> LOCATION: (7)..(7)
<223> OTHER INFORMATION: cm
<220> FEATURE:
<221> NAME/KEY: modified_base
<222> LOCATION: (8)..(8)
<223> OTHER INFORMATION: 2'-fluoro-adenosine
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (10)..(10)
<223> OTHER INFORMATION: 2'-fluoro-adenosine
<220> FEATURE:
<221> NAME/KEY: modified_base
<222> LOCATION: (11)..(11)
<223> OTHER INFORMATION: 2'-OMe adenosine
<220> FEATURE:
<221> NAME/KEY: modified_base
<222> LOCATION: (12)..(12)
<223> OTHER INFORMATION: 2'-fluoro-cytidine
<220> FEATURE:
<221> NAME/KEY: modified_base
<222> LOCATION: (13)..(13)
<223> OTHER INFORMATION: 2'-OMe adenosine
<220> FEATURE:
<221> NAME/KEY: misc_feature
<222> LOCATION: (13)..(20)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-fluoro-uridine
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (16)..(16)
<223> OTHER INFORMATION: 2'-fluoro-guanosine
<220> FEATURE:
<221> NAME/KEY: modified_base
<222> LOCATION: (16)..(16)
<223> OTHER INFORMATION: 2'-fluoro-guanosine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: 2'-fluoro-guanosine
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (20)..(20)
<223> OTHER INFORMATION: 2'-fluoro-uridine

<400> SEQUENCE: 47
uccggucaca acauuguggu 20

<210> SEQ ID NO 48
<211> LENGTH: 20
<212> TYPE: RNA
<213> ORGANISM: Artificial Sequence
<220> FEATURE:
<223> OTHER INFORMATION: AS-8
<220> FEATURE:
<221> NAME/KEY: modified_base
<222> LOCATION: (1)..(1)
<223> OTHER INFORMATION: 2'-OMe adenosine
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-uridine
<220> FEATURE:
<221> NAME/KEY: modified_base
<222> LOCATION: (3)..(3)
<223> OTHER INFORMATION: 2'-OMe adenosine
<220> FEATURE:
<221> NAME/KEY: modified_base
<222> LOCATION: (4)..(4)
<223> OTHER INFORMATION: 2'-fluoro-adenosine
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: 2'-fluoro-cytidine
<220> FEATURE:
<221> NAME/KEY: modified_base
<222> LOCATION: (7)..(7)

<223> OTHER INFORMATION: um
<220> FEATURE:
<221> NAME/KEY: modified_base
<222> LOCATION: (8)..(8)
<223> OTHER INFORMATION: 2'-fluoro-cytidine
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(10)
<223> OTHER INFORMATION: 2'-fluoro-uridine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-fluoro-adenosine
<220> FEATURE:
<221> NAME/KEY: modified_base
<222> LOCATION: (13)..(13)
<223> OTHER INFORMATION: cm
<220> FEATURE:
<221> NAME/KEY: misc_feature
<222> LOCATION: (13)..(20)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-fluoro-uridine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: 2'-fluoro-adenosine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: 2'-fluoro-adenosine
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(20)
<223> OTHER INFORMATION: 2'-fluoro-adenosine

<400> SEQUENCE: 48
auaaucucuu uacugauaua 20

<210> SEQ ID NO 49
<211> LENGTH: 15
<212> TYPE: RNA
<213> ORGANISM: Artificial Sequence
<220> FEATURE:
<223> OTHER INFORMATION: SS-1
<220> FEATURE:
<221> NAME/KEY: modified_base
<222> LOCATION: (1)..(1)
<223> OTHER INFORMATION: 2'-fluoro-cytidine
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-OMe adenosine
<220> FEATURE:
<221> NAME/KEY: modified_base
<222> LOCATION: (3)..(3)
<223> OTHER INFORMATION: 2'-fluoro-guanosine
<220> FEATURE:
<221> NAME/KEY: modified_base
<222> LOCATION: (4)..(4)
<223> OTHER INFORMATION: um
<220> FEATURE:
<221> NAME/KEY: modified_base
<222> LOCATION: (5)..(5)
<223> OTHER INFORMATION: 2'-fluoro-adenosine
<220> FEATURE:
<221> NAME/KEY: modified_base
<222> LOCATION: (6)..(6)
<223> OTHER INFORMATION: 2'-OMe adenosine
<220> FEATURE:
<221> NAME/KEY: modified_base
<222> LOCATION: (7)..(7)
<223> OTHER INFORMATION: 2'-fluoro-adenosine
<220> FEATURE:
<221> NAME/KEY: modified_base
<222> LOCATION: (8)..(8)
<223> OTHER INFORMATION: gm
<220> FEATURE:
<221> NAME/KEY: modified_base
<222> LOCATION: (9)..(9)
<223> OTHER INFORMATION: 2'-fluoro-adenosine
<220> FEATURE:
<221> NAME/KEY: modified_base
<222> LOCATION: (10)..(10)
<223> OTHER INFORMATION: gm
<220> FEATURE:
<221> NAME/KEY: modified_base
<222> LOCATION: (11)..(11)
<223> OTHER INFORMATION: 2'-fluoro-adenosine
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: 2'-fluoro-uridine
<220> FEATURE:
<221> NAME/KEY: misc_feature
<222> LOCATION: (13)..(15)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-OMe adenosine
<220> FEATURE:
<221> NAME/KEY: modified_base
<222> LOCATION: (15)..(15)
<223> OTHER INFORMATION: 2'-fluoro-adenosine

<400> SEQUENCE: 49
caguaaagag auuaa 15

<210> SEQ ID NO 50
<211> LENGTH: 15
<212> TYPE: RNA
<213> ORGANISM: Artificial Sequence
<220> FEATURE:
<223> OTHER INFORMATION: SS-2
<220> FEATURE:
<221> NAME/KEY: modified_base
<222> LOCATION: (1)..(1)
<223> OTHER INFORMATION: 2'-fluoro-cytidine
<220> FEATURE:
<221> NAME/KEY: misc_feature
<222> LOCATION: (1)..(3)
<223> OTHER INFORMATION: Phosphorothioate Linkage
<220> FEATURE:

<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: 2'-fluoro-cytidine
<220> FEATURE:
<221> NAME/KEY: modified_base
<222> LOCATION: (4)..(4)
<223> OTHER INFORMATION: 2'-OMe adenosine
<220> FEATURE:
<221> NAME/KEY: modified_base
<222> LOCATION: (5)..(5)
<223> OTHER INFORMATION: 2'-fluoro-guanosine
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (7)..(7)
<223> OTHER INFORMATION: 2'-fluoro-adenosine
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(9)
<223> OTHER INFORMATION: 2'-fluoro-uridine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (11)..(11)
<223> OTHER INFORMATION: 2'-fluoro-adenosine
<220> FEATURE:
<221> NAME/KEY: modified_base
<222> LOCATION: (12)..(12)
<223> OTHER INFORMATION: 2'-OMe adenosine
<220> FEATURE:
<221> NAME/KEY: modified_base
<222> LOCATION: (13)..(13)
<223> OTHER INFORMATION: 2'-fluoro-adenosine
<220> FEATURE:
<221> NAME/KEY: misc_feature
<222> LOCATION: (13)..(15)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-OMe adenosine
<220> FEATURE:
<221> NAME/KEY: modified_base
<222> LOCATION: (15)..(15)
<223> OTHER INFORMATION: 2'-fluoro-adenosine

<400> SEQUENCE: 50
cucaggauuu aaaaa 15

<210> SEQ ID NO 51
<211> LENGTH: 15
<212> TYPE: RNA
<213> ORGANISM: Artificial Sequence
<220> FEATURE:
<223> OTHER INFORMATION: SS-3
<220> FEATURE:
<221> NAME/KEY: modified_base
<222> LOCATION: (1)..(1)
<223> OTHER INFORMATION: 2'-fluoro-uridine
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-fluoro-adenosine
<220> FEATURE:
<221> NAME/KEY: modified_base
<222> LOCATION: (4)..(4)
<223> OTHER INFORMATION: 2'-OMe adenosine
<220> FEATURE:
<221> NAME/KEY: modified_base
<222> LOCATION: (5)..(5)
<223> OTHER INFORMATION: 2'-fluoro-adenosine
<220> FEATURE:
<221> NAME/KEY: modified_base
<222> LOCATION: (6)..(6)
<223> OTHER INFORMATION: 2'-OMe adenosine
<220> FEATURE:
<221> NAME/KEY: modified_base
<222> LOCATION: (7)..(7)
<223> OTHER INFORMATION: 2'-fluoro-cytidine
<220> FEATURE:
<221> NAME/KEY: modified_base
<222> LOCATION: (8)..(8)
<223> OTHER INFORMATION: 2'-OMe adenosine
<220> FEATURE:
<221> NAME/KEY: modified_base
<222> LOCATION: (9)..(9)
<223> OTHER INFORMATION: 2'-fluoro-uridine
<220> FEATURE:
<221> NAME/KEY: modified_base
<222> LOCATION: (10)..(10)
<223> OTHER INFORMATION: 2'-OMe adenosine
<220> FEATURE:
<221> NAME/KEY: modified_base
<222> LOCATION: (11)..(11)
<223> OTHER INFORMATION: 2'-fluoro-guanosine
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: 2'-fluoro-guanosine
<220> FEATURE:
<221> NAME/KEY: misc_feature
<222> LOCATION: (13)..(15)
<223> OTHER INFORMATION: Phosphorothioate Linkage
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-fluoro-adenosine

<400> SEQUENCE: 51
ugaaaacaua gugga 15

<210> SEQ ID NO 52
<211> LENGTH: 15
<212> TYPE: RNA
<213> ORGANISM: Artificial Sequence
<220> FEATURE:
<223> OTHER INFORMATION: SS-4
<220> FEATURE:
<221> NAME/KEY: modified_base
<222> LOCATION: (1)..(1)
<223> OTHER INFORMATION: 2'-fluoro-adenosine
<220> FEATURE:
<221> NAME/KEY: misc_feature
<222> LOCATION: (1)..(3)

<223> OTHER INFORMATION: Phosphorothioate Linkage
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: 2'-fluoro-guanosine
<220> FEATURE:
<221> NAME/KEY: modified_base
<222> LOCATION: (4)..(4)
<223> OTHER INFORMATION: um
<220> FEATURE:
<221> NAME/KEY: modified_base
<222> LOCATION: (5)..(5)
<223> OTHER INFORMATION: 2'-fluoro-guanosine
<220> FEATURE:
<221> NAME/KEY: modified_base
<222> LOCATION: (6)..(6)
<223> OTHER INFORMATION: cm
<220> FEATURE:
<221> NAME/KEY: modified_base
<222> LOCATION: (7)..(7)
<223> OTHER INFORMATION: 2'-fluoro-uridine
<220> FEATURE:
<221> NAME/KEY: modified_base
<222> LOCATION: (8)..(8)
<223> OTHER INFORMATION: cm
<220> FEATURE:
<221> NAME/KEY: modified_base
<222> LOCATION: (9)..(9)
<223> OTHER INFORMATION: 2'-fluoro-uridine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (11)..(11)
<223> OTHER INFORMATION: 2'-fluoro-adenosine
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: 2'-fluoro-guanosine
<220> FEATURE:
<221> NAME/KEY: misc_feature
<222> LOCATION: (13)..(15)
<223> OTHER INFORMATION: Phosphorothioate Linkage
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(15)
<223> OTHER INFORMATION: 2'-fluoro-adenosine

<400> SEQUENCE: 52
augugcucuu aggca 15

<210> SEQ ID NO 53
<211> LENGTH: 15
<212> TYPE: RNA
<213> ORGANISM: Artificial Sequence
<220> FEATURE:
<223> OTHER INFORMATION: SS-5
<220> FEATURE:
<221> NAME/KEY: modified_base
<222> LOCATION: (1)..(1)
<223> OTHER INFORMATION: 2'-fluoro-cytidine
<220> FEATURE:
<221> NAME/KEY: misc_feature -continued
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: 2'-fluoro-guanosine
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (5)..(5)
<223> OTHER INFORMATION: 2'-fluoro-adenosine
<220> FEATURE:
<221> NAME/KEY: modified_base
<222> LOCATION: (6)..(6)
<223> OTHER INFORMATION: 2'-OMe adenosine
<220> FEATURE:
<221> NAME/KEY: modified_base
<222> LOCATION: (7)..(7)
<223> OTHER INFORMATION: 2'-fluoro-adenosine
<220> FEATURE:
<221> NAME/KEY: modified_base
<222> LOCATION: (8)..(8)
<223> OTHER INFORMATION: 2'-OMe adenosine
<220> FEATURE:
<221> NAME/KEY: modified_base
<222> LOCATION: (9)..(9)
<223> OTHER INFORMATION: 2'-fluoro-guanosine
<220> FEATURE:
<221> NAME/KEY: modified_base
<222> LOCATION: (10)..(10)
<223> OTHER INFORMATION: cm
<220> FEATURE:
<221> NAME/KEY: modified_base
<222> LOCATION: (11)..(11)
<223> OTHER INFORMATION: 2'-fluoro-uridine
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: 2'-fluoro-adenosine
<220> FEATURE:
<221> NAME/KEY: misc_feature
<222> LOCATION: (13)..(15)
<223> OTHER INFORMATION: Phosphorothioate Linkage
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (15)..(15)
<223> OTHER INFORMATION: 2'-fluoro-adenosine

<400> SEQUENCE: 53
cuggaaaagc ugaua 15

<210> SEQ ID NO 54
<211> LENGTH: 15
<212> TYPE: RNA
<213> ORGANISM: Artificial Sequence
<220> FEATURE:
<223> OTHER INFORMATION: SS-6
<220> FEATURE:
<221> NAME/KEY: modified_base
<222> LOCATION: (1)..(1)
<223> OTHER INFORMATION: 2'-fluoro-adenosine
<220> FEATURE:

<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-OMe adenosine
<220> FEATURE:
<221> NAME/KEY: modified_base
<222> LOCATION: (3)..(3)
<223> OTHER INFORMATION: 2'-fluoro-uridine
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (5)..(5)
<223> OTHER INFORMATION: 2'-fluoro-uridine
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (7)..(7)
<223> OTHER INFORMATION: 2'-fluoro-guanosine
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(9)
<223> OTHER INFORMATION: 2'-fluoro-guanosine
<220> FEATURE:
<221> NAME/KEY: modified_base
<222> LOCATION: (10)..(10)
<223> OTHER INFORMATION: 2'-OMe adenosine
<220> FEATURE:
<221> NAME/KEY: modified_base
<222> LOCATION: (11)..(11)
<223> OTHER INFORMATION: 2'-fluoro-cytidine
<220> FEATURE:
<221> NAME/KEY: modified_base
<222> LOCATION: (12)..(12)
<223> OTHER INFORMATION: cm
<220> FEATURE:
<221> NAME/KEY: modified_base
<222> LOCATION: (13)..(13)
<223> OTHER INFORMATION: 2'-fluoro-guanosine
<220> FEATURE:
<221> NAME/KEY: misc_feature
<222> LOCATION: (13)..(15)
<223> OTHER INFORMATION: Phosphorothioate Linkage
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-fluoro-adenosine

<400> SEQUENCE: 54
aauguuguga ccgga 15

<210> SEQ ID NO 55
<211> LENGTH: 15
<212> TYPE: RNA
<213> ORGANISM: Artificial Sequence
<220> FEATURE:
<223> OTHER INFORMATION: SS-7
<220> FEATURE:
<221> NAME/KEY: modified_base
<222> LOCATION: (1)..(1)
<223> OTHER INFORMATION: 2'-fluoro-cytidine
<220> FEATURE:
<221> NAME/KEY: modified_base
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-OMe adenosine
<220> FEATURE:
<221> NAME/KEY: modified_base
<222> LOCATION: (3)..(3)
<223> OTHER INFORMATION: 2'-fluoro-guanosine
<220> FEATURE:
<221> NAME/KEY: modified_base
<222> LOCATION: (4)..(4)
<223> OTHER INFORMATION: um
<220> FEATURE:
<221> NAME/KEY: modified_base
<222> LOCATION: (5)..(5)
<223> OTHER INFORMATION: 2'-fluoro-adenosine
<220> FEATURE:
<221> NAME/KEY: modified_base
<222> LOCATION: (6)..(6)
<223> OTHER INFORMATION: 2'-OMe adenosine
<220> FEATURE:
<221> NAME/KEY: modified_base
<222> LOCATION: (7)..(7)
<223> OTHER INFORMATION: 2'-fluoro-adenosine
<220> FEATURE:
<221> NAME/KEY: modified_base
<222> LOCATION: (8)..(8)
<223> OTHER INFORMATION: gm
<220> FEATURE:
<221> NAME/KEY: modified_base
<222> LOCATION: (9)..(9)
<223> OTHER INFORMATION: 2'-fluoro-adenosine
<220> FEATURE:
<221> NAME/KEY: modified_base
<222> LOCATION: (10)..(10)
<223> OTHER INFORMATION: gm
<220> FEATURE:
<221> NAME/KEY: modified_base
<222> LOCATION: (11)..(11)
<223> OTHER INFORMATION: 2'-fluoro-adenosine
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: 2'-fluoro-uridine
<220> FEATURE:
<221> NAME/KEY: modified_base
<222> LOCATION: (13)..(15)
<223> OTHER INFORMATION: Phosphorothioate Linkage
<220> FEATURE:
<221> NAME/KEY: modified_base
<222> LOCATION: (14)..(14)
<223> OTHER INFORMATION: 2'-OMe adenosine
<220> FEATURE:
<221> NAME/KEY: modified_base
<222> LOCATION: (15)..(15)
<223> OTHER INFORMATION: 2'-fluoro-uridine

<400> SEQUENCE: 55
caguaaagag auuau 15

<210> SEQ ID NO 56
<211> LENGTH: 20
<212> TYPE: RNA
<213> ORGANISM: Artificial Sequence
<220> FEATURE:
<223> OTHER INFORMATION: FAM-Ctrl-PO
<220> FEATURE:
<221> NAME/KEY: modified_base
<222> LOCATION: (1)..(20)
<223> OTHER INFORMATION: um

<400> SEQUENCE: 56
uuuuuuuuuu uuuuuuuuuu 20

<210> SEQ ID NO 57
<211> LENGTH: 20
<212> TYPE: RNA
<213> ORGANISM: Artificial Sequence
<220> FEATURE:
<223> OTHER INFORMATION: FAM-PO-ex1
<220> FEATURE:
<221> NAME/KEY: modified_base
<222> LOCATION: (1)..(19)
<223> OTHER INFORMATION: um
<220> FEATURE:
<221> NAME/KEY: modified_base
<222> LOCATION: (20)..(20)
<223> OTHER INFORMATION: 2'-OMe-ex-uridine

<400> SEQUENCE: 57
uuuuuuuuuu uuuuuuuuuu 20

<210> SEQ ID NO 58
<211> LENGTH: 20
<212> TYPE: RNA
<213> ORGANISM: Artificial Sequence
<220> FEATURE:
<223> OTHER INFORMATION: FAM-PO-ex2
<220> FEATURE:
<221> NAME/KEY: modified_base
<222> LOCATION: (1)..(18)
<223> OTHER INFORMATION: um
<220> FEATURE:
<221> NAME/KEY: modified_base
<222> LOCATION: (19)..(20)
<223> OTHER INFORMATION: 2'-OMe-ex-uridine

<400> SEQUENCE: 58
uuuuuuuuuu uuuuuuuuuu 20

<210> SEQ ID NO 59
<211> LENGTH: 20
<212> TYPE: RNA
<213> ORGANISM: Artificial Sequence
<220> FEATURE:
<223> OTHER INFORMATION: FAM-PO-ex3
<220> FEATURE:
<221> NAME/KEY: modified_base
<222> LOCATION: (1)..(17)
<223> OTHER INFORMATION: um
<220> FEATURE:
<221> NAME/KEY: modified_base
<222> LOCATION: (18)..(20)
<223> OTHER INFORMATION: 2'-OMe-ex-uridine

<400> SEQUENCE: 59
uuuuuuuuuu uuuuuuuuuu 20

<210> SEQ ID NO 60

<211> LENGTH: 20
<212> TYPE: RNA
<213> ORGANISM: Artificial Sequence
<220> FEATURE:
<223> OTHER INFORMATION: FAM-PO-ex4
<220> FEATURE:
<221> NAME/KEY: modified_base
<222> LOCATION: (1)..(16)
<223> OTHER INFORMATION: um
<220> FEATURE:
<221> NAME/KEY: modified_base
<222> LOCATION: (17)..(20)
<223> OTHER INFORMATION: 2'-OMe-ex-uridine

<400> SEQUENCE: 60
uuuuuuuuuu uuuuuuuuuu 20

<210> SEQ ID NO 61
<211> LENGTH: 20
<212> TYPE: RNA
<213> ORGANISM: Artificial Sequence
<220> FEATURE:
<223> OTHER INFORMATION: FAM-PO-ex5
<220> FEATURE:
<221> NAME/KEY: modified_base
<222> LOCATION: (1)..(15)
<223> OTHER INFORMATION: um
<220> FEATURE:
<221> NAME/KEY: modified_base
<222> LOCATION: (16)..(20)
<223> OTHER INFORMATION: 2'-OMe-ex-uridine

<400> SEQUENCE: 61
uuuuuuuuuu uuuuuuuuuu 20

<210> SEQ ID NO 62
<211> LENGTH: 20
<212> TYPE: RNA
<213> ORGANISM: Artificial Sequence
<220> FEATURE:
<223> OTHER INFORMATION: FAM-Ctrl-PS
<220> FEATURE:
<221> NAME/KEY: modified_base
<222> LOCATION: (1)..(20)
<223> OTHER INFORMATION: um
<220> FEATURE:
<221> NAME/KEY: misc_feature
<222> LOCATION: (15)..(20)
<223> OTHER INFORMATION: Phosphorothioate Linkage

<400> SEQUENCE: 62
uuuuuuuuuu uuuuuuuuuu 20

<210> SEQ ID NO 63
<211> LENGTH: 20
<212> TYPE: RNA
<213> ORGANISM: Artificial Sequence
<220> FEATURE:
<223> OTHER INFORMATION: FAM-PS-ex1
<220> FEATURE:
<221> NAME/KEY: modified_base
<222> LOCATION: (1)..(19)
<223> OTHER INFORMATION: um
<220> FEATURE:
<221> NAME/KEY: misc_feature
<222> LOCATION: (15)..(20)
<223> OTHER INFORMATION: Phosphorothioate Linkage
<220> FEATURE:
<221> NAME/KEY: modified_base
<222> LOCATION: (20)..(20)
<223> OTHER INFORMATION: 2'-OMe-ex-uridine

<400> SEQUENCE: 63
uuuuuuuuuu uuuuuuuuuu 20

<210> SEQ ID NO 64
<211> LENGTH: 20
<212> TYPE: RNA
<213> ORGANISM: Artificial Sequence
<220> FEATURE:
<223> OTHER INFORMATION: FAM-PS-ex2
<220> FEATURE:
<221> NAME/KEY: modified_base
<222> LOCATION: (1)..(18)
<223> OTHER INFORMATION: um
<220> FEATURE:
<221> NAME/KEY: misc_feature
<222> LOCATION: (15)..(20)
<223> OTHER INFORMATION: Phosphorothioate Linkage
<220> FEATURE:
<221> NAME/KEY: modified_base
<222> LOCATION: (19)..(20)
<223> OTHER INFORMATION: 2'-OMe-ex-uridine

<400> SEQUENCE: 64
uuuuuuuuuu uuuuuuuuuu 20

<210> SEQ ID NO 65
<211> LENGTH: 20
<212> TYPE: RNA
<213> ORGANISM: Artificial Sequence
<220> FEATURE:
<223> OTHER INFORMATION: FAM-PS-ex3
<220> FEATURE:
<221> NAME/KEY: modified_base
<222> LOCATION: (1)..(17)
<223> OTHER INFORMATION: um
<220> FEATURE:
<221> NAME/KEY: misc_feature
<222> LOCATION: (15)..(20)
<223> OTHER INFORMATION: Phosphorothioate Linkage
<220> FEATURE:
<221> NAME/KEY: modified_base
<222> LOCATION: (18)..(20)
<223> OTHER INFORMATION: 2'-OMe-ex-uridine

<400> SEQUENCE: 65
uuuuuuuuuu uuuuuuuuuu 20

<210> SEQ ID NO 66
<211> LENGTH: 20
<212> TYPE: RNA
<213> ORGANISM: Artificial Sequence
<220> FEATURE:
<223> OTHER INFORMATION: FAM-PS-ex4
<220> FEATURE:
<221> NAME/KEY: modified_base
<222> LOCATION: (1)..(16)
<223> OTHER INFORMATION: um
<220> FEATURE:
<221> NAME/KEY: misc_feature
<222> LOCATION: (15)..(20)
<223> OTHER INFORMATION: Phosphorothioate Linkage
<220> FEATURE:
<221> NAME/KEY: modified_base
<222> LOCATION: (17)..(20)
<223> OTHER INFORMATION: 2'-OMe-ex-uridine

<400> SEQUENCE: 66
uuuuuuuuuu uuuuuuuuuu 20

<210> SEQ ID NO 67
<211> LENGTH: 20
<212> TYPE: RNA
<213> ORGANISM: Artificial Sequence
<220> FEATURE:
<223> OTHER INFORMATION: FAM-PS-ex5
<220> FEATURE:
<221> NAME/KEY: modified_base
<222> LOCATION: (1)..(15)
<223> OTHER INFORMATION: um
<220> FEATURE:
<221> NAME/KEY: misc_feature
<222> LOCATION: (15)..(20)
<223> OTHER INFORMATION: Phosphorothioate Linkage
<220> FEATURE:
<221> NAME/KEY: modified_base
<222> LOCATION: (16)..(20)
<223> OTHER INFORMATION: 2'-OMe-ex-uridine

<400> SEQUENCE: 67
uuuuuuuuuu uuuuuuuuuu 20

<210> SEQ ID NO 68
<211> LENGTH: 20
<212> TYPE: RNA
<213> ORGANISM: Artificial Sequence
<220> FEATURE:
<223> OTHER INFORMATION: ON1
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (2)..(2)
<223> OTHER INFORMATION: 2'-fluoro-uridine
<220> FEATURE:
<221> NAME/KEY: modified_base
<222> LOCATION: (3)..(3)
<223> OTHER INFORMATION: 2'-OMe adenosine
<220> FEATURE:
<221> NAME/KEY: modified_base
<222> LOCATION: (4)..(4)
<223> OTHER INFORMATION: 2'-fluoro-adenosine
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: 2'-fluoro-cytidine
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (8)..(8)
<223> OTHER INFORMATION: 2'-fluoro-cytidine
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(10)
<223> OTHER INFORMATION: 2'-fluoro-uridine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-fluoro-adenosine
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (14)..(14)
<223> OTHER INFORMATION: 2'-fluoro-uridine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: 2'-fluoro-adenosine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: 2'-fluoro-uridine
<220> FEATURE:
<221> NAME/KEY: modified_base
<222> LOCATION: (19)..(20)
<223> OTHER INFORMATION: um

<400> SEQUENCE: 68
uuaaucucuu uacugauuuu 20

<210> SEQ ID NO 69
<211> LENGTH: 20
<212> TYPE: RNA
<213> ORGANISM: Artificial Sequence
<220> FEATURE:
<223> OTHER INFORMATION: ON2
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (2)..(2)
<223> OTHER INFORMATION: 2'-OMe-ex-uridine
<220> FEATURE:
<221> NAME/KEY: modified_base
<222> LOCATION: (3)..(3)
<223> OTHER INFORMATION: 2'-OMe adenosine
<220> FEATURE:
<221> NAME/KEY: modified_base
<222> LOCATION: (4)..(4)
<223> OTHER INFORMATION: 2'-fluoro-adenosine
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: 2'-fluoro-cytidine
<220> FEATURE:
<221> NAME/KEY: modified_base
<222> LOCATION: (7)..(7)

<223> OTHER INFORMATION: um
<220> FEATURE:
<221> NAME/KEY: modified_base
<222> LOCATION: (8)..(8)
<223> OTHER INFORMATION: 2'-fluoro-cytidine
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(10)
<223> OTHER INFORMATION: 2'-fluoro-uridine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-fluoro-adenosine
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (14)..(14)
<223> OTHER INFORMATION: 2'-fluoro-uridine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: 2'-fluoro-adenosine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: 2'-fluoro-uridine
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(20)
<223> OTHER INFORMATION: 2'-OMe-ex-uridine

<400> SEQUENCE: 69
uuaaucucuu uacugauuuu 20

<210> SEQ ID NO 70
<211> LENGTH: 20
<212> TYPE: RNA
<213> ORGANISM: Artificial Sequence
<220> FEATURE:
<223> OTHER INFORMATION: ON3
<220> FEATURE:
<221> NAME/KEY: modified_base
<222> LOCATION: (1)..(1)
<223> OTHER INFORMATION: um
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-uridine
<220> FEATURE:
<221> NAME/KEY: modified_base
<222> LOCATION: (3)..(3)
<223> OTHER INFORMATION: 2'-OMe adenosine
<220> FEATURE:
<221> NAME/KEY: modified_base
<222> LOCATION: (4)..(4)
<223> OTHER INFORMATION: 2'-fluoro-adenosine
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: 2'-fluoro-cytidine
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (8)..(8)
<223> OTHER INFORMATION: 2'-fluoro-cytidine
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(10)
<223> OTHER INFORMATION: 2'-fluoro-uridine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-fluoro-adenosine
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (14)..(14)
<223> OTHER INFORMATION: 2'-fluoro-uridine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: 2'-fluoro-adenosine
<220> FEATURE:
<221> NAME/KEY: misc_feature
<222> LOCATION: (16)..(20)
<223> OTHER INFORMATION: Phosphorothioate Linkage
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: 2'-fluoro-uridine
<220> FEATURE:
<221> NAME/KEY: modified_base
<222> LOCATION: (19)..(20)
<223> OTHER INFORMATION: um

<400> SEQUENCE: 70
uuaaucucuu uacugauuuu 20

<210> SEQ ID NO 71
<211> LENGTH: 21
<212> TYPE: RNA
<213> ORGANISM: Artificial Sequence
<220> FEATURE:
<223> OTHER INFORMATION: P5_Ctrl
<220> FEATURE:
<221> NAME/KEY: modified_base
<222> LOCATION: (1)..(1)
<223> OTHER INFORMATION: 5 vinyl phosphonate-2'-OMe uridine
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-uridine
<220> FEATURE:
<221> NAME/KEY: modified_base
<222> LOCATION: (3)..(4)
<223> OTHER INFORMATION: gm
<220> FEATURE:
<221> NAME/KEY: modified_base
<222> LOCATION: (5)..(5)
<223> OTHER INFORMATION: 2'-OMe adenosine
<220> FEATURE:
<221> NAME/KEY: modified_base
<222> LOCATION: (6)..(6)
<223> OTHER INFORMATION: 2'-fluoro-uridine
<220> FEATURE:
<221> NAME/KEY: modified_base
<222> LOCATION: (7)..(7)
<223> OTHER INFORMATION: 2'-OMe adenosine
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(10)
<223> OTHER INFORMATION: gm
<220> FEATURE:
<221> NAME/KEY: modified_base
<222> LOCATION: (11)..(11)
<223> OTHER INFORMATION: 2'-OMe adenosine
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: 2'-fluoro-uridine
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (16)..(16)
<223> OTHER INFORMATION: 2'-fluoro-guanosine
<220> FEATURE:
<221> NAME/KEY: modified_base
<222> LOCATION: (17)..(21)
<223> OTHER INFORMATION: um
<220> FEATURE:
<221> NAME/KEY: misc_feature
<222> LOCATION: (19)..(21)
<223> OTHER INFORMATION: Phosphorothioate Linkage

<400> SEQUENCE: 71
uuggauaugg auguuguuuu u 21

<210> SEQ ID NO 72
<211> LENGTH: 16
<212> TYPE: RNA
<213> ORGANISM: Artificial Sequence
<220> FEATURE:
<223> OTHER INFORMATION: P5_Ctrl
<220> FEATURE:
<221> NAME/KEY: modified_base
<222> LOCATION: (1)..(1)
<223> OTHER INFORMATION: cm
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(3)
<223> OTHER INFORMATION: 2'-OMe adenosine
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (5)..(5)
<223> OTHER INFORMATION: 2'-OMe adenosine
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (7)..(7)
<223> OTHER INFORMATION: cm
<220> FEATURE:
<221> NAME/KEY: modified_base
<222> LOCATION: (8)..(8)
<223> OTHER INFORMATION: 2'-fluoro-cytidine
<220> FEATURE:
<221> NAME/KEY: modified_base
<222> LOCATION: (9)..(9)
<223> OTHER INFORMATION: 2'-OMe adenosine
<220> FEATURE:
<221> NAME/KEY: modified_base
<222> LOCATION: (10)..(10)
<223> OTHER INFORMATION: 2'-fluoro-uridine
<220> FEATURE:
<221> NAME/KEY: modified_base
<222> LOCATION: (11)..(11)
<223> OTHER INFORMATION: 2'-fluoro-adenosine
<220> FEATURE:
<221> NAME/KEY: modified_base
<222> LOCATION: (12)..(12)
<223> OTHER INFORMATION: 2'-fluoro-uridine
<220> FEATURE:
<221> NAME/KEY: modified_base
<222> LOCATION: (13)..(14)
<223> OTHER INFORMATION: cm
<220> FEATURE:
<221> NAME/KEY: misc_feature
<222> LOCATION: (14)..(16)
<223> OTHER INFORMATION: Phosphorothioate Linkage
<220> FEATURE:
<221> NAME/KEY: modified_base
<222> LOCATION: (15)..(16)
<223> OTHER INFORMATION: 2'-OMe adenosine

<400> SEQUENCE: 72
caacauccau auccaa 16

<210> SEQ ID NO 73

-continued

<211> LENGTH: 21
<212> TYPE: RNA
<213> ORGANISM: Artificial Sequence
<220> FEATURE:
<223> OTHER INFORMATION: P2_Ctrl
<220> FEATURE:
<221> NAME/KEY: modified_base
<222> LOCATION: (1)..(1)
<223> OTHER INFORMATION: 5 vinyl phosphonate-2'-OMe uridine
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-uridine
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(4)
<223> OTHER INFORMATION: 2'-fluoro-guanosine
<220> FEATURE:
<221> NAME/KEY: modified_base
<222> LOCATION: (5)..(5)
<223> OTHER INFORMATION: 2'-OMe adenosine
<220> FEATURE:
<221> NAME/KEY: modified_base
<222> LOCATION: (6)..(6)
<223> OTHER INFORMATION: 2'-fluoro-uridine
<220> FEATURE:
<221> NAME/KEY: modified_base
<222> LOCATION: (7)..(7)
<223> OTHER INFORMATION: 2'-OMe adenosine
<220> FEATURE:
<221> NAME/KEY: modified_base
<222> LOCATION: (8)..(8)
<223> OTHER INFORMATION: 2'-fluoro-uridine
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (10)..(10)
<223> OTHER INFORMATION: 2'-fluoro-guanosine
<220> FEATURE:
<221> NAME/KEY: modified_base
<222> LOCATION: (11)..(11)
<223> OTHER INFORMATION: 2'-OMe adenosine
<220> FEATURE:
<221> NAME/KEY: modified_base
<222> LOCATION: (12)..(12)
<223> OTHER INFORMATION: 2'-fluoro-uridine
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: 2'-fluoro-uridine
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (16)..(16)
<223> OTHER INFORMATION: 2'-fluoro-guanosine
<220> FEATURE:
<221> NAME/KEY: modified_base
<222> LOCATION: (17)..(21)
<223> OTHER INFORMATION: um
<220> FEATURE:
<221> NAME/KEY: misc_feature -continued
<222> LOCATION: (19)..(21)
<223> OTHER INFORMATION: Phosphorothioate Linkage

<400> SEQUENCE: 73
uuggauaugg auguuguuuu u 21

<210> SEQ ID NO 74
<211> LENGTH: 16
<212> TYPE: RNA
<213> ORGANISM: Artificial Sequence
<220> FEATURE:
<223> OTHER INFORMATION: P2_Ctrl
<220> FEATURE:
<221> NAME/KEY: modified_base
<222> LOCATION: (1)..(1)
<223> OTHER INFORMATION: cm
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-adenosine
<220> FEATURE:
<221> NAME/KEY: modified_base
<222> LOCATION: (3)..(3)
<223> OTHER INFORMATION: 2'-OMe adenosine
<220> FEATURE:
<221> NAME/KEY: modified_base
<222> LOCATION: (4)..(4)
<223> OTHER INFORMATION: 2'-fluoro-cytidine
<220> FEATURE:
<221> NAME/KEY: modified_base
<222> LOCATION: (5)..(5)
<223> OTHER INFORMATION: 2'-OMe adenosine
<220> FEATURE:
<221> NAME/KEY: modified_base
<222> LOCATION: (6)..(6)
<223> OTHER INFORMATION: 2'-fluoro-uridine
<220> FEATURE:
<221> NAME/KEY: modified_base
<222> LOCATION: (7)..(7)
<223> OTHER INFORMATION: cm
<220> FEATURE:
<221> NAME/KEY: modified_base
<222> LOCATION: (8)..(8)
<223> OTHER INFORMATION: 2'-fluoro-cytidine
<220> FEATURE:
<221> NAME/KEY: modified_base
<222> LOCATION: (9)..(9)
<223> OTHER INFORMATION: 2'-OMe adenosine
<220> FEATURE:
<221> NAME/KEY: modified_base
<222> LOCATION: (10)..(10)
<223> OTHER INFORMATION: 2'-fluoro-uridine
<220> FEATURE:
<221> NAME/KEY: modified_base
<222> LOCATION: (11)..(11)
<223> OTHER INFORMATION: 2'-OMe adenosine
<220> FEATURE:
<221> NAME/KEY: modified_base
<222> LOCATION: (12)..(12)
<223> OTHER INFORMATION: 2'-fluoro-uridine
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (14)..(14)
<223> OTHER INFORMATION: 2'-fluoro-cytidine
<220> FEATURE:
<221> NAME/KEY: misc_feature
<222> LOCATION: (14)..(16)
<223> OTHER INFORMATION: Phosphorothioate Linkage
<220> FEATURE:

<221> NAME/KEY: modified_base
<222> LOCATION: (15)..(16)
<223> OTHER INFORMATION: 2'-OMe adenosine

<400> SEQUENCE: 74
caacauccau auccaa 16

<210> SEQ ID NO 75
<211> LENGTH: 21
<212> TYPE: RNA
<213> ORGANISM: Artificial Sequence
<220> FEATURE:
<223> OTHER INFORMATION: P5_Ctrl
<220> FEATURE:
<221> NAME/KEY: modified_base
<222> LOCATION: (1)..(1)
<223> OTHER INFORMATION: 5 vinyl phosphonate-2'-OMe uridine
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-uridine
<220> FEATURE:
<221> NAME/KEY: modified_base
<222> LOCATION: (3)..(4)
<223> OTHER INFORMATION: gm
<220> FEATURE:
<221> NAME/KEY: modified_base
<222> LOCATION: (5)..(5)
<223> OTHER INFORMATION: 2'-OMe adenosine
<220> FEATURE:
<221> NAME/KEY: modified_base
<222> LOCATION: (6)..(6)
<223> OTHER INFORMATION: 2'-fluoro-uridine
<220> FEATURE:
<221> NAME/KEY: modified_base
<222> LOCATION: (7)..(7)
<223> OTHER INFORMATION: 2'-OMe adenosine
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(10)
<223> OTHER INFORMATION: gm
<220> FEATURE:
<221> NAME/KEY: modified_base
<222> LOCATION: (11)..(11)
<223> OTHER INFORMATION: 2'-OMe adenosine
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: 2'-fluoro-uridine
<220> FEATURE:
<221> NAME/KEY: misc_feature
<222> LOCATION: (14)..(21)
<223> OTHER INFORMATION: Phosphorothioate Linkage
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (16)..(16)
<223> OTHER INFORMATION: 2'-fluoro-guanosine
<220> FEATURE:
<221> NAME/KEY: modified_base
<222> LOCATION: (17)..(21)
<223> OTHER INFORMATION: um

<400> SEQUENCE: 75
uuggauaugg auguuguuuu u 21

<210> SEQ ID NO 76
<211> LENGTH: 21
<212> TYPE: RNA
<213> ORGANISM: Artificial Sequence
<220> FEATURE:
<223> OTHER INFORMATION: P2_Ctrl
<220> FEATURE:
<221> NAME/KEY: modified_base
<222> LOCATION: (1)..(1)
<223> OTHER INFORMATION: 5 vinyl phosphonate-2'-OMe uridine
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-uridine
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(4)
<223> OTHER INFORMATION: 2'-fluoro-guanosine
<220> FEATURE:
<221> NAME/KEY: modified_base
<222> LOCATION: (5)..(5)
<223> OTHER INFORMATION: 2'-OMe adenosine
<220> FEATURE:
<221> NAME/KEY: modified_base
<222> LOCATION: (6)..(6)
<223> OTHER INFORMATION: 2'-fluoro-uridine
<220> FEATURE:
<221> NAME/KEY: modified_base
<222> LOCATION: (7)..(7)
<223> OTHER INFORMATION: 2'-OMe adenosine
<220> FEATURE:
<221> NAME/KEY: modified_base
<222> LOCATION: (8)..(8)
<223> OTHER INFORMATION: 2'-fluoro-uridine
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (10)..(10)
<223> OTHER INFORMATION: 2'-fluoro-guanosine
<220> FEATURE:
<221> NAME/KEY: modified_base
<222> LOCATION: (11)..(11)
<223> OTHER INFORMATION: 2'-OMe adenosine
<220> FEATURE:
<221> NAME/KEY: modified_base
<222> LOCATION: (12)..(12)
<223> OTHER INFORMATION: 2'-fluoro-uridine
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: 2'-fluoro-uridine
<220> FEATURE:
<221> NAME/KEY: misc_feature
<222> LOCATION: (14)..(21)

<223> OTHER INFORMATION: Phosphorothioate Linkage
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (16)..(16)
<223> OTHER INFORMATION: 2'-fluoro-guanosine
<220> FEATURE:
<221> NAME/KEY: modified_base
<222> LOCATION: (17)..(21)
<223> OTHER INFORMATION: um

<400> SEQUENCE: 76
uuggauaugg auguuguuuu u 21

<210> SEQ ID NO 77
<211> LENGTH: 21
<212> TYPE: RNA
<213> ORGANISM: Artificial Sequence
<220> FEATURE:
<223> OTHER INFORMATION: P5_ex
<220> FEATURE:
<221> NAME/KEY: modified_base
<222> LOCATION: (1)..(1)
<223> OTHER INFORMATION: 5 vinyl phosphonate-2'-OMe uridine
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-uridine
<220> FEATURE:
<221> NAME/KEY: modified_base
<222> LOCATION: (3)..(4)
<223> OTHER INFORMATION: gm
<220> FEATURE:
<221> NAME/KEY: modified_base
<222> LOCATION: (5)..(5)
<223> OTHER INFORMATION: 2'-OMe adenosine
<220> FEATURE:
<221> NAME/KEY: modified_base
<222> LOCATION: (6)..(6)
<223> OTHER INFORMATION: 2'-fluoro-uridine
<220> FEATURE:
<221> NAME/KEY: modified_base
<222> LOCATION: (7)..(7)
<223> OTHER INFORMATION: 2'-OMe adenosine
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(10)
<223> OTHER INFORMATION: gm
<220> FEATURE:
<221> NAME/KEY: modified_base
<222> LOCATION: (11)..(11)
<223> OTHER INFORMATION: 2'-OMe adenosine
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: 2'-fluoro-uridine
<220> FEATURE:
<221> NAME/KEY: modified_base

```
<222> LOCATION: (15)..(15)
<223> OTHER INFORMATION: um
<220> FEATURE:
<221> NAME/KEY: modified_base
<222> LOCATION: (16)..(16)
<223> OTHER INFORMATION: 2'-fluoro-guanosine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(21)
<223> OTHER INFORMATION: 2-O-methyl modified uridine and exNA
      internucleotide linkage
<220> FEATURE:
<221> NAME/KEY: misc_feature
<222> LOCATION: (19)..(21)
<223> OTHER INFORMATION: Phosphorothioate Linkage

<400> SEQUENCE: 77

uuggauaugg auguuguuuu u                                              21


<210> SEQ ID NO 78
<211> LENGTH: 21
<212> TYPE: RNA
<213> ORGANISM: Artificial Sequence
<220> FEATURE:
<223> OTHER INFORMATION: P5_ex
<220> FEATURE:
<221> NAME/KEY: modified_base
<222> LOCATION: (1)..(1)
<223> OTHER INFORMATION: 5 vinyl phosphonate-2'-OMe uridine
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-uridine
<220> FEATURE:
<221> NAME/KEY: modified_base
<222> LOCATION: (3)..(4)
<223> OTHER INFORMATION: gm
<220> FEATURE:
<221> NAME/KEY: modified_base
<222> LOCATION: (5)..(5)
<223> OTHER INFORMATION: 2'-OMe adenosine
<220> FEATURE:
<221> NAME/KEY: modified_base
<222> LOCATION: (6)..(6)
<223> OTHER INFORMATION: 2'-fluoro-uridine
<220> FEATURE:
<221> NAME/KEY: modified_base
<222> LOCATION: (7)..(7)
<223> OTHER INFORMATION: 2'-OMe adenosine
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(10)
<223> OTHER INFORMATION: gm
<220> FEATURE:
<221> NAME/KEY: modified_base
<222> LOCATION: (11)..(11)
<223> OTHER INFORMATION: 2'-OMe adenosine
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: gm
```

```
<220> FEATURE:
<221> NAME/KEY: modified_base
<222> LOCATION: (14)..(14)
<223> OTHER INFORMATION: 2'-fluoro-uridine
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (16)..(16)
<223> OTHER INFORMATION: 2'-fluoro-guanosine
<220> FEATURE:
<221> NAME/KEY: modified_base
<222> LOCATION: (17)..(19)
<223> OTHER INFORMATION: um
<220> FEATURE:
<221> NAME/KEY: misc_feature
<222> LOCATION: (19)..(21)
<223> OTHER INFORMATION: Phosphorothioate Linkage
<220> FEATURE:
<221> NAME/KEY: modified_base
<222> LOCATION: (20)..(21)
<223> OTHER INFORMATION: 2-O-methyl modified uridine and exNA
      internucleotide linkage

<400> SEQUENCE: 78

uuggauaugg auguuguuuu u                                              21


<210> SEQ ID NO 79
<211> LENGTH: 21
<212> TYPE: RNA
<213> ORGANISM: Artificial Sequence
<220> FEATURE:
<223> OTHER INFORMATION: P2_ex
<220> FEATURE:
<221> NAME/KEY: modified_base
<222> LOCATION: (1)..(1)
<223> OTHER INFORMATION: 5 vinyl phosphonate-2'-OMe uridine
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-uridine
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(4)
<223> OTHER INFORMATION: 2'-fluoro-guanosine
<220> FEATURE:
<221> NAME/KEY: modified_base
<222> LOCATION: (5)..(5)
<223> OTHER INFORMATION: 2'-OMe adenosine
<220> FEATURE:
<221> NAME/KEY: modified_base
<222> LOCATION: (6)..(6)
<223> OTHER INFORMATION: 2'-fluoro-uridine
<220> FEATURE:
<221> NAME/KEY: modified_base
<222> LOCATION: (7)..(7)
<223> OTHER INFORMATION: 2'-OMe adenosine
<220> FEATURE:
<221> NAME/KEY: modified_base
<222> LOCATION: (8)..(8)
<223> OTHER INFORMATION: 2'-fluoro-uridine
<220> FEATURE:
<221> NAME/KEY: modified_base
<222> LOCATION: (9)..(9)
<223> OTHER INFORMATION: gm
<220> FEATURE:
<221> NAME/KEY: modified_base
```

<222> LOCATION: (10)..(10)
<223> OTHER INFORMATION: 2'-fluoro-guanosine
<220> FEATURE:
<221> NAME/KEY: modified_base
<222> LOCATION: (11)..(11)
<223> OTHER INFORMATION: 2'-OMe adenosine
<220> FEATURE:
<221> NAME/KEY: modified_base
<222> LOCATION: (12)..(12)
<223> OTHER INFORMATION: 2'-fluoro-uridine
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: 2'-fluoro-uridine
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (16)..(16)
<223> OTHER INFORMATION: 2'-fluoro-guanosine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(21)
<223> OTHER INFORMATION: 2-O-methyl modified uridine and exNA
      internucleotide linkage
<220> FEATURE:
<221> NAME/KEY: misc_feature
<222> LOCATION: (19)..(21)
<223> OTHER INFORMATION: Phosphorothioate Linkage

<400> SEQUENCE: 79
uuggauaugg auguuguuuu u                                              21

<210> SEQ ID NO 80
<211> LENGTH: 21
<212> TYPE: RNA
<213> ORGANISM: Artificial Sequence
<220> FEATURE:
<223> OTHER INFORMATION: P5_ex
<220> FEATURE:
<221> NAME/KEY: modified_base
<222> LOCATION: (1)..(1)
<223> OTHER INFORMATION: 5 vinyl phosphonate-2'-OMe uridine
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-uridine
<220> FEATURE:
<221> NAME/KEY: modified_base
<222> LOCATION: (3)..(4)
<223> OTHER INFORMATION: gm
<220> FEATURE:
<221> NAME/KEY: modified_base
<222> LOCATION: (5)..(5)
<223> OTHER INFORMATION: 2'-OMe adenosine
<220> FEATURE:
<221> NAME/KEY: modified_base
<222> LOCATION: (6)..(6)
<223> OTHER INFORMATION: 2'-fluoro-uridine
<220> FEATURE:
<221> NAME/KEY: modified_base
<222> LOCATION: (7)..(7)
<223> OTHER INFORMATION: 2'-OMe adenosine

```
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(10)
<223> OTHER INFORMATION: gm
<220> FEATURE:
<221> NAME/KEY: modified_base
<222> LOCATION: (11)..(11)
<223> OTHER INFORMATION: 2'-OMe adenosine
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: 2'-fluoro-uridine
<220> FEATURE:
<221> NAME/KEY: misc_feature
<222> LOCATION: (14)..(21)
<223> OTHER INFORMATION: Phosphorothioate Linkage
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (16)..(16)
<223> OTHER INFORMATION: 2'-fluoro-guanosine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(21)
<223> OTHER INFORMATION: 2-O-methyl modified uridine and exNA
      internucleotide linkage

<400> SEQUENCE: 80

uuggauaugg auguuguuuu u                                              21


<210> SEQ ID NO 81
<211> LENGTH: 21
<212> TYPE: RNA
<213> ORGANISM: Artificial Sequence
<220> FEATURE:
<223> OTHER INFORMATION: P2_ex
<220> FEATURE:
<221> NAME/KEY: modified_base
<222> LOCATION: (1)..(1)
<223> OTHER INFORMATION: 5 vinyl phosphonate-2'-OMe uridine
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (2)..(2)
<223> OTHER INFORMATION: 2'-fluoro-uridine
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(4)
<223> OTHER INFORMATION: 2'-fluoro-guanosine
<220> FEATURE:
<221> NAME/KEY: modified_base
```

<222> LOCATION: (5)..(5)
<223> OTHER INFORMATION: 2'-OMe adenosine
<220> FEATURE:
<221> NAME/KEY: modified_base
<222> LOCATION: (6)..(6)
<223> OTHER INFORMATION: 2'-fluoro-uridine
<220> FEATURE:
<221> NAME/KEY: modified_base
<222> LOCATION: (7)..(7)
<223> OTHER INFORMATION: 2'-OMe adenosine
<220> FEATURE:
<221> NAME/KEY: modified_base
<222> LOCATION: (8)..(8)
<223> OTHER INFORMATION: 2'-fluoro-uridine
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (10)..(10)
<223> OTHER INFORMATION: 2'-fluoro-guanosine
<220> FEATURE:
<221> NAME/KEY: modified_base
<222> LOCATION: (11)..(11)
<223> OTHER INFORMATION: 2'-OMe adenosine
<220> FEATURE:
<221> NAME/KEY: modified_base
<222> LOCATION: (12)..(12)
<223> OTHER INFORMATION: 2'-fluoro-uridine
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: 2'-fluoro-uridine
<220> FEATURE:
<221> NAME/KEY: misc_feature
<222> LOCATION: (14)..(21)
<223> OTHER INFORMATION: Phosphorothioate Linkage
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (16)..(16)
<223> OTHER INFORMATION: 2'-fluoro-guanosine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(21)
<223> OTHER INFORMATION: 2-O-methyl modified uridine and exNA
internucleotide linkage

<400> SEQUENCE: 81
uuggauaugg auguuguuuu u 21

<210> SEQ ID NO 82
<211> LENGTH: 21
<212> TYPE: RNA
<213> ORGANISM: Artificial Sequence
<220> FEATURE:
<223> OTHER INFORMATION: P5_ex
<220> FEATURE:
<221> NAME/KEY: modified_base
<222> LOCATION: (1)..(1)
<223> OTHER INFORMATION: 5 vinyl phosphonate-2'-OMe uridine
<220> FEATURE:
<221> NAME/KEY: misc_feature
<222> LOCATION: (1)..(3)
<223> OTHER INFORMATION: Phosphorothioate Linkage

```
<220> FEATURE:
<221> NAME/KEY: modified_base
<222> LOCATION: (2)..(2)
<223> OTHER INFORMATION: 2'-fluoro-adenosine
<220> FEATURE:
<221> NAME/KEY: modified_base
<222> LOCATION: (3)..(3)
<223> OTHER INFORMATION: 2'-OMe adenosine
<220> FEATURE:
<221> NAME/KEY: modified_base
<222> LOCATION: (4)..(4)
<223> OTHER INFORMATION: um
<220> FEATURE:
<221> NAME/KEY: modified_base
<222> LOCATION: (5)..(5)
<223> OTHER INFORMATION: cm
<220> FEATURE:
<221> NAME/KEY: modified_base
<222> LOCATION: (6)..(6)
<223> OTHER INFORMATION: 2'-fluoro-guanosine
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (8)..(8)
<223> OTHER INFORMATION: 2'-OMe adenosine
<220> FEATURE:
<221> NAME/KEY: modified_base
<222> LOCATION: (9)..(11)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (14)..(14)
<223> OTHER INFORMATION: 2'-fluoro-cytidine
<220> FEATURE:
<221> NAME/KEY: modified_base
<222> LOCATION: (15)..(15)
<223> OTHER INFORMATION: 2'-OMe adenosine
<220> FEATURE:
<221> NAME/KEY: modified_base
<222> LOCATION: (16)..(16)
<223> OTHER INFORMATION: 2'-fluoro-adenosine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(21)
<223> OTHER INFORMATION: 2-O-methyl modified uridine and exNA
      internucleotide linkage
<220> FEATURE:
<221> NAME/KEY: misc_feature
<222> LOCATION: (19)..(21)
<223> OTHER INFORMATION: Phosphorothioate Linkage

<400> SEQUENCE: 82

uaaucguauu ugucaauuuu u                                              21


<210> SEQ ID NO 83
<211> LENGTH: 16
<212> TYPE: RNA
<213> ORGANISM: Artificial Sequence
<220> FEATURE:
<223> OTHER INFORMATION: P5_ex
<220> FEATURE:
<221> NAME/KEY: modified_base
```

<222> LOCATION: (1)..(2)
<223> OTHER INFORMATION: um
<220> FEATURE:
<221> NAME/KEY: misc_feature
<222> LOCATION: (1)..(3)
<223> OTHER INFORMATION: Phosphorothioate Linkage
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(4)
<223> OTHER INFORMATION: 2'-OMe adenosine
<220> FEATURE:
<221> NAME/KEY: modified_base
<222> LOCATION: (5)..(5)
<223> OTHER INFORMATION: cm
<220> FEATURE:
<221> NAME/KEY: modified_base
<222> LOCATION: (6)..(7)
<223> OTHER INFORMATION: 2'-OMe adenosine
<220> FEATURE:
<221> NAME/KEY: modified_base
<222> LOCATION: (8)..(8)
<223> OTHER INFORMATION: 2'-fluoro-adenosine
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(10)
<223> OTHER INFORMATION: 2'-fluoro-adenosine
<220> FEATURE:
<221> NAME/KEY: modified_base
<222> LOCATION: (11)..(11)
<223> OTHER INFORMATION: 2'-fluoro-cytidine
<220> FEATURE:
<221> NAME/KEY: modified_base
<222> LOCATION: (12)..(12)
<223> OTHER INFORMATION: 2'-fluoro-guanosine
<220> FEATURE:
<221> NAME/KEY: modified_base
<222> LOCATION: (13)..(13)
<223> OTHER INFORMATION: 2'-OMe adenosine
<220> FEATURE:
<221> NAME/KEY: modified_base
<222> LOCATION: (14)..(15)
<223> OTHER INFORMATION: um
<220> FEATURE:
<221> NAME/KEY: misc_feature
<222> LOCATION: (14)..(16)
<223> OTHER INFORMATION: Phosphorothioate Linkage
<220> FEATURE:
<221> NAME/KEY: modified_base
<222> LOCATION: (16)..(16)
<223> OTHER INFORMATION: 2'-OMe adenosine

<400> SEQUENCE: 83
uugacaaaua cgauua 16

<210> SEQ ID NO 84
<211> LENGTH: 21
<212> TYPE: RNA
<213> ORGANISM: Artificial Sequence
<220> FEATURE:
<223> OTHER INFORMATION: P5_ex
<220> FEATURE:
<221> NAME/KEY: modified_base
<222> LOCATION: (1)..(1)
<223> OTHER INFORMATION: 5 vinyl phosphonate-2'-OMe uridine
<220> FEATURE:
<221> NAME/KEY: misc_feature
<222> LOCATION: (1)..(3)
<223> OTHER INFORMATION: Phosphorothioate Linkage
<220> FEATURE:

<221> NAME/KEY: modified_base
<222> LOCATION: (2)..(2)
<223> OTHER INFORMATION: 2'-fluoro-adenosine
<220> FEATURE:
<221> NAME/KEY: modified_base
<222> LOCATION: (3)..(3)
<223> OTHER INFORMATION: 2'-OMe adenosine
<220> FEATURE:
<221> NAME/KEY: modified_base
<222> LOCATION: (4)..(4)
<223> OTHER INFORMATION: um
<220> FEATURE:
<221> NAME/KEY: modified_base
<222> LOCATION: (5)..(5)
<223> OTHER INFORMATION: cm
<220> FEATURE:
<221> NAME/KEY: modified_base
<222> LOCATION: (6)..(6)
<223> OTHER INFORMATION: 2'-fluoro-guanosine
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (8)..(8)
<223> OTHER INFORMATION: 2'-OMe adenosine
<220> FEATURE:
<221> NAME/KEY: modified_base
<222> LOCATION: (9)..(11)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (14)..(14)
<223> OTHER INFORMATION: 2'-fluoro-cytidine
<220> FEATURE:
<221> NAME/KEY: misc_feature
<222> LOCATION: (14)..(21)
<223> OTHER INFORMATION: Phosphorothioate Linkage
<220> FEATURE:
<221> NAME/KEY: modified_base
<222> LOCATION: (15)..(15)
<223> OTHER INFORMATION: 2'-OMe adenosine
<220> FEATURE:
<221> NAME/KEY: modified_base
<222> LOCATION: (16)..(16)
<223> OTHER INFORMATION: 2'-fluoro-adenosine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(21)
<223> OTHER INFORMATION: 2-O-methyl modified uridine and exNA
      internucleotide linkage

<400> SEQUENCE: 84
uaaucguauu ugucaauuuu u                                              21

<210> SEQ ID NO 85
<211> LENGTH: 11
<212> TYPE: RNA
<213> ORGANISM: Artificial Sequence
<220> FEATURE:
<223> OTHER INFORMATION: Themo-ex1a
<220> FEATURE:
<221> NAME/KEY: modified_base
<222> LOCATION: (1)..(1)

<223> OTHER INFORMATION: 2-OH ribocytidine
<220> FEATURE:
<221> NAME/KEY: modified_base
<222> LOCATION: (2)..(2)
<223> OTHER INFORMATION: 2-OH riboguanosine
<220> FEATURE:
<221> NAME/KEY: modified_base
<222> LOCATION: (3)..(3)
<223> OTHER INFORMATION: 2-OH ribocytidine
<220> FEATURE:
<221> NAME/KEY: modified_base
<222> LOCATION: (4)..(4)
<223> OTHER INFORMATION: 2-OH riboadenosine
<220> FEATURE:
<221> NAME/KEY: modified_base
<222> LOCATION: (5)..(5)
<223> OTHER INFORMATION: 2-OH ribouridine
<220> FEATURE:
<221> NAME/KEY: modified_base
<222> LOCATION: (6)..(6)
<223> OTHER INFORMATION: exNA ribo-uridine
<220> FEATURE:
<221> NAME/KEY: modified_base
<222> LOCATION: (7)..(7)
<223> OTHER INFORMATION: 2-OH riboadenosine
<220> FEATURE:
<221> NAME/KEY: modified_base
<222> LOCATION: (8)..(8)
<223> OTHER INFORMATION: 2-OH riboguanosine
<220> FEATURE:
<221> NAME/KEY: modified_base
<222> LOCATION: (9)..(10)
<223> OTHER INFORMATION: 2-OH ribocytidine
<220> FEATURE:
<221> NAME/KEY: modified_base
<222> LOCATION: (11)..(11)
<223> OTHER INFORMATION: 2-OH riboguanosine

<400> SEQUENCE: 85
cgcauuagcc g 11

<210> SEQ ID NO 86
<211> LENGTH: 11
<212> TYPE: RNA
<213> ORGANISM: Artificial Sequence
<220> FEATURE:
<223> OTHER INFORMATION: Themo-ex1b
<220> FEATURE:
<221> NAME/KEY: modified_base
<222> LOCATION: (1)..(1)
<223> OTHER INFORMATION: 2-OH ribocytidine
<220> FEATURE:
<221> NAME/KEY: modified_base
<222> LOCATION: (2)..(2)
<223> OTHER INFORMATION: 2-OH riboguanosine
<220> FEATURE:
<221> NAME/KEY: modified_base
<222> LOCATION: (3)..(3)
<223> OTHER INFORMATION: 2-OH ribocytidine
<220> FEATURE:
<221> NAME/KEY: modified_base
<222> LOCATION: (4)..(4)
<223> OTHER INFORMATION: 2-OH riboadenosine
<220> FEATURE:
<221> NAME/KEY: modified_base
<222> LOCATION: (5)..(5)
<223> OTHER INFORMATION: 2-OH ribouridine
<220> FEATURE:
<221> NAME/KEY: modified_base
<222> LOCATION: (6)..(6)
<223> OTHER INFORMATION: exNA ribo-uridine
<220> FEATURE:
<221> NAME/KEY: modified_base
<222> LOCATION: (7)..(7)
<223> OTHER INFORMATION: 2-OH riboadenosine
<220> FEATURE:
<221> NAME/KEY: modified_base
<222> LOCATION: (8)..(8)
<223> OTHER INFORMATION: 2-OH riboguanosine
<220> FEATURE:
<221> NAME/KEY: modified_base
<222> LOCATION: (9)..(10)
<223> OTHER INFORMATION: 2-OH ribocytidine
<220> FEATURE:
<221> NAME/KEY: modified_base
<222> LOCATION: (11)..(11)
<223> OTHER INFORMATION: 2-OH riboguanosine

<400> SEQUENCE: 86
cgcauuagcc g 11

<210> SEQ ID NO 87
<211> LENGTH: 11
<212> TYPE: RNA
<213> ORGANISM: Artificial Sequence
<220> FEATURE:
<223> OTHER INFORMATION: Themo-ex2
<220> FEATURE:
<221> NAME/KEY: modified_base
<222> LOCATION: (1)..(1)
<223> OTHER INFORMATION: 2-OH ribocytidine
<220> FEATURE:
<221> NAME/KEY: modified_base
<222> LOCATION: (2)..(2)
<223> OTHER INFORMATION: 2-OH riboguanosine
<220> FEATURE:
<221> NAME/KEY: modified_base
<222> LOCATION: (3)..(3)
<223> OTHER INFORMATION: 2-OH ribocytidine
<220> FEATURE:
<221> NAME/KEY: modified_base
<222> LOCATION: (4)..(4)
<223> OTHER INFORMATION: 2-OH riboadenosine
<220> FEATURE:
<221> NAME/KEY: modified_base
<222> LOCATION: (5)..(5)
<223> OTHER INFORMATION: 2-OH riboguanosine
<220> FEATURE:
<221> NAME/KEY: modified_base
<222> LOCATION: (6)..(6)
<223> OTHER INFORMATION: exNA ribo-uridine
<220> FEATURE:
<221> NAME/KEY: modified_base
<222> LOCATION: (7)..(7)
<223> OTHER INFORMATION: 2-OH riboadenosine
<220> FEATURE:
<221> NAME/KEY: modified_base
<222> LOCATION: (8)..(8)
<223> OTHER INFORMATION: 2-OH riboguanosine
<220> FEATURE:
<221> NAME/KEY: modified_base
<222> LOCATION: (9)..(10)
<223> OTHER INFORMATION: 2-OH ribocytidine
<220> FEATURE:
<221> NAME/KEY: modified_base
<222> LOCATION: (11)..(11)
<223> OTHER INFORMATION: 2-OH riboguanosine

<400> SEQUENCE: 87
cgcaguagcc g 11

<210> SEQ ID NO 88
<211> LENGTH: 11
<212> TYPE: RNA
<213> ORGANISM: Artificial Sequence
<220> FEATURE:
<223> OTHER INFORMATION: Themo-ex3
<220> FEATURE:
<221> NAME/KEY: modified_base
<222> LOCATION: (1)..(1)
<223> OTHER INFORMATION: 2-OH ribocytidine
<220> FEATURE:

<221> NAME/KEY: modified_base
<222> LOCATION: (2)..(2)
<223> OTHER INFORMATION: 2-OH riboguanosine
<220> FEATURE:
<221> NAME/KEY: modified_base
<222> LOCATION: (3)..(3)
<223> OTHER INFORMATION: 2-OH ribocytidine
<220> FEATURE:
<221> NAME/KEY: modified_base
<222> LOCATION: (4)..(5)
<223> OTHER INFORMATION: 2-OH riboadenosine
<220> FEATURE:
<221> NAME/KEY: modified_base
<222> LOCATION: (6)..(6)
<223> OTHER INFORMATION: exNA ribo-uridine
<220> FEATURE:
<221> NAME/KEY: modified_base
<222> LOCATION: (7)..(7)
<223> OTHER INFORMATION: 2-OH riboadenosine
<220> FEATURE:
<221> NAME/KEY: modified_base
<222> LOCATION: (8)..(8)
<223> OTHER INFORMATION: 2-OH riboguanosine
<220> FEATURE:
<221> NAME/KEY: modified_base
<222> LOCATION: (9)..(10)
<223> OTHER INFORMATION: 2-OH ribocytidine
<220> FEATURE:
<221> NAME/KEY: modified_base
<222> LOCATION: (11)..(11)
<223> OTHER INFORMATION: 2-OH riboguanosine

<400> SEQUENCE: 88
cgcaauagcc g 11

<210> SEQ ID NO 89
<211> LENGTH: 11
<212> TYPE: RNA
<213> ORGANISM: Artificial Sequence
<220> FEATURE:
<223> OTHER INFORMATION: Themo-ex4
<220> FEATURE:
<221> NAME/KEY: modified_base
<222> LOCATION: (1)..(1)
<223> OTHER INFORMATION: 2-OH ribocytidine
<220> FEATURE:
<221> NAME/KEY: modified_base
<222> LOCATION: (2)..(2)
<223> OTHER INFORMATION: 2-OH riboguanosine
<220> FEATURE:
<221> NAME/KEY: modified_base
<222> LOCATION: (3)..(3)
<223> OTHER INFORMATION: 2-OH ribocytidine
<220> FEATURE:
<221> NAME/KEY: modified_base
<222> LOCATION: (4)..(4)
<223> OTHER INFORMATION: 2-OH riboadenosine
<220> FEATURE:
<221> NAME/KEY: modified_base
<222> LOCATION: (5)..(5)
<223> OTHER INFORMATION: 2-OH ribocytidine
<220> FEATURE:
<221> NAME/KEY: modified_base
<222> LOCATION: (6)..(6)
<223> OTHER INFORMATION: exNA ribo-uridine
<220> FEATURE:
<221> NAME/KEY: modified_base
<222> LOCATION: (7)..(7)
<223> OTHER INFORMATION: 2-OH riboadenosine
<220> FEATURE:
<221> NAME/KEY: modified_base
<222> LOCATION: (8)..(8)
<223> OTHER INFORMATION: 2-OH riboguanosine
<220> FEATURE:
<221> NAME/KEY: modified_base
<222> LOCATION: (9)..(10)
<223> OTHER INFORMATION: 2-OH ribocytidine
<220> FEATURE:
<221> NAME/KEY: modified_base
<222> LOCATION: (11)..(11)
<223> OTHER INFORMATION: 2-OH riboguanosine

<400> SEQUENCE: 89
cgcacuagcc g 11

<210> SEQ ID NO 90
<211> LENGTH: 11
<212> TYPE: RNA
<213> ORGANISM: Artificial Sequence
<220> FEATURE:
<223> OTHER INFORMATION: UC-seq-ex1
<220> FEATURE:
<221> NAME/KEY: modified_base
<222> LOCATION: (1)..(1)
<223> OTHER INFORMATION: 2-OH ribouridine
<220> FEATURE:
<221> NAME/KEY: modified_base
<222> LOCATION: (2)..(2)
<223> OTHER INFORMATION: 2-OH ribocytidine
<220> FEATURE:
<221> NAME/KEY: modified_base
<222> LOCATION: (3)..(3)
<223> OTHER INFORMATION: 2-OH ribouridine
<220> FEATURE:
<221> NAME/KEY: modified_base
<222> LOCATION: (4)..(4)
<223> OTHER INFORMATION: 2-OH ribocytidine
<220> FEATURE:
<221> NAME/KEY: modified_base
<222> LOCATION: (5)..(5)
<223> OTHER INFORMATION: 2-OH ribouridine
<220> FEATURE:
<221> NAME/KEY: modified_base
<222> LOCATION: (6)..(6)
<223> OTHER INFORMATION: exNA ribo-uridine
<220> FEATURE:
<221> NAME/KEY: modified_base
<222> LOCATION: (7)..(7)
<223> OTHER INFORMATION: 2-OH ribouridine
<220> FEATURE:
<221> NAME/KEY: modified_base
<222> LOCATION: (8)..(8)
<223> OTHER INFORMATION: 2-OH ribocytidine
<220> FEATURE:
<221> NAME/KEY: modified_base
<222> LOCATION: (9)..(9)
<223> OTHER INFORMATION: 2-OH ribouridine
<220> FEATURE:
<221> NAME/KEY: modified_base
<222> LOCATION: (10)..(10)
<223> OTHER INFORMATION: 2-OH ribocytidine
<220> FEATURE:
<221> NAME/KEY: modified_base
<222> LOCATION: (11)..(11)
<223> OTHER INFORMATION: 2-OH ribouridine

<400> SEQUENCE: 90
ucucuuucuc u 11

<210> SEQ ID NO 91
<211> LENGTH: 11
<212> TYPE: RNA
<213> ORGANISM: Artificial Sequence
<220> FEATURE:
<223> OTHER INFORMATION: UC-seq-ex2
<220> FEATURE:
<221> NAME/KEY: modified_base
<222> LOCATION: (1)..(1)
<223> OTHER INFORMATION: 2-OH ribouridine
<220> FEATURE:
<221> NAME/KEY: modified_base
<222> LOCATION: (2)..(2)

<223> OTHER INFORMATION: 2-OH ribocytidine
<220> FEATURE:
<221> NAME/KEY: modified_base
<222> LOCATION: (3)..(3)
<223> OTHER INFORMATION: 2-OH ribouridine
<220> FEATURE:
<221> NAME/KEY: modified_base
<222> LOCATION: (4)..(4)
<223> OTHER INFORMATION: 2-OH ribocytidine
<220> FEATURE:
<221> NAME/KEY: modified_base
<222> LOCATION: (5)..(7)
<223> OTHER INFORMATION: exNA ribo-uridine
<220> FEATURE:
<221> NAME/KEY: modified_base
<222> LOCATION: (8)..(8)
<223> OTHER INFORMATION: 2-OH ribocytidine
<220> FEATURE:
<221> NAME/KEY: modified_base
<222> LOCATION: (9)..(9)
<223> OTHER INFORMATION: 2-OH ribouridine
<220> FEATURE:
<221> NAME/KEY: modified_base
<222> LOCATION: (10)..(10)
<223> OTHER INFORMATION: 2-OH ribocytidine
<220> FEATURE:
<221> NAME/KEY: modified_base
<222> LOCATION: (11)..(11)
<223> OTHER INFORMATION: 2-OH ribouridine

<400> SEQUENCE: 91
ucucuuucuc u 11

<210> SEQ ID NO 92
<211> LENGTH: 11
<212> TYPE: RNA
<213> ORGANISM: Artificial Sequence
<220> FEATURE:
<223> OTHER INFORMATION: UC-seq-ex3
<220> FEATURE:
<221> NAME/KEY: modified_base
<222> LOCATION: (1)..(1)
<223> OTHER INFORMATION: exNA ribo-uridine
<220> FEATURE:
<221> NAME/KEY: modified_base
<222> LOCATION: (2)..(2)
<223> OTHER INFORMATION: 2-OH ribocytidine
<220> FEATURE:
<221> NAME/KEY: modified_base
<222> LOCATION: (3)..(3)
<223> OTHER INFORMATION: exNA ribo-uridine
<220> FEATURE:
<221> NAME/KEY: modified_base
<222> LOCATION: (4)..(4)
<223> OTHER INFORMATION: 2-OH ribocytidine
<220> FEATURE:
<221> NAME/KEY: modified_base
<222> LOCATION: (5)..(5)
<223> OTHER INFORMATION: exNA ribo-uridine
<220> FEATURE:
<221> NAME/KEY: modified_base
<222> LOCATION: (6)..(6)
<223> OTHER INFORMATION: 2-OH ribouridine
<220> FEATURE:
<221> NAME/KEY: modified_base
<222> LOCATION: (7)..(7)
<223> OTHER INFORMATION: exNA ribo-uridine
<220> FEATURE:
<221> NAME/KEY: modified_base
<222> LOCATION: (8)..(8)
<223> OTHER INFORMATION: 2-OH ribocytidine
<220> FEATURE:
<221> NAME/KEY: modified_base
<222> LOCATION: (9)..(9)
<223> OTHER INFORMATION: exNA ribo-uridine
<220> FEATURE:
<221> NAME/KEY: modified_base -continued

```
<222> LOCATION: (10)..(10)
<223> OTHER INFORMATION: 2-OH ribocytidine
<220> FEATURE:
<221> NAME/KEY: modified_base
<222> LOCATION: (11)..(11)
<223> OTHER INFORMATION: exNA ribo-uridine

<400> SEQUENCE: 92

ucucuuucuc u                                                          11
```

SYNTHETIC OLIGONUCLEOTIDES HAVING REGIONS OF BLOCK AND CLUSTER MODIFICATIONS

CROSS-REFERENCE TO RELATED APPLICATIONS

This application claims the benefit of U.S. Provisional Application Ser. No. 63/029,880, filed May 26, 2020, and U.S. Provisional Application Ser. No. 63/166,459, filed Mar. 26, 2021, the entire disclosures of which are incorporated herein by reference.

STATEMENT REGARDING FEDERALLY SPONSORED RESEARCH OR DEVELOPMENT

This disclosure was made with government support under grant numbers NS104022 and OD020012 awarded by the National Institutes of Health. The Government has certain rights in the disclosure.

FIELD OF THE DISCLOSURE

This disclosure relates to the use of novel intersubunit linkages to increase stability of modified oligonucleotides.

SEQUENCE LISTING

The instant application contains a Sequence Listing which has been submitted electronically in ASCII format and is hereby incorporated by reference in its entirety. Said ASCII file, created on Oct. 26, 2023, is named 718617_UM9-255_ST25 and is 126,484 bytes in size.

BACKGROUND

Currently, the most common metabolically stable backbone modification used in complex therapeutic RNAs is the Phosphorothioate (PS) modification. While other available backbone modification alternatives, such as Peptide Nucleic Acid (PNA) and Phosphorodiamidate Morpholino Oligonucleotide (PMO), work well as steric-blocking antisense oligonucleotides, they are not tolerated in many promising RNA-based therapeutic strategies. These strategies include siRNAs, miRNAs, RNaseH-dependent antisense oligonucleotides, and aptamer-based therapeutics. This poor tolerance is due to PNA's and PMO's inability to withstand biological machineries, such as Argonaute proteins (siRNA/miRNA), and RNaseH that strictly recognize RNA structures when they form "functional" RNA-protein complexes.

One of the most common RNA-based therapeutic strategies is the use of metabolically stable, PS-modified RNAs or PS/PO-modified chimeric oligonucleotides. One severe drawback in this strategy, however, is toxicity due to non-specific binding of the RNAs to a variety of proteins in vivo. Another drawback is that the PS-modified and even more so, PS/PO-modified RNAs are decomposed by endogenous nucleases. Thus, additional backbone modifications that provide higher metabolic stabilization without compromising drug efficacy are urgently needed in the field of RNA therapeutics.

Synthetic accessibility is also an important factor in a development of therapeutic oligonucleotides. A variety of other modified backbones have been reported (e.g. boranophosphate, phosphoroamidate, etc.) but many of those require their own specific synthetic procedure, which is not compatible with the conventional phosphoramidite oligonucleotide synthesis cycle. This incompatibility makes it difficult to freely synthesize/design chimeric backbones having these modifications in a similar manner as mixing PS/PO backbone with other sugar modified backbones. This difficulty in the synthesis limits additively diversifying the designing pattern of functional therapeutic oligonucleotides. Thus, having a new chemical tool that is easy to synthesize and is compatible with currently validated chemical modification is in high demand in the field.

SUMMARY

Provided herein is a new variety of backbone modification wherein one or more carbon chains are inserted in the backbone structure. The backbone modifications provided herein are not expected to have a profound impact on the structure of RNA, and can therefore provide compatibility with a variety of RNA-binding biological machineries. Further, these modifications are not expected to display toxic, non-specific binding to proteins, and thus can be incorporated into a wide range of therapeutic RNAs. The modifications herein are capable of enhancing oligonucleotide stability.

As used herein, the term "block" refers to at least two consecutive modified intersubunit linkages of the disclosure present at one or both of a 5' end and a 3' end of a modified oligonucleotide. In certain embodiments, the block comprises three consecutive modified intersubunit linkages at the 5' end of a modified oligonucleotide. In certain embodiments, the block comprises four consecutive modified intersubunit linkages at the 5' end of a modified oligonucleotide. In certain embodiments, the block comprises five consecutive modified intersubunit linkages at the 5' end of a modified oligonucleotide. In certain embodiments, the block comprises three consecutive modified intersubunit linkages at the 3' end of a modified oligonucleotide. In certain embodiments, the block comprises four consecutive modified intersubunit linkages at the 3' end of a modified oligonucleotide. In certain embodiments, the block comprises five consecutive modified intersubunit linkages at the 3' end of a modified oligonucleotide. The consecutive modified intersubunit linkages of the disclosure form a block at the termini of an oligonucleotide and confer enhanced stability (e.g., nuclease stability) to the oligonucleotide.

As used herein, the term "cluster" refers to at least two modified intersubunit linkages of the disclosure present at one or both of a 5' end and a 3' end of a modified oligonucleotide. The cluster of modified intersubunit linkages need not be consecutive. For example, but in no way limiting, a cluster of modified intersubunit linkages can include alternating modified intersubunit linkages. In certain embodiments, the cluster comprises three total modified intersubunit linkages at the 5' end of a modified oligonucleotide. In certain embodiments, the cluster comprises four total modified intersubunit linkages at the 5' end of a modified oligonucleotide. In certain embodiments, the cluster comprises five total modified intersubunit linkages at the 5' end of a modified oligonucleotide. In certain embodiments, the cluster comprises three total modified intersubunit linkages at the 3' end of a modified oligonucleotide. In certain embodiments, the cluster comprises four total modified intersubunit linkages at the 3' end of a modified oligonucleotide. In certain embodiments, the cluster comprises five total modified intersubunit linkages at the 3' end of a modified oligonucleotide. The cluster of modified intersubunit linkages of the disclosure at the termini of an oligonucleotide confer enhanced stability (e.g., nuclease stability) to the oligonucleotide.

In one aspect, the disclosure provides a modified oligonucleotide comprising a 5' end, a 3' end and at least two modified intersubunit linkages of Formula Ia:

(Ia)

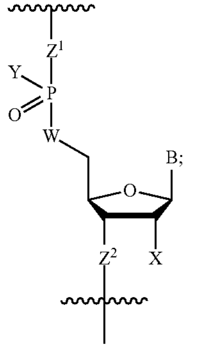

wherein:

B is a base moiety;

W is O or $O(CH_2)_n{}^1$, wherein $n^1$ is 1 to 10;

X is selected from the group consisting of H, OH, $OR^1$, $R^1$, F, Cl, Br, I, SH, $SR^1$, $NH_2$, $NHR^1$, $NR^1{}_2$, and $COOR^1$;

Y is selected from the group consisting of $O^-$, OH, $OR^2$, $NH^-$, $NH_2$, $NR^2{}_2$, $BH_3$, $S^-$, $R^2$, and SH;

$Z^1$ is O or $O(CH_2)_n{}^2$ wherein $n^2$ is 1 to 10;

$Z^2$ is O or $O(CH_2)_n{}^3$ wherein $n^3$ is 1 to 10;

$R^1$ is a substituted or unsubstituted $C_1$-$C_6$ alkyl, alkenyl, alkynyl, aryl, or mixtures thereof;

$R^2$ is a substituted or unsubstituted $C_1$-$C_6$ alkyl, alkenyl, alkynyl, aryl, or mixtures thereof; and wherein at least two of the modified intersubunit linkages are present at one or both of the 5' end and the 3' end of the modified oligonucleotide.

In an embodiment of Formula Ia, $Z^1$ is $O(CH_2)_n{}^2$, $n^2$ is 1, W is O, and Y is $O^-$. In an embodiment of Formula Ia, $Z^1$ is O, W is $O(CH_2)n^1$, $n^1$ is 1, and Y is $O^-$. In an embodiment of Formula Ia, $Z^1$ is $O(CH_2)_n{}^2$, $n^2$ is 1, W is O, and Y is $O^-$. In an embodiment of Formula Ia, $Z^1$ is $O(CH_2)_n{}^2$, $n^2$ is 1, W is $O(CH_2)n^1$, and Y is $O^-$. In an embodiment of Formula Ia, $Z^1$ is $O(CH_2)_n{}^2$, $n^2$ is 1, W is $O(CH_2)n^1$, and Y is $S^-$.

In an embodiment of Formula Ia, the base moiety B is selected from the group consisting of adenine, guanine, cytosine, and uracil.

In an embodiment of Formula Ia, the base moiety B forms a base pairing interaction with another base moiety in the target RNA. In another embodiment of Formula Ia, the base moiety B does not base pair with the target RNA.

In an embodiment of Formula Ia, between two and ten (i.e., 2, 3, 4, 5, 6, 7, 8, 9, or 10) of the modified intersubunit linkages are present at one or both of the 5' end and 3' end of the modified oligonucleotide.

In an embodiment of Formula Ia, between two and five (i.e., 2, 3, 4, or 5) of the modified intersubunit linkages are present at one or both of the 5' end and 3' end of the modified oligonucleotide.

In an embodiment of Formula Ia, two of the modified intersubunit linkages are present at one or both of the 5' end and 3' end of the modified oligonucleotide.

In an embodiment of Formula Ia, three of the modified intersubunit linkages are present at one or both of the 5' end and 3' end of the modified oligonucleotide.

In an embodiment of Formula Ia, four of the modified intersubunit linkages are present at one or both of the 5' end and 3' end of the modified oligonucleotide.

In an embodiment of Formula Ia, five of the modified intersubunit linkages are present at one or both of the 5' end and 3' end of the modified oligonucleotide.

In an embodiment of Formula Ia, six of the modified intersubunit linkages are present at one or both of the 5' end and 3' end of the modified oligonucleotide.

In an embodiment of Formula Ia, seven of the modified intersubunit linkages are present at one or both of the 5' end and 3' end of the modified oligonucleotide.

In an embodiment of Formula Ia, eight of the modified intersubunit linkages are present at one or both of the 5' end and 3' end of the modified oligonucleotide.

In an embodiment of Formula Ia, nine of the modified intersubunit linkages are present at one or both of the 5' end and 3' end of the modified oligonucleotide.

In an embodiment of Formula Ia, ten of the modified intersubunit linkages are present at one or both of the 5' end and 3' end of the modified oligonucleotide.

In an embodiment of Formula Ia, the at least two modified intersubunit linkages are consecutive. In an embodiment of Formula Ia, three, four, or five of the modified intersubunit linkages are present at one or both of the 5' end and 3' end of the modified oligonucleotide and the intersubunit linkages are consecutive.

In an embodiment of Formula Ia, Y is $S^-$. In an embodiment of Formula Ia, X is $OR^1$ or F.

In an embodiment of Formula Ia, the oligonucleotide is selected from the group consisting of an siRNA, a miRNA, an antisense oligonucleotide, a ribozyme, and a mRNA.

In an embodiment of Formula Ia, the siRNA comprises an antisense strand and a sense strand, and wherein one or both of the antisense strand and the sense strand comprise the modified intersubunit linkages.

In an embodiment of Formula Ia, the antisense strand comprises or consists of 8 or fewer (e.g., 8, 7, 6, 5, 4, 3, 2, 1, or 0) phosphorothioate modifications. In an embodiment of Formula Ia, the antisense strand comprises or consists of 8 phosphorothioate modifications. In an embodiment of Formula Ia, the antisense strand comprises or consists of 7 phosphorothioate modifications. In an embodiment of Formula Ia, the antisense strand comprises or consists of 6 phosphorothioate modifications. In an embodiment of Formula Ia, the antisense strand comprises or consists of 5 phosphorothioate modifications. In an embodiment of Formula Ia, the antisense strand comprises or consists of 4 phosphorothioate modifications. In an embodiment of Formula Ia, the antisense strand comprises or consists of 3 phosphorothioate modifications. In an embodiment of Formula Ia, the antisense strand comprises or consists of 2 phosphorothioate modifications. In an embodiment of Formula Ia, the antisense strand comprises or consists of 1 phosphorothioate modifications. In an embodiment of Formula Ia, the antisense strand comprises or consists of 0 phosphorothioate modifications.

In an embodiment of Formula Ia, the sense strand comprises or consists of 8 or fewer (e.g., 8, 7, 6, 5, 4, 3, 2, 1, or 0) phosphorothioate modifications. In an embodiment of Formula Ia, the sense strand comprises or consists of 8 phosphorothioate modifications. In an embodiment of Formula Ia, the sense strand comprises or consists of 7 phosphorothioate modifications. In an embodiment of Formula Ia, the sense strand comprises or consists of 6 phosphorothioate modifications. In an embodiment of Formula Ia, the sense strand comprises or consists of 5 phosphorothioate modifications. In an embodiment of Formula Ia, the sense strand comprises or consists of 4 phosphorothioate modifications. In an embodiment of Formula Ia, the sense strand comprises or consists of 3 phosphorothioate modifications. In an embodiment of Formula Ia, the sense strand comprises or consists of 2 phosphorothioate modifications. In an embodiment of Formula Ia, the sense strand comprises or consists of 1 phosphorothioate modifications. In an embodiment of Formula Ia, the sense strand comprises or consists of 0 phosphorothioate modifications.

In one aspect, the disclosure provides a modified oligonucleotide comprising a 5' end, a 3' end and at least two modified intersubunit linkages of Formula I:

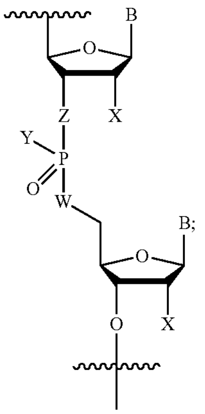

(I)

wherein:

B is a base moiety;

W is O or $O(CH_2)_n^{\ 1}$, wherein $n^1$ is 1 to 10;

X is selected from the group consisting of H, OH, $OR^1$, $R^1$, F, Cl, Br, I, SH, $SR^1$, $NH_2$, $NHR^1$, $NR^1_2$, and $COOR^1$;

Y is selected from the group consisting of $O^-$, OH, $OR^2$, $NH^-$, $NH_2$, $NR^2_2$, $BH_3$, $S^-$, $R^2$, and SH;

Z is O or $O(CH_2)_n^{\ 2}$ wherein $n^2$ is 1 to 10;

$R^1$ is a substituted or unsubstituted $C_1$-$C_6$ alkyl, alkenyl, alkynyl, aryl, or mixtures thereof;

$R^2$ is a substituted or unsubstituted $C_1$-$C_6$ alkyl, alkenyl, alkynyl, aryl, or mixtures thereof; and wherein at least two of the modified intersubunit linkages are present at one or both of the 5' end and the 3' end of the modified oligonucleotide.

In an embodiment of Formula I, Z is $O(CH_2)_n^{\ 2}$, $n^2$ is 1, W is O, and Y is $O^-$. In an embodiment of Formula I, Z is O, W is $O(CH_2)_n^{\ 1}$, $n^1$ is 1, and Y is $O^-$. In an embodiment of Formula I, Z is $O(CH_2)_n^{\ 2}$, $n^2$ is 1, W is O, and Y is $O^-$. In an embodiment of Formula I, Z is $O(CH_2)_n^{\ 2}$, $n^2$ is 1, W is $O(CH_2)_n^{\ 1}$, and Y is $O^-$. In an embodiment of Formula I, Z is $O(CH_2)_n^{\ 2}$, $n^2$ is 1, W is $O(CH_2)_n^{\ 1}$, and Y is $S^-$.

In an embodiment of Formula I, the base moiety B is selected from the group consisting of adenine, guanine, cytosine, and uracil.

In an embodiment of Formula I, the base moiety B forms a base pairing interaction with another base moiety in the target RNA. In another embodiment of Formula Ia, the base moiety B does not base pair with the target RNA.

In an embodiment of Formula I, between two and ten (i.e., 2, 3, 4, 5, 6, 7, 8, 9, or 10) of the modified intersubunit linkages are present at one or both of the 5' end and 3' end of the modified oligonucleotide. In an embodiment of Formula I, between two and five (i.e., 2, 3, 4, or 5) of the modified intersubunit linkages are present at one or both of the 5' end and 3' end of the modified oligonucleotide. In an embodiment of Formula I, two of the modified intersubunit linkages are present at one or both of the 5' end and 3' end of the modified oligonucleotide. In an embodiment of Formula I, three of the modified intersubunit linkages are present at one or both of the 5' end and 3' end of the modified oligonucleotide. In an embodiment of Formula I, four of the modified intersubunit linkages are present at one or both of the 5' end and 3' end of the modified oligonucleotide. In an embodiment of Formula I, five of the modified intersubunit linkages are present at one or both of the 5' end and 3' end of the modified oligonucleotide. In an embodiment of Formula I, six of the modified intersubunit linkages are present at one or both of the 5' end and 3' end of the modified oligonucleotide. In an embodiment of Formula I, seven of the modified intersubunit linkages are present at one or both of the 5' end and 3' end of the modified oligonucleotide. In an embodiment of Formula I, eight of the modified intersubunit linkages are present at one or both of the 5' end and 3' end of the modified oligonucleotide. In an embodiment of Formula I, nine of the modified intersubunit linkages are present at one or both of the 5' end and 3' end of the modified oligonucleotide. In an embodiment of Formula I, ten of the modified intersubunit linkages are present at one or both of the 5' end and 3' end of the modified oligonucleotide.

In an embodiment of Formula I, the at least two modified intersubunit linkages are consecutive. In an embodiment of Formula I, three, four, or five of the modified intersubunit linkages are present at one or both of the 5' end and 3' end of the modified oligonucleotide and the intersubunit linkages are consecutive.

In an embodiment of Formula I, Y is $S^-$. In an embodiment of Formula I, X is $OR^1$ or F.

In an embodiment of Formula I, the oligonucleotide is selected from the group consisting of an siRNA, a miRNA, an antisense oligonucleotide, a ribozyme, and a mRNA.

In an embodiment of Formula I, the siRNA comprises an antisense strand and a sense strand, and wherein one or both of the antisense strand and the sense strand comprise the modified intersubunit linkages.

In an embodiment of Formula I, the antisense strand comprises or consists of 8 or fewer (e.g., 8, 7, 6, 5, 4, 3, 2, 1, or 0) phosphorothioate modifications. In an embodiment of Formula I, the antisense strand comprises or consists of 8 phosphorothioate modifications. In an embodiment of Formula I, the antisense strand comprises or consists of 7 phosphorothioate modifications. In an embodiment of Formula I, the antisense strand comprises or consists of 6 phosphorothioate modifications. In an embodiment of Formula I, the antisense strand comprises or consists of 5 phosphorothioate modifications. In an embodiment of Formula I, the antisense strand comprises or consists of 4 phosphorothioate modifications. In an embodiment of Formula I, the antisense strand comprises or consists of 3 phosphorothioate modifications. In an embodiment of Formula I, the antisense strand comprises or consists of 2 phosphorothioate modifications. In an embodiment of Formula I, the antisense strand comprises or consists of 1 phosphorothioate modifications. In an embodiment of Formula I, the antisense strand comprises or consists of 0 phosphorothioate modifications.

In an embodiment of Formula I, the sense strand comprises or consists of 8 or fewer (e.g., 8, 7, 6, 5, 4, 3, 2, 1, or 0) phosphorothioate modifications. In an embodiment of Formula I, the sense strand comprises or consists of 8 phosphorothioate modifications. In an embodiment of Formula I, the sense strand comprises or consists of 7 phosphorothioate modifications. In an embodiment of Formula I, the sense strand comprises or consists of 6 phosphorothioate modifications. In an embodiment of Formula I, the sense strand comprises or consists of 5 phosphorothioate modifications. In an embodiment of Formula I, the sense strand comprises or consists of 4 phosphorothioate modifications. In an embodiment of Formula I, the sense strand comprises or consists of 3 phosphorothioate modifications. In an embodiment of Formula I, the sense strand comprises or consists of 2 phosphorothioate modifications. In an embodiment of Formula I, the sense strand comprises or consists of 1 phosphorothioate modifications. In an embodiment of Formula I, the sense strand comprises or consists of 0 phosphorothioate modifications.

In one aspect, the disclosure provides a modified oligonucleotide comprising a 5' end, a 3' end and at least two modified intersubunit linkages of Formula IIa:

(IIa)

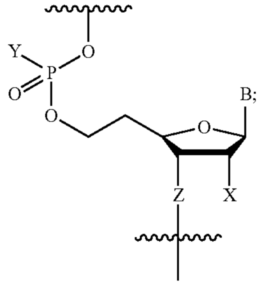

wherein:

B is a base moiety;

X is selected from the group consisting of H, OH, OR, $R^1$, F, Cl, Br, I, SH, $SR^1$, $NH_2$, $NHR^1$, $NR^1_2$, and $COOR^1$;

Y is selected from the group consisting of $O^-$, OH, $OR^2$, $NH^-$, $NH_2$, $NR^2_2$, $BH_3$, $S^-$, $R^2$, and SH;

Z is O or $O(CH_2)_{n^2}$ wherein $n^2$ is 1 to 10;

$R^1$ is a substituted or unsubstituted $C_1$-$C_6$ alkyl, alkenyl, alkynyl, aryl, or mixtures thereof;

$R^2$ is a substituted or unsubstituted $C_1$-$C_6$ alkyl, alkenyl, alkynyl, aryl, or mixtures thereof; and wherein at least two of the modified intersubunit linkages are present at one or both of the 5' end and the 3' end of the modified oligonucleotide.

In an embodiment of Formula IIa, between two and ten (i.e., 2, 3, 4, 5, 6, 7, 8, 9, or 10) of the modified intersubunit linkages are present at one or both of the 5' end and 3' end of the modified oligonucleotide.

In an embodiment of Formula IIa, between two and five of the modified intersubunit linkages are present at one or both of the 5' end and 3' end of the modified oligonucleotide.

In an embodiment of Formula IIa, two of the modified intersubunit linkages are present at one or both of the 5' end and 3' end of the modified oligonucleotide.

In an embodiment of Formula IIa, three of the modified intersubunit linkages are present at one or both of the 5' end and 3' end of the modified oligonucleotide.

In an embodiment of Formula IIa, four of the modified intersubunit linkages are present at one or both of the 5' end and 3' end of the modified oligonucleotide.

In an embodiment of Formula IIa, five of the modified intersubunit linkages are present at one or both of the 5' end and 3' end of the modified oligonucleotide. In an embodiment of Formula IIa, six of the modified intersubunit linkages are present at one or both of the 5' end and 3' end of the modified oligonucleotide. In an embodiment of Formula IIa, seven of the modified intersubunit linkages are present at one or both of the 5' end and 3' end of the modified oligonucleotide. In an embodiment of Formula IIa, eight of the modified intersubunit linkages are present at one or both of the 5' end and 3' end of the modified oligonucleotide. In an embodiment of Formula IIa, nine of the modified intersubunit linkages are present at one or both of the 5' end and 3' end of the modified oligonucleotide. In an embodiment of Formula IIa, ten of the modified intersubunit linkages are present at one or both of the 5' end and 3' end of the modified oligonucleotide.

In an embodiment of Formula IIa, the at least two modified intersubunit linkages are consecutive. In an embodiment of Formula IIa, three, four, or five of the modified intersubunit linkages are present at one or both of the 5' end and 3' end of the modified oligonucleotide and the intersubunit linkages are consecutive.

In an embodiment of Formula IIa, Y is $S^-$. In an embodiment of Formula IIa, Y is $O^-$. In an embodiment of Formula IIa, X is $OR^1$ or F.

In an embodiment of Formula IIa, the base moiety B is selected from the group consisting of adenine, guanine, cytosine, and uracil.

In an embodiment of Formula IIa, the base moiety B forms a base pairing interaction with another base moiety in the target RNA. In another embodiment of Formula Ia, the base moiety B does not base pair with the target RNA.

In one aspect, the disclosure provides a modified oligonucleotide comprising a 5' end, a 3' end and at least two modified intersubunit linkages of Formula II:

(II)

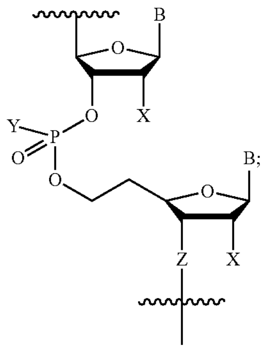

wherein:

B is a base moiety;

X is selected from the group consisting of H, OH, $OR^1$, $R^1$, F, Cl, Br, I, SH, $SR^1$, $NH_2$, $NHR^1$, $NR^1_2$, and $COOR^1$;

Y is selected from the group consisting of $O^-$, OH, $OR^2$, $NH^-$, $NH_2$, $NR^2_2$, $BH_3$, $S^-$, $R^2$, and SH;

Z is O or $O(CH_2)_n^2$ wherein $n^2$ is 1 to 10;

$R^1$ is a substituted or unsubstituted $C_1$-$C_6$ alkyl, alkenyl, alkynyl, aryl, or mixtures thereof;

$R^2$ is a substituted or unsubstituted $C_1$-$C_6$ alkyl, alkenyl, alkynyl, aryl, or mixtures thereof; and wherein at least two of the modified intersubunit linkages are present at one or both of the 5' end and the 3' end of the modified oligonucleotide.

In an embodiment of Formula II, between two and ten (i.e., 2, 3, 4, 5, 6, 7, 8, 9, or 10) of the modified intersubunit linkages are present at one or both of the 5' end and 3' end of the modified oligonucleotide. In an embodiment of Formula II, between two and five of the modified intersubunit linkages are present at one or both of the 5' end and 3' end of the modified oligonucleotide. In an embodiment of Formula II, two of the modified intersubunit linkages are present at one or both of the 5' end and 3' end of the modified oligonucleotide. In an embodiment of Formula II, three of the modified intersubunit linkages are present at one or both of the 5' end and 3' end of the modified oligonucleotide. In an embodiment of Formula II, four of the modified intersubunit linkages are present at one or both of the 5' end and 3' end of the modified oligonucleotide. In an embodiment of Formula II, five of the modified intersubunit linkages are present at one or both of the 5' end and 3' end of the modified oligonucleotide. In an embodiment of Formula II, six of the modified intersubunit linkages are present at one or both of the 5' end and 3' end of the modified oligonucleotide. In an embodiment of Formula II, seven of the modified intersubunit linkages are present at one or both of the 5' end and 3' end of the modified oligonucleotide. In an embodiment of Formula II, eight of the modified intersubunit linkages are present at one or both of the 5' end and 3' end of the modified oligonucleotide. In an embodiment of Formula II, nine of the modified intersubunit linkages are present at one or both of the 5' end and 3' end of the modified oligonucleotide. In an embodiment of Formula II, ten of the modified intersubunit linkages are present at one or both of the 5' end and 3' end of the modified oligonucleotide.

In an embodiment of Formula II, the at least two modified intersubunit linkages are consecutive. In an embodiment of Formula II, three, four, or five of the modified intersubunit linkages are present at one or both of the 5' end and 3' end of the modified oligonucleotide and the intersubunit linkages are consecutive.

In an embodiment of Formula II, Y is $S^-$. In an embodiment of Formula II, Y is O. In an embodiment of Formula II, X is $OR^1$ or F.

In an embodiment of Formula II, the base moiety B is selected from the group consisting of adenine, guanine, cytosine, and uracil.

In an embodiment of Formula II, the base moiety B forms a base pairing interaction with another base moiety in the target RNA. In another embodiment of Formula Ia, the base moiety B does not base pair with the target RNA.

In one aspect, the disclosure provides a modified oligonucleotide comprising a 5' end, a 3' end and at least two modified intersubunit linkages of Formula IIIa:

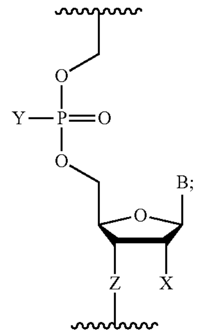

(IIIa)

wherein:

B is a base moiety;

X is selected from the group consisting of H, OH, $OR^1$, $R^1$, F, Cl, Br, I, SH, $SR^1$, $NH_2$, $NHR^1$, $NR^1_2$, and $COOR^1$;

Y is selected from the group consisting of $O^-$, OH, $OR^2$, $NH^-$, $NH_2$, $NR^2_2$, $BH_3$, $S^-$, $R^2$, and SH;

Z is O or $O(CH_2)_n^2$ wherein $n^2$ is 1 to 10;

$R^1$ is a substituted or unsubstituted $C_1$-$C_6$ alkyl, alkenyl, alkynyl, aryl, or mixtures thereof;

$R^2$ is a substituted or unsubstituted $C_1$-$C_6$ alkyl, alkenyl, alkynyl, aryl, or mixtures thereof; and wherein at least two of the modified intersubunit linkages are present at one or both of the 5' end and the 3' end of the modified oligonucleotide.

In an embodiment of Formula IIIa, between two and ten (i.e., 2, 3, 4, 5, 6, 7, 8, 9, or 10) of the modified intersubunit linkages are present at one or both of the 5' end and 3' end of the modified oligonucleotide.

In an embodiment of Formula IIIa, between two and five of the modified intersubunit linkages are present at one or both of the 5' end and 3' end of the modified oligonucleotide.

In an embodiment of Formula IIIa, two of the modified intersubunit linkages are present at one or both of the 5' end and 3' end of the modified oligonucleotide. In an embodiment of Formula IIIa, three of the modified intersubunit linkages are present at one or both of the 5' end and 3' end of the modified oligonucleotide. In an embodiment of Formula IIIa, four of the modified intersubunit linkages are present at one or both of the 5' end and 3' end of the modified oligonucleotide. In an embodiment of Formula IIIa, five of the modified intersubunit linkages are present at one or both of the 5' end and 3' end of the modified oligonucleotide. In an embodiment of Formula IIIa, six of the modified intersubunit linkages are present at one or both of the 5' end and 3' end of the modified oligonucleotide. In an embodiment of Formula IIIa, seven of the modified intersubunit linkages are present at one or both of the 5' end and 3' end of the modified oligonucleotide. In an embodiment of Formula IIIa, eight of the modified intersubunit linkages are present at one or both of the 5' end and 3' end of the modified oligonucleotide. In an embodiment of Formula IIIa, nine of the modified intersubunit linkages are present at one or both of the 5' end and 3' end of the modified oligonucleotide. In an embodiment of Formula IIIa, ten of the modified intersubunit linkages are present at one or both of the 5' end and 3' end of the modified oligonucleotide.

In an embodiment of Formula IIIa, the at least two modified intersubunit linkages are consecutive. In an embodiment of Formula IIIa, three, four, or five of the modified intersubunit linkages are present at one or both of the 5' end and 3' end of the modified oligonucleotide and the intersubunit linkages are consecutive.

In an embodiment of Formula IIIa, the base moiety B is selected from the group consisting of adenine, guanine, cytosine, and uracil.

In an embodiment of Formula IIIa, the base moiety B forms a base pairing interaction with another base moiety.

In one aspect, the disclosure provides a modified oligonucleotide comprising a 5' end, a 3' end and at least two modified intersubunit linkages of Formula III:

(III)

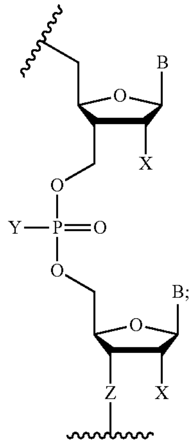

wherein:

B is a base moiety;

X is selected from the group consisting of H, OH, $OR^1$, $R^1$, F, Cl, Br, I, SH, $SR^1$, $NH_2$, $NHR^1$, $NR^1_2$, and $COOR^1$;

Y is selected from the group consisting of $O^-$, OH, $OR^2$, $NH^-$, $NH_2$, $NR^2_2$, $BH_3$, $S^-$, $R^2$, and SH;

Z is O or $O(CH_2)_n{}^2$ wherein $n^2$ is 1 to 10;

$R^1$ is a substituted or unsubstituted $C_1$-$C_6$ alkyl, alkenyl, alkynyl, aryl, or mixtures thereof;

$R^2$ is a substituted or unsubstituted $C_1$-$C_6$ alkyl, alkenyl, alkynyl, aryl, or mixtures thereof; and wherein at least two of the modified intersubunit linkages are present at one or both of the 5' end and the 3' end of the modified oligonucleotide.

In an embodiment of Formula III, between two and ten (i.e., 2, 3, 4, 5, 6, 7, 8, 9, or 10) of the modified intersubunit linkages are present at one or both of the 5' end and 3' end of the modified oligonucleotide. In an embodiment of Formula III, between two and five of the modified intersubunit linkages are present at one or both of the 5' end and 3' end of the modified oligonucleotide.

In an embodiment of Formula III, two of the modified intersubunit linkages are present at one or both of the 5' end and 3' end of the modified oligonucleotide. In an embodiment of Formula III, three of the modified intersubunit linkages are present at one or both of the 5' end and 3' end of the modified oligonucleotide. In an embodiment of Formula III, four of the modified intersubunit linkages are present at one or both of the 5' end and 3' end of the modified oligonucleotide. In an embodiment of Formula III, five of the modified intersubunit linkages are present at one or both of the 5' end and 3' end of the modified oligonucleotide. In an embodiment of Formula III, six of the modified intersubunit linkages are present at one or both of the 5' end and 3' end of the modified oligonucleotide. In an embodiment of Formula III, seven of the modified intersubunit linkages are present at one or both of the 5' end and 3' end of the modified oligonucleotide. In an embodiment of Formula III, eight of the modified intersubunit linkages are present at one or both of the 5' end and 3' end of the modified oligonucleotide. In an embodiment of Formula III, nine of the modified intersubunit linkages are present at one or both of the 5' end and 3' end of the modified oligonucleotide. In an embodiment of Formula III, ten of the modified intersubunit linkages are present at one or both of the 5' end and 3' end of the modified oligonucleotide.

In an embodiment of Formula III, the at least two modified intersubunit linkages are consecutive. In an embodiment of Formula III, three, four, or five of the modified intersubunit linkages are present at one or both of the 5' end and 3' end of the modified oligonucleotide and the intersubunit linkages are consecutive.

In an embodiment of Formula III, the base moiety B is selected from the group consisting of adenine, guanine, cytosine, and uracil.

In an embodiment of Formula III, the base moiety B forms a base pairing interaction with another base moiety in the target RNA. In another embodiment of Formula Ia, the base moiety B does not base pair with the target RNA.

In one aspect, the disclosure provides a modified oligonucleotide comprising a 5' end, a 3' end and at least two modified intersubunit linkages of Formula IVa:

(IVa)

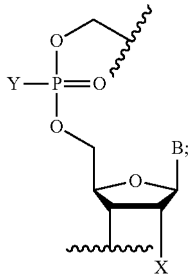

wherein:

B is a base moiety;

X is selected from the group consisting of H, OH, $OR^1$, $R^1$, F, Cl, Br, I, SH, $SR^1$, $NH_2$, $NHR^1$, $NR^1_2$, and $COOR^1$;

Y is selected from the group consisting of $O^-$, OH, $OR^2$, $NH^-$, $NH_2$, $NR^2_2$, $BH_3$, $S^-$, $R^2$, and SH;

Z is O or $O(CH_2)_n{}^2$ wherein $n^2$ is 1 to 10;

$R^1$ is a substituted or unsubstituted $C_1$-$C_6$ alkyl, alkenyl, alkynyl, aryl, or mixtures thereof;

$R^2$ is a substituted or unsubstituted $C_1$-$C_6$ alkyl, alkenyl, alkynyl, aryl, or mixtures thereof; and wherein at least two of the modified intersubunit linkages are present at one or both of the 5' end and the 3' end of the modified oligonucleotide.

In an embodiment of Formula IVa, between two and ten (i.e., 2, 3, 4, 5, 6, 7, 8, 9, or 10) of the modified intersubunit linkages are present at one or both of the 5' end and 3' end of the modified oligonucleotide.

In an embodiment of Formula IVa, between two and five of the modified intersubunit linkages are present at one or both of the 5' end and 3' end of the modified oligonucleotide.

In an embodiment of Formula IVa, two of the modified intersubunit linkages are present at one or both of the 5' end and 3' end of the modified oligonucleotide. In an embodiment of Formula IVa, three of the modified intersubunit linkages are present at one or both of the 5' end and 3' end of the modified oligonucleotide. In an embodiment of Formula IVa, four of the modified intersubunit linkages are present at one or both of the 5' end and 3' end of the modified oligonucleotide. In an embodiment of Formula IVa, five of the modified intersubunit linkages are present at one or both of the 5' end and 3' end of the modified oligonucleotide. In an embodiment of Formula IVa, six of the modified intersubunit linkages are present at one or both of the 5' end and 3' end of the modified oligonucleotide. In an embodiment of Formula IVa, seven of the modified intersubunit linkages are present at one or both of the 5' end and 3' end of the modified oligonucleotide. In an embodiment of Formula IVa, eight of the modified intersubunit linkages are present at one or both of the 5' end and 3' end of the modified oligonucleotide. In an embodiment of Formula IVa, nine of the modified intersubunit linkages are present at one or both of the 5' end and 3' end of the modified oligonucleotide. In an embodiment of Formula IVa, ten of the modified intersubunit linkages are present at one or both of the 5' end and 3' end of the modified oligonucleotide.

In an embodiment of Formula IVa, the at least two modified intersubunit linkages are consecutive. In an embodiment of Formula IVa, three, four, or five of the modified intersubunit linkages are present at one or both of the 5' end and 3' end of the modified oligonucleotide and the intersubunit linkages are consecutive.

In an embodiment of Formula IVa, the base moiety B is selected from the group consisting of adenine, guanine, cytosine, and uracil.

In an embodiment of Formula IVa, the base moiety B forms a base pairing interaction with another base moiety.

In one aspect, the disclosure provides a modified oligonucleotide comprising a 5' end, a 3' end and at least two modified intersubunit linkages of Formula IV:

(IV)

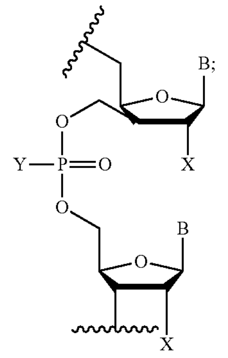

wherein:

B is a base moiety;

X is selected from the group consisting of H, OH, $OR^1$, $R^1$, F, Cl, Br, I, SH, $SR^1$, $NH_2$, $NHR^1$, $NR^1_2$, and $COOR^1$;

Y is selected from the group consisting of $O^-$, OH, $OR^2$, $NH^-$, $NH_2$, $NR^2_2$, $BH_3$, $S^-$, $R^2$, and SH;

$R^1$ is a substituted or unsubstituted $C_1$-$C_6$ alkyl, alkenyl, alkynyl, aryl, or mixtures thereof;

$R^2$ is a substituted or unsubstituted $C_1$-$C_6$ alkyl, alkenyl, alkynyl, aryl, or mixtures thereof; and wherein at least two of the modified intersubunit linkages are present at one or both of the 5' end and the 3' end of the modified oligonucleotide.

In an embodiment of Formula IV, between two and ten (i.e., 2, 3, 4, 5, 6, 7, 8, 9, or 10) of the modified intersubunit linkages are present at one or both of the 5' end and 3' end of the modified oligonucleotide.

In an embodiment of Formula IV, between two and five of the modified intersubunit linkages are present at one or both of the 5' end and 3' end of the modified oligonucleotide.

In an embodiment of Formula IV, two of the modified intersubunit linkages are present at one or both of the 5' end and 3' end of the modified oligonucleotide. In an embodiment of Formula IV, three of the modified intersubunit linkages are present at one or both of the 5' end and 3' end of the modified oligonucleotide. In an embodiment of Formula IV, four of the modified intersubunit linkages are present at one or both of the 5' end and 3' end of the modified oligonucleotide. In an embodiment of Formula IV, five of the modified intersubunit linkages are present at one or both of the 5' end and 3' end of the modified oligonucleotide. In an embodiment of Formula IV, six of the modified intersubunit linkages are present at one or both of the 5' end and 3' end of the modified oligonucleotide. In an embodiment of Formula IV, seven of the modified intersubunit linkages are present at one or both of the 5' end and 3' end of the modified oligonucleotide. In an embodiment of Formula IV, eight of the modified intersubunit linkages are present at one or both of the 5' end and 3' end of the modified oligonucleotide. In an embodiment of Formula IV, nine of the modified intersubunit linkages are present at one or both of the 5' end and 3' end of the modified oligonucleotide. In an embodiment of Formula IV, ten of the modified intersubunit linkages are present at one or both of the 5' end and 3' end of the modified oligonucleotide.

In an embodiment of Formula IV, the at least two modified intersubunit linkages are consecutive. In an embodiment of Formula IV, three, four, or five of the modified intersubunit linkages are present at one or both of the 5' end and 3' end of the modified oligonucleotide and the intersubunit linkages are consecutive.

In an embodiment of Formula IV, the base moiety B is selected from the group consisting of adenine, guanine, cytosine, and uracil.

In an embodiment of Formula IV, the base moiety B forms a base pairing interaction with another base moiety in the target RNA. In another embodiment of Formula Ia, the base moiety B does not base pair with the target RNA.

In one aspect, the disclosure provides a modified oligonucleotide comprising a 5' end, a 3' end and at least two modified intersubunit linkages of Formula Va:

(Va)

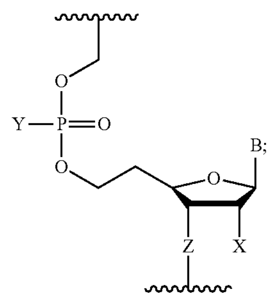

wherein:

B is a base moiety;

X is selected from the group consisting of H, OH, $OR^1$, $R^1$, F, Cl, Br, I, SH, $SR^1$, $NH_2$, $NHR^1$, $NR^1_2$, and $COOR^1$;

Y is selected from the group consisting of $O^-$, OH, $OR^2$, $NH^-$, $NH_2$, $NR^2_2$, $BH_3$, $S^-$, $R^2$, and SH;

Z is O or $O(CH_2)_n{}^2$ wherein $n^2$ is 1 to 10;

$R^1$ is a substituted or unsubstituted $C_1$-$C_6$ alkyl, alkenyl, alkynyl, aryl, or mixtures thereof;

$R^2$ is a substituted or unsubstituted $C_1$-$C_6$ alkyl, alkenyl, alkynyl, aryl, or mixtures thereof; and wherein at least two of the modified intersubunit linkages are present at one or both of the 5' end and the 3' end of the modified oligonucleotide.

In an embodiment of Formula Va, between two and ten (i.e., 2, 3, 4, 5, 6, 7, 8, 9, or 10) of the modified intersubunit linkages are present at one or both of the 5' end and 3' end of the modified oligonucleotide.

In an embodiment of Formula Va, between two and five of the modified intersubunit linkages are present at one or both of the 5' end and 3' end of the modified oligonucleotide.

In an embodiment of Formula Va, two of the modified intersubunit linkages are present at one or both of the 5' end and 3' end of the modified oligonucleotide. In an embodiment of Formula Va, three of the modified intersubunit linkages are present at one or both of the 5' end and 3' end of the modified oligonucleotide. In an embodiment of Formula Va, four of the modified intersubunit linkages are present at one or both of the 5' end and 3' end of the modified oligonucleotide. In an embodiment of Formula Va, five of the modified intersubunit linkages are present at one or both of the 5' end and 3' end of the modified oligonucleotide. In an embodiment of Formula Va, six of the modified intersubunit linkages are present at one or both of the 5' end and 3' end of the modified oligonucleotide. In an embodiment of Formula Va, seven of the modified intersubunit linkages are present at one or both of the 5' end and 3' end of the modified oligonucleotide. In an embodiment of Formula Va, eight of the modified intersubunit linkages are present at one or both of the 5' end and 3' end of the modified oligonucleotide. In an embodiment of Formula Va, nine of the modified intersubunit linkages are present at one or both of the 5' end and 3' end of the modified oligonucleotide. In an embodiment of Formula Va, ten of the modified intersubunit linkages are present at one or both of the 5' end and 3' end of the modified oligonucleotide.

In an embodiment of Formula Va, the at least two modified intersubunit linkages are consecutive. In an embodiment of Formula Va, three, four, or five of the modified intersubunit linkages are present at one or both of the 5' end and 3' end of the modified oligonucleotide and the intersubunit linkages are consecutive.

In an embodiment of Formula Va, the base moiety B is selected from the group consisting of adenine, guanine, cytosine, and uracil.

In an embodiment of Formula Va, the base moiety B forms abase pairing interaction with another base moiety in the target RNA. In another embodiment of Formula Ia, the base moiety B does not base pair with the target RNA.

In one aspect, the disclosure provides a modified oligonucleotide comprising a 5' end, a 3' end and at least two modified intersubunit linkages of Formula V:

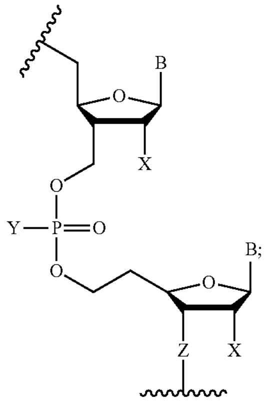

(V)

wherein:

B is a base moiety;

X is selected from the group consisting of H, OH, $OR^1$, $R^1$, F, Cl, Br, I, SH, $SR^1$, $NH_2$, $NHR^1$, $NR^1_2$, and $COOR^1$;

Y is selected from the group consisting of $O^-$, OH, $OR^2$, $NH^-$, $NH_2$, $NR^2_2$, $BH_3$, $S^-$, $R^2$, and SH;

Z is O or $O(CH_2)_n{}^2$ wherein $n^2$ is 1 to 10;

$R^1$ is a substituted or unsubstituted $C_1$-$C_6$ alkyl, alkenyl, alkynyl, aryl, or mixtures thereof;

$R^2$ is a substituted or unsubstituted $C_1$-$C_6$ alkyl, alkenyl, alkynyl, aryl, or mixtures thereof; and wherein at least two of the modified intersubunit linkages are present at one or both of the 5' end and the 3' end of the modified oligonucleotide.

In an embodiment of Formula V, between two and ten (i.e., 2, 3, 4, 5, 6, 7, 8, 9, or 10) of the modified intersubunit linkages are present at one or both of the 5' end and 3' end of the modified oligonucleotide. In an embodiment of Formula V, between two and five of the modified intersubunit linkages are present at one or both of the 5' end and 3' end of the modified oligonucleotide. In an embodiment of Formula V, two of the modified intersubunit linkages are present at one or both of the 5' end and 3' end of the modified oligonucleotide. In an embodiment of Formula V, three of the modified intersubunit linkages are present at one or both of the 5' end and 3' end of the modified oligonucleotide. In an embodiment of Formula V, four of the modified intersubunit linkages are present at one or both of the 5' end and 3' end of the modified oligonucleotide. In an embodiment of Formula V, five of the modified intersubunit linkages are present at one or both of the 5' end and 3' end of the modified oligonucleotide. In an embodiment of Formula V, six of the modified intersubunit linkages are present at one or both of the 5' end and 3' end of the modified oligonucleotide. In an embodiment of Formula V, seven of the modified intersubunit linkages are present at one or both of the 5' end and 3' end of the modified oligonucleotide. In an embodiment of Formula V, eight of the modified intersubunit linkages are present at one or both of the 5' end and 3' end of the modified oligonucleotide. In an embodiment of Formula V, nine of the modified intersubunit linkages are present at one or both of the 5' end and 3' end of the modified oligonucleotide. In an embodiment of Formula V, ten of the modified intersubunit linkages are present at one or both of the 5' end and 3' end of the modified oligonucleotide.

In an embodiment of Formula V, the at least two modified intersubunit linkages are consecutive. In an embodiment of Formula V, three, four, or five of the modified intersubunit linkages are present at one or both of the 5' end and 3' end of the modified oligonucleotide and the intersubunit linkages are consecutive.

In an embodiment of Formula V, the base moiety B is selected from the group consisting of adenine, guanine, cytosine, and uracil.

In an embodiment of Formula V, the base moiety B forms a base pairing interaction with another base moiety in the target RNA. In another embodiment of Formula Ia, the base moiety B does not base pair with the target RNA.

In one aspect, the disclosure provides a modified oligonucleotide comprising a 5' end, a 3' end and at least two modified intersubunit linkages of Formula VIa:

(VIa)

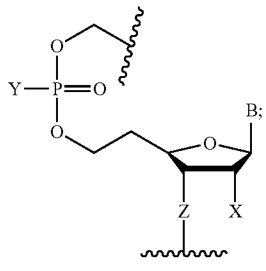

wherein:

B is a base moiety;

X is selected from the group consisting of H, OH, $OR^1$, $R^1$, F, Cl, Br, I, SH, $SR^1$, $NH_2$, $NHR^1$, $NR^1_2$, and $COOR^1$;

Y is selected from the group consisting of $O^-$, OH, $OR^2$, $NH^-$, $NH_2$, $NR^2_2$, $BH_3$, $S^-$, $R^2$, and SH;

Z is O or $O(CH_2)_{n^2}$ wherein $n^2$ is 1 to 10;

$R^1$ is a substituted or unsubstituted $C_1$-$C_6$ alkyl, alkenyl, alkynyl, aryl, or mixtures thereof;

$R^2$ is a substituted or unsubstituted $C_1$-$C_6$ alkyl, alkenyl, alkynyl, aryl, or mixtures thereof; and wherein at least two of the modified intersubunit linkages are present at one or both of the 5' end and the 3' end of the modified oligonucleotide.

In an embodiment of Formula VIa, between two and ten (i.e., 2, 3, 4, 5, 6, 7, 8, 9, or 10) of the modified intersubunit linkages are present at one or both of the 5' end and 3' end of the modified oligonucleotide.

In an embodiment of Formula VIa, between two and five of the modified intersubunit linkages are present at one or both of the 5' end and 3' end of the modified oligonucleotide.

In an embodiment of Formula VIa, two of the modified intersubunit linkages are present at one or both of the 5' end and 3' end of the modified oligonucleotide. In an embodiment of Formula VIa, three of the modified intersubunit linkages are present at one or both of the 5' end and 3' end of the modified oligonucleotide. In an embodiment of Formula VIa, four of the modified intersubunit linkages are present at one or both of the 5' end and 3' end of the modified oligonucleotide. In an embodiment of Formula VIa, five of the modified intersubunit linkages are present at one or both of the 5' end and 3' end of the modified oligonucleotide. In an embodiment of Formula VIa, six of the modified intersubunit linkages are present at one or both of the 5' end and 3' end of the modified oligonucleotide. In an embodiment of Formula VIa, seven of the modified intersubunit linkages are present at one or both of the 5' end and 3' end of the modified oligonucleotide. In an embodiment of Formula VIa, eight of the modified intersubunit linkages are present at one or both of the 5' end and 3' end of the modified oligonucleotide. In an embodiment of Formula VIa, nine of the modified intersubunit linkages are present at one or both of the 5' end and 3' end of the modified oligonucleotide. In an embodiment of Formula VIa, ten of the modified intersubunit linkages are present at one or both of the 5' end and 3' end of the modified oligonucleotide.

In one aspect, the disclosure provides a modified oligonucleotide comprising a 5' end, a 3' end and at least two modified intersubunit linkages of Formula VI:

(VI)

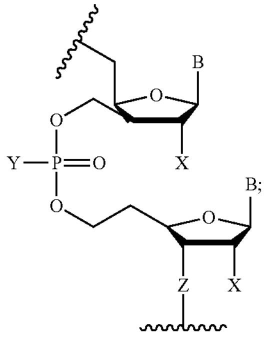

wherein:

B is a base moiety;

X is selected from the group consisting of H, OH, $OR^1$, $R^1$, F, Cl, Br, I, SH, $SR^1$, $NH_2$, $NHR^1$, $NR^1_2$, and $COOR^1$;

Y is selected from the group consisting of $O^-$, OH, $OR^2$, $NH^-$, $NH_2$, $NR^2_2$, $BH_3$, $S^-$, $R^2$, and SH;

Z is O or $O(CH_2)_{n^2}$ wherein $n^2$ is 1 to 10;

$R^1$ is a substituted or unsubstituted $C_1$-$C_6$ alkyl, alkenyl, alkynyl, aryl, or mixtures thereof;

$R^2$ is a substituted or unsubstituted $C_1$-$C_6$ alkyl, alkenyl, alkynyl, aryl, or mixtures thereof; and wherein at least two of the modified intersubunit linkages are present at one or both of the 5' end and the 3' end of the modified oligonucleotide.

In an embodiment of Formula VI, between two and ten (i.e., 2, 3, 4, 5, 6, 7, 8, 9, or 10) of the modified intersubunit linkages are present at one or both of the 5' end and 3' end of the modified oligonucleotide.

In an embodiment of Formula VI, between two and five of the modified intersubunit linkages are present at one or both of the 5' end and 3' end of the modified oligonucleotide.

In an embodiment of Formula VI, two of the modified intersubunit linkages are present at one or both of the 5' end and 3' end of the modified oligonucleotide. In an embodiment of Formula VI, three of the modified intersubunit linkages are present at one or both of the 5' end and 3' end of the modified oligonucleotide. In an embodiment of Formula VI, four of the modified intersubunit linkages are present at one or both of the 5' end and 3' end of the modified oligonucleotide. In an embodiment of Formula VI, five of the modified intersubunit linkages are present at one or both of the 5' end and 3' end of the modified oligonucleotide. In an embodiment of Formula VI, six of the modified intersubunit linkages are present at one or both of the 5' end and 3' end of the modified oligonucleotide. In an embodiment of Formula VI, seven of the modified intersubunit linkages are present at one or both of the 5' end and 3' end of the modified oligonucleotide. In an embodiment of Formula VI, eight of the modified intersubunit linkages are present at one or both of the 5' end and 3' end of the modified oligonucleotide. In an embodiment of Formula VI, nine of the modified intersubunit linkages are present at one or both of the 5' end and 3' end of the modified oligonucleotide. In an embodiment of Formula VI, ten of the modified intersubunit linkages are present at one or both of the 5' end and 3' end of the modified oligonucleotide.

In an embodiment of Formula VI, the at least two modified intersubunit linkages are consecutive. In an embodiment of Formula VI, three, four, or five of the modified intersubunit linkages are present at one or both of the 5' end and 3' end of the modified oligonucleotide and the intersubunit linkages are consecutive.

In an embodiment of Formula VI, the base moiety B is selected from the group consisting of adenine, guanine, cytosine, and uracil.

In an embodiment of Formula VI, the base moiety B forms a base pairing interaction with another base moiety in the target RNA. In another embodiment of Formula Ia, the base moiety B does not base pair with the target RNA.

In one aspect, the disclosure provides a method of increasing the stability of an oligonucleotide, comprising introducing at least one modified intersubunit linkage of Formula Ia:

(Ia)

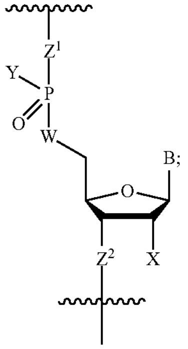

wherein:

B is a base moiety;

W is O or $O(CH_2)_n$, wherein $n^1$ is 1 to 10;

X is selected from the group consisting of H, OH, $OR^1$, $R^1$, F, Cl, Br, I, SH, $SR^1$, $NH_2$, $NHR^1$, $NR^1_2$, and $COOR^1$;

Y is selected from the group consisting of $O^-$, OH, $OR^2$, $NH^-$, $NH_2$, $NR^2_2$, $BH_3$, $S^-$, $R^2$, and SH;

$Z^1$ is O or $O(CH_2)_n{}^2$ wherein $n^2$ is 1 to 10;

$Z^2$ is O or $O(CH_2)_{n3}{}^2$ wherein $n^3$ is 1 to 10;

$R^1$ is a substituted or unsubstituted $C_1$-$C_6$ alkyl, alkenyl, alkynyl, aryl, or mixtures thereof; and $R^2$ is a substituted or unsubstituted $C_1$-$C_6$ alkyl, alkenyl, alkynyl, aryl, or mixtures thereof, thereby increasing the stability of the oligonucleotide.

In an embodiment of the method, the oligonucleotide has increased stability relative to an oligonucleotide that does not comprise at least one modified intersubunit linkage of Formula Ia.

In an embodiment of the method, the oligonucleotide has increased serum stability relative to an oligonucleotide that does not comprise at least one modified intersubunit linkage of Formula Ia.

In an embodiment of the method, the oligonucleotide comprises a 5' end and a 3' end, and wherein the at least one modified intersubunit linkage of Formula Ia is present at the one or both of the 5' end and 3' end.

In an embodiment of the method, the oligonucleotide comprises at least one modified intersubunit linkage of Formula Ia at the 5' end of the oligonucleotide.

In an embodiment of the method, the oligonucleotide comprises at least two modified intersubunit linkages of Formula Ia at the 5' end of the oligonucleotide.

In an embodiment of the method, the oligonucleotide comprises at least three modified intersubunit linkages of Formula Ia at the 5' end of the oligonucleotide.

In an embodiment of the method, the oligonucleotide comprises at least four modified intersubunit linkages of Formula Ia at the 5' end of the oligonucleotide.

In an embodiment of the method, the oligonucleotide comprises at least five modified intersubunit linkages of Formula Ia at the 5' end of the oligonucleotide.

In an embodiment of the method, the oligonucleotide comprises one, two, three, four, or five modified intersubunit linkages of Formula Ia at the 5' end of the oligonucleotide.

In an embodiment of the method, the oligonucleotide comprises at least two consecutive modified intersubunit linkages of Formula Ia at the 5' end of the oligonucleotide.

In an embodiment of the method, the oligonucleotide comprises two, three, four, or five consecutive modified intersubunit linkages of Formula Ia at the 5' end of the oligonucleotide.

In an embodiment of the method, the oligonucleotide comprises four consecutive modified intersubunit linkages of Formula Ia at the 5' end of the oligonucleotide.

In an embodiment of the method, the oligonucleotide comprises at least one modified intersubunit linkage of Formula Ia at the 3' end of the oligonucleotide.

In an embodiment of the method, the oligonucleotide comprises at least two modified intersubunit linkages of Formula Ia at the 3' end of the oligonucleotide.

In an embodiment of the method, the oligonucleotide comprises at least three modified intersubunit linkages of Formula Ia at the 3' end of the oligonucleotide.

In an embodiment of the method, the oligonucleotide comprises at least four modified intersubunit linkages of Formula Ia at the 3' end of the oligonucleotide.

In an embodiment of the method, the oligonucleotide comprises at least five modified intersubunit linkages of Formula Ia at the 3' end of the oligonucleotide.

In an embodiment of the method, the oligonucleotide comprises one, two, three, four, or five modified intersubunit linkages of Formula Ia at the 3' end of the oligonucleotide.

In an embodiment of the method, the oligonucleotide comprises at least two consecutive modified intersubunit linkages of Formula Ia at the 3' end of the oligonucleotide.

In an embodiment of the method, the oligonucleotide comprises two, three, four, or five consecutive modified intersubunit linkages of Formula Ia at the 3' end of the oligonucleotide.

In an embodiment of the method, the oligonucleotide comprises four consecutive modified intersubunit linkages of Formula Ia at the 3' end of the oligonucleotide.

In an embodiment of the method, the oligonucleotide comprises increased resistance to degradation by one or more of a 5' exonuclease, a 3' exonuclease, and an endonuclease.

In an embodiment of the method, the oligonucleotide comprises increased resistance to degradation by a 5' exonuclease. In an embodiment of the method, the oligonucleotide comprises increased resistance to degradation by a 3' exonuclease. In an embodiment of the method, the oligonucleotide comprises increased resistance to degradation by an endonuclease.

In an embodiment of the method, the oligonucleotide comprises or consists of 8 or fewer (e.g., 8, 7, 6, 5, 4, 3, 2, 1, or 0) phosphorothioate modifications. In an embodiment of the method, the oligonucleotide comprises or consists of 8 phosphorothioate modifications. In an embodiment of the method, the oligonucleotide comprises or consists of 7 phosphorothioate modifications. In an embodiment of the method, the oligonucleotide comprises or consists of 6 phosphorothioate modifications. In an embodiment of the method, the oligonucleotide comprises or consists of 5 phosphorothioate modifications. In an embodiment of the method, the oligonucleotide comprises or consists of 4 phosphorothioate modifications. In an embodiment of the method, the oligonucleotide comprises or consists of 3 phosphorothioate modifications. In an embodiment of the method, the oligonucleotide comprises or consists of 2 phosphorothioate modifications. In an embodiment of the method, the oligonucleotide comprises or consists of 1 phosphorothioate modifications. In an embodiment of the method, the oligonucleotide comprises or consists of 0 phosphorothioate modifications.

In one aspect, the disclosure provides a method of increasing the stability of an oligonucleotide, comprising introducing at least one modified intersubunit linkage of Formula I:

(I)

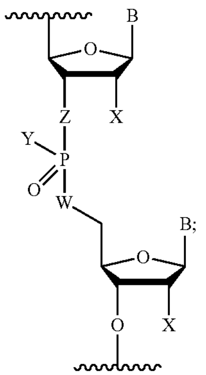

wherein:

B is a base moiety;

W is O or $O(CH_2)_{n^1}$, wherein $n^1$ is 1 to 10;

X is selected from the group consisting of H, OH, $OR^1$, $R^1$, F, Cl, Br, I, SH, $SR^1$, $NH_2$, $NHR^1$, $NR^1_2$, and $COOR^1$;

Y is selected from the group consisting of $O^-$, OH, $OR^2$, $NH^-$, $NH_2$, $NR^2_2$, $BH_3$, $S^-$, $R^2$, and SH;

Z is O or $O(CH_2)_{n^2}$ wherein $n^2$ is 1 to 10;

$R^1$ is a substituted or unsubstituted $C_1$-$C_6$ alkyl, alkenyl, alkynyl, aryl, or mixtures thereof; and $R^2$ is a substituted or unsubstituted $C_1$-$C_6$ alkyl, alkenyl, alkynyl, aryl, or mixtures thereof; thereby increasing the stability of the oligonucleotide.

In an embodiment of the method, the oligonucleotide has increased stability relative to an oligonucleotide that does not comprise at least one modified intersubunit linkage of Formula I.

In an embodiment of the method, the oligonucleotide has increased serum stability relative to an oligonucleotide that does not comprise at least one modified intersubunit linkage of Formula I.

In an embodiment of the method, the oligonucleotide comprises a 5' end and a 3' end, and wherein the at least one modified intersubunit linkage of Formula I is present at the one or both of the 5' end and 3' end. In an embodiment of the method, the oligonucleotide comprises at least one modified intersubunit linkage of Formula I at the 5' end of the oligonucleotide. In an embodiment of the method, the oligonucleotide comprises at least two modified intersubunit linkages of Formula I at the 5' end of the oligonucleotide. In an embodiment of the method, the oligonucleotide comprises at least three modified intersubunit linkages of Formula I at the 5' end of the oligonucleotide. In an embodiment of the method, the oligonucleotide comprises at least four modified intersubunit linkages of Formula I at the 5' end of the oligonucleotide. In an embodiment of the method, the oligonucleotide comprises at least five modified intersubunit linkages of Formula I at the 5' end of the oligonucleotide. In an embodiment of the method, the oligonucleotide comprises one, two, three, four, or five modified intersubunit linkages of Formula I at the 5' end of the oligonucleotide. In an embodiment of the method, the oligonucleotide comprises at least two consecutive modified intersubunit linkages of Formula I at the 5' end of the oligonucleotide. In an embodiment of the method, the oligonucleotide comprises four consecutive modified intersubunit linkages of Formula I at the 5' end of the oligonucleotide. In an embodiment of the method, the oligonucleotide comprises at least one modified intersubunit linkage of Formula I at the 3' end of the oligonucleotide. In an embodiment of the method, the oligonucleotide comprises at least two modified intersubunit linkages of Formula I at the 3' end of the oligonucleotide. In an embodiment of the method, the oligonucleotide comprises at least three modified intersubunit linkages of Formula I at the 3' end of the oligonucleotide. In an embodiment of the method, the oligonucleotide comprises at least four modified intersubunit linkages of Formula I at the 3' end of the oligonucleotide. In an embodiment of the method, the oligonucleotide comprises at least five modified intersubunit linkages of Formula I at the 3' end of the oligonucleotide. In an embodiment of the method, the oligonucleotide comprises one, two, three, four, or five modified intersubunit linkages of Formula I at the 3' end of the oligonucleotide. In an embodiment of the method, the oligonucleotide comprises at least two consecutive modified intersubunit linkages of Formula I at the 3' end of the oligonucleotide. In an embodiment of the method, the oligonucleotide comprises four consecutive modified intersubunit linkages of Formula I at the 3' end of the oligonucleotide.

In an embodiment of the method, the oligonucleotide comprises increased resistance to degradation by one or more of a 5' exonuclease, a 3' exonuclease, and an endonuclease. In an embodiment of the method, the oligonucleotide comprises increased resistance to degradation by a 5' exonuclease. In an embodiment of the method, the oligonucleotide comprises increased resistance to degradation by a 3' exonuclease. In an embodiment of the method, the oligonucleotide comprises increased resistance to degradation by an endonuclease.

In one aspect, the disclosure provides a modified universal sequence, comprising at least two modified intersubunit linkages of Formula Ia:

(Ia)

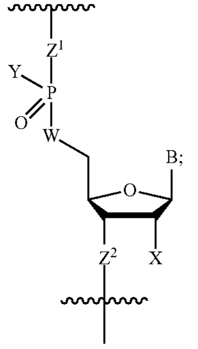

wherein:

B is a base moiety;

W is O or $O(CH_2)_n$, wherein $n^1$ is 1 to 10;

X is selected from the group consisting of H, OH, $OR^1$, $R^1$, F, Cl, Br, I, SH, $SR^1$, $NH_2$, $NHR^1$, $NR^1_2$, and $COOR^1$;

Y is selected from the group consisting of $O^-$, OH, $OR^2$, $NH^-$, $NH_2$, $NR^2_2$, $BH_3$, $S^-$, $R^2$, and SH;

$Z^1$ is O or $O(CH_2)_n{}^2$ wherein $n^2$ is 1 to 10;

$Z^2$ is O or $O(CH_2)_n{}^3$ wherein $n^3$ is 1 to 10;

$R^1$ is a substituted or unsubstituted $C_1$-$C_6$ alkyl, alkenyl, alkynyl, aryl, or mixtures thereof; and $R^2$ is a substituted or unsubstituted $C_1$-$C_6$ alkyl, alkenyl, alkynyl, aryl, or mixtures thereof.

In an embodiment, the modified universal sequence comprises between two to ten consecutive nucleotides in length.

In an embodiment, the modified universal sequence comprises four consecutive nucleotides in length. In an embodiment, the modified universal sequence comprises five consecutive nucleotides in length.

In an embodiment, the modified universal sequence comprises at least two consecutive modified intersubunit linkages of Formula Ia. In an embodiment, the modified universal sequence comprises four consecutive modified intersubunit linkages of Formula Ia. In an embodiment, the modified universal sequence comprises five consecutive modified intersubunit linkages of Formula Ia.

In an embodiment, the modified universal sequence comprises a nucleotide sequence selected from the group consisting of: UUUU, AAAA, CCCC, UUUUU, AAAAA, and CCCCC.

In an embodiment, $Z^1$ is $O(CH_2)_n{}^2$, $n^2$ is 1, W is O, and Y is $O^-$. In an embodiment, $Z^1$ is O, W is $O(CH_2)_n{}^1$, $n^1$ is 1, and Y is $O^-$. In an embodiment, $Z^1$ is $O(CH_2)_n{}^2$, $n^2$ is 1, W is O, and Y is $O^-$. In an embodiment, $Z^1$ is $O(CH_2)_n{}^2$, $n^2$ is 1, W is $O(CH_2)_n{}^1$, and Y is $O^-$. In an embodiment, $Z^1$ is $O(CH_2)_n{}^2$, $n^2$ is 1, W is $O(CH_2)_n$, and Y is $S^-$. In an embodiment, Y is $S^-$. In an embodiment, X is $OR^1$ or F.

In an embodiment, the base moiety B is selected from the group consisting of adenine, guanine, cytosine, and uracil.

In an embodiment the base moiety B forms a base pairing interaction with another base moiety in the target RNA. In another embodiment of Formula Ia, the base moiety B does not base pair with the target RNA.

In another aspect, the disclosure provides an oligonucleotide comprising the modified universal sequence comprising at least two modified intersubunit linkages of Formula Ia recited above, wherein the modified universal sequence is present at one or both of a 5' end and a 3' end of the oligonucleotide.

In an embodiment, the oligonucleotide is selected from the group consisting of an siRNA, a miRNA, an antisense oligonucleotide, a ribozyme, and a mRNA.

In an embodiment, the siRNA comprises an antisense strand and a sense strand, and wherein one or both of the antisense strand and the sense strand comprise the modified intersubunit linkages.

In an embodiment, the antisense strand comprises or consists of 8 or fewer (e.g., 8, 7, 6, 5, 4, 3, 2, 1, or 0) phosphorothioate modifications. In an embodiment, the antisense strand comprises or consists of 8 phosphorothioate modifications. In an embodiment, the antisense strand comprises or consists of 7 phosphorothioate modifications. In an embodiment, the antisense strand comprises or consists of 6 phosphorothioate modifications. In an embodiment, the antisense strand comprises or consists of 5 phosphorothioate modifications. In an embodiment, the antisense strand comprises or consists of 4 phosphorothioate modifications. In an embodiment, the antisense strand comprises or consists of 3 phosphorothioate modifications. In an embodiment, the antisense strand comprises or consists of 2 phosphorothioate modifications. In an embodiment, the antisense strand comprises or consists of 1 phosphorothioate modifications. In an embodiment, the antisense strand comprises or consists of 0 phosphorothioate modifications.

In an embodiment, the sense strand comprises or consists of 8 or fewer (e.g., 8, 7, 6, 5, 4, 3, 2, 1, or 0) phosphorothioate modifications. In an embodiment, the sense strand comprises or consists of 8 phosphorothioate modifications. In an embodiment, the sense strand comprises or consists of 7 phosphorothioate modifications. In an embodiment, the sense strand comprises or consists of 6 phosphorothioate modifications. In an embodiment, the sense strand comprises or consists of 5 phosphorothioate modifications. In an embodiment, the sense strand comprises or consists of 4 phosphorothioate modifications. In an embodiment, the sense strand comprises or consists of 3 phosphorothioate modifications. In an embodiment, the sense strand comprises or consists of 2 phosphorothioate modifications. In an embodiment, the sense strand comprises or consists of 1 phosphorothioate modifications. In an embodiment, the sense strand comprises or consists of 0 phosphorothioate modifications.

In one aspect, the disclosure provides a modified universal sequence, comprising at least two modified intersubunit linkages of Formula X:

(X)

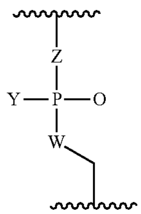

;

wherein:

B is a base moiety;

W is O or $O(CH_2)_n{}^1$, wherein $n^1$ is 1 to 10;

Y is selected from the group consisting of $O^-$, OH, $OR^2$, $NH^-$, $NH_2$, $NR^2_2$, $BH_3$, $S^-$, $R^2$, and SH;

Z is O or $O(CH_2)_n{}^2$ wherein $n^2$ is 1 to 10;

$R^1$ is a substituted or unsubstituted $C_1$-$C_6$ alkyl, alkenyl, alkynyl, aryl, or mixtures thereof; and $R^2$ is a substituted or unsubstituted $C_1$-$C_6$ alkyl, alkenyl, alkynyl, aryl, or mixtures thereof.

In an embodiment, the intersubunit linkage of Formula X bridges two nucleosides.

In an embodiment of Formula X, Z is OH and Y is $O^-$ or $S^-$.

In another aspect, the disclosure provides an oligonucleotide comprising the modified universal sequence comprising at least two modified intersubunit linkages of Formula X recited above, wherein the modified universal sequence is present at one or both of a 5' end and a 3' end of the oligonucleotide.

In one aspect, the disclosure provides a method of increasing the stability of an oligonucleotide, comprising attaching the modified universal sequence recited above to one or both of a 5' end and a 3' end of the oligonucleotide.

In an embodiment of the modified oligonucleotide, the modified universal sequence, or the method recited above, the base moiety B forms does not form a base pairing interaction with another base moiety.

BRIEF DESCRIPTION OF THE DRAWINGS

The foregoing and other features and advantages of the present disclosure will be more fully understood from the following detailed description of illustrative embodiments taken in conjunction with the accompanying drawings.

FIG. 2 provides a synthesis of a 2'-OMe-exNA phosphoramidite 9a.

FIG. 13 (SEQ ID NO: 85-92) provides a chart of exNA-modified RNA nucleotides that have been synthesized.

DETAILED DESCRIPTION OF CERTAIN EXEMPLARY EMBODIMENTS

Figure 1:
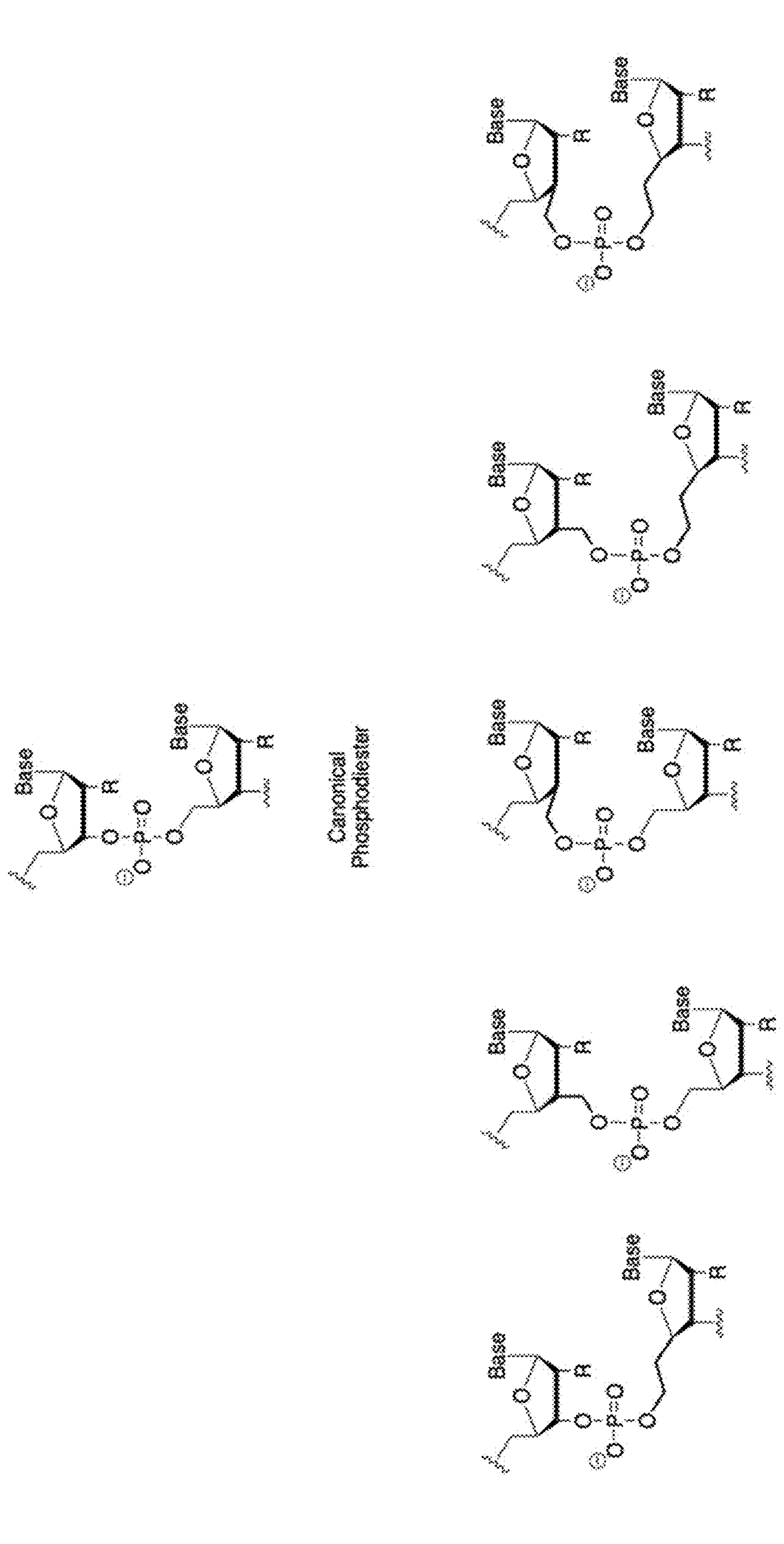
FIG. 1 summarizes the modified intersubunit linkages provided herein.

Novel oligonucleotide intersubunit linkages and their use for increasing oligonucleotide stability are provided.

Unless otherwise specified, nomenclature used in connection with cell and tissue culture, molecular biology, immunology, microbiology, genetics and protein and nucleic acid chemistry and hybridization described herein are those well-known and commonly used in the art. In addition, the methods and techniques provided herein are performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, delivery, and treatment of patients.

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

So that the disclosure may be more readily understood, certain terms are first defined.

As used herein, the term "universal" or "conserved" or "fixed" refers to a standard nucleotide sequence that remains unchanged at one or both of the 5' end and 3' end of an oligonucleotide of the disclosure. The universal sequence may be a region of a larger oligonucleotide (e.g., an antisense oligonucleotide, the sense and/or antisense strand of an siRNA duplex, or an mRNA). In certain embodiments, the universal region of a target oligonucleotide is fully complementary to, partially complementary to, or not complementary to a target mRNA.

When a universal nucleotide sequence is applied to an antisense strand of an siRNA, the universal nucleotide sequence is located at the 3' end of the antisense strand. In certain embodiments, the universal nucleotide sequence is located from nucleotide position 17 onward counted from the antisense 5' end. In this embodiment, positions 1 through 16 of the antisense strand have complementarity to a target mRNA, and position 17 onward comprise the universal nucleotide sequence and can be fully complementary to, partially complementary to, or not complementary to the target mRNA. In certain embodiments, the universal nucleotide sequence is present at positions 17-20 counted from the 5' end of the antisense strand. In certain embodiments, the universal nucleotide sequence is present at positions 17-21 counted from the 5' end of the antisense strand and comprises a nucleotide sequence selected from the group consisting of: UUUU, AAAA, CCCC, UUUUU, AAAAA, and CCCCC.

When a universal nucleotide sequence is applied to an antisense oligonucleotide (ASO), the universal nucleotide sequence is located at one or both of the 5' end and 3' end of the ASO. In certain embodiments, the universal sequence contains one or more modified intersubunit linkages of the disclosure.

In one aspect, the disclosure provides a modified universal sequence, comprising at least two modified intersubunit linkages of Formula Ia:

(Ia)

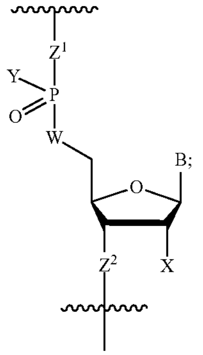

wherein:

B is a base moiety;

W is O or $O(CH_2)_n$, wherein $n^1$ is 1 to 10;

X is selected from the group consisting of H, OH, $OR^1$, $R^1$, F, Cl, Br, I, SH, $SR^1$, $NH_2$, $NHR^1$, $NR^1_2$, and $COOR^1$;

Y is selected from the group consisting of $O^-$, OH, $OR^2$, $NH^-$, $NH_2$, $NR^2_2$, $BH_3$, $S^-$, $R^2$, and SH;

$Z^1$ is O or $O(CH_2)_n{}^2$ wherein $n^2$ is 1 to 10;

$Z^2$ is O or $O(CH_2)_n{}^3$ wherein $n^3$ is 1 to 10;

$R^1$ is a substituted or unsubstituted $C_1$-$C_6$ alkyl, alkenyl, alkynyl, aryl, or mixtures thereof; and $R^2$ is a substituted or unsubstituted $C_1$-$C_6$ alkyl, alkenyl, alkynyl, aryl, or mixtures thereof, wherein the modified universal sequence is present at one or both of an oligonucleotide 5' end and a 3' end.

In an embodiment, the modified universal sequence comprises between two to ten consecutive nucleotides in length.

In an embodiment, the modified universal sequence comprises four consecutive nucleotides in length. In an embodiment, the modified universal sequence comprises five consecutive nucleotides in length.

In an embodiment, the modified universal sequence comprises at least two consecutive modified intersubunit linkages of Formula Ia. In an embodiment, the modified universal sequence comprises four consecutive modified intersubunit linkages of Formula Ia. In an embodiment, the modified universal sequence comprises five consecutive modified intersubunit linkages of Formula Ia.

In an embodiment, the modified universal sequence comprises a nucleotide sequence selected from the group consisting of: UUUU, AAAA, CCCC, UUUUU, AAAAA, and CCCCC.

In an embodiment, $Z^1$ is $O(CH_2)_n{}^2$, $n^2$ is 1, W is O, and Y is $O^-$. In an embodiment, $Z^1$ is O, W is $O(CH_2)_n{}^1$, $n^1$ is 1, and Y is $O^-$. In an embodiment, $Z^1$ is $O(CH_2)_n{}^2$, $n^2$ is 1, W is O, and Y is $O^-$. In an embodiment, $Z^1$ is $O(CH_2)_n{}^2$, $n^2$ is 1, W is $O(CH_2)_n{}^1$, and Y is $O^-$. In an embodiment, $Z^1$ is $O(CH_2)_n{}^2$, $n^2$ is 1, W is $O(CH_2)_n{}^1$, and Y is $S^-$. In an embodiment, Y is $S^-$. In an embodiment, X is $OR^1$ or F.

In an embodiment, the base moiety B is selected from the group consisting of adenine, guanine, cytosine, and uracil.

In an embodiment, the oligonucleotide is selected from the group consisting of an siRNA, a miRNA, an antisense oligonucleotide, a ribozyme, and a mRNA.

In an embodiment, the siRNA comprises an antisense strand and a sense strand, and wherein one or both of the antisense strand and the sense strand comprise the modified intersubunit linkages.

In one aspect, the disclosure provides a modified universal sequence, comprising at least two modified intersubunit linkages of Formula X:

(X)

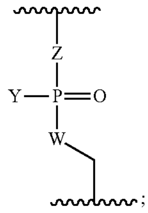

;

wherein:

B is a base moiety;

W is O or $O(CH_2)_{n}{}^{1}$, wherein $n^1$ is 1 to 10;

Y is selected from the group consisting of $O^-$, OH, $OR^2$, $NH^-$, $NH_2$, $NR^2{}_2$, $BH_3$, $S^-$, $R^2$, and SH;

Z is O or $O(CH_2)_{n}{}^{2}$ wherein $n^2$ is 1 to 10;

$R^1$ is a substituted or unsubstituted $C_1$-$C_6$ alkyl, alkenyl, alkynyl, aryl, or mixtures thereof; and $R^2$ is a substituted or unsubstituted $C_1$-$C_6$ alkyl, alkenyl, alkynyl, aryl, or mixtures thereof, wherein the modified universal sequence is present at one or both of an oligonucleotide 5' end and a 3' end.

In an embodiment, the intersubunit linkage of Formula X bridges two nucleosides.

In an embodiment of Formula X, Z is O and Y is $O^-$ or $S^-$.

In one aspect, the disclosure provides a method of increasing the stability of an oligonucleotide, comprising attaching the modified universal sequence recited above to one or both of a 5' end and a 3' end of the oligonucleotide.

In an embodiment, the modified universal sequence is attached to one or both of a 5' end and a 3' end of the oligonucleotide with a phosphodiester intersubunit linkage, a phosphorothioate intersubunit linkage, or any one of the modified intersubunit linkages of the disclosure. In an embodiment, the modified universal sequence is attached to one or both of a 5' end and a 3' end of the oligonucleotide with a nucleotide linker. In an embodiment, the modified universal sequence is attached to one or both of a 5' end and a 3' end of the oligonucleotide with a non-nucleotide linker.

The term "nucleoside" refers to a molecule having a purine or pyrimidine base covalently linked to a ribose or deoxyribose sugar. Exemplary nucleosides include adenosine, guanosine, cytidine, uridine and thymidine. Additional exemplary nucleosides include inosine, 1-methyl inosine, pseudouridine, 5,6-dihydrouridine, ribothymidine, 2N-methylguanosine and N2,N2-dimethylguanosine (also referred to as "rare" nucleosides). The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by an unmodified phosphodiester or chemically-modified intersubunit linkage between 5' and 3' carbon atoms.

The term "RNA" or "RNA molecule" or "ribonucleic acid molecule" refers to a polymer of ribonucleotides (e.g., 2, 3, 4, 5, 10, 15, 20, 25, 30, or more ribonucleotides). The term "DNA" or "DNA molecule" or "deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

As used herein, the term "small interfering RNA" ("siRNA") (also referred to in the art as "short interfering RNAs") refers to an RNA (or RNA analog) comprising between about 10-50 nucleotides (or nucleotide analogs), which is capable of directing or mediating RNA interference. In certain embodiments, a siRNA comprises between about 15-30 nucleotides or nucleotide analogs, or between about 16-25 nucleotides (or nucleotide analogs), or between about 18-23 nucleotides (or nucleotide analogs), or between about 19-22 nucleotides (or nucleotide analogs) (e.g., 19, 20, 21 or 22 nucleotides or nucleotide analogs). The term "short" siRNA refers to a siRNA comprising about 21 nucleotides (or nucleotide analogs), for example, 19, 20, 21 or 22 nucleotides. The term "long" siRNA refers to a siRNA comprising about 24-25 nucleotides, for example, 23, 24, 25 or 26 nucleotides. Short siRNAs may, in some instances, include fewer than 19 nucleotides, e.g., 16, 17 or 18 nucleotides, provided that the shorter siRNA retains the ability to mediate RNAi. Likewise, long siRNAs may, in some instances, include more than 26 nucleotides, provided that the longer siRNA retains the ability to mediate RNAi absent further processing, e.g., enzymatic processing, to a short siRNA.

The term "nucleotide analog" or "altered nucleotide" or "modified nucleotide" refers to a non-standard nucleotide, including non-naturally occurring ribonucleotides or deoxyribonucleotides. Exemplary nucleotide analogs are modified at any position so as to alter certain chemical properties of the nucleotide yet retain the ability of the nucleotide analog to perform its intended function. Examples of positions of the nucleotide, which may be derivatized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O– and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310.

Nucleotide analogs may also comprise modifications to the sugar portion of the nucleotides. For example, the 2' OH-group may be replaced by a group selected from H, OR, R, F, Cl, Br, I, SH, SR, $NH_2$, NHR, $NR_2$, or COOR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions, which allow the nucleotide to perform its intended function such as described in, for example, Eckstein, Antisense Nucleic Acid Drug Dev. 2000 Apr. 10(2):117-21, Rusckowski et al. Antisense Nucleic Acid Drug Dev. 2000 Oct. 10(5):333-45, Stein, Antisense Nucleic Acid Drug Dev. 2001 Oct. 11(5): 317-25, Vorobjev et al. Antisense Nucleic Acid Drug Dev. 2001 Apr. 11(2): 77-85, and U.S. Pat. No. 5,684,143. Certain of the above-referenced modifications (e.g., phosphate group modifications) decrease the rate of hydrolysis of, for example, polynucleotides comprising said analogs in vivo or in vitro.

The term "oligonucleotide" refers to a polymer of nucleotides and/or nucleotide analogs. Oligonucleotides include, but are not limited to, siRNAs, antisense oligonucleotides, miRNAs, ribozymes, and mRNA.

The term "RNA analog" refers to a polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. As discussed above, the oligonucleotides may be linked with linkages which result in a lower rate of hydrolysis of the RNA analog as compared to an RNA molecule with phosphodiester linkages. For example, the nucleotides of the analog may comprise methylenediol, ethylene diol, oxymethylthio, oxyethylthio, oxycarbonyloxy, phosphorodiamidate, phosphoroamidate, and/or phosphorothioate linkages. Examples of RNA analogues include, but are not limited to, sugar- and/or backbone-modified ribonucleotides and/or deoxyribonucleotides. Such alterations or modifications can further include the addition of non-nucleotide material, such as to the end(s) of the RNA or internally (at one or more nucleotides of the RNA). An RNA analog need only be sufficiently similar to natural RNA that it has the ability to mediate (mediates) RNA interference.

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA, which direct the degradative mechanism to other similar RNA sequences. Alternatively, RNAi can be initiated by the hand of man, for example, to silence the expression of target genes.

An RNAi agent, e.g., an RNA silencing agent, having a strand, which contains a "sequence sufficiently complementary to a target mRNA sequence to direct target-specific RNA interference (RNAi)" means that the strand has a sequence sufficient to trigger the destruction of the target mRNA by the RNAi machinery or process.

As used herein, the term "isolated RNA" (e.g., "isolated siRNA" or "isolated siRNA precursor") refers to RNA molecules, which are substantially free of other cellular material, or culture medium when produced by recombinant techniques, or substantially free of chemical precursors or other chemicals when chemically synthesized.

As used herein, the term "RNA silencing" refers to a group of sequence-specific regulatory mechanisms (e.g. RNA interference (RNAi), transcriptional gene silencing (TGS), post-transcriptional gene silencing (PTGS), quelling, co-suppression, and translational repression) mediated by RNA molecules which result in the inhibition or "silencing" of the expression of a corresponding protein-coding gene. RNA silencing has been observed in many types of organisms, including plants, animals, and fungi.

The term "discriminatory RNA silencing" refers to the ability of an RNA molecule to substantially inhibit the expression of a "first" or "target" polynucleotide sequence while not substantially inhibiting the expression of a "second" or "non-target" polynucleotide sequence," e.g., when both polynucleotide sequences are present in the same cell. In certain embodiments, the target polynucleotide sequence corresponds to a target gene, while the non-target polynucleotide sequence corresponds to a non-target gene. In other embodiments, the target polynucleotide sequence corresponds to a target allele, while the non-target polynucleotide sequence corresponds to a non-target allele. In certain embodiments, the target polynucleotide sequence is the DNA sequence encoding the regulatory region (e.g. promoter or enhancer elements) of a target gene. In other embodiments, the target polynucleotide sequence is a target mRNA encoded by a target gene.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

As used herein, the term "transgene" refers to any nucleic acid molecule, which is inserted by artifice into a cell, and becomes part of the genome of the organism that develops from the cell. Such a transgene may include a gene that is partly or entirely heterologous (i.e., foreign) to the transgenic organism, or may represent a gene homologous to an endogenous gene of the organism. The term "transgene" also means a nucleic acid molecule that includes one or more selected nucleic acid sequences, e.g., DNAs, that encode one or more engineered RNA precursors, to be expressed in a transgenic organism, e.g., animal, which is partly or entirely heterologous, i.e., foreign, to the transgenic animal, or homologous to an endogenous gene of the transgenic animal, but which is designed to be inserted into the animal's genome at a location which differs from that of the natural gene. A transgene includes one or more promoters and any other DNA, such as introns, necessary for expression of the selected nucleic acid sequence, all operably linked to the selected sequence, and may include an enhancer sequence.

A gene "involved" in a disease or disorder includes a gene, the normal or aberrant expression or function of which effects or causes the disease or disorder or at least one symptom of said disease or disorder.

The term "gain-of-function mutation" as used herein, refers to any mutation in a gene in which the protein encoded by said gene (i.e., the mutant protein) acquires a function not normally associated with the protein (i.e., the wild type protein) causes or contributes to a disease or disorder. The gain-of-function mutation can be a deletion, addition, or substitution of a nucleotide or nucleotides in the gene which gives rise to the change in the function of the encoded protein. In one embodiment, the gain-of-function mutation changes the function of the mutant protein or causes interactions with other proteins. In another embodiment, the gain-of-function mutation causes a decrease in or removal of normal wild-type protein, for example, by interaction of the altered, mutant protein with said normal, wild-type protein.

As used herein, the term "target gene" is a gene whose expression is to be substantially inhibited or "silenced." This silencing can be achieved by RNA silencing, e.g., by cleaving the mRNA of the target gene or translational repression of the target gene. The term "non-target gene" is a gene whose expression is not to be substantially silenced. In one embodiment, the polynucleotide sequences of the target and non-target gene (e.g. mRNA encoded by the target and non-target genes) can differ by one or more nucleotides. In another embodiment, the target and non-target genes can differ by one or more polymorphisms (e.g., Single Nucleotide Polymorphisms or SNPs). In another embodiment, the target and non-target genes can share less than 100% sequence identity. In another embodiment, the non-target gene may be a homologue (e.g. an orthologue or paralogue) of the target gene.

A "target allele" is an allele (e.g., a SNP allele) whose expression is to be selectively inhibited or "silenced." This silencing can be achieved by RNA silencing, e.g., by cleaving the mRNA of the target gene or target allele by a siRNA. The term "non-target allele" is an allele whose expression is not to be substantially silenced. In certain embodiments, the target and non-target alleles can correspond to the same target gene. In other embodiments, the target allele corresponds to, or is associated with, a target gene, and the non-target allele corresponds to, or is associated with, a non-target gene. In one embodiment, the polynucleotide sequences of the target and non-target alleles can differ by one or more nucleotides. In another embodiment, the target and non-target alleles can differ by one or more allelic polymorphisms (e.g., one or more SNPs). In another embodiment, the target and non-target alleles can share less than 100% sequence identity.

The term "polymorphism" as used herein, refers to a variation (e.g., one or more deletions, insertions, or substitutions) in a gene sequence that is identified or detected when the same gene sequence from different sources or subjects (but from the same organism) are compared. For example, a polymorphism can be identified when the same gene sequence from different subjects are compared. Identification of such polymorphisms is routine in the art, the methodologies being similar to those used to detect, for example, breast cancer point mutations. Identification can be made, for example, from DNA extracted from a subject's lymphocytes, followed by amplification of polymorphic regions using specific primers to said polymorphic region. Alternatively, the polymorphism can be identified when two alleles of the same gene are compared. In particular embodiments, the polymorphism is a single nucleotide polymorphism (SNP).

A variation in sequence between two alleles of the same gene within an organism is referred to herein as an "allelic polymorphism." In certain embodiments, the allelic polymorphism corresponds to a SNP allele. For example, the allelic polymorphism may comprise a single nucleotide variation between the two alleles of a SNP. The polymorphism can be at a nucleotide within a coding region but, due to the degeneracy of the genetic code, no change in amino acid sequence is encoded. Alternatively, polymorphic sequences can encode a different amino acid at a particular position, but the change in the amino acid does not affect protein function. Polymorphic regions can also be found in non-encoding regions of the gene. In exemplary embodiments, the polymorphism is found in a coding region of the gene or in an untranslated region (e.g., a 5' UTR or 3' UTR) of the gene.

As used herein, the term "allelic frequency" is a measure (e.g., proportion or percentage) of the relative frequency of an allele (e.g., a SNP allele) at a single locus in a population of individuals. For example, where a population of individuals carry n loci of a particular chromosomal locus (and the gene occupying the locus) in each of their somatic cells, then the allelic frequency of an allele is the fraction or percentage of loci that the allele occupies within the population. In particular embodiments, the allelic frequency of an allele (e.g., an SNP allele) is at least 10% (e.g., at least 15%, 20%, 25%, 30%, 35%, 40% or more) in a sample population.

As used herein, the term "sample population" refers to a population of individuals comprising a statistically significant number of individuals. For example, the sample population may comprise 50, 75, 100, 200, 500, 1000 or more individuals. In particular embodiments, the sample population may comprise individuals which share at least on common disease phenotype (e.g., a gain-of-function disorder) or mutation (e.g., a gain-of-function mutation).

As used herein, the term "heterozygosity" refers to the fraction of individuals within a population that are heterozygous (e.g., contain two or more different alleles) at a particular locus (e.g., at a SNP). Heterozygosity may be calculated for a sample population using methods that are well known to those skilled in the art.

The phrase "examining the function of a gene in a cell or organism" refers to examining or studying the expression, activity, function or phenotype arising therefrom.

As used herein, the term "RNA silencing agent" refers to an RNA, which is capable of inhibiting or "silencing" the expression of a target gene. In certain embodiments, the RNA silencing agent is capable of preventing complete processing (e.g., the full translation and/or expression) of a mRNA molecule through a post-transcriptional silencing mechanism. RNA silencing agents include small (<50 b.p.), noncoding RNA molecules, for example RNA duplexes comprising paired strands, as well as precursor RNAs from which such small non-coding RNAs can be generated. Exemplary RNA silencing agents include siRNAs, miRNAs, siRNA-like duplexes, antisense oligonucleotides, GAPMER molecules, and dual-function oligonucleotides as well as precursors thereof. In one embodiment, the RNA silencing agent is capable of inducing RNA interference. In another embodiment, the RNA silencing agent is capable of mediating translational repression.

As used herein, the term "rare nucleotide" refers to a naturally occurring nucleotide that occurs infrequently, including naturally occurring deoxyribonucleotides or ribonucleotides that occur infrequently, e.g., a naturally occurring ribonucleotide that is not guanosine, adenosine, cytosine, or uridine. Examples of rare nucleotides include, but are not limited to, inosine, 1-methyl inosine, pseudouridine, 5,6-dihydrouridine, ribothymidine, 2N-methylguanosine and 2,2N,N-dimethylguanosine.

The term "engineered," as in an engineered RNA precursor, or an engineered nucleic acid molecule, indicates that the precursor or molecule is not found in nature, in that all or a portion of the nucleic acid sequence of the precursor or molecule is created or selected by a human. Once created or selected, the sequence can be replicated, translated, transcribed, or otherwise processed by mechanisms within a cell. Thus, an RNA precursor produced within a cell from a transgene that includes an engineered nucleic acid molecule is an engineered RNA precursor.

As used herein, the term "microRNA" ("miRNA"), also referred to in the art as "small temporal RNAs" ("stRNAs"), refers to a small (10-50 nucleotide) RNA which are genetically encoded (e.g., by viral, mammalian, or plant genomes) and are capable of directing or mediating RNA silencing. An "miRNA disorder" shall refer to a disease or disorder characterized by an aberrant expression or activity of an miRNA.

As used herein, the term "dual functional oligonucleotide" refers to a RNA silencing agent having the formula T-L-μ, wherein T is an mRNA targeting moiety, L is a linking moiety, and is a miRNA recruiting moiety. As used herein, the terms "mRNA targeting moiety," "targeting moiety," "mRNA targeting portion" or "targeting portion" refer to a domain, portion or region of the dual functional oligonucleotide having sufficient size and sufficient complementarity to a portion or region of an mRNA chosen or targeted for silencing (i.e., the moiety has a sequence sufficient to capture the target mRNA). As used herein, the term "linking moiety" or "linking portion" refers to a domain, portion or region of the RNA-silencing agent which covalently joins or links the mRNA.

As used herein, the term "antisense strand" of an RNA silencing agent, e.g., an siRNA or RNA silencing agent, refers to a strand that is substantially complementary to a section of about 10-50 nucleotides, e.g., about 15-30, 16-25, 18-23 or 19-22 nucleotides of the mRNA of the gene targeted for silencing. The antisense strand or first strand has sequence sufficiently complementary to the desired target mRNA sequence to direct target-specific silencing, e.g., complementarity sufficient to trigger the destruction of the desired target mRNA by the RNAi machinery or process (RNAi interference) or complementarity sufficient to trigger translational repression of the desired target mRNA.

The term "sense strand" or "second strand" of an RNA silencing agent, e.g., an siRNA or RNA silencing agent, refers to a strand that is complementary to the antisense strand or first strand. Antisense and sense strands can also be referred to as first or second strands, the first or second strand having complementarity to the target sequence and the respective second or first strand having complementarity to said first or second strand. miRNA duplex intermediates or siRNA-like duplexes include a miRNA strand having sufficient complementarity to a section of about 10-50 nucleotides of the mRNA of the gene targeted for silencing and a miRNA* strand having sufficient complementarity to form a duplex with the miRNA strand.

As used herein, the term "guide strand" refers to a strand of an RNA silencing agent, e.g., an antisense strand of an siRNA duplex or siRNA sequence, that enters into the RISC complex and directs cleavage of the target mRNA.

As used herein, the term "asymmetry," as in the asymmetry of the duplex region of an RNA silencing agent (e.g., the stem of an shRNA), refers to an inequality of bond strength or base pairing strength between the termini of the RNA silencing agent (e.g., between terminal nucleotides on a first strand or stem portion and terminal nucleotides on an opposing second strand or stem portion), such that the 5' end of one strand of the duplex is more frequently in a transient unpaired, e.g., single-stranded, state than the 5' end of the complementary strand. This structural difference determines that one strand of the duplex is preferentially incorporated into a RISC complex. The strand whose 5' end is less tightly paired to the complementary strand will preferentially be incorporated into RISC and mediate RNAi.

As used herein, the term "bond strength" or "base pair strength" refers to the strength of the interaction between pairs of nucleotides (or nucleotide analogs) on opposing strands of an oligonucleotide duplex (e.g., an siRNA duplex), due primarily to H-bonding, van der Waals interactions, and the like between said nucleotides (or nucleotide analogs).

As used herein, the "5' end," as in the 5' end of an oligonucleotide (e.g., an antisense strand or a sense strand of an siRNA), refers to the 5' terminal nucleotides, e.g., between one and about five nucleotides at the 5' terminus of an oligonucleotide. In certain embodiments, the 5' end of an oligonucleotide corresponds to the first five nucleotides of the oligonucleotide. In certain embodiments, the 5' end of an oligonucleotide is the first nucleotide. In certain embodiments, the 5' end of an oligonucleotide is the first two consecutive nucleotides. In certain embodiments, the 5' end of an oligonucleotide is the first three consecutive nucleotides. In certain embodiments, the 5' end of an oligonucleotide is the first four consecutive nucleotides. In certain embodiments, the 5' end of an oligonucleotide is the first five consecutive nucleotides.

As used herein, the "3' end," as in the 3' end of an oligonucleotide (e.g., an antisense strand or a sense strand of an siRNA), refers to the 3' terminal nucleotides, e.g., of between one and about five nucleotides at the 3' terminus of an oligonucleotide. In certain embodiments, the 3' end of an oligonucleotide corresponds to the last five nucleotides of the oligonucleotide. In certain embodiments, the 3' end of an oligonucleotide is the last nucleotide. In certain embodiments, the 3' end of an oligonucleotide is the last two consecutive nucleotides. In certain embodiments, the 3' end of an oligonucleotide is the last three consecutive nucleotides. In certain embodiments, the 3' end of an oligonucleotide is the last four consecutive nucleotides. In certain embodiments, the 3' end of an oligonucleotide is the last five consecutive nucleotides.

As used herein the term "destabilizing nucleotide" refers to a first nucleotide or nucleotide analog capable of forming a base pair with second nucleotide or nucleotide analog such that the base pair is of lower bond strength than a conventional base pair (i.e., Watson-Crick base pair). In certain embodiments, the destabilizing nucleotide is capable of forming a mismatch base pair with the second nucleotide. In other embodiments, the destabilizing nucleotide is capable of forming a wobble base pair with the second nucleotide. In yet other embodiments, the destabilizing nucleotide is capable of forming an ambiguous base pair with the second nucleotide.

As used herein, the term "base pair" refers to the interaction between pairs of nucleotides (or nucleotide analogs) on opposing strands of an oligonucleotide duplex (e.g., a duplex formed by a strand of a RNA silencing agent and a target mRNA sequence), due primarily to H-bonding, van der Waals interactions, and the like between said nucleotides (or nucleotide analogs). As used herein, the term "bond strength" or "base pair strength" refers to the strength of the base pair.

As used herein, the term "mismatched base pair" refers to a base pair consisting of non-complementary or non-Watson-Crick base pairs, for example, not normal complementary G:C, A:T or A:U base pairs. As used herein the term "ambiguous base pair" (also known as a non-discriminatory base pair) refers to a base pair formed by a universal nucleotide.

As used herein, term "universal nucleotide" (also known as a "neutral nucleotide") include those nucleotides (e.g. certain destabilizing nucleotides) having a base (a "universal base" or "neutral base") that does not significantly discriminate between bases on a complementary polynucleotide when forming a base pair. Universal nucleotides are predominantly hydrophobic molecules that can pack efficiently into antiparallel duplex nucleic acids (e.g., double-stranded DNA or RNA) due to stacking interactions. The base portion of universal nucleotides typically comprise a nitrogen-containing aromatic heterocyclic moiety.

As used herein, the terms "sufficient complementarity" or "sufficient degree of complementarity" mean that the RNA silencing agent has a sequence (e.g. in the antisense strand, mRNA targeting moiety or miRNA recruiting moiety) which is sufficient to bind the desired target RNA, respectively, and to trigger the RNA silencing of the target mRNA.

As used herein, the term "translational repression" refers to a selective inhibition of mRNA translation. Natural translational repression proceeds via miRNAs cleaved from shRNA precursors. Both RNAi and translational repression are mediated by RISC. Both RNAi and translational repression occur naturally or can be initiated by the hand of man, for example, to silence the expression of target genes.

As used herein, the term "alkoxy," refers to the group —O-alkyl, wherein alkyl is as defined herein. Alkoxy includes, by way of example, methoxy, ethoxy, n-propoxy, isopropoxy, n-butoxy, sec-butoxy, t-butoxy and the like. In an embodiment, C1-C6 alkoxy groups are provided herein.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "hydroxy" alone or as part of another substituent means, unless otherwise stated, an alcohol moiety having the formula —OH.

As used herein, the term "exNA" or "ex-NA" refers to an "extended nucleic acid" that contains an intersubunit linkage that contains one or more additional $CH_2$ groups at the 3' position, at the 5' position, or both.

Preparation of linkers can involve the protection and deprotection of various chemical groups. The need for protection and deprotection, and the selection of appropriate protecting groups can be readily determined by one skilled in the art. The chemistry of protecting groups can be found, for example, in Greene, et al., Protective Groups in Organic Synthesis, 4d. Ed., Wiley & Sons, 2007, which is incorporated herein by reference in its entirety. Adjustments to the protecting groups and formation and cleavage methods described herein may be adjusted as necessary in light of the various substituents.

Various methodologies of the instant disclosure include step that involves comparing a value, level, feature, characteristic, property, etc. to a "suitable control," referred to interchangeably herein as an "appropriate control." A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing an RNA silencing agent of the disclosure into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and example are illustrative only and not intended to be limiting.

Various aspects of the disclosure are described in further detail in the following subsections.

I. Novel Modified Oligonucleotide Synthesis

Here we describe a portfolio of synthetic procedures for oligonucleotides modified with a novel backbone modification, Extended Nucleic Acid (exNA). This chemical modification of the backbone significantly enhances oligonucleotide metabolic stability. The chemical modification includes one or more carbon atoms or chains inserted in the backbone at the 5'-position, 3'-position, or both. This structural modulation forms non-canonical stretched/flexible structure on oligo-backbones, which protect oligonucleotides from cleavage by various nucleases.

The novel exNA-modification is widely compatible in any oligonucleotide, such as an siRNA, antisense oligonucleotide, and mRNA. The combination of an exNA-phosphorothioate (exNA-PS) backbone enables drastic enhancement of metabolic stability (10-50 orders of magnitude as compared to unmodified oligonucleotides) without compromising the function of the oligonucleotide (e.g., siRNA-mediated silencing efficacy). For example, 5'-[exNA-PS]4-3' modification induce NO negative impact on siRNA efficacy while inducing drastically high exonuclease stability, as will be shown below. Moreover, an exNA-phosphodiester (exNA-PO) backbone also enables drastic enhancement of metabolic stability without compromising the function of the oligonucleotide. It has been previously shown that phosphorothioate-containing backbones in oligonucleotides are toxic when administered in vivo. Accordingly, the exNA-PO backbone can be employed to enhancement of metabolic stability while decreasing toxicity. Thus, this metabolically stabilizing exNA modification is widely and robustly improves the performance of therapeutic oligonucleotide candidates in vivo.

In this disclosure, the synthesis protocol for exNA-modified oligonucleotide is described. Importantly, the exNA monomer phosphoramidite synthesis can be realized from commercially available nucleosides and the exNA-modified oligonucleotide can be made using conventional oligonucleotide solid phase synthesis procedures on an automatic oligo synthesizer.

This synthetic procedure provides following noteworthy benefits. For example, the conversion of a regular nucleoside to an "exNA-format" is applicable to many diverse modified nucleosides. Thus, this expands the possibilities to synthesize and create many more types of modified oligonucleotides with compatibility of the chemical synthesis. Secondly, there is no need of a separate specific synthesis procedure during an oligonucleotide synthesis cycle. This is a huge benefit in the ease of use of these oligos, especially with an automated synthesizer where a bottle of exNA phosphoramidite could easily be added to the machine. Thirdly, there is no need of a specific oligonucleotide deprotection condition because the exNA phosphoramidites and oligos are compatible with conventional deprotection conditions. Again, this is beneficial for the ease of synthesis and in the use of an automated synthesizer. Fourthly, it is possible to synthesize mix-mer oligonucleotide having both exNA and clinically validated modified nucleotides (e.g., 2'-OMe, 2'-F, phosphorothioate, various ligand conjugates, lipid conjugates, etc).

In one aspect, the disclosure provides a modified oligonucleotide comprising a 5' end, a 3' end and at least two modified intersubunit linkages of Formula Ia:

(Ia)

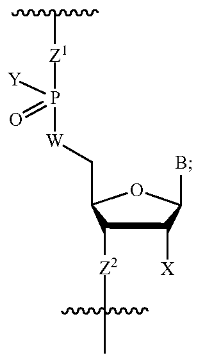

wherein:

B is a base moiety;

W is O or $O(CH_2)_n$, wherein $n^1$ is 1 to 10;

X is selected from the group consisting of H, OH, $OR^1$, $R^1$, F, Cl, Br, I, SH, $SR^1$, $NH_2$, $NHR^1$, $NR^1{}_2$, and $COOR^1$;

Y is selected from the group consisting of $O^-$, OH, $OR^2$, $NH^-$, $NH_2$, $NR^2{}_2$, $BH_3$, $S^-$, $R^2$, and SH;

$Z^1$ is O or $O(CH_2)_n{}^2$ wherein $n^2$ is 1 to 10;

$Z^2$ is O or $O(CH_2)_n{}^3$ wherein $n^3$ is 1 to 10;

$R^1$ is a substituted or unsubstituted $C_1$-$C_6$ alkyl, alkenyl, alkynyl, aryl, or mixtures thereof;

$R^2$ is a substituted or unsubstituted $C_1$-$C_6$ alkyl, alkenyl, alkynyl, aryl, or mixtures thereof; and wherein at least two of the modified intersubunit linkages are present at one or both of the 5' end and 3' end of the modified oligonucleotide.

In an embodiment, $Z^1$ is $O(CH_2)_n{}^2$, $n^2$ is 1, W is O, and Y is $O^-$. In an embodiment, $Z^1$ is O, W is $O(CH_2)_n{}^1$, $n^1$ is 1, and Y is $O^-$. In an embodiment, $Z^1$ is $O(CH_2)_n{}^2$, $n^2$ is 1, W is O, and Y is $O^-$. In an embodiment, $Z^1$ is $O(CH_2)_n{}^2$, $n^2$ is 1, W is $O(CH_2)_n{}^1$, and Y is $O^-$. In an embodiment, $Z^1$ is $O(CH_2)_n{}^2$, $n^2$ is 1, W is $O(CH_2)_1$, and Y is $S^-$. In an embodiment, Y is $S^-$. In an embodiment, X is $OR^1$ or F.

In an embodiment, between two and ten of the modified intersubunit linkages are present at one or both of the 5' end and the 3' end of the modified oligonucleotide.

In an embodiment, between two and five of the modified intersubunit linkages are present at one or both of the 5' end and the 3' end of the modified oligonucleotide.

In an embodiment, between two and five of the modified intersubunit linkages are present at the 5' end of the modified oligonucleotide.

In an embodiment, between two and five of the modified intersubunit linkages are present at the 3' end of the modified oligonucleotide.

In an embodiment, two of the modified intersubunit linkages are present at one or both of the 5' end and the 3' end of the modified oligonucleotide. In an embodiment, two of the modified intersubunit linkages are present at the 5' end of the modified oligonucleotide. In an embodiment, two of the modified intersubunit linkages are present at the 3' end of the modified oligonucleotide.

In an embodiment, three of the modified intersubunit linkages are present at one or both of the 5' end and the 3' end of the modified oligonucleotide. In an embodiment, three of the modified intersubunit linkages are present at the 5' end of the modified oligonucleotide. In an embodiment, three of the modified intersubunit linkages are present at the 3' end of the modified oligonucleotide.

In an embodiment, four of the modified intersubunit linkages are present at one or both of the 5' end and the 3' end of the modified oligonucleotide. In an embodiment, four of the modified intersubunit linkages are present at the 5' end of the modified oligonucleotide. In an embodiment, four of the modified intersubunit linkages are present at the 3' end of the modified oligonucleotide.

In an embodiment, five of the modified intersubunit linkages are present at one or both of the 5' end and the 3' end of the modified oligonucleotide. In an embodiment, five of the modified intersubunit linkages are present at the 5' end of the modified oligonucleotide. In an embodiment, five of the modified intersubunit linkages are present at the 3' end of the modified oligonucleotide.

In an embodiment, the at least two modified intersubunit linkages are consecutive. In an embodiment, the modified oligonucleotide comprises three consecutive modified intersubunit linkages at one or both of the 5' end and the 3' end of the modified oligonucleotide. In an embodiment, the modified oligonucleotide comprises four consecutive modified intersubunit linkages at one or both of the 5' end and the 3' end of the modified oligonucleotide. In an embodiment, the modified oligonucleotide comprises five consecutive modified intersubunit linkages at one or both of the 5' end and the 3' end of the modified oligonucleotide.

In an embodiment, the oligonucleotide is selected from the group consisting of an siRNA, a miRNA, an antisense oligonucleotide, a ribozyme, and a mRNA.

In an embodiment, the siRNA comprises an antisense strand and a sense strand, and wherein one or both of the antisense strand and the sense strand comprise the modified intersubunit linkages.

In another aspect, the disclosure provides a modified oligonucleotide comprising a 5' end, a 3' end and at least two modified intersubunit linkages of Formula II:

(IIa)

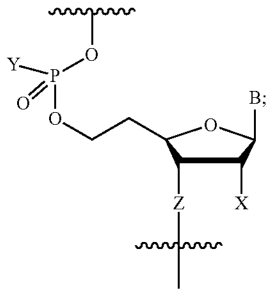

wherein:

B is a base moiety;

X is selected from the group consisting of H, OH, $OR^1$, $R^1$, F, Cl, Br, I, SH, $SR^1$, $NH_2$, $NHR^1$, $NR^1{}_2$, and $COOR^1$;

Y is selected from the group consisting of $O^-$, OH, $OR^2$, $NH^-$, $NH_2$, $NR^2{}_2$, $BH_3$, $S^-$, $R^2$, and SH;

Z is O or $O(CH_2)_n$ wherein n is 1 to 10;

$R^1$ is a substituted or unsubstituted $C_1$-$C_6$ alkyl, alkenyl, alkynyl, aryl, or mixtures thereof;

$R^2$ is a substituted or unsubstituted $C_1$-$C_6$ alkyl, alkenyl, alkynyl, aryl, or mixtures thereof; and wherein at least two of the modified intersubunit linkages are present at one or both of the 5' end and the 3' end of the modified oligonucleotide.

In another aspect, the disclosure provides a modified oligonucleotide comprising a 5' end, a 3' end and at least two modified intersubunit linkages of Formula II:

(II)

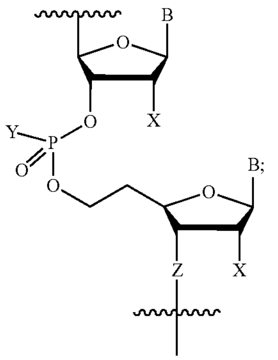

wherein:
- B is a base moiety;
- X is selected from the group consisting of H, OH, $OR^1$, $R^1$, F, Cl, Br, I, SH, $SR^1$, $NH_2$, $NHR^1$, $NR^1_2$, and $COOR^1$;
- Y is selected from the group consisting of $O^-$, OH, $OR^2$, $NH^-$, $NH_2$, $NR^2_2$, $BH_3$, $S^-$, $R^2$, and SH;
- Z is O or $O(CH_2)_n$ wherein n is 1 to 10;
- $R^1$ is a substituted or unsubstituted $C_1$-$C_6$ alkyl, alkenyl, alkynyl, aryl, or mixtures thereof;
- $R^2$ is a substituted or unsubstituted $C_1$-$C_6$ alkyl, alkenyl, alkynyl, aryl, or mixtures thereof; and wherein at least two of the modified intersubunit linkages are present at one or both of the 5' end and the 3' end of the modified oligonucleotide.

In an embodiment, Y is $S^-$. In an embodiment, Y is $O^-$. In an embodiment, X is $OR^1$ or F.

In an embodiment, between two and ten of the modified intersubunit linkages are present at one or both of the 5' end and the 3' end of the modified oligonucleotide.

In an embodiment, between two and five of the modified intersubunit linkages are present at one or both of the 5' end and the 3' end of the modified oligonucleotide. In an embodiment, between two and five of the modified intersubunit linkages are present at the 5' end of the modified oligonucleotide. In an embodiment, between two and five of the modified intersubunit linkages are present at the 3' end of the modified oligonucleotide.

In an embodiment, two of the modified intersubunit linkages are present at one or both of the 5' end and the 3' end of the modified oligonucleotide. In an embodiment, two of the modified intersubunit linkages are present at the 5' end of the modified oligonucleotide. In an embodiment, two of the modified intersubunit linkages are present at the 3' end of the modified oligonucleotide.

In an embodiment, three of the modified intersubunit linkages are present at one or both of the 5' end and the 3' end of the modified oligonucleotide. In an embodiment, three of the modified intersubunit linkages are present at the 5' end of the modified oligonucleotide. In an embodiment, three of the modified intersubunit linkages are present at the 3' end of the modified oligonucleotide.

In an embodiment, four of the modified intersubunit linkages are present at one or both of the 5' end and the 3' end of the modified oligonucleotide. In an embodiment, four of the modified intersubunit linkages are present at the 5' end of the modified oligonucleotide. In an embodiment, four of the modified intersubunit linkages are present at the 3' end of the modified oligonucleotide.

In an embodiment, five of the modified intersubunit linkages are present at one or both of the 5' end and the 3' end of the modified oligonucleotide. In an embodiment, five of the modified intersubunit linkages are present at the 5' end of the modified oligonucleotide. In an embodiment, five of the modified intersubunit linkages are present at the 3' end of the modified oligonucleotide.

In an embodiment, the at least two modified intersubunit linkages are consecutive. In an embodiment, the modified oligonucleotide comprises three consecutive modified intersubunit linkages at one or both of the 5' end and the 3' end of the modified oligonucleotide. In an embodiment, the modified oligonucleotide comprises four consecutive modified intersubunit linkages at one or both of the 5' end and the 3' end of the modified oligonucleotide. In an embodiment, the modified oligonucleotide comprises five consecutive modified intersubunit linkages at one or both of the 5' end and the 3' end of the modified oligonucleotide.

In an embodiment, the oligonucleotide is selected from the group consisting of an siRNA, a miRNA, an antisense oligonucleotide, a ribozyme, and a mRNA.

In an embodiment, the siRNA comprises an antisense strand and a sense strand, and wherein one or both of the antisense strand and the sense strand comprise the modified intersubunit linkages.

In another aspect, the disclosure provides a modified oligonucleotide comprising a 5' end, a 3' end and at least two modified intersubunit linkages of Formula IIIa:

(IIIa)

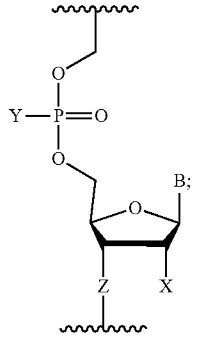

wherein:
- B is a base moiety;
- X is selected from the group consisting of H, OH, $OR^1$, $R^1$, F, Cl, Br, I, SH, $SR^1$, $NH_2$, $NHR^1$, $NR^1_2$, and $COOR^1$;
- Y is selected from the group consisting of $O^-$, OH, $OR^2$, $NH^-$, $NH_2$, $NR^2_2$, $BH_3$, $S^-$, $R^2$ and SH;
- Z is O or $O(CH_2)_n$ wherein n is 1 to 10;
- $R^1$ is a substituted or unsubstituted $C_1$-$C_6$ alkyl, alkenyl, alkynyl, aryl, or mixtures thereof;
- $R^2$ is a substituted or unsubstituted $C_1$-$C_6$ alkyl, alkenyl, alkynyl, aryl, or mixtures thereof; and wherein at least two of the modified intersubunit linkages are present at one or both of the 5' end and the 3' end of the modified oligonucleotide.

In another aspect, the disclosure provides a modified oligonucleotide comprising a 5' end, a 3' end and at least two modified intersubunit linkages of Formula III:

(III)

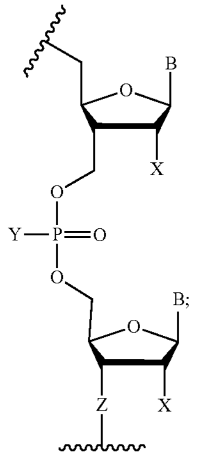

wherein:

B is a base moiety;

X is selected from the group consisting of H, OH, $OR^1$, $R^1$, F, Cl, Br, I, SH, $SR^1$, $NH_2$, $NHR^1$, $NR^1_2$, and $COOR^1$;

Y is selected from the group consisting of $O^-$, OH, $OR^2$, $NH^-$, $NH_2$, $NR^2_2$, $BH_3$, $S^-$, $R^2$ and SH;

Z is O or $O(CH_2)_n$ wherein n is 1 to 10;

$R^1$ is a substituted or unsubstituted $C_1$-$C_6$ alkyl, alkenyl, alkynyl, aryl, or mixtures thereof;

$R^2$ is a substituted or unsubstituted $C_1$-$C_6$ alkyl, alkenyl, alkynyl, aryl, or mixtures thereof; and wherein at least two of the modified intersubunit linkages are present at one or both of the 5' end and the 3' end of the modified oligonucleotide.

In an embodiment, Y is $S^-$. In an embodiment, Y is $O^-$. In an embodiment, X is $OR^1$ or F.

In an embodiment, between two and ten of the modified intersubunit linkages are present at one or both of the 5' end and the 3' end of the modified oligonucleotide.

In an embodiment, between two and five of the modified intersubunit linkages are present at one or both of the 5' end and the 3' end of the modified oligonucleotide. In an embodiment, between two and five of the modified intersubunit linkages are present at the 5' end of the modified oligonucleotide. In an embodiment, between two and five of the modified intersubunit linkages are present at the 3' end of the modified oligonucleotide.

In an embodiment, two of the modified intersubunit linkages are present at one or both of the 5' end and the 3' end of the modified oligonucleotide. In an embodiment, two of the modified intersubunit linkages are present at the 5' end of the modified oligonucleotide. In an embodiment, two of the modified intersubunit linkages are present at the 3' end of the modified oligonucleotide.

In an embodiment, three of the modified intersubunit linkages are present at one or both of the 5' end and the 3' end of the modified oligonucleotide. In an embodiment, three of the modified intersubunit linkages are present at the 5' end of the modified oligonucleotide. In an embodiment, three of the modified intersubunit linkages are present at the 3' end of the modified oligonucleotide.

In an embodiment, four of the modified intersubunit linkages are present at one or both of the 5' end and the 3' end of the modified oligonucleotide. In an embodiment, four of the modified intersubunit linkages are present at the 5' end of the modified oligonucleotide. In an embodiment, four of the modified intersubunit linkages are present at the 3' end of the modified oligonucleotide.

In an embodiment, five of the modified intersubunit linkages are present at one or both of the 5' end and the 3' end of the modified oligonucleotide. In an embodiment, five of the modified intersubunit linkages are present at the 5' end of the modified oligonucleotide. In an embodiment, five of the modified intersubunit linkages are present at the 3' end of the modified oligonucleotide.

In an embodiment, the at least two modified intersubunit linkages are consecutive. In an embodiment, the modified oligonucleotide comprises three consecutive modified intersubunit linkages at one or both of the 5' end and the 3' end of the modified oligonucleotide. In an embodiment, the modified oligonucleotide comprises four consecutive modified intersubunit linkages at one or both of the 5' end and the 3' end of the modified oligonucleotide. In an embodiment, the modified oligonucleotide comprises five consecutive modified intersubunit linkages at one or both of the 5' end and the 3' end of the modified oligonucleotide.

In an embodiment, the oligonucleotide is selected from the group consisting of an siRNA, a miRNA, an antisense oligonucleotide, a ribozyme, and a mRNA.

In an embodiment, the siRNA comprises an antisense strand and a sense strand, and wherein one or both of the antisense strand and the sense strand comprise the modified intersubunit linkages.

In one aspect, the disclosure provides a modified oligonucleotide comprising a 5' end, a 3' end and at least two modified intersubunit linkages of Formula IV:

(IV)

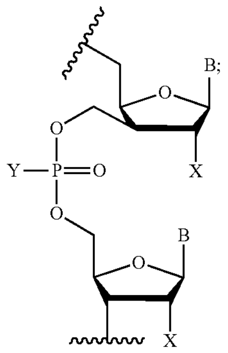

wherein:

B is a base moiety;

X is selected from the group consisting of H, OH, OR, $R^1$, F, Cl, Br, I, SH, $SR^1$, $NH_2$, $NHR^1$, $NR^1_2$, and $COOR^1$;

Y is selected from the group consisting of $O^-$, OH, $OR^2$, $NH^-$, $NH_2$, $NR^2_2$, $BH_3$, $S^-$, $R^2$, and SH;

$R^1$ is a substituted or unsubstituted $C_1$-$C_6$ alkyl, alkenyl, alkynyl, aryl, or mixtures thereof;

$R^2$ is a substituted or unsubstituted $C_1$-$C_6$ alkyl, alkenyl, alkynyl, aryl, or mixtures thereof; and wherein at least two of the modified intersubunit linkages are present at one or both of the 5' end and the 3' end of the modified oligonucleotide.

In an embodiment, Y is $S^-$. In an embodiment, Y is $O^-$. In an embodiment, X is $OR^1$ or F.

In an embodiment, between two and ten of the modified intersubunit linkages are present at one or both of the 5' end and the 3' end of the modified oligonucleotide.

In an embodiment, between two and five of the modified intersubunit linkages are present at one or both of the 5' end and the 3' end of the modified oligonucleotide. In an embodiment, between two and five of the modified intersubunit linkages are present at the 5' end of the modified oligonucleotide. In an embodiment, between two and five of the modified intersubunit linkages are present at the 3' end of the modified oligonucleotide.

In an embodiment, two of the modified intersubunit linkages are present at one or both of the 5' end and the 3' end of the modified oligonucleotide. In an embodiment, two of the modified intersubunit linkages are present at the 5' end of the modified oligonucleotide. In an embodiment, two of the modified intersubunit linkages are present at the 3' end of the modified oligonucleotide.

In an embodiment, three of the modified intersubunit linkages are present at one or both of the 5' end and the 3' end of the modified oligonucleotide. In an embodiment, three of the modified intersubunit linkages are present at the 5' end of the modified oligonucleotide. In an embodiment, three of the modified intersubunit linkages are present at the 3' end of the modified oligonucleotide.

In an embodiment, four of the modified intersubunit linkages are present at one or both of the 5' end and the 3' end of the modified oligonucleotide. In an embodiment, four of the modified intersubunit linkages are present at the 5' end of the modified oligonucleotide. In an embodiment, four of the modified intersubunit linkages are present at the 3' end of the modified oligonucleotide.

In an embodiment, five of the modified intersubunit linkages are present at one or both of the 5' end and the 3' end of the modified oligonucleotide. In an embodiment, five of the modified intersubunit linkages are present at the 5' end of the modified oligonucleotide. In an embodiment, five of the modified intersubunit linkages are present at the 3' end of the modified oligonucleotide.

In an embodiment, the at least two modified intersubunit linkages are consecutive. In an embodiment, the modified oligonucleotide comprises three consecutive modified intersubunit linkages at one or both of the 5' end and the 3' end of the modified oligonucleotide. In an embodiment, the modified oligonucleotide comprises four consecutive modified intersubunit linkages at one or both of the 5' end and the 3' end of the modified oligonucleotide. In an embodiment, the modified oligonucleotide comprises five consecutive modified intersubunit linkages at one or both of the 5' end and the 3' end of the modified oligonucleotide.

In an embodiment, the oligonucleotide is selected from the group consisting of an siRNA, a miRNA, an antisense oligonucleotide, a ribozyme, and a mRNA.

In an embodiment, the siRNA comprises an antisense strand and a sense strand, and wherein one or both of the antisense strand and the sense strand comprise the modified intersubunit linkages.

In one aspect, the disclosure provides a modified oligonucleotide comprising a 5' end, a 3' end and at least two modified intersubunit linkages of Formula Va:

(Va)

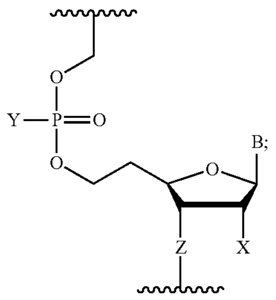

wherein:

B is a base moiety;

X is selected from the group consisting of H, OH, $OR^1$, $R^1$, F, Cl, Br, I, SH, $SR^1$, $NH_2$, $NHR^1$, $NR^1_2$, and $COOR^1$;

Y is selected from the group consisting of $O^-$, OH, $OR^2$, $NH^-$, $NH_2$, $NR^2_2$, $BH_3$, $S^-$, $R^2$ and SH;

Z is O or $O(CH_2)_n$ wherein n is 1 to 10;

$R^1$ is a substituted or unsubstituted $C_1$-$C_6$ alkyl, alkenyl, alkynyl, aryl, or mixtures thereof;

$R^2$ is a substituted or unsubstituted $C_1$-$C_6$ alkyl, alkenyl, alkynyl, aryl, or mixtures thereof; and wherein at least two of the modified intersubunit linkages are present at one or both of the 5' end and 3' end of the modified oligonucleotide.

In one aspect, the disclosure provides a modified oligonucleotide comprising a 5' end, a 3' end and at least two modified intersubunit linkages of Formula V:

(V)

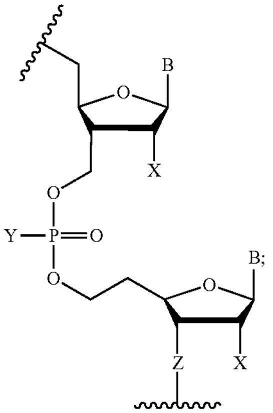

wherein:

B is a base moiety;

X is selected from the group consisting of H, OH, $OR^1$, $R^1$, F, Cl, Br, I, SH, $SR^1$, $NH_2$, $NHR^1$, $NR^1_2$, and $COOR^1$;

Y is selected from the group consisting of $O^-$, OH, $OR^2$, $NH^-$, $NH_2$, $NR^2_2$, $BH_3$, $S^-$, $R^2$ and SH;

Z is O or $O(CH_2)_n$ wherein n is 1 to 10;

$R^1$ is a substituted or unsubstituted $C_1$-$C_6$ alkyl, alkenyl, alkynyl, aryl, or mixtures thereof;

$R^2$ is a substituted or unsubstituted $C_1$-$C_6$ alkyl, alkenyl, alkynyl, aryl, or mixtures thereof; and wherein at least two of the modified intersubunit linkages are present at one or both of the 5' end and 3' end of the modified oligonucleotide.

In an embodiment, Y is S. In an embodiment, Y is $O^-$. In an embodiment, X is $OR^1$ or F.

In an embodiment, between two and ten of the modified intersubunit linkages are present at one or both of the 5' end and the 3' end of the modified oligonucleotide.

In an embodiment, between two and five of the modified intersubunit linkages are present at one or both of the 5' end and the 3' end of the modified oligonucleotide. In an embodiment, between two and five of the modified intersubunit linkages are present at the 5' end of the modified oligonucleotide. In an embodiment, between two and five of the modified intersubunit linkages are present at the 3' end of the modified oligonucleotide.

In an embodiment, two of the modified intersubunit linkages are present at one or both of the 5' end and the 3' end of the modified oligonucleotide. In an embodiment, two of the modified intersubunit linkages are present at the 5' end of the modified oligonucleotide. In an embodiment, two of the modified intersubunit linkages are present at the 3' end of the modified oligonucleotide.

In an embodiment, three of the modified intersubunit linkages are present at one or both of the 5' end and the 3' end of the modified oligonucleotide. In an embodiment, three of the modified intersubunit linkages are present at the 5' end of the modified oligonucleotide. In an embodiment, three of the modified intersubunit linkages are present at the 3' end of the modified oligonucleotide.

In an embodiment, four of the modified intersubunit linkages are present at one or both of the 5' end and the 3' end of the modified oligonucleotide. In an embodiment, four of the modified intersubunit linkages are present at the 5' end of the modified oligonucleotide. In an embodiment, four of the modified intersubunit linkages are present at the 3' end of the modified oligonucleotide.

In an embodiment, five of the modified intersubunit linkages are present at one or both of the 5' end and the 3' end of the modified oligonucleotide. In an embodiment, five of the modified intersubunit linkages are present at the 5' end of the modified oligonucleotide. In an embodiment, five of the modified intersubunit linkages are present at the 3' end of the modified oligonucleotide.

In an embodiment, the at least two modified intersubunit linkages are consecutive. In an embodiment, the modified oligonucleotide comprises three consecutive modified intersubunit linkages at one or both of the 5' end and the 3' end of the modified oligonucleotide. In an embodiment, the modified oligonucleotide comprises four consecutive modified intersubunit linkages at one or both of the 5' end and the 3' end of the modified oligonucleotide. In an embodiment, the modified oligonucleotide comprises five consecutive modified intersubunit linkages at one or both of the 5' end and the 3' end of the modified oligonucleotide.

In an embodiment, the oligonucleotide is selected from the group consisting of an siRNA, a miRNA, an antisense oligonucleotide, a ribozyme, and a mRNA.

In an embodiment, the siRNA comprises an antisense strand and a sense strand, and wherein one or both of the antisense strand and the sense strand comprise the modified intersubunit linkages.

In another aspect, the disclosure provides a modified oligonucleotide comprising a 5' end, a 3' end and at least two modified intersubunit linkages of Formula (VI)

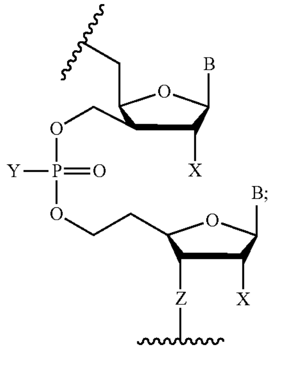

wherein:

B is a base moiety;

X is selected from the group consisting of H, OH, $OR^1$, $R^1$, F, Cl, Br, I, SH, $SR^1$, $NH_2$, $NHR^1$, $NR^1_2$, and $COOR^1$;

Y is selected from the group consisting of $O^-$, OH, $OR^2$, $NH^-$, $NH_2$, $NR^2_2$, $BH_3$, $S^-$, $R^2$ and SH;

Z is O or $O(CH_2)_n$ wherein n is 1 to 10;

$R^1$ is a substituted or unsubstituted $C_1$-$C_6$ alkyl, alkenyl, alkynyl, aryl, or mixtures thereof;

$R^2$ is a substituted or unsubstituted $C_1$-$C_6$ alkyl, alkenyl, alkynyl, aryl, or mixtures thereof; and wherein at least two of the modified intersubunit linkages are present at one or both of the 5' end and the 3' end of the modified oligonucleotide.

In an embodiment, Y is $S^-$. In an embodiment, Y is $O^-$. In an embodiment, X is $OR^1$ or F.

In an embodiment, between two and ten of the modified intersubunit linkages are present at one or both of the 5' end and the 3' end of the modified oligonucleotide.

In an embodiment, between two and five of the modified intersubunit linkages are present at one or both of the 5' end and the 3' end of the modified oligonucleotide. In an embodiment, between two and five of the modified intersubunit linkages are present at the 5' end of the modified oligonucleotide. In an embodiment, between two and five of the modified intersubunit linkages are present at the 3' end of the modified oligonucleotide.

In an embodiment, two of the modified intersubunit linkages are present at one or both of the 5' end and the 3' end of the modified oligonucleotide. In an embodiment, two of the modified intersubunit linkages are present at the 5' end of the modified oligonucleotide. In an embodiment, two of the modified intersubunit linkages are present at the 3' end of the modified oligonucleotide.

In an embodiment, three of the modified intersubunit linkages are present at one or both of the 5' end and the 3' end of the modified oligonucleotide. In an embodiment, three of the modified intersubunit linkages are present at the 5' end of the modified oligonucleotide. In an embodiment, three of the modified intersubunit linkages are present at the 3' end of the modified oligonucleotide.

In an embodiment, four of the modified intersubunit linkages are present at one or both of the 5' end and the 3' end of the modified oligonucleotide. In an embodiment, four of the modified intersubunit linkages are present at the 5' end of the modified oligonucleotide. In an embodiment, four of the modified intersubunit linkages are present at the 3' end of the modified oligonucleotide.

In an embodiment, five of the modified intersubunit linkages are present at one or both of the 5' end and the 3' end of the modified oligonucleotide. In an embodiment, five of the modified intersubunit linkages are present at the 5' end of the modified oligonucleotide. In an embodiment, five of the modified intersubunit linkages are present at the 3' end of the modified oligonucleotide.

In an embodiment, the at least two modified intersubunit linkages are consecutive. In an embodiment, the modified oligonucleotide comprises three consecutive modified intersubunit linkages at one or both of the 5' end and the 3' end of the modified oligonucleotide. In an embodiment, the modified oligonucleotide comprises four consecutive modified intersubunit linkages at one or both of the 5' end and the 3' end of the modified oligonucleotide. In an embodiment, the modified oligonucleotide comprises five consecutive modified intersubunit linkages at one or both of the 5' end and the 3' end of the modified oligonucleotide.

In an embodiment, the oligonucleotide is selected from the group consisting of an siRNA, a miRNA, an antisense oligonucleotide, a ribozyme, and a mRNA.

In an embodiment, the siRNA comprises an antisense strand and a sense strand, and wherein one or both of the antisense strand and the sense strand comprise the modified intersubunit linkages.

In an embodiment of any of the above aspects of the disclosure, the base moiety B is selected from the group consisting of adenine, guanine, cytosine, and uracil.

In another aspect, the disclosure provides a method for synthesizing a modified oligonucleotide comprising a 5' end, a 3' end and at least one modified intersubunit linkage comprising:

(a) providing a nucleoside having a 5'-protecting group linked to a solid support;
(b) removal of the protecting group;
(c) combining the deprotected nucleoside with a phosphoramidite derivative of Formula (VII) to form a phosphite triester;

(VII)

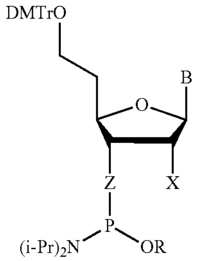

(d) capping the phosphite triester;
(e) oxidizing the phosphite triester;
(f) repeating steps (b) through (e) using an additional phosphoramidite; and
(g) cleaving from the solid support.

II. Novel Phosphoramidite Derivative Synthesis

Figure 11:
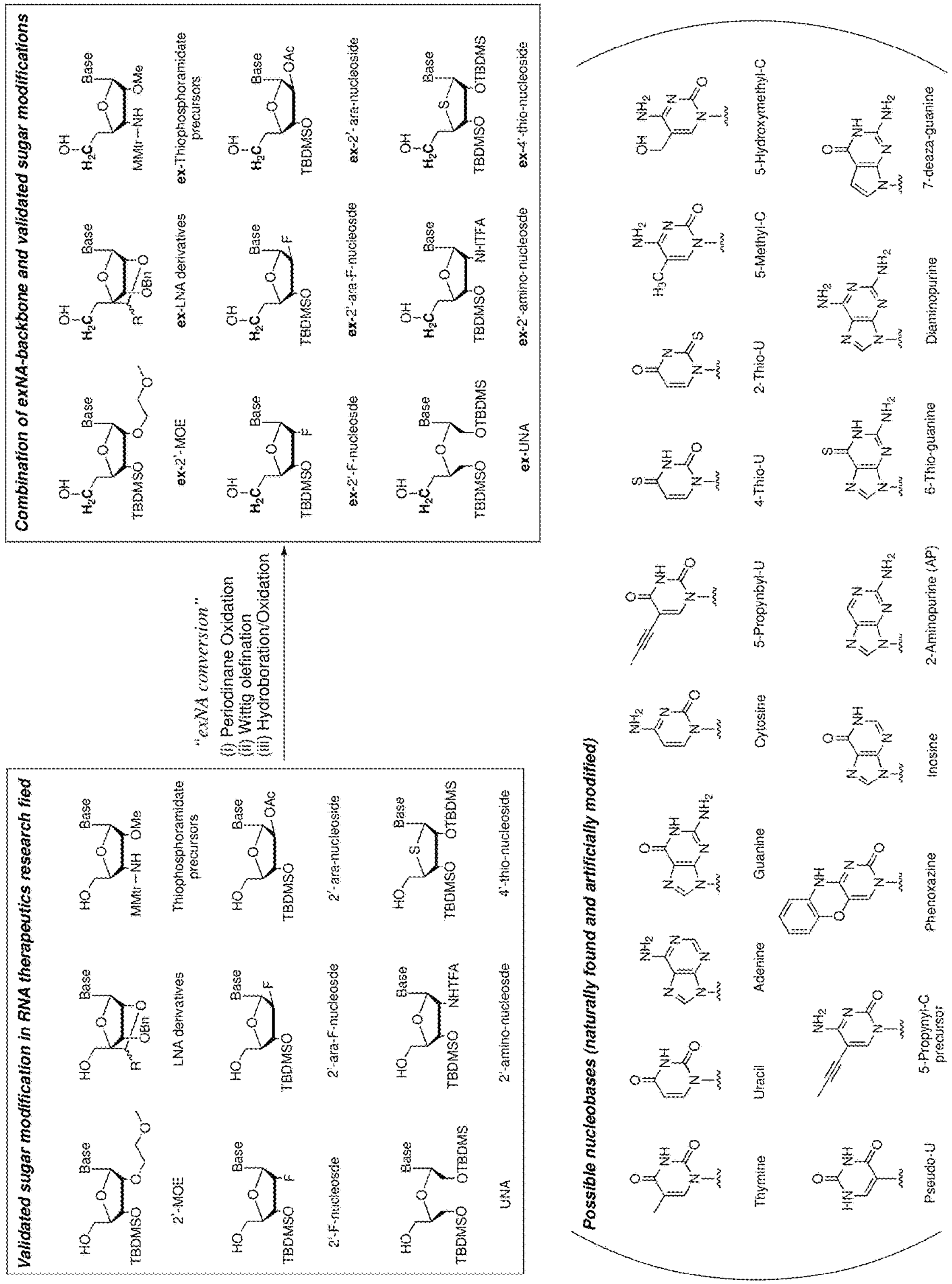
FIG. 11 provides a universal scheme for exNA conversion of sugar-modified nucleotides.

Here we describe a collection of synthetic procedures for novel phosphoramidite derivatives used to make oligonucleotides modified with the novel backbone modification, Extended Nucleic Acid (exNA). As shown in FIG. 11, this modification is very versatile and can be combined with many existing nucleosides to greatly enhance the diversity of oligonucleotides having an enhanced stability. In this aspect, the disclosure provides a phosphoramidite derivative of Formula (VII):

(VII)

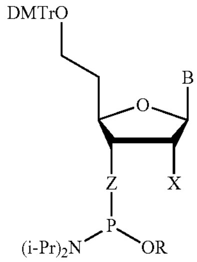

wherein:

B is a base moiety;

X is selected from the group consisting of H, OH, OR, F, SH, SR, $NR^2{}_2$, MOE, alkyl, allyl, aryl, and $C_{1-6}$-alkoxy;

Z is O or $OCH_2$; R is OMe or OCE (cyanoethyl):

$R^1$ is alkyl, allyl or aryl; and $R^2$ is alkyl, allyl or aryl.

In an embodiment of Formula VII, the base moiety B is selected from the group consisting of adenine, guanine, cytosine, and uracil.

In another aspect, the disclosure provides a phosphoramidite derivative of Formula (VIII):

(VIII)

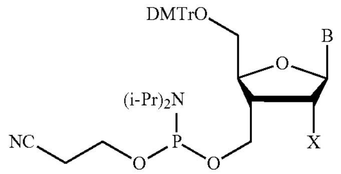

wherein:

B is a base moiety;

X is selected from the group consisting of H, OH, OR, F, SH, SR, $NR^2{}_2$, MOE, alkyl, allyl, aryl, and $C_{1-6}$-alkoxy;

$R^1$ is alkyl, allyl or aryl; and $R^2$ is alkyl, allyl or aryl.

In an embodiment of Formula (VIII), the base moiety B is selected from the group consisting of adenine, guanine, cytosine, and uracil.

In another aspect, the disclosure provides phosphoramidite derivative of Formula (IX):

(IX)

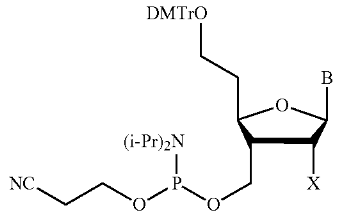

wherein:

B is a base moiety;

X is selected from the group consisting of H, OH, OR, F, SH, SR, $NR^2{}_2$, MOE, alkyl, allyl, aryl, and $C_{1-6}$-alkoxy;

$R^1$ is alkyl, allyl or aryl; and $R^2$ is alkyl, allyl or aryl.

In an embodiment of Formula (IX) wherein the base moiety B is selected from the group consisting of adenine, guanine, cytosine, and uracil.

In another aspect, the disclosure provides method for coupling a phosphoramidite derivative of Formula (VII):

(VII)

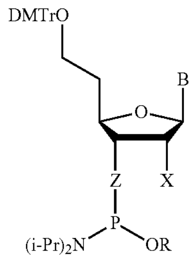

to a 5'-terminus of a nucleoside or an oligonucleotide comprising adding the phosphoramidite derivative of Formula (VII) to the nucleoside or the oligonucleotide in an organic solvent comprising an aromatic heterocyclic acid.

In another aspect, the disclosure provides a method for synthesizing a exNA phosphoramidite:

(a) providing a nucleoside having 3'-protecting group;
(b) oxidizing 5'-hydroxyl group of the nucleoside to a 5'-aldehyde group;
(c) converting 5'-aldehyde group of the nucleoside to a 5'-vinyl group by Wittig olefination;
(d) conducting hydroboration/oxidation on the 5'-vinyl group to produce a 6'-hydroxyl group;
(e) protecting the 6'-hydroxyl group with a DMTr group;
(f) removing the 3'-protecting group of the nucleoside;
(g) phosphitylating 3'-hydroxyl group to produce a 3'-phosphoramidite.

III. siRNA Design

In some embodiments, siRNAs are designed as follows. First, a portion of a target gene is selected. Cleavage of mRNA at these sites should eliminate translation of corresponding protein. Antisense strands were designed based on the target sequence and sense strands were designed to be complementary to the antisense strand. Hybridization of the antisense and sense strands forms the siRNA duplex. The antisense strand includes about 19 to 25 nucleotides, e.g., 19, 20, 21, 22, 23, 24 or 25 nucleotides. In other embodiments, the antisense strand includes 20, 21, 22 or 23 nucleotides. The sense strand includes about 14 to 25 nucleotides, e.g., 14, 15, 16, 17, 18, 19, 20, 21, 22, 23, 24 or 25 nucleotides. In other embodiments, the sense strand is 15 nucleotides. In other embodiments, the sense strand is 16 nucleotides. In other embodiments, the sense strand is 17 nucleotides. In other embodiments, the sense strand is 18 nucleotides. In other embodiments, the sense strand is 19 nucleotides. In other embodiments, the sense strand is 20 nucleotides. The skilled artisan will appreciate, however, that siRNAs having antisense strands with a length of less than 19 nucleotides or greater than 25 nucleotides can also function to mediate RNAi. Accordingly, siRNAs of such length are also within the scope of the instant disclosure, provided that they retain the ability to mediate RNAi. Longer RNAi agents have been demonstrated to elicit an interferon or PKR response in certain mammalian cells, which may be undesirable. In certain embodiments, the RNAi agents of the disclosure do not elicit a PKR response (i.e., are of a sufficiently short length). However, longer RNAi agents may be useful, for example, in cell types incapable of generating a PKR response or in situations where the PKR response has been down-regulated or dampened by alternative means.

The sense strand sequence can be designed such that the target sequence is essentially in the middle of the strand. Moving the target sequence to an off-center position can, in some instances, reduce efficiency of cleavage by the siRNA. Such compositions, i.e., less efficient compositions, may be desirable for use if off-silencing of the wild-type mRNA is detected.

The antisense strand can be the same length as the sense strand and includes complementary nucleotides. In one embodiment, the strands are fully complementary, i.e., the strands are blunt-ended when aligned or annealed. In another embodiment, the strands align or anneal such that 1-, 2-, 3-, 4-, 5-, 6-, 7-, or 8-nucleotide overhangs are generated, i.e., the 3' end of the sense strand extends 1, 2, 3, 4, 5, 6, 7, or 8 nucleotides further than the 5' end of the antisense strand and/or the 3' end of the antisense strand extends 1, 2, 3, 4, 5, 6, 7, or 8 nucleotides further than the 5' end of the sense strand. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material.

To facilitate entry of the antisense strand into RISC (and thus increase or improve the efficiency of target cleavage and silencing), the base pair strength between the 5' end of the sense strand and 3' end of the antisense strand can be altered, e.g., lessened or reduced, as described in detail in U.S. Pat. Nos. 7,459,547, 7,772,203 and 7,732,593, entitled "Methods and Compositions for Controlling Efficacy of RNA Silencing" (filed Jun. 2, 2003) and U.S. Pat. Nos. 8,309,704, 7,750,144, 8,304,530, 8,329,892 and 8,309,705, entitled "Methods and Compositions for Enhancing the Efficacy and Specificity of RNAi" (filed Jun. 2, 2003), the contents of which are incorporated in their entirety by this reference. In one embodiment of these aspects of the disclosure, the base-pair strength is less due to fewer G:C base pairs between the 5' end of the first or antisense strand and the 3' end of the second or sense strand than between the 3' end of the first or antisense strand and the 5' end of the second or sense strand. In another embodiment, the base pair strength is less due to at least one mismatched base pair between the 5' end of the first or antisense strand and the 3' end of the second or sense strand. In certain exemplary embodiments, the mismatched base pair is selected from the group consisting of G:A, C:A, C:U, G:G, A:A, C:C and U:U. In another embodiment, the base pair strength is less due to at least one wobble base pair, e.g., G:U, between the 5' end of the first or antisense strand and the 3' end of the second or sense strand. In another embodiment, the base pair strength is less due to at least one base pair comprising a rare nucleotide, e.g., inosine (I). In certain exemplary embodiments, the base pair is selected from the group consisting of an I:A, I:U and I:C. In yet another embodiment, the base pair strength is less due to at least one base pair comprising a modified nucleotide. In certain exemplary embodiments, the modified nucleotide is selected from the group consisting of 2-amino-G, 2-amino-A, 2,6-diamino-G, and 2,6-diamino-A.

To validate the effectiveness by which siRNAs destroy mRNAs (e.g., mRNA expressed from a target gene), the siRNA can be incubated with cDNA (e.g., cDNA derived from a target gene) in a *Drosophila*-based in vitro mRNA expression system. Radiolabeled with $^{32}P$, newly synthesized mRNAs (e.g., target mRNA) are detected autoradiographically on an agarose gel. The presence of cleaved mRNA indicates mRNA nuclease activity. Suitable controls include omission of siRNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence. Sites of siRNA-mRNA complementation are selected which result in optimal mRNA specificity and maximal mRNA cleavage.

IV. RNAi Agents

The present disclosure includes siRNA molecules designed, for example, as described above. The siRNA molecules of the disclosure can be chemically synthesized, or can be transcribed in vitro from a DNA template, or in vivo from e.g., shRNA, or by using recombinant human DICER enzyme, to cleave in vitro transcribed dsRNA templates into pools of 20-, 21- or 23-bp duplex RNA mediating RNAi. The siRNA molecules can be designed using any method known in the art.

In one aspect, instead of the RNAi agent being an interfering ribonucleic acid, e.g., an siRNA or shRNA as described above, the RNAi agent can encode an interfering ribonucleic acid, e.g., an shRNA, as described above. In other words, the RNAi agent can be a transcriptional template of the interfering ribonucleic acid. Thus, RNAi agents of the present disclosure can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21-23 nucleotides (Brummelkamp et al., 2002; Lee et al., 2002, Supra; Miyagishi et al., 2002; Paddison et al., 2002, *supra*; Paul et al., 2002, *supra*; Sui et al., 2002 *supra*; Yu et al., 2002, *supra*. More information about shRNA design and use can be found on the internet at the following addresses: katandin.cshl.org:9331/RNAi/docs/BseRI-BamHI_Strategy.pdf and katandin.cshl.org:9331/RNAi/docs/Web_version_of_PCR_strategyl.pdf).

Expression constructs of the present disclosure include any construct suitable for use in the appropriate expression system and include, but are not limited to, retroviral vectors, linear expression cassettes, plasmids and viral or virally-derived vectors, as known in the art. Such expression constructs can include one or more inducible promoters, RNA Pol III promoter systems such as U6 snRNA promoters or H1 RNA polymerase III promoters, or other promoters known in the art. The constructs can include one or both strands of the siRNA. Expression constructs expressing both strands can also include loop structures linking both strands, or each strand can be separately transcribed from separate promoters within the same construct. Each strand can also be transcribed from a separate expression construct. (Tuschl, T., 2002, *Supra*).

Synthetic siRNAs can be delivered into cells by methods known in the art, including cationic liposome transfection and electroporation. To obtain longer term suppression of the target genes and to facilitate delivery under certain circumstances, one or more siRNA can be expressed within cells from recombinant DNA constructs. Such methods for expressing siRNA duplexes within cells from recombinant DNA constructs to allow longer-term target gene suppression in cells are known in the art, including mammalian Pol III promoter systems (e.g., H1 or U6/snRNA promoter systems (Tuschl, T., 2002, *supra*) capable of expressing functional double-stranded siRNAs; (Bagella et al., 1998; Lee et al., 2002, *supra*; Miyagishi et al., 2002, *supra*; Paul et al., 2002, *supra*; Yu et al., 2002, *supra*; Sui et al., 2002, *supra*). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al., 1998; Lee et al., 2002, *supra*; Miyagishi et al., 2002, *supra*; Paul et al., 2002, *supra*; Yu et al., 2002), *supra*; Sui et al., 2002, *supra*). Constructs containing siRNA sequence under the control of T7 promoter also make functional siRNAs when co-transfected into the cells with a vector expressing T7 RNA polymerase (Jacque et al., 2002, *supra*). A single construct may contain multiple sequences coding for siRNAs, such as multiple regions of the target gene, targeting the same gene or multiple genes, and can be driven, for example, by separate PolIII promoter sites.

Animal cells express a range of noncoding RNAs of approximately 22 nucleotides termed micro RNA (miRNAs) which can regulate gene expression at the post transcriptional or translational level during animal development. One common feature of miRNAs is that they are all excised from an approximately 70 nucleotide precursor RNA stem-loop, probably by Dicer, an RNase III-type enzyme, or a homolog thereof. By substituting the stem sequences of the miRNA precursor with sequence complementary to the target mRNA, a vector construct that expresses the engineered precursor can be used to produce siRNAs to initiate RNAi against specific mRNA targets in mammalian cells (Zeng et al., 2002, *supra*). When expressed by DNA vectors containing polymerase III promoters, micro-RNA designed hairpins can silence gene expression (McManus et al., 2002, *supra*). MicroRNAs targeting polymorphisms may also be useful for blocking translation of mutant proteins, in the absence of siRNA-mediated gene-silencing. Such applications may be useful in situations, for example, where a designed siRNA caused off-target silencing of wild type protein.

Viral-mediated delivery mechanisms can also be used to induce specific silencing of targeted genes through expression of siRNA, for example, by generating recombinant adenoviruses harboring siRNA under RNA Pol II promoter transcription control (Xia et al., 2002, *supra*). Infection of HeLa cells by these recombinant adenoviruses allows for diminished endogenous target gene expression. Injection of the recombinant adenovirus vectors into transgenic mice expressing the target genes of the siRNA results in in vivo reduction of target gene expression. Id. In an animal model, whole-embryo electroporation can efficiently deliver synthetic siRNA into post-implantation mouse embryos (Calegari et al., 2002). In adult mice, efficient delivery of siRNA can be accomplished by “high-pressure” delivery technique, a rapid injection (within 5 seconds) of a large volume of siRNA containing solution into animal via the tail vein (Liu et al., 1999, *supra*; McCaffrey et al., 2002, *supra*; Lewis et al., 2002. Nanoparticles and liposomes can also be used to deliver siRNA into animals. In certain exemplary embodiments, recombinant adeno-associated viruses (rAAVs) and their associated vectors can be used to deliver one or more siRNAs into cells, e.g., neural cells (e.g., brain cells) (US Patent Applications 2014/0296486, 2010/0186103, 2008/0269149, 2006/0078542 and 2005/0220766).

The nucleic acid compositions of the disclosure include both unmodified siRNAs and modified siRNAs as known in the art, such as crosslinked siRNA derivatives or derivatives having non-nucleotide moieties linked, for example to their 3' or 5' ends. Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Engineered RNA precursors, introduced into cells or whole organisms as described herein, will lead to the production of a desired siRNA molecule. Such an siRNA molecule will then associate with endogenous protein components of the RNAi pathway to bind to and target a specific mRNA sequence for cleavage and destruction. In this fashion, the mRNA to be targeted by the siRNA generated from the engineered RNA precursor will be depleted from the cell or organism, leading to a decrease in the concentration of the protein encoded by that mRNA in the cell or organism. The RNA precursors are typically nucleic acid molecules that individually encode either one strand of a dsRNA or encode the entire nucleotide sequence of an RNA hairpin loop structure.

The nucleic acid compositions of the disclosure can be unconjugated or can be conjugated to another moiety, such as a nanoparticle, to enhance a property of the compositions, e.g., a pharmacokinetic parameter such as absorption, efficacy, bioavailability and/or half-life. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

The nucleic acid molecules of the present disclosure can also be labeled using any method known in the art. For instance, the nucleic acid compositions can be labeled with a fluorophore, e.g., Cy3, fluorescein, or rhodamine. The labeling can be carried out using a kit, e.g., the SILENCERm siRNA labeling kit (Ambion). Additionally, the siRNA can be radiolabeled, e.g., using $^{3}H$, $^{32}P$ or another appropriate isotope.

Moreover, because RNAi is believed to progress via at least one single-stranded RNA intermediate, the skilled artisan will appreciate that ss-siRNAs (e.g., the antisense strand of a ds-siRNA) can also be designed (e.g., for chemical synthesis) generated (e.g., enzymatically generated) or expressed (e.g., from a vector or plasmid) as described herein and utilized according to the claimed methodologies. Moreover, in invertebrates, RNAi can be triggered effectively by long dsRNAs (e.g., dsRNAs about 100-1000 nucleotides in length, preferably about 200-500, for example, about 250, 300, 350, 400 or 450 nucleotides in length) acting as effectors of RNAi. (Brondani et al., Proc Natl Acad Sci USA. 2001 Dec. 4; 98(25):14428-33. Epub 2001 Nov. 27.)

V. RNA Silencing Agents

In one embodiment, the present disclosure provides novel RNA silencing agents (e.g., siRNA and shRNAs), methods of making said RNA silencing agents, and methods (e.g., research and/or therapeutic methods) for using said improved RNA silencing agents (or portions thereof) for RNA silencing of a target gene. The RNA silencing agents comprise an antisense strand (or portions thereof), wherein the antisense strand has sufficient complementary to a heterozygous single nucleotide polymorphism to mediate an RNA-mediated silencing mechanism (e.g. RNAi).

In certain embodiments, siRNA compounds are provided having one or any combination of the following properties: (1) fully chemically-stabilized (i.e., no unmodified 2'-OH residues); (2) asymmetry; (3) 11-20 base pair duplexes; (4) greater than 50% 2'-methoxy modifications, such as 70%-100% 2'-methoxy modifications, although an alternating pattern of chemically-modified nucleotides (e.g., 2'-fluoro and 2'-methoxy modifications), are also contemplated; and (5) single-stranded, fully phosphorothioated tails of 5-8 bases. In certain embodiments, the number of phosphorothioate modifications is varied from 4 to 16 total. In certain embodiments, the number of phosphorothioate modifications is varied from 8 to 13 total. In certain embodiments, the siRNA comprises or consists of 4 phosphorothioate modifications. In certain embodiments, the siRNA comprises or consists of 5 phosphorothioate modifications. In certain embodiments, the siRNA comprises or consists of 6 phosphorothioate modifications. In certain embodiments, the siRNA comprises or consists of 7 phosphorothioate modifications. In certain embodiments, the siRNA comprises or consists of 8 phosphorothioate modifications. In certain embodiments, the siRNA comprises or consists of 9 phosphorothioate modifications. In certain embodiments, the siRNA comprises or consists of 10 phosphorothioate modifications. In certain embodiments, the siRNA comprises or consists of 11 phosphorothioate modifications. In certain embodiments, the siRNA comprises or consists of 12 phosphorothioate modifications. In certain embodiments, each phosphorothioate modification is combined with an exNA modification. In certain embodiments, the siRNA comprises no phosphorothioate modifications.

In certain embodiments, the siRNA compounds described herein can be conjugated to a variety of targeting agents, including, but not limited to, cholesterol, docosahexaenoic acid (DHA), phenyltropanes, cortisol, vitamin A, vitamin D, N-acetylgalactosamine (GalNac), and gangliosides. The cholesterol-modified version showed 5-10 fold improvement in efficacy in vitro versus previously used chemical stabilization patterns (e.g., wherein all purine but not pyrimidines are modified) in wide range of cell types (e.g., HeLa, neurons, hepatocytes, trophoblasts).

Certain compounds of the disclosure having the structural properties described above and herein may be referred to as "hsiRNA-ASP" (hydrophobically-modified, small interfering RNA, featuring an advanced stabilization pattern). In addition, this hsiRNA-ASP pattern showed a dramatically improved distribution through the brain, spinal cord, delivery to liver, placenta, kidney, spleen and several other tissues, making them accessible for therapeutic intervention.

In liver hsiRNA-ASP delivery specifically to endothelial and kupper cells, but not hepatocytes, making this chemical modification pattern complimentary rather than competitive technology to GalNac conjugates.

The compounds of the disclosure can be described in the following aspects and embodiments.

In a first aspect, provided herein is an oligonucleotide of at least 16 contiguous nucleotides, said oligonucleotide having a 5' end, a 3' end and complementarity to a target, wherein: (1) the oligonucleotide comprises at least 70% 2'-O-methyl modifications; (2) the nucleotide at position 14 from the 5' end is not a 2'-methoxy-ribonucleotide; and (3) the nucleotides are connected via modified linkages as shown in FIG. 1.

In a second aspect, provided herein is a dsRNA comprising an antisense strand and a sense strand, each strand comprising at least 14 contiguous nucleotides, with a 5' end and a 3' end, wherein: (1) the antisense strand comprises a sequence substantially complementary to a target nucleic acid sequence; (2) the antisense strand comprises at least 70% 2'-O-methyl modifications; (3) the nucleotide at position 14 from the 5' end of the antisense strand is not 2'-methoxy-ribonucleotide; (4) a portion of the antisense strand is complementary to a portion of the sense strand; (5) the sense strand comprises at least 70% 2'-O-methyl modifications; and (6) the nucleotides are connected via modified linkages as shown in FIG. 1.

a) Design of siRNA Molecules

An siRNA molecule of the disclosure is a duplex consisting of a sense strand and complementary antisense strand, the antisense strand having sufficient complementary to a target mRNA to mediate RNAi. In certain embodiments, the siRNA molecule has a length from about 10-50 or more nucleotides, i.e., each strand comprises 10-50 nucleotides (or nucleotide analogs). In other embodiments, the siRNA molecule has a length from about 15-30, e.g., 15, 16, 17, 18, 19, 20, 21, 22, 23, 24, 25, 26, 27, 28, 29, or 30 nucleotides in each strand, wherein one of the strands is sufficiently complementary to a target region. In certain embodiments, the strands are aligned such that there are at least 1, 2, 3, 4, 5, 6, 7, 8, 9, or 10 bases at the end of the strands, which do not align (i.e., for which no complementary bases occur in the opposing strand), such that an overhang of 1, 2, 3, 4, 5, 6, 7, 8, 9, or 10 residues occurs at one or both ends of the duplex when strands are annealed.

Usually, siRNAs can be designed by using any method known in the art, for instance, by using the following protocol:

1. The siRNA should be specific for a target sequence, e.g., a target sequence set forth in the Examples. The first strand should be complementary to the target sequence, and the other strand is substantially complementary to the first strand. (See Examples for exemplary sense and antisense strands.) Exemplary target sequences are selected from any region of the target gene that leads to potent gene silencing. Regions of the target gene include, but are not limited to, the 5' untranslated region (5'-UTR) of a target gene, the 3' untranslated region (3'-UTR) of a target gene, an exon of a target gene, or an intron of a target gene. Cleavage of mRNA at these sites should eliminate translation of corresponding target protein. Target sequences from other regions of the target gene are also suitable for targeting. A sense strand is designed based on the target sequence.

2. The sense strand of the siRNA is designed based on the sequence of the selected target site. In certain embodiments, the sense strand includes about 15 to 25 nucleotides, e.g., 15, 16, 17, 18, 19, 20, 21, 22, 23, 24 or 25 nucleotides. In certain embodiments, the sense strand includes 15, 16, 17, 18, 19, or 20 nucleotides. In certain embodiments, the sense strand is 15 nucleotides in length. In certain embodiments, the sense strand is 18 nucleotides in length. In certain embodiments, the sense strand is 20 nucleotides in length. The skilled artisan will appreciate, however, that siRNAs having a length of less than 15 nucleotides or greater than 25 nucleotides can also function to mediate RNAi. Accordingly, siRNAs of such length are also within the scope of the instant disclosure, provided that they retain the ability to mediate RNAi. Longer RNA silencing agents have been demonstrated to elicit an interferon or Protein Kinase R (PKR) response in certain mammalian cells which may be undesirable. In certain embodiments, the RNA silencing agents of the disclosure do not elicit a PKR response (i.e., are of a sufficiently short length). However, longer RNA silencing agents may be useful, for example, in cell types incapable of generating a PKR response or in situations where the PKR response has been down-regulated or dampened by alternative means.

The siRNA molecules of the disclosure have sufficient complementarity with the target sequence such that the siRNA can mediate RNAi. In general, siRNA containing nucleotide sequences sufficiently identical to a target sequence portion of the target gene to effect RISC-mediated cleavage of the target gene are preferred. Accordingly, in a preferred embodiment, the sense strand of the siRNA is designed to have a sequence sufficiently identical to a portion of the target. For example, the sense strand may have 100% identity to the target site. However, 100% identity is not required. Greater than 80% identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% identity, between the sense strand and the target RNA sequence is preferred. The disclosure has the advantage of being able to tolerate certain sequence variations to enhance efficiency and specificity of RNAi. In one embodiment, the sense strand has 4, 3, 2, 1, or 0 mismatched nucleotide(s) with a target region, such as a target region that differs by at least one base pair between a wild-type and mutant allele, e.g., a target region comprising the gain-of-function mutation, and the other strand is identical or substantially identical to the first strand. Moreover, siRNA sequences with small insertions or deletions of 1 or 2 nucleotides may also be effective for mediating RNAi. Alternatively, siRNA sequences with nucleotide analog substitutions or insertions can be effective for inhibition.

Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=number of identical positions/total number of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

3. The antisense or guide strand of the siRNA is routinely the same length as the sense strand and includes complementary nucleotides. In one embodiment, the guide and sense strands are fully complementary, i.e., the strands are blunt-ended when aligned or annealed. In another embodiment, the strands of the siRNA can be paired in such a way as to have a 3' overhang of 1 to 7 (e.g., 2, 3, 4, 5, 6 or 7), or 1 to 4, e.g., 2, 3 or 4 nucleotides. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material. Thus, in another embodiment, the nucleic acid molecules may have a 3' overhang of 2 nucleotides, such as TT. The overhanging nucleotides may be either RNA or DNA. As noted above, it is desirable to choose a target region wherein the mutant:wild type mismatch is a purine:purine mismatch.

4. Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at National Center for Biotechnology Information website.

5. Select one or more sequences that meet your criteria for evaluation.

Further general information about the design and use of siRNA may be found in "The siRNA User Guide," available at The Max-Plank-Institut fur Biophysikalische Chemie website.

Alternatively, the siRNA may be defined functionally as a nucleotide sequence (or oligonucleotide sequence) that is capable of hybridizing with the target sequence (e.g., 400 mM NaCl, 40 mM PIPES pH 6.4, 1 mM EDTA, 50° C. or 70° C. hybridization for 12-16 hours; followed by washing). Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6(log 10[Na+])+0.41(% G+C)-(600/N), where N is the number of bases in the hybrid, and $[Na^+]$ is the concentration of sodium ions in the hybridization buffer ($[Na^+]$ for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference.

Negative control siRNAs should have the same nucleotide composition as the selected siRNA, but without significant sequence complementarity to the appropriate genome. Such negative controls may be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

6. To validate the effectiveness by which siRNAs destroy target mRNAs (e.g., wild-type or mutant mRNA), the siRNA may be incubated with target cDNA in a *Drosophila*-based in vitro mRNA expression system. Radiolabeled with $^{32}P$, newly synthesized target mRNAs are detected autoradiographically on an agarose gel. The presence of cleaved target mRNA indicates mRNA nuclease activity. Suitable controls include omission of siRNA and use of non-target cDNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

siRNAs may be designed to target any of the target sequences described *supra*. Said siRNAs comprise an antisense strand which is sufficiently complementary with the target sequence to mediate silencing of the target sequence. In certain embodiments, the RNA silencing agent is a siRNA.

In certain embodiments, the siRNA comprises a sense strand comprising a linkage set forth at FIG. 1, or an antisense strand comprising a linkage set forth at FIG. 1.

Sites of siRNA-mRNA complementation are selected which result in optimal mRNA specificity and maximal mRNA cleavage.

b) siRNA-Like Molecules siRNA-like molecules of the disclosure have a sequence (i.e., have a strand having a sequence) that is "sufficiently complementary" to a target sequence of an mRNA to direct gene silencing either by RNAi or translational repression. siRNA-like molecules are designed in the same way as siRNA molecules, but the degree of sequence identity between the sense strand and target RNA approximates that observed between an miRNA and its target. In general, as the degree of sequence identity between a miRNA sequence and the corresponding target gene sequence is decreased, the tendency to mediate post-transcriptional gene silencing by translational repression rather than RNAi is increased. Therefore, in an alternative embodiment, where post-transcriptional gene silencing by translational repression of the target gene is desired, the miRNA sequence has partial complementarity with the target gene sequence. In certain embodiments, the miRNA sequence has partial complementarity with one or more short sequences (complementarity sites) dispersed within the target mRNA (e.g. within the 3'-UTR of the target mRNA) (Hutvagner and Zamore, Science, 2002; Zeng et al., Mol. Cell, 2002; Zeng et al., RNA, 2003; Doench et al., Genes & Dev., 2003). Since the mechanism of translational repression is cooperative, multiple complementarity sites (e.g., 2, 3, 4, 5, or 6) may be targeted in certain embodiments.

The capacity of a siRNA-like duplex to mediate RNAi or translational repression may be predicted by the distribution of non-identical nucleotides between the target gene sequence and the nucleotide sequence of the silencing agent at the site of complementarity. In one embodiment, where gene silencing by translational repression is desired, at least one non-identical nucleotide is present in the central portion of the complementarity site so that duplex formed by the miRNA guide strand and the target mRNA contains a central "bulge" (Doench J G et al., Genes & Dev., 2003). In another embodiment 2, 3, 4, 5, or 6 contiguous or non-contiguous non-identical nucleotides are introduced. The non-identical nucleotide may be selected such that it forms a wobble base pair (e.g., G:U) or a mismatched base pair (G:A, C:A, C:U, G:G, A:A, C:C, U:U). In a further preferred embodiment, the "bulge" is centered at nucleotide positions 12 and 13 from the 5' end of the miRNA molecule.

c) Short Hairpin RNA (shRNA) Molecules

In certain featured embodiments, the instant disclosure provides shRNAs capable of mediating RNA silencing of a target sequence with enhanced selectivity. In contrast to siRNAs, shRNAs mimic the natural precursors of micro RNAs (miRNAs) and enter at the top of the gene silencing pathway. For this reason, shRNAs are believed to mediate gene silencing more efficiently by being fed through the entire natural gene silencing pathway.

miRNAs are noncoding RNAs of approximately 22 nucleotides which can regulate gene expression at the post transcriptional or translational level during plant and animal development. One common feature of miRNAs is that they are all excised from an approximately 70 nucleotide precursor RNA stem-loop termed pre-miRNA, probably by Dicer, an RNase III-type enzyme, or a homolog thereof. Naturally-occurring miRNA precursors (pre-miRNA) have a single strand that forms a duplex stem including two portions that are generally complementary, and a loop, that connects the two portions of the stem. In typical pre-miRNAs, the stem includes one or more bulges, e.g., extra nucleotides that create a single nucleotide "loop" in one portion of the stem, and/or one or more unpaired nucleotides that create a gap in the hybridization of the two portions of the stem to each other. Short hairpin RNAs, or engineered RNA precursors, of the disclosure are artificial constructs based on these naturally occurring pre-miRNAs, but which are engineered to deliver desired RNA silencing agents (e.g., siRNAs of the disclosure). By substituting the stem sequences of the pre-miRNA with sequence complementary to the target mRNA, a shRNA is formed. The shRNA is processed by the entire gene silencing pathway of the cell, thereby efficiently mediating RNAi.

The requisite elements of a shRNA molecule include a first portion and a second portion, having sufficient complementarity to anneal or hybridize to form a duplex or double-stranded stem portion. The two portions need not be fully or perfectly complementary. The first and second "stem" portions are connected by a portion having a sequence that has insufficient sequence complementarity to anneal or hybridize to other portions of the shRNA. This latter portion is referred to as a "loop" portion in the shRNA molecule. The shRNA molecules are processed to generate siRNAs. shRNAs can also include one or more bulges, i.e., extra nucleotides that create a small nucleotide "loop" in a portion of the stem, for example a one-, two- or three-nucleotide loop. The stem portions can be the same length, or one portion can include an overhang of, for example, 1-5 nucleotides. The overhanging nucleotides can include, for example, uracils (Us), e.g., all Us. Such Us are notably encoded by thymidines (Ts) in the shRNA-encoding DNA which signal the termination of transcription.

In shRNAs (or engineered precursor RNAs) of the instant disclosure, one portion of the duplex stem is a nucleic acid sequence that is complementary (or anti-sense) to the target sequence. Preferably, one strand of the stem portion of the shRNA is sufficiently complementary (e.g., antisense) to a target RNA (e.g., mRNA) sequence to mediate degradation or cleavage of said target RNA via RNA interference (RNAi). Thus, engineered RNA precursors include a duplex stem with two portions and a loop connecting the two stem portions. The antisense portion can be on the 5' or 3' end of the stem. The stem portions of a shRNA are preferably about 15 to about 50 nucleotides in length. Preferably the two stem portions are about 18 or 19 to about 21, 22, 23, 24, 25, 30, 35, 37, 38, 39, or 40 or more nucleotides in length. In preferred embodiments, the length of the stem portions should be 21 nucleotides or greater. When used in mammalian cells, the length of the stem portions should be less than about 30 nucleotides to avoid provoking non-specific responses like the interferon pathway. In non-mammalian cells, the stem can be longer than 30 nucleotides. In fact, the stem can include much larger sections complementary to the target mRNA (up to, and including the entire mRNA). In fact, a stem portion can include much larger sections complementary to the target mRNA (up to, and including the entire mRNA).

The two portions of the duplex stem must be sufficiently complementary to hybridize to form the duplex stem. Thus, the two portions can be, but need not be, fully or perfectly complementary. In addition, the two stem portions can be the same length, or one portion can include an overhang of 1, 2, 3, or 4 nucleotides. The overhanging nucleotides can include, for example, uracils (Us), e.g., all Us. The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop in the shRNAs or engineered RNA precursors can be 2, 3, 4, 5, 6, 7, 8, 9, or more, e.g., 15 or 20, or more nucleotides in length.

The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop portion in the shRNA can be about 2 to about 20 nucleotides in length, i.e., about 2, 3, 4, 5, 6, 7, 8, 9, or more, e.g., 15 or 20, or more nucleotides in length. A preferred loop consists of or comprises a "tetraloop" sequences. Exemplary tetraloop sequences include, but are not limited to, the sequences GNRA, where N is any nucleotide and R is a purine nucleotide, GGGG, and UUUU.

In certain embodiments, shRNAs of the disclosure include the sequences of a desired siRNA molecule described *supra*. In other embodiments, the sequence of the antisense portion of a shRNA can be designed essentially as described above or generally by selecting an 18, 19, 20, 21 nucleotides, or longer, sequence from within the target RNA, for example, from a region 100 to 200 or 300 nucleotides upstream or downstream of the start of translation. In general, the sequence can be selected from any portion of the target RNA (e.g., mRNA) including the 5' UTR (untranslated region), coding sequence, or 3' UTR. This sequence can optionally follow immediately after a region of the target gene containing two adjacent AA nucleotides. The last two nucleotides of the nucleotide sequence can be selected to be UU. This 21 or so nucleotide sequence is used to create one portion of a duplex stem in the shRNA. This sequence can replace a stem portion of a wild-type pre-miRNA sequence, e.g., enzymatically, or is included in a complete sequence that is synthesized. For example, one can synthesize DNA oligonucleotides that encode the entire stem-loop engineered RNA precursor, or that encode just the portion to be inserted into the duplex stem of the precursor, and using restriction enzymes to build the engineered RNA precursor construct, e.g., from a wild-type pre-miRNA.

Engineered RNA precursors include in the duplex stem the 21-22 or so nucleotide sequences of the siRNA or siRNA-like duplex desired to be produced in vivo. Thus, the stem portion of the engineered RNA precursor includes at least 18 or 19 nucleotide pairs corresponding to the sequence of an exonic portion of the gene whose expression is to be reduced or inhibited. The two 3' nucleotides flanking this region of the stem are chosen so as to maximize the production of the siRNA from the engineered RNA precursor and to maximize the efficacy of the resulting siRNA in targeting the corresponding mRNA for translational repression or destruction by RNAi in vivo and in vitro.

In certain embodiments, shRNAs of the disclosure include miRNA sequences, optionally end-modified miRNA sequences, to enhance entry into RISC. The miRNA sequence can be similar or identical to that of any naturally occurring miRNA (see e.g. The miRNA Registry; Griffiths-Jones S, Nuc. Acids Res., 2004). Over one thousand natural miRNAs have been identified to date and together they are thought to comprise about 1% of all predicted genes in the genome. Many natural miRNAs are clustered together in the introns of pre-mRNAs and can be identified in silico using homology-based searches (Pasquinelli et al., 2000; Lagos-Quintana et al., 2001; Lau et al., 2001; Lee and Ambros, 2001) or computer algorithms (e.g. MiRScan, MiRSeeker) that predict the capability of a candidate miRNA gene to form the stem loop structure of a pri-mRNA (Grad et al., Mol. Cell., 2003; Lim et al., Genes Dev., 2003; Lim et al., Science, 2003; Lai E C et al., Genome Bio., 2003). An online registry provides a searchable database of all published miRNA sequences (The miRNA Registry at the Sanger Institute website; Griffiths-Jones S, Nuc. Acids Res., 2004). Exemplary, natural miRNAs include lin-4, let-7, miR-10, mirR-15, miR-16, miR-168, miR-175, miR-196 and their homologs, as well as other natural miRNAs from humans and certain model organisms including *Drosophila melanogaster, Caenorhabditis elegans*, zebrafish, *Arabidopsis* thalania, *Mus musculus*, and *Rattus norvegicus* as described in International PCT Publication No. WO 03/029459.

Naturally-occurring miRNAs are expressed by endogenous genes in vivo and are processed from a hairpin or stem-loop precursor (pre-miRNA or pri-miRNAs) by Dicer or other RNAses (Lagos-*Quintana* et al., Science, 2001; Lau et al., Science, 2001; Lee and Ambros, Science, 2001; Lagos-Quintana et al., Curr. Biol., 2002; Mourelatos et al., Genes Dev., 2002; Reinhart et al., Science, 2002; Ambros et al., Curr. Biol., 2003; Brennecke et al., 2003; Lagos-Quintana et al., RNA, 2003; Lim et al., Genes Dev., 2003; Lim et al., Science, 2003). miRNAs can exist transiently in vivo as a double-stranded duplex, but only one strand is taken up by the RISC complex to direct gene silencing. Certain miRNAs, e.g., plant miRNAs, have perfect or near-perfect complementarity to their target mRNAs and, hence, direct cleavage of the target mRNAs. Other miRNAs have less than perfect complementarity to their target mRNAs and, hence, direct translational repression of the target mRNAs. The degree of complementarity between an miRNA and its target mRNA is believed to determine its mechanism of action. For example, perfect or near-perfect complementarity between a miRNA and its target mRNA is predictive of a cleavage mechanism (Yekta et al., Science, 2004), whereas less than perfect complementarity is predictive of a translational repression mechanism. In particular embodiments, the miRNA sequence is that of a naturally-occurring miRNA sequence, the aberrant expression or activity of which is correlated with an miRNA disorder.

d) Dual Functional Oligonucleotide Tethers

In other embodiments, the RNA silencing agents of the present disclosure include dual functional oligonucleotide tethers useful for the intercellular recruitment of a miRNA. Animal cells express a range of miRNAs, noncoding RNAs of approximately 22 nucleotides which can regulate gene expression at the post transcriptional or translational level. By binding a miRNA bound to RISC and recruiting it to a target mRNA, a dual functional oligonucleotide tether can repress the expression of genes involved e.g., in the arteriosclerotic process. The use of oligonucleotide tethers offers several advantages over existing techniques to repress the expression of a particular gene. First, the methods described herein allow an endogenous molecule (often present in abundance), an miRNA, to mediate RNA silencing. Accordingly, the methods described herein obviate the need to introduce foreign molecules (e.g., siRNAs) to mediate RNA silencing. Second, the RNA-silencing agents and, in particular, the linking moiety (e.g., oligonucleotides such as the 2'-O-methyl oligonucleotide), can be made stable and resistant to nuclease activity. As a result, the tethers of the present disclosure can be designed for direct delivery, obviating the need for indirect delivery (e.g. viral) of a precursor molecule or plasmid designed to make the desired agent within the cell. Third, tethers and their respective moieties, can be designed to conform to specific mRNA sites and specific miRNAs. The designs can be cell and gene product specific. Fourth, the methods disclosed herein leave the mRNA intact, allowing one skilled in the art to block protein synthesis in short pulses using the cell's own machinery. As a result, these methods of RNA silencing are highly regulatable.

The dual functional oligonucleotide tethers ("tethers") of the disclosure are designed such that they recruit miRNAs (e.g., endogenous cellular miRNAs) to a target mRNA so as to induce the modulation of a gene of interest. In preferred embodiments, the tethers have the formula T-L-μ, wherein T is an mRNA targeting moiety, L is a linking moiety, and is an miRNA recruiting moiety. Any one or more moiety may be double stranded. Preferably, however, each moiety is single stranded.

Moieties within the tethers can be arranged or linked (in the 5' to 3' direction) as depicted in the formula T-L-μ (i.e., the 3' end of the targeting moiety linked to the 5' end of the linking moiety and the 3' end of the linking moiety linked to the 5' end of the miRNA recruiting moiety). Alternatively, the moieties can be arranged or linked in the tether as follows: μ-T-L (i.e., the 3' end of the miRNA recruiting moiety linked to the 5' end of the linking moiety and the 3' end of the linking moiety linked to the 5' end of the targeting moiety).

The mRNA targeting moiety, as described above, is capable of capturing a specific target mRNA. According to the disclosure, expression of the target mRNA is undesirable, and, thus, translational repression of the mRNA is desired. The mRNA targeting moiety should be of sufficient size to effectively bind the target mRNA. The length of the targeting moiety will vary greatly depending, in part, on the length of the target mRNA and the degree of complementarity between the target mRNA and the targeting moiety. In various embodiments, the targeting moiety is less than about 200, 100, 50, 30, 25, 20, 19, 18, 17, 16, 15, 14, 13, 12, 11, 10, 9, 8, 7, 6, or 5 nucleotides in length. In a particular embodiment, the targeting moiety is about 15 to about 25 nucleotides in length.

The miRNA recruiting moiety, as described above, is capable of associating with a miRNA. According to the disclosure, the miRNA may be any miRNA capable of repressing the target mRNA. Mammals are reported to have over 250 endogenous miRNAs (Lagos-Quintana et al. (2002) Current Biol. 12:735-739; Lagos-Quintana et al. (2001) Science 294:858-862; and Lim et al. (2003) Science 299:1540). In various embodiments, the miRNA may be any art-recognized miRNA.

The linking moiety is any agent capable of linking the targeting moieties such that the activity of the targeting moieties is maintained. Linking moieties are preferably oligonucleotide moieties comprising a sufficient number of nucleotides such that the targeting agents can sufficiently interact with their respective targets. Linking moieties have little or no sequence homology with cellular mRNA or miRNA sequences. Exemplary linking moieties include one or more 2'-O-methylnucleotides, e.g., 2'-β-methyladenosine, 2'-O-methylthymidine, 2'-O-methylguanosine or 2'-O-methyluridine.

e) Gene Silencing Oligonucleotides

In certain exemplary embodiments, gene expression (e.g., target gene expression) can be modulated using oligonucleotide-based compounds comprising two or more single stranded antisense oligonucleotides that are linked through their 5'-ends that allow the presence of two or more accessible 3'-ends to effectively inhibit or decrease target gene expression. Such linked oligonucleotides are also known as Gene Silencing Oligonucleotides (GSOs). (See, e.g., U.S. Pat. No. 8,431,544 assigned to Idera Pharmaceuticals, Inc., incorporated herein by reference in its entirety for all purposes.) Provided herein are novel and improved GSOs comprising intersubunit linkages according to Formula (I) and its embodiments.

The linkage at the 5' ends of the GSOs is independent of the other oligonucleotide linkages and may be directly via 5', 3' or 2' hydroxyl groups, or indirectly, via a non-nucleotide linker or a nucleoside, utilizing either the 2' or 3' hydroxyl positions of the nucleoside. Linkages may also utilize a functionalized sugar or nucleobase of a 5' terminal nucleotide.

GSOs can comprise two identical or different sequences conjugated at their 5'-5' ends via a phosphodiester, phosphorothioate or non-nucleoside linker. Such compounds may comprise 15 to 27 nucleotides that are complementary to specific portions of mRNA targets of interest for antisense down regulation of gene product. GSOs that comprise identical sequences can bind to a specific mRNA via Watson-Crick hydrogen bonding interactions and inhibit protein expression. GSOs that comprise different sequences are able to bind to two or more different regions of one or more mRNA target and inhibit protein expression. Such compounds are comprised of heteronucleotide sequences complementary to target mRNA and form stable duplex structures through Watson-Crick hydrogen bonding. Under certain conditions, GSOs containing two free 3'-ends (5'-5'-attached antisense) can be more potent inhibitors of gene expression than those containing a single free 3'-end or no free 3'-end.

In some embodiments, the non-nucleotide linker is glycerol or a glycerol homolog of the formula HO—$(CH_2)_o$—CH(OH)—$(CH_2)_p$—OH, wherein o and p independently are integers from 1 to about 6, from 1 to about 4 or from 1 to about 3. In some other embodiments, the non-nucleotide linker is a derivative of 1,3-diamino-2-hydroxypropane. Some such derivatives have the formula HO—$(CH_2)_m$—C(O)NH—$CH_2$—CH(OH)—$CH_2$—NHC(O)—$(CH_2)_m$—OH, wherein m is an integer from 0 to about 10, from 0 to about 6, from 2 to about 6 or from 2 to about 4.

Some non-nucleotide linkers permit attachment of more than two GSO components. For example, the non-nucleotide linker glycerol has three hydroxyl groups to which GSO components may be covalently attached. Some oligonucleotide-based compounds of the disclosure, therefore, comprise two or more oligonucleotides linked to a nucleotide or anon-nucleotide linker. Such oligonucleotides according to the disclosure are referred to as being "branched."

In certain embodiments, GSOs are at least 14 nucleotides in length. In certain exemplary embodiments, GSOs are 15 to 40 nucleotides long or 20 to 30 nucleotides in length. Thus, the component oligonucleotides of GSOs can independently be 14, 15, 16, 17, 18, 19, 20, 21, 22, 23, 24, 25, 26, 27, 28, 29, 30, 31, 32, 33, 34, 35, 36, 37, 38, 39 or 40 nucleotides in length.

These oligonucleotides can be prepared by the art recognized methods such as phosphoramidate or H-phosphonate chemistry which can be carried out manually or by an automated synthesizer. These oligonucleotides may also be modified in a number of ways without compromising their ability to hybridize to mRNA. Such modifications may include at least one intemucleotide linkage of the oligonucleotide being an alkylphosphonate, phosphorothioate, phosphorodithioate, methylphosphonate, phosphate ester, alkylphosphonothioate, phosphoramidate, carbamate, carbonate, phosphate hydroxyl, acetamidate or carboxymethyl ester or a combination of these and other intemucleotide linkages between the 5' end of one nucleotide and the 3' end of another nucleotide in which the 5' nucleotide phosphodiester linkage has been replaced with any number of chemical groups.

VI. Modified Oligonucleotides

In certain aspects of the present application, an oligonucleotide, such as an RNA silencing agent (or any portion thereof), as described *supra*, may be modified, such that the activity of the agent is further improved. For example, the RNA silencing agents described in Section II *supra*, may be modified with any of the modifications described infra. The modifications can, in part, serve to further enhance target discrimination, to enhance stability of the agent (e.g., to prevent degradation), to promote cellular uptake, to enhance the target efficiency, to improve efficacy in binding (e.g., to the targets), to improve patient tolerance to the agent, and/or to reduce toxicity.

1) Modifications to Enhance Target Discrimination

In certain embodiments, the oligonucleotides, siRNA, and RNA silencing agents of the disclosure may be substituted with a destabilizing nucleotide to enhance single nucleotide target discrimination (see U.S. application Ser. No. 11/698,689, filed Jan. 25, 2007 and U.S. Provisional Application No. 60/762,225 filed Jan. 25, 2006, both of which are incorporated herein by reference). Such a modification may be sufficient to abolish the specificity of the RNA silencing agent for a non-target mRNA (e.g. wild-type mRNA), without appreciably affecting the specificity of the RNA silencing agent for a target mRNA (e.g. gain-of-function mutant mRNA).

In certain embodiments, the RNA silencing agents of the present application are modified by the introduction of at least one universal nucleotide in the antisense strand thereof. Universal nucleotides comprise base portions that are capable of base pairing indiscriminately with any of the four conventional nucleotide bases (e.g. A, G, C, U). A universal nucleotide is contemplated because it has relatively minor effect on the stability of the RNA duplex or the duplex formed by the guide strand of the RNA silencing agent and the target mRNA. Exemplary universal nucleotides include those having an inosine base portion or an inosine analog base portion selected from the group consisting of deoxyinosine (e.g. 2'-deoxyinosine), 7-deaza-2'-deoxyinosine, 2'-aza-2'-deoxyinosine, PNA-inosine, morpholino-inosine, LNA-inosine, phosphoramidate-inosine, 2'-O-methoxyethyl-inosine, and 2'-OMe-inosine. In certain embodiments, the universal nucleotide is an inosine residue or a naturally occurring analog thereof.

In certain embodiments, the RNA silencing agents of the disclosure are modified by the introduction of at least one destabilizing nucleotide within 5 nucleotides from a specificity-determining nucleotide (i.e., the nucleotide which recognizes the disease-related polymorphism). For example, the destabilizing nucleotide may be introduced at a position that is within 5, 4, 3, 2, or 1 nucleotide(s) from a specificity-determining nucleotide. In exemplary embodiments, the destabilizing nucleotide is introduced at a position which is 3 nucleotides from the specificity-determining nucleotide (i.e., such that there are 2 stabilizing nucleotides between the destablilizing nucleotide and the specificity-determining nucleotide). In RNA silencing agents having two strands or strand portions (e.g. siRNAs and shRNAs), the destabilizing nucleotide may be introduced in the strand or strand portion that does not contain the specificity-determining nucleotide. In certain embodiments, the destabilizing nucleotide is introduced in the same strand or strand portion that contains the specificity-determining nucleotide.

2) Modifications to Enhance Efficacy and Specificity

In certain embodiments, the RNA silencing agents of the disclosure may be altered to facilitate enhanced efficacy and specificity in mediating RNAi according to asymmetry design rules (see U.S. Pat. Nos. 8,309,704, 7,750,144, 8,304,530, 8,329,892 and 8,309,705). Such alterations facilitate entry of the antisense strand of the siRNA (e.g., a siRNA designed using the methods of the present application or an siRNA produced from a shRNA) into RISC in favor of the sense strand, such that the antisense strand preferentially guides cleavage or translational repression of a target mRNA, and thus increasing or improving the efficiency of target cleavage and silencing. In certain embodiments, the asymmetry of an RNA silencing agent is enhanced by lessening the base pair strength between the antisense strand 5' end (AS 5') and the sense strand 3' end (S 3') of the RNA silencing agent relative to the bond strength or base pair strength between the antisense strand 3' end (AS 3') and the sense strand 5' end (S '5) of said RNA silencing agent.

In one embodiment, the asymmetry of an RNA silencing agent of the present application may be enhanced such that there are fewer G:C base pairs between the 5' end of the first or antisense strand and the 3' end of the sense strand portion than between the 3' end of the first or antisense strand and the 5' end of the sense strand portion. In another embodiment, the asymmetry of an RNA silencing agent of the disclosure may be enhanced such that there is at least one mismatched base pair between the 5' end of the first or antisense strand and the 3' end of the sense strand portion. In certain embodiments, the mismatched base pair is selected from the group consisting of G:A, C:A, C:U, G:G, A:A, C:C and U:U. In another embodiment, the asymmetry of an RNA silencing agent of the disclosure may be enhanced such that there is at least one wobble base pair, e.g., G:U, between the 5' end of the first or antisense strand and the 3' end of the sense strand portion. In another embodiment, the asymmetry of an RNA silencing agent of the disclosure may be enhanced such that there is at least one base pair comprising a rare nucleotide, e.g., inosine (I). In certain embodiments, the base pair is selected from the group consisting of an I:A, I:U and I:C. In yet another embodiment, the asymmetry of an RNA silencing agent of the disclosure may be enhanced such that there is at least one base pair comprising a modified nucleotide. In certain embodiments, the modified nucleotide is selected from the group consisting of 2-amino-G, 2-amino-A, 2,6-diamino-G, and 2,6-diamino-A.

3) RNA Silencing Agents with Enhanced Stability

The RNA silencing agents of the present application can be modified to improve stability in serum or in growth medium for cell cultures. The modifications described below may be used in combination with the exNA intersubunit linkages of the disclosure to further enhance or improve stability. In order to enhance the stability, the 3'-residues may be stabilized against degradation, e.g., they may be selected such that they consist of purine nucleotides, such as adenosine or guanosine nucleotides. Alternatively, substitution of pyrimidine nucleotides by modified analogues, e.g., substitution of uridine by 2'-deoxythymidine is tolerated and does not affect the efficiency of RNA interference.

In a one aspect, the present application features RNA silencing agents that include first and second strands wherein the second strand and/or first strand is modified by the substitution of internal nucleotides with modified nucleotides, such that in vivo stability is enhanced as compared to a corresponding unmodified RNA silencing agent. As defined herein, an "internal" nucleotide is one occurring at any position other than the 5' end or 3' end of nucleic acid molecule, polynucleotide or oligonucleotide. An internal nucleotide can be within a single-stranded molecule or within a strand of a duplex or double-stranded molecule. In one embodiment, the sense strand and/or antisense strand is modified by the substitution of at least one internal nucleotide. In another embodiment, the sense strand and/or antisense strand is modified by the substitution of at least 2, 3, 4, 5, 6, 7, 8, 9, 10, 11, 12, 13, 14, 15, 16, 17, 18, 19, 20, 21, 22, 23, 24, 25 or more internal nucleotides. In another embodiment, the sense strand and/or antisense strand is modified by the substitution of at least 5%, 10%, 15%, 20%, 25%, 30%, 35%, 40%, 45%, 50%, 55%, 60%, 65%, 70%, 75%, 80%, 85%, 90%, 95% or more of the internal nucleotides. In yet another embodiment, the sense strand and/or antisense strand is modified by the substitution of all of the internal nucleotides.

In one aspect, the present application features RNA silencing agents that are at least 80% chemically modified.

In certain embodiments, the RNA silencing agents may be fully chemically modified, i.e., 100% of the nucleotides are chemically modified. In another aspect, the present application features RNA silencing agents comprising 2'-OH ribose groups that are at least 80% chemically modified. In certain embodiments, the RNA silencing agents comprise 2'-OH ribose groups that are about 80%, 85%, 90%, 95%, or 100% chemically modified.

In certain embodiments, the RNA silencing agents may contain at least one modified nucleotide analogue. The nucleotide analogues may be located at positions where the target-specific silencing activity, e.g., the RNAi mediating activity or translational repression activity is not substantially affected, e.g., in a region at the 5'-end and/or the 3'-end of the siRNA molecule. Moreover, the ends may be stabilized by incorporating modified nucleotide analogues.

Exemplary nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In exemplary backbone-modified ribonucleotides, the phosphodiester group connecting to adjacent ribonucleotides is replaced by a modified group, e.g., of phosphorothioate group. In exemplary sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

In certain embodiments, the modifications are 2'-fluoro, 2'-amino and/or 2'-thio modifications. Modifications include 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine, 2,6-diaminopurine, 4-thio-uridine, and/or 5-amino-allyl-uridine. In a certain embodiment, the 2'-fluoro ribonucleotides are every uridine and cytidine. Additional exemplary modifications include 5-bromo-uridine, 5-iodo-uridine, 5-methyl-cytidine, ribo-thymidine, 2-aminopurine, 2'-amino-butyryl-pyrene-uridine, 5-fluoro-cytidine, and 5-fluoro-uridine. 2'-deoxy-nucleotides and 2'-Ome nucleotides can also be used within modified RNA-silencing agents moities of the instant disclosure. Additional modified residues include, deoxy-abasic, inosine, N3-methyl-uridine, N6,N6-dimethyl-adenosine, pseudouridine, purine ribonucleoside and ribavirin. In a certain embodiment, the 2' moiety is a methyl group such that the linking moiety is a 2'-O-methyl oligonucleotide.

In a certain embodiment, the RNA silencing agent of the present application comprises Locked Nucleic Acids (LNAs). LNAs comprise sugar-modified nucleotides that resist nuclease activities (are highly stable) and possess single nucleotide discrimination for mRNA (Elmen et al., Nucleic Acids Res., (2005), 33(1): 439-447; Braasch et al. (2003) Biochemistry 42:7967-7975, Petersen et al. (2003) Trends Biotechnol 21:74-81). These molecules have 2'-0,4'-C-ethylene-bridged nucleic acids, with possible modifications such as 2'-deoxy-2"-fluorouridine. Moreover, LNAs increase the specificity of oligonucleotides by constraining the sugar moiety into the 3'-endo conformation, thereby pre-organizing the nucleotide for base pairing and increasing the melting temperature of the oligonucleotide by as much as 10° C. per base.

In another exemplary embodiment, the RNA silencing agent of the present application comprises Peptide Nucleic Acids (PNAs). PNAs comprise modified nucleotides in which the sugar-phosphate portion of the nucleotide is replaced with a neutral 2-amino ethylglycine moiety capable of forming a polyamide backbone, which is highly resistant to nuclease digestion and imparts improved binding specificity to the molecule (Nielsen, et al., Science, (2001), 254: 1497-1500).

Also contemplated are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O– and N-alkylated nucleotides, e.g., N6-methyl adenosine are suitable. It should be noted that the above modifications may be combined.

In other embodiments, cross-linking can be employed to alter the pharmacokinetics of the RNA silencing agent, for example, to increase half-life in the body. Thus, the present application includes RNA silencing agents having two complementary strands of nucleic acid, wherein the two strands are crosslinked. The present application also includes RNA silencing agents which are conjugated or unconjugated (e.g., at its 3' terminus) to another moiety (e.g. a non-nucleic acid moiety such as a peptide), an organic compound (e.g., a dye), or the like). Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Other exemplary modifications include: (a) 2' modification, e.g., provision of a 2' OMe moiety on a U in a sense or antisense strand, but especially on a sense strand, or provision of a 2' OMe moiety in a 3' overhang, e.g., at the 3' terminus (3' terminus means at the 3' atom of the molecule or at the most 3' moiety, e.g., the most 3' P or 2' position, as indicated by the context); (b) modification of the backbone, e.g., with the replacement of an 0 with an S, in the phosphate backbone, e.g., the provision of a phosphorothioate modification, on the U or the A or both, especially on an antisense strand; e.g., with the replacement of a O with an S; (c) replacement of the U with a C5 amino linker; (d) replacement of an A with a G (sequence changes can be located on the sense strand and not the antisense strand in certain embodiments); and (d) modification at the 2', 6', 7', or 8' position. Exemplary embodiments are those in which one or more of these modifications are present on the sense but not the antisense strand, or embodiments where the antisense strand has fewer of such modifications. Yet other exemplary modifications include the use of a methylated P in a 3' overhang, e.g., at the 3' terminus; combination of a 2' modification, e.g., provision of a 2' 0 Me moiety and modification of the backbone, e.g., with the replacement of a O with an S, e.g., the provision of a phosphorothioate modification, or the use of a methylated P, in a 3' overhang, e.g., at the 3' terminus; modification with a 3' alkyl; modification with an abasic pyrrolidone in a 3' overhang, e.g., at the 3' terminus; modification with naproxen, ibuprofen, or other moieties which inhibit degradation at the 3' terminus.

Heavily Modified RNA Silencing Agents

In certain embodiments, the RNA silencing agent comprises at least 80% chemically modified nucleotides. In certain embodiments, the RNA silencing agent is fully chemically modified, i.e., 100% of the nucleotides are chemically modified.

In certain embodiments, the RNA silencing agent is 2'-O-methyl rich, i.e., comprises greater than 50% 2'-O-methyl content. In certain embodiments, the RNA silencing agent comprises at least about 55%, 60%, 65%, 70%, 75%, 80%, 85%, 90%, 95%, or 100% 2'-O-methyl nucleotide content. In certain embodiments, the RNA silencing agent comprises at least about 70% 2'-O-methyl nucleotide modifications. In certain embodiments, the RNA silencing agent comprises between about 70% and about 90% 2'-O-methyl nucleotide modifications. In certain embodiments, the RNA silencing agent is a dsRNA comprising an antisense strand and sense strand. In certain embodiments, the antisense strand comprises at least about 70% 2'-O-methyl nucleotide modifications. In certain embodiments, the antisense strand comprises between about 70% and about 90% 2'-O-methyl nucleotide modifications. In certain embodiments, the sense strand comprises at least about 70% 2'-O-methyl nucleotide modifications. In certain embodiments, the sense strand comprises between about 70% and about 90% 2'-O-methyl nucleotide modifications. In certain embodiments, the sense strand comprises between 100% 2'-O-methyl nucleotide modifications.

2'-O-methyl rich RNA silencing agents and specific chemical modification patterns are further described in U.S. Ser. No. 16/550,076 (filed Aug. 23, 2019) and U.S. Ser. No. 62/891,185 (filed Aug. 23, 2019), each of which is incorporated herein by reference.

4) Conjugated Functional Moieties

In other embodiments, RNA silencing agents may be modified with one or more functional moieties. A functional moiety is a molecule that confers one or more additional activities to the RNA silencing agent. In certain embodiments, the functional moieties enhance cellular uptake by target cells (e.g., neuronal cells). Thus, the disclosure includes RNA silencing agents which are conjugated or unconjugated (e.g., at its 5' and/or 3' terminus) to another moiety (e.g. a non-nucleic acid moiety such as a peptide), an organic compound (e.g., a dye), or the like. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

In a certain embodiment, the functional moiety is a hydrophobic moiety. In a certain embodiment, the hydrophobic moiety is selected from the group consisting of fatty acids, steroids, secosteroids, lipids, gangliosides and nucleoside analogs, endocannabinoids, and vitamins. In a certain embodiment, the steroid selected from the group consisting of cholesterol and Lithocholic acid (LCA). In a certain embodiment, the fatty acid selected from the group consisting of Eicosapentaenoic acid (EPA), Docosahexaenoic acid (DHA) and Docosanoic acid (DCA). In a certain embodiment, the vitamin selected from the group consisting of choline, vitamin A, vitamin E, and derivatives or metabolites thereof. In a certain embodiment, the vitamin is selected from the group consisting of retinoic acid and alpha-tocopheryl succinate.

In a certain embodiment, an RNA silencing agent of disclosure is conjugated to a lipophilic moiety. In one embodiment, the lipophilic moiety is a ligand that includes a cationic group. In another embodiment, the lipophilic moiety is attached to one or both strands of an siRNA. In an exemplary embodiment, the lipophilic moiety is attached to one end of the sense strand of the siRNA. In another exemplary embodiment, the lipophilic moiety is attached to the 3' end of the sense strand. In certain embodiments, the lipophilic moiety is selected from the group consisting of cholesterol, vitamin E, vitamin K, vitamin A, folic acid, a cationic dye (e.g., Cy3). In an exemplary embodiment, the lipophilic moiety is cholesterol. Other lipophilic moieties include cholic acid, adamantane acetic acid, 1-pyrene butyric acid, dihydrotestosterone, 1,3-Bis-O(hexadecyl) glycerol, geranyloxyhexyl group, hexadecylglycerol, bomeol, menthol, 1,3-propanediol, heptadecyl group, palmitic acid, myristic acid, O3-(oleoyl)lithocholic acid, O3-(oleoyl)cholenic acid, dimethoxytrityl, or phenoxazine.

In certain embodiments, the functional moieties may comprise one or more ligands tethered to an RNA silencing agent to improve stability, hybridization thermodynamics with a target nucleic acid, targeting to a particular tissue or cell-type, or cell permeability, e.g., by an endocytosis-dependent or -independent mechanism. Ligands and associated modifications can also increase sequence specificity and consequently decrease off-site targeting. A tethered ligand can include one or more modified bases or sugars that can function as intercalators. These can be located in an internal region, such as in a bulge of RNA silencing agent/target duplex. The intercalator can be an aromatic, e.g., a polycyclic aromatic or heterocyclic aromatic compound. A polycyclic intercalator can have stacking capabilities, and can include systems with 2, 3, or 4 fused rings. The universal bases described herein can be included on a ligand. In one embodiment, the ligand can include a cleaving group that contributes to target gene inhibition by cleavage of the target nucleic acid. The cleaving group can be, for example, a bleomycin (e.g., bleomycin-A5, bleomycin-A2, or bleomycin-B2), pyrene, phenanthroline (e.g., 0-phenanthroline), a polyamine, a tripeptide (e.g., lys-tyr-lys tripeptide), or a metal ion chelating group. The metal ion chelating group can include, e.g., an Lu(III) or EU(III) macrocyclic complex, a Zn(II) 2,9-dimethylphenanthroline derivative, a Cu(II) terpyridine, or acridine, which can promote the selective cleavage of target RNA at the site of the bulge by free metal ions, such as Lu(III). In some embodiments, a peptide ligand can be tethered to a RNA silencing agent to promote cleavage of the target RNA, e.g., at the bulge region. For example, 1,8-dimethyl-1,3,6,8,10,13-hexaazacyclotetradecane (cyclam) can be conjugated to a peptide (e.g., by an amino acid derivative) to promote target RNA cleavage. A tethered ligand can be an aminoglycoside ligand, which can cause an RNA silencing agent to have improved hybridization properties or improved sequence specificity. Exemplary aminoglycosides include glycosylated polylysine, galactosylated polylysine, neomycin B, tobramycin, kanamycin A, and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity. An acridine analog, neo-5-acridine, has an increased affinity for the HIV Rev-response element (RRE). In some embodiments, the guanidine analog (the guanidinoglycoside) of an aminoglycoside ligand is tethered to an RNA silencing agent. In a guanidinoglycoside, the amine group on the amino acid is exchanged for a guanidine group. Attachment of a guanidine analog can enhance cell permeability of an RNA silencing agent. A tethered ligand can be a poly-arginine peptide, peptoid or peptidomimetic, which can enhance the cellular uptake of an oligonucleotide agent.

Exemplary ligands are coupled, either directly or indirectly, via an intervening tether, to a ligand-conjugated carrier. In certain embodiments, the coupling is through a covalent bond. In certain embodiments, the ligand is attached to the carrier via an intervening tether. In certain embodiments, a ligand alters the distribution, targeting or lifetime of an RNA silencing agent into which it is incorporated. In certain embodiments, a ligand provides an enhanced affinity for a selected target, e.g., molecule, cell or cell type, compartment, e.g., a cellular or organ compartment, tissue, organ or region of the body, as, e.g., compared to a species absent such a ligand.

Exemplary ligands can improve transport, hybridization, and specificity properties and may also improve nuclease resistance of the resultant natural or modified RNA silencing agent, or a polymeric molecule comprising any combination of monomers described herein and/or natural or modified ribonucleotides. Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophiles, lipids, steroids (e.g., uvaol, hecigenin, diosgenin), terpenes (e.g., triterpenes, e.g., sarsasapogenin, Friedelin, epifriedelanol derivatized lithocholic acid), vitamins (e.g., folic acid, vitamin A, biotin, pyridoxal), carbohydrates, proteins, protein binding agents, integrin targeting molecules, polycationics, peptides, polyamines, and peptide mimics. Ligands can include a naturally occurring substance, (e.g., human serum albumin (HSA), low-density lipoprotein (LDL), or globulin); carbohydrate (e.g., a dextran, pullulan, chitin, chitosan, inulin, cyclodextrin or hyaluronic acid); amino acid, or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, mucin carbohydrate, multivalent lactose, multivalent galactose, N-acetyl-galactosamine (GalNAc) or derivatives thereof, N-acetyl-glucosamine, multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic. Other examples of ligands include dyes, intercalating agents (e.g. acridines and substituted acridines), cross-linkers (e.g. psoralene, mitomycin C), porphyrins (TPPC4, texaphyrin, Sapphyrin), polycyclic aromatic hydrocarbons (e.g., phenazine, dihydrophenazine, phenanthroline, pyrenes), lys-tyr-lys tripeptide, aminoglycosides, guanidium aminoglycodies, artificial endonucleases (e.g. EDTA), lipophilic molecules, e.g, cholesterol (and thio analogs thereof), cholic acid, cholanic acid, lithocholic acid, adamantane acetic acid, 1-pyrene butyric acid, dihydrotestosterone, glycerol (e.g., esters (e.g., mono, bis, or tris fatty acid esters, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ fatty acids) and ethers thereof, e.g., $C_{10}$, $C_{11}$, $C_{12}$, $C_{13}$, $C_{14}$, $C_{51}$, $C_{16}$, $C_{17}$, $C_{18}$, $C_{19}$, or $C_{20}$ alkyl; e.g., 1,3-bis-O(hexadecyl) glycerol, 1,3-bis-O(octaadecyl)glycerol), geranyloxyhexyl group, hexadecylglycerol, bomeol, menthol, 1,3-propanediol, heptadecyl group, palmitic acid, stearic acid (e.g., glyceryl distearate), oleic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g. biotin), transport/absorption facilitators (e.g., aspirin, naproxen, vitamin E, folic acid), synthetic ribonucleases (e.g., imidazole, bisimidazole, histamine, imidazole clusters, acridine-imidazole conjugates, $Eu^{3+}$ complexes of tetraazamacrocycles), dinitrophenyl, HRP or AP. In certain embodiments, the ligand is GalNAc or a derivative thereof.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-kB.

The ligand can be a substance, e.g., a drug, which can increase the uptake of the RNA silencing agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin. The ligand can increase the uptake of the RNA silencing agent into the cell by activating an inflammatory response, for example. Exemplary ligands that would have such an effect include tumor necrosis factor alpha (TNF$\alpha$), interleukin-1 beta, or gamma interferon. In one aspect, the ligand is a lipid or lipid-based molecule. Such a lipid or lipid-based molecule can bind a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA. A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney. In a certain embodiment, the lipid based ligand binds HSA. A lipid-based ligand can bind HSA with a sufficient affinity such that the conjugate will be distributed to a non-kidney tissue. However, it is contemplated that the affinity not be so strong that the HSA-ligand binding cannot be reversed. In another embodiment, the lipid based ligand binds HSA weakly or not at all, such that the conjugate will be distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These can be useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

In another aspect, the ligand is a cell-permeation agent, such as a helical cell-permeation agent. In certain embodiments, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent can be an alpha-helical agent, which may have a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to oligonucleotide agents can affect pharmacokinetic distribution of the RNA silencing agent, such as by enhancing cellular recognition and absorption. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. The peptide moiety can be an L-peptide or D-peptide. In another alternative, the peptide moiety can include a hydrophobic membrane translocation sequence (MTS). A peptide or peptidomimetic can be encoded by a random sequence of DNA, such as a peptide identified from a phage-display library, or one-bead-one-compound (OBOC) combinatorial library (Lam et al., Nature 354:82-84, 1991). In exemplary embodiments, the peptide or peptidomimetic tethered to an RNA silencing agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

In certain embodiments, the functional moiety is linked to the 5' end and/or 3' end of the RNA silencing agent of the disclosure. In certain embodiments, the functional moiety is linked to the 5' end and/or 3' end of an antisense strand of the RNA silencing agent of the disclosure. In certain embodiments, the functional moiety is linked to the 5' end and/or 3' end of a sense strand of the RNA silencing agent of the disclosure. In certain embodiments, the functional moiety is linked to the 3' end of a sense strand of the RNA silencing agent of the disclosure.

In certain embodiments, the functional moiety is linked to the RNA silencing agent by a linker. In certain embodiments, the functional moiety is linked to the antisense strand and/or sense strand by a linker. In certain embodiments, the functional moiety is linked to the 3' end of a sense strand by a linker. In certain embodiments, the linker comprises a divalent or trivalent linker. In certain embodiments, the linker comprises an ethylene glycol chain, an alkyl chain, a peptide, RNA, DNA, a phosphodiester, a phosphorothioate, a phosphoramidate, an amide, a carbamate, or a combination thereof. In certain embodiments, the divalent or trivalent linker is selected from:

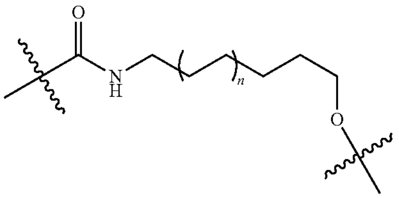
;
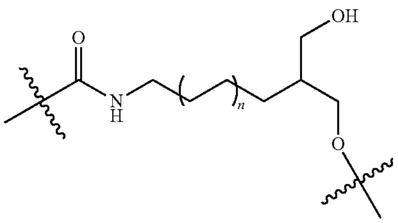
;

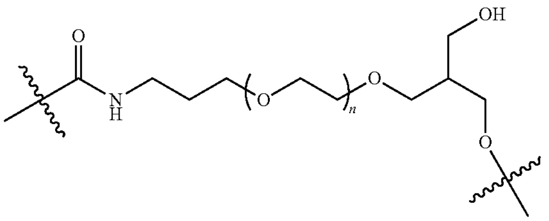
;

-continued

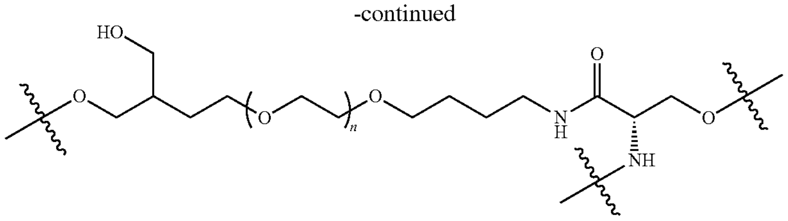

;  or

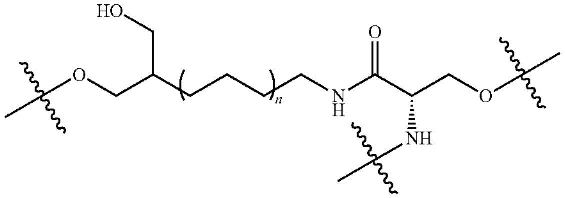

wherein n is 1, 2, 3, 4, or 5.

In certain embodiments, the linker further comprises a phosphodiester or phosphodiester derivative. In certain embodiments, the phosphodiester or phosphodiester derivative is selected from the group consisting of:

(Zc1)

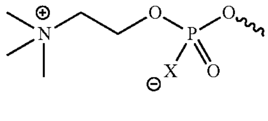

;

(Zc2)

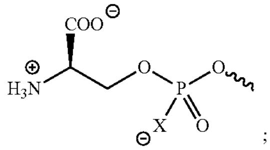

;

(Zc3)

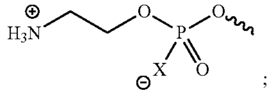

;  and (Zc4)

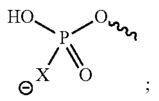

;

wherein X is O, S or $BH_3$.

The various functional moieties of the disclosure and means to conjugate them to RNA silencing agents are described in further detail in WO2017/030973A1 and WO2018/031933A2, incorporated herein by reference.

VI. Branched Oligonucleotides

Two or more RNA silencing agents as disclosed *supra*, for example oligonucleotide constructs such as siRNAs, may be connected to one another by one or more moieties independently selected from a linker, a spacer and a branching point, to form a branched oligonucleotide RNA silencing agent. In certain embodiments, the branched oligonucleotide RNA silencing agent consists of two siRNAs to form a di-branched siRNA ("di-siRNA") scaffolding for delivering two siRNAs. In representative embodiments, the nucleic acids of the branched oligonucleotide each comprise an antisense strand (or portions thereof), wherein the antisense strand has sufficient complementarity to a target mRNA to mediate an RNA-mediated silencing mechanism (e.g. RNAi).

In exemplary embodiments, the branched oligonucleotides may have two to eight RNA silencing agents attached through a linker. The linker may be hydrophobic. In an embodiment, branched oligonucleotides of the present application have two to three oligonucleotides. In an embodiment, the oligonucleotides independently have substantial chemical stabilization (e.g., at least 40% of the constituent bases are chemically-modified). In an exemplary embodiment, the oligonucleotides have full chemical stabilization (i.e., all the constituent bases are chemically-modified). In some embodiments, branched oligonucleotides comprise one or more single-stranded phosphorothioated tails, each independently having two to twenty nucleotides. In a non-limiting embodiment, each single-stranded tail has two to ten nucleotides.

In certain embodiments, branched oligonucleotides are characterized by three properties: (1) a branched structure, (2) full metabolic stabilization, and (3) the presence of a single-stranded tail comprising phosphorothioate linkers. In certain embodiments, branched oligonucleotides have 2 or 3 branches. It is believed that the increased overall size of the branched structures promotes increased uptake. Also, without being bound by a particular theory of activity, multiple adjacent branches (e.g., 2 or 3) are believed to allow each branch to act cooperatively and thus dramatically enhance rates of internalization, trafficking and release.

Branched oligonucleotides are provided in various structurally diverse embodiments. In some embodiments nucleic acids attached at the branching points are single stranded or double stranded and consist of miRNA inhibitors, gapmers, mixmers, SSOs, PMOs, or PNAs. These single strands can be attached at their 3' or 5' end. Combinations of siRNA and single stranded oligonucleotides could also be used for dual function. In another embodiment, short nucleic acids complementary to the gapmers, mixmers, miRNA inhibitors, SSOs, PMOs, and PNAs are used to carry these active single-stranded nucleic acids and enhance distribution and cellular internalization. The short duplex region has a low melting temperature (Tm ~37° C.) for fast dissociation upon internalization of the branched structure into the cell.

The Di-siRNA branched oligonucleotides may comprise chemically diverse conjugates, such as the functional moieties described above. Conjugated bioactive ligands may be used to enhance cellular specificity and to promote membrane association, internalization, and serum protein binding. Examples of bioactive moieties to be used for conjugation include DHA, GalNAc, and cholesterol. These moieties can be attached to Di-siRNA either through the connecting linker or spacer, or added via an additional linker or spacer attached to another free siRNA end.

The presence of a branched structure improves the level of tissue retention in the brain more than 100-fold compared to non-branched compounds of identical chemical composition, suggesting a new mechanism of cellular retention and distribution. Branched oligonucleotides have unexpectedly uniform distribution throughout the spinal cord and brain. Moreover, branched oligonucleotides exhibit unexpectedly efficient systemic delivery to a variety of tissues, and very high levels of tissue accumulation.

Branched oligonucleotides comprise a variety of therapeutic nucleic acids, including siRNAs, ASOs, miRNAs, miRNA inhibitors, splice switching, PMOs, PNAs. In some embodiments, branched oligonucleotides further comprise conjugated hydrophobic moieties and exhibit unprecedented silencing and efficacy in vitro and in vivo.

Linkers

In an embodiment of the branched oligonucleotide, each linker is independently selected from an ethylene glycol chain, an alkyl chain, a peptide, RNA, DNA, a phosphate, a phosphonate, a phosphoramidate, an ester, an amide, a triazole, and combinations thereof; wherein any carbon or oxygen atom of the linker is optionally replaced with a nitrogen atom, bears a hydroxyl substituent, or bears an oxo substituent. In one embodiment, each linker is an ethylene glycol chain. In another embodiment, each linker is an alkyl chain. In another embodiment, each linker is a peptide. In another embodiment, each linker is RNA. In another embodiment, each linker is DNA. In another embodiment, each linker is a phosphate. In another embodiment, each linker is a phosphonate. In another embodiment, each linker is a phosphoramidate. In another embodiment, each linker is an ester. In another embodiment, each linker is an amide. In another embodiment, each linker is a triazole.

VII. Compound of Formula (I)

In another aspect, provided herein is a branched oligonucleotide compound of formula (I):

$$L\text{-}(N)_n \qquad (I)$$

wherein L is selected from an ethylene glycol chain, an alkyl chain, a peptide, RNA, DNA, a phosphate, a phosphonate, a phosphoramidate, an ester, an amide, a triazole, and combinations thereof, wherein formula (I) optionally further comprises one or more branch point B, and one or more spacer S; wherein B is independently for each occurrence a polyvalent organic species or derivative thereof; S is independently for each occurrence selected from an ethylene glycol chain, an alkyl chain, a peptide, RNA, DNA, a phosphate, a phosphonate, a phosphoramidate, an ester, an amide, a triazole, and combinations thereof.

Moiety N is an RNA duplex comprising a sense strand and an antisense strand; and n is 2, 3, 4, 5, 6, 7 or 8. In an embodiment, the antisense strand of N comprises a sequence substantially complementary to a target nucleic acid sequence of interest. The sense strand and antisense strand may each independently comprise one or more chemical modifications.

In an embodiment, the compound of formula (I) has a structure selected from formulas (I-1)-(I-9) of Table 1.

TABLE 1

N—L—N (I-1)

N—S—L—S—N (I-2)

TABLE 1-continued

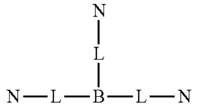
(I-3)

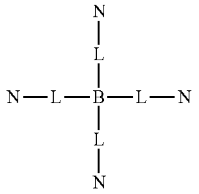
(1-4)

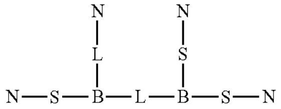
(I-5)

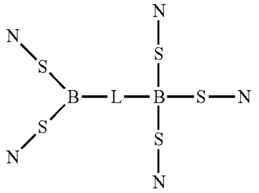
(I-6)

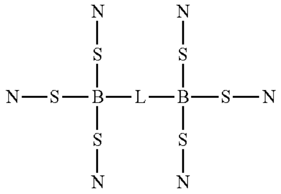
(1-7)

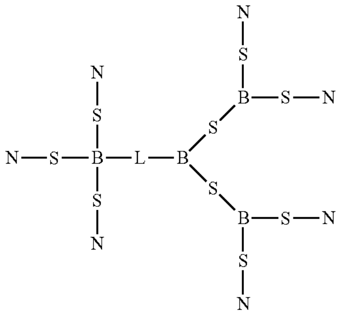
(I-8)

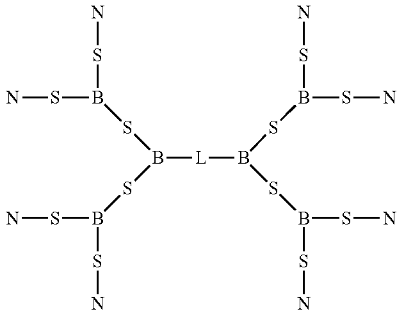
(I-9)

In one embodiment, the compound of formula (I) is formula (I-1). In another embodiment, the compound of formula (I) is formula (1-2). In another embodiment, the compound of formula (I) is formula (1-3). In another embodiment, the compound of formula (I) is formula (1-4). In another embodiment, the compound of formula (I) is formula (1-5). In another embodiment, the compound of formula (I) is formula (1-6). In another embodiment, the compound of formula (I) is formula (1-7). In another embodiment, the compound of formula (I) is formula (1-8). In another embodiment, the compound of formula (I) is formula (1-9).

In an embodiment of the compound of formula (I), each linker is independently selected from an ethylene glycol chain, an alkyl chain, a peptide, RNA, DNA, a phosphate, a phosphonate, a phosphoramidate, an ester, an amide, a triazole, and combinations thereof, wherein any carbon or oxygen atom of the linker is optionally replaced with a nitrogen atom, bears a hydroxyl substituent, or bears an oxo substituent. In one embodiment of the compound of formula (I), each linker is an ethylene glycol chain. In another embodiment, each linker is an alkyl chain. In another embodiment of the compound of formula (I), each linker is a peptide. In another embodiment of the compound of formula (I), each linker is RNA. In another embodiment of the compound of formula (I), each linker is DNA. In another embodiment of the compound of formula (I), each linker is a phosphate. In another embodiment, each linker is a phosphonate. In another embodiment of the compound of formula (I), each linker is a phosphoramidate. In another embodiment of the compound of formula (I), each linker is an ester. In another embodiment of the compound of formula (I), each linker is an amide. In another embodiment of the compound of formula (I), each linker is a triazole.

In one embodiment of the compound of formula (I), B is a polyvalent organic species. In another embodiment of the compound of formula (I), B is a derivative of a polyvalent organic species. In one embodiment of the compound of formula (I), B is a triol or tetrol derivative. In another embodiment, B is a tri- or tetra-carboxylic acid derivative. In another embodiment, B is an amine derivative. In another embodiment, B is a tri- or tetra-amine derivative. In another embodiment, B is an amino acid derivative. In another embodiment of the compound of formula (I), B is selected from the formulas of:

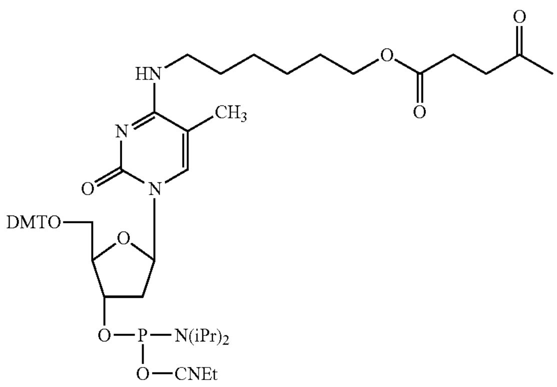

;

-continued

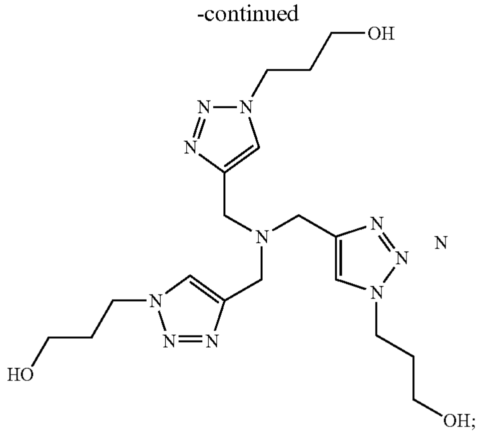

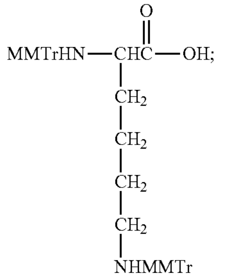

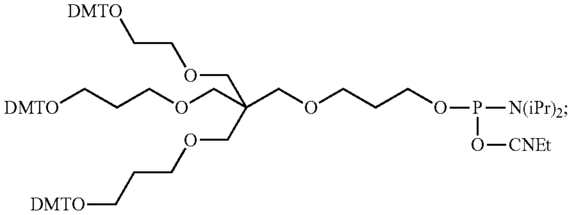

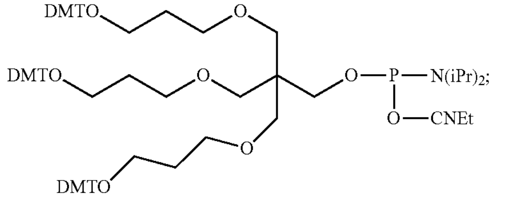

or

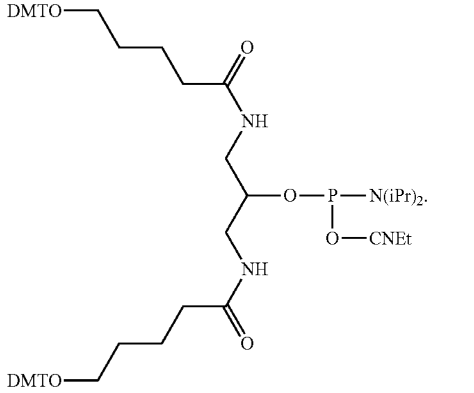

Polyvalent organic species are moieties comprising carbon and three or more valencies (i.e., points of attachment with moieties such as S, L or N, as defined above). Non-limiting examples of polyvalent organic species include triols (e.g., glycerol, phloroglucinol, and the like), tetrols (e.g., ribose, pentaerythritol, 1,2,3,5-tetrahydroxybenzene, and the like), tri-carboxylic acids (e.g., citric acid, 1,3,5-cyclohexanetricarboxylic acid, trimesic acid, and the like), tetra-carboxylic acids (e.g., ethylenediaminetetraacetic acid, pyromellitic acid, and the like), tertiary amines (e.g., tripropargylamine, triethanolamine, and the like), triamines (e.g., diethylenetriamine and the like), tetramines, and species comprising a combination of hydroxyl, thiol, amino, and/or carboxyl moieties (e.g., amino acids such as lysine, serine, cysteine, and the like).

In an embodiment of the compound of formula (I), each nucleic acid comprises one or more chemically-modified nucleotides. In an embodiment of the compound of formula (I), each nucleic acid consists of chemically-modified nucleotides. In certain embodiments of the compound of formula (I), >95%, >90%, >85%, >80%, >75%, >70%, >65%, >60%, >55% or >50% of each nucleic acid comprises chemically-modified nucleotides.

In an embodiment, each antisense strand independently comprises a 5' terminal group R selected from the groups of Table 2.

TABLE 2

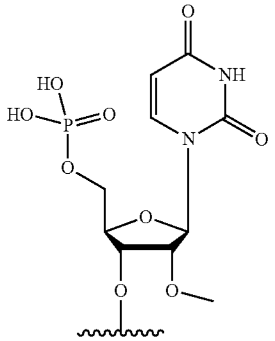

$R^1$

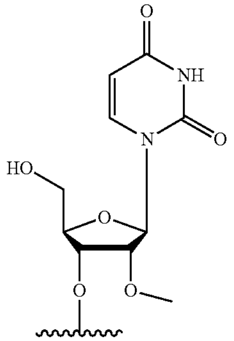

$R^2$

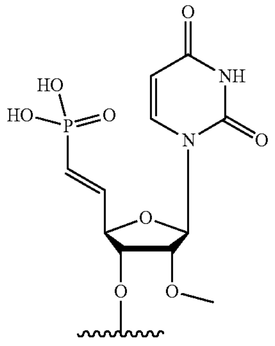

$R^3$

TABLE 2-continued

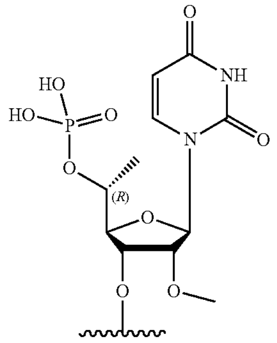

$R^4$

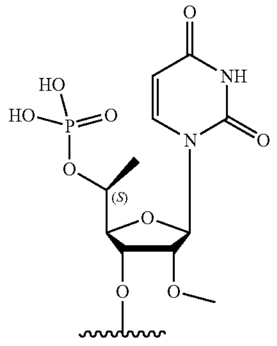

$R^5$

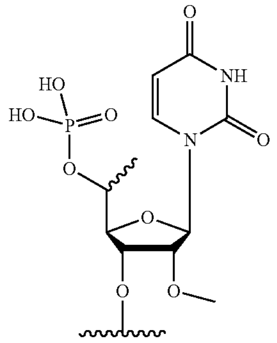

$R^6$

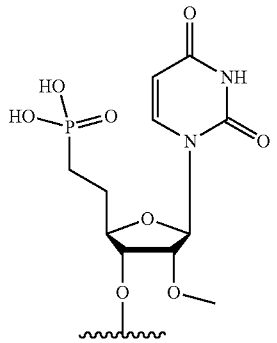

$R^7$

TABLE 2-continued

| |
|---|
| 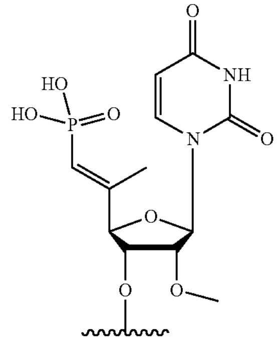<br>$R^8$ |

In one embodiment, R is $R_1$. In another embodiment, R is $R_2$. In another embodiment, R is $R_3$. In another embodiment, R is $R_4$. In another embodiment, R is $R_5$. In another embodiment, R is $R_6$. In another embodiment, R is $R_7$. In another embodiment, R is $R_8$.

Structure of Formula (II)

In an embodiment, the compound of formula (I) has the structure of formula (II):

(II)

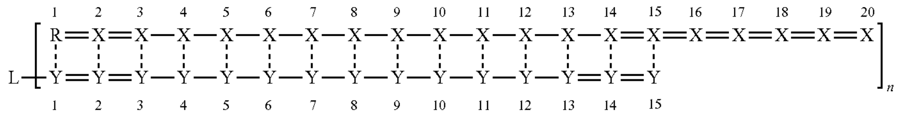

wherein X, for each occurrence, independently, is selected from adenosine, guanosine, uridine, cytidine, and chemically-modified derivatives thereof; Y, for each occurrence, independently, is selected from adenosine, guanosine, uridine, cytidine, and chemically-modified derivatives thereof, - represents a phosphodiester internucleoside linkage; = represents a phosphorothioate internucleoside linkage; and - - - represents, individually for each occurrence, a base-pairing interaction or a mismatch.

In certain embodiments, the structure of formula (II) does not contain mismatches. In one embodiment, the structure of formula (II) contains 1 mismatch. In another embodiment, the compound of formula (II) contains 2 mismatches. In another embodiment, the compound of formula (II) contains 3 mismatches. In another embodiment, the compound of formula (II) contains 4 mismatches. In an embodiment, each nucleic acid consists of chemically-modified nucleotides.

In certain embodiments, >95%, >90%, >85%, >80%, >75%, >70%, >65%, >60%, >55% or >50% of X's of the structure of formula (II) are chemically-modified nucleotides. In other embodiments, >95%, >90%, >85%, >80%, >75%, >70%, >65%, >60%, >55% or >50% of X's of the structure of formula (II) are chemically-modified nucleotides.

Structure of Formula (III)

In an embodiment, the compound of formula (I) has the structure of formula (III):

(III)

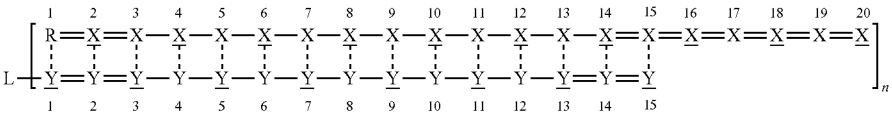

wherein X, for each occurrence, independently, is a nucleotide comprising a 2'-deoxy-2'-fluoro modification; X, for each occurrence, independently, is a nucleotide comprising a 2'-O-methyl modification; Y, for each occurrence, independently, is a nucleotide comprising a 2'-deoxy-2'-fluoro modification; and Y, for each occurrence, independently, is a nucleotide comprising a 2'-O-methyl modification.

In an embodiment, X is chosen from the group consisting of 2'-deoxy-2'-fluoro modified adenosine, guanosine, uridine or cytidine. In an embodiment, X is chosen from the group consisting of 2'-O-methyl modified adenosine, guanosine, uridine or cytidine. In an embodiment, Y is chosen from the group consisting of 2'-deoxy-2'-fluoro modified adenosine, guanosine, uridine or cytidine. In an embodiment, Y is chosen from the group consisting of 2'-O-methyl modified adenosine, guanosine, uridine or cytidine.

In certain embodiments, the structure of formula (III) does not contain mismatches. In one embodiment, the structure of formula (III) contains 1 mismatch. In another embodiment, the compound of formula (III) contains 2 mismatches. In another embodiment, the compound of formula (III) contains 3 mismatches. In another embodiment, the compound of formula (III) contains 4 mismatches.

Structure of Formula (IV)

In an embodiment, the compound of formula (I) has the structure of formula (IV):

(IV)

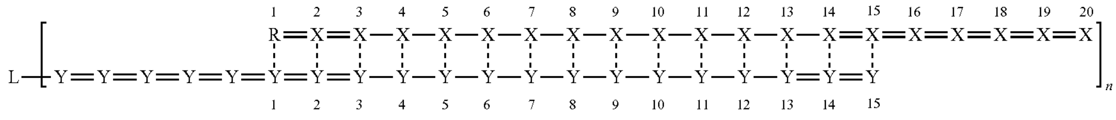

wherein X, for each occurrence, independently, is selected from adenosine, guanosine, uridine, cytidine, and chemically-modified derivatives thereof, Y, for each occurrence, independently, is selected from adenosine, guanosine, uridine, cytidine, and chemically-modified derivatives thereof, - represents a phosphodiester internucleoside linkage; = represents a phosphorothioate internucleoside linkage; and - - - represents, individually for each occurrence, a base-pairing interaction or a mismatch.

In certain embodiments, the structure of formula (IV) does not contain mismatches. In one embodiment, the structure of formula (IV) contains 1 mismatch. In another embodiment, the compound of formula (IV) contains 2 mismatches. In another embodiment, the compound of formula (IV) contains 3 mismatches. In another embodiment, the compound of formula (IV) contains 4 mismatches. In an embodiment, each nucleic acid consists of chemically-modified nucleotides.

In certain embodiments, >95%, >90%, >85%, >80%, >75%, >70%, >65%, >60%, >55% or >50% of X's of the structure of formula (IV) are chemically-modified nucleotides. In other embodiments, >95%, >90%, >85%, >80%, >75%, >70%, >65%, >60%, >55% or >50% of X's of the structure of formula (IV) are chemically-modified nucleotides.

Structure of Formula (V)

In an embodiment, the compound of formula (I) has the structure of formula (V):

(V)

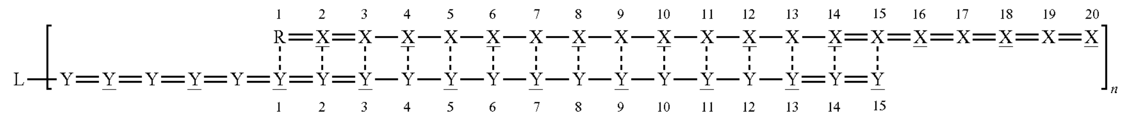

wherein X, for each occurrence, independently, is a nucleotide comprising a 2'-deoxy-2'-fluoro modification; X, for each occurrence, independently, is a nucleotide comprising a 2'-O-methyl modification; Y, for each occurrence, independently, is a nucleotide comprising a 2'-deoxy-2'-fluoro modification; and Y, for each occurrence, independently, is a nucleotide comprising a 2'-O-methyl modification.

In certain embodiments, X is chosen from the group consisting of 2'-deoxy-2'-fluoro modified adenosine, guanosine, uridine or cytidine. In an embodiment, X is chosen from the group consisting of 2'-O-methyl modified adenosine, guanosine, uridine or cytidine. In an embodiment, Y is chosen from the group consisting of 2'-deoxy-2'-fluoro modified adenosine, guanosine, uridine or cytidine. In an embodiment, Y is chosen from the group consisting of 2'-O-methyl modified adenosine, guanosine, uridine or cytidine.

In certain embodiments, the structure of formula (V) does not contain mismatches. In one embodiment, the structure of formula (V) contains 1 mismatch. In another embodiment, the compound of formula (V) contains 2 mismatches. In another embodiment, the compound of formula (V) contains 3 mismatches. In another embodiment, the compound of formula (V) contains 4 mismatches.

Variable Linkers

In an embodiment of the compound of formula (I), L has the structure of L1:

delivery system, L is a peptide. In another embodiment of the delivery system, L is RNA. In another embodiment of the delivery system, L is DNA. In another embodiment of (L1)

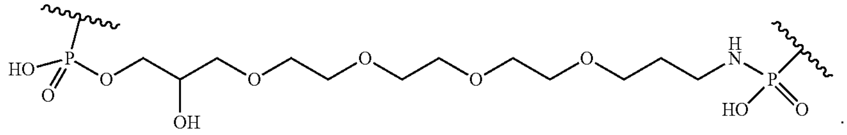

In an embodiment of L1, R is $R^3$ and n is 2.

In an embodiment of the structure of formula (II), L has the structure of L1. In an embodiment of the structure of formula (III), L has the structure of L1. In an embodiment of the structure of formula (IV), L has the structure of L1. In an embodiment of the structure of formula (V), L has the structure of L1. In an embodiment of the structure of formula (VI), L has the structure of L1. In an embodiment of the structure of formula (VI), L has the structure of L1.

In an embodiment of the compound of formula (I), L has the structure of L2:

the delivery system, L is a phosphate. In another embodiment of the delivery system, L is a phosphonate. In another embodiment of the delivery system, L is a phosphoramidate. In another embodiment of the delivery system, L is an ester. In another embodiment of the delivery system, L is an amide. In another embodiment of the delivery system, L is a triazole.

In one embodiment of the delivery system, S is an ethylene glycol chain. In another embodiment, S is an alkyl chain. In another embodiment of the delivery system, S is a peptide. In another embodiment, S is RNA. In another (L2)

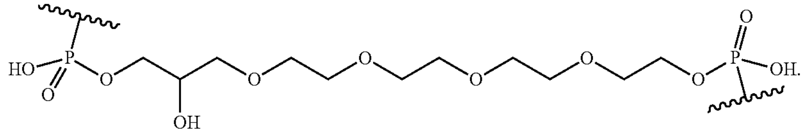

In an embodiment of L2, R is R3 and n is 2. In an embodiment of the structure of formula (II), L has the structure of L2. In an embodiment of the structure of formula (III), L has the structure of L2. In an embodiment of the structure of formula (IV), L has the structure of L2. In an embodiment of the structure of formula (V), L has the structure of L2. In an embodiment of the structure of formula (VI), L has the structure of L2. In an embodiment of the structure of formula (VI), L has the structure of L2.

Delivery System

In a third aspect, provided herein is a delivery system for therapeutic nucleic acids having the structure of formula (VI):

$$L\text{-}(cNA)_n \qquad (VI)$$

wherein L is selected from an ethylene glycol chain, an alkyl chain, a peptide, RNA, DNA, a phosphate, a phosphonate, a phosphoramidate, an ester, an amide, a triazole, and combinations thereof, wherein formula (VI) optionally further comprises one or more branch point B, and one or more spacer S; wherein B is independently for each occurrence a polyvalent organic species or derivative thereof; S is independently for each occurrence selected from an ethylene glycol chain, an alkyl chain, a peptide, RNA, DNA, a phosphate, a phosphonate, a phosphoramidate, an ester, an amide, a triazole, and combinations thereof; each cNA, independently, is a carrier nucleic acid comprising one or more chemical modifications; and n is 2, 3, 4, 5, 6, 7 or 8.

In one embodiment of the delivery system, L is an ethylene glycol chain. In another embodiment of the delivery system, L is an alkyl chain. In another embodiment of the embodiment of the delivery system, S is DNA. In another embodiment of the delivery system, S is a phosphate. In another embodiment of the delivery system, S is a phosphonate. In another embodiment of the delivery system, S is a phosphoramidate. In another embodiment of the delivery system, S is an ester. In another embodiment, S is an amide. In another embodiment, S is a triazole.

In one embodiment of the delivery system, n is 2. In another embodiment of the delivery system, n is 3. In another embodiment of the delivery system, n is 4. In another embodiment of the delivery system, n is 5. In another embodiment of the delivery system, n is 6. In another embodiment of the delivery system, n is 7. In another embodiment of the delivery system, n is 8.

In certain embodiments, each cNA comprises >95%, >90%, >85%, >80%, >75%, >70%, >65%, >60%, >55% or >50% chemically-modified nucleotides.

In an embodiment, the compound of formula (VI) has a structure selected from formulas (VI-1)-(VI-9) of Table 3:

TABLE 3

| | |
|---|---|
| ANc—L—cNA | (VI-1) |
| ANc—S—L—S—cNA | (VI-2) |
| 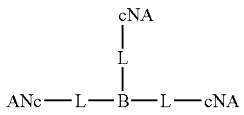 | (VI-3) |

TABLE 3-continued

| | |
|---|---|
| 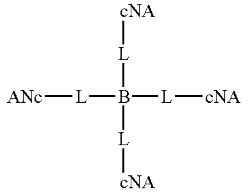 | (VI-4) |
| 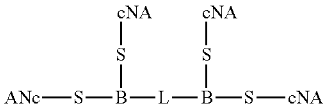 | (VI-5) |
| 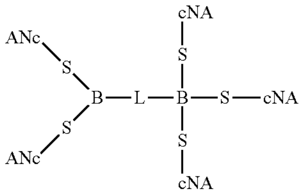 | (VI-6) |
| 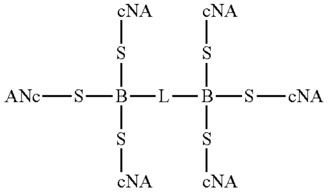 | (VI-7) |
| 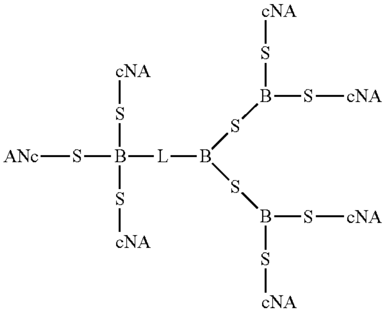 | (VI-8) |
| 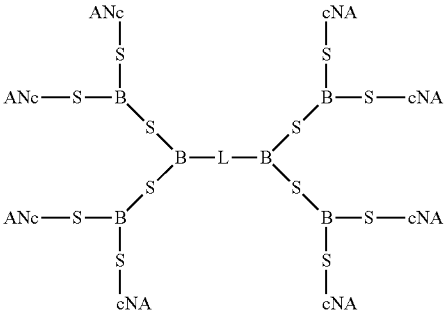 | (VI-9) |

In an embodiment, the compound of formula (VI) is the structure of formula (VI-1). In an embodiment, the compound of formula (VI) is the structure of formula (VI-2). In an embodiment, the compound of formula (VI) is the structure of formula (VI-3). In an embodiment, the compound of formula (VI) is the structure of formula (VI-4). In an embodiment, the compound of formula (VI) is the structure of formula (VI-5). In an embodiment, the compound of formula (VI) is the structure of formula (VI-6). In an embodiment, the compound of formula (VI) is the structure of formula (VI-7). In an embodiment, the compound of formula (VI) is the structure of formula (VI-8). In an embodiment, the compound of formula (VI) is the structure of formula (VI-9).

In an embodiment, the compound of formulas (VI) (including, e.g., formulas (VI-1)-(VI-9), each cNA independently comprises at least 15 contiguous nucleotides. In an embodiment, each cNA independently consists of chemically-modified nucleotides.

In an embodiment, the delivery system further comprises n therapeutic nucleic acids (NA), wherein each NA comprises a sequence substantially complementary to a target nucleic acid sequence of interest.

Also, each NA is hybridized to at least one cNA. In one embodiment, the delivery system is comprised of 2 NAs. In another embodiment, the delivery system is comprised of 3 NAs. In another embodiment, the delivery system is comprised of 4 NAs. In another embodiment, the delivery system is comprised of 5 NAs. In another embodiment, the delivery system is comprised of 6 NAs. In another embodiment, the delivery system is comprised of 7 NAs. In another embodiment, the delivery system is comprised of 8 NAs.

In an embodiment, each NA independently comprises at least 15 contiguous nucleotides. In an embodiment, each NA independently comprises 15-25 contiguous nucleotides. In an embodiment, each NA independently comprises 15 contiguous nucleotides. In an embodiment, each NA independently comprises 16 contiguous nucleotides. In another embodiment, each NA independently comprises 17 contiguous nucleotides. In another embodiment, each NA independently comprises 18 contiguous nucleotides. In another embodiment, each NA independently comprises 19 contiguous nucleotides. In another embodiment, each NA independently comprises 20 contiguous nucleotides. In an embodiment, each NA independently comprises 21 contiguous nucleotides. In an embodiment, each NA independently comprises 22 contiguous nucleotides. In an embodiment, each NA independently comprises 23 contiguous nucleotides. In an embodiment, each NA independently comprises 24 contiguous nucleotides. In an embodiment, each NA independently comprises 25 contiguous nucleotides.

In an embodiment, each NA comprises an unpaired overhang of at least 2 nucleotides. In another embodiment, each NA comprises an unpaired overhang of at least 3 nucleotides. In another embodiment, each NA comprises an unpaired overhang of at least 4 nucleotides. In another embodiment, each NA comprises an unpaired overhang of at least 5 nucleotides. In another embodiment, each NA comprises an unpaired overhang of at least 6 nucleotides. In an embodiment, the nucleotides of the overhang are connected via phosphorothioate linkages.

In an embodiment, each NA, independently, is selected from the group consisting of: DNA, siRNAs, antagomiRs, miRNAs, gapmers, mixmers, or guide RNAs. In one embodiment, each NA, independently, is a DNA. In another embodiment, each NA, independently, is a siRNA. In another embodiment, each NA, independently, is an antagomiR. In another embodiment, each NA, independently, is a miRNA. In another embodiment, each NA, independently, is a gapmer. In another embodiment, each NA, independently, is a mixmer. In another embodiment, each NA, independently, is a guide RNA. In an embodiment, each NA is the same. In an embodiment, each NA is not the same.

In an embodiment, the delivery system further comprising n therapeutic nucleic acids (NA) has a structure selected from formulas (I), (II), (III), (IV), (V), (VI), and embodiments thereof described herein. In one embodiment, the delivery system has a structure selected from formulas (I), (II), (III), (IV), (V), (VI), and embodiments thereof described herein further comprising 2 therapeutic nucleic acids (NA). In another embodiment, the delivery system has a structure selected from formulas (I), (II), (III), (IV), (V), (VI), and embodiments thereof described herein further comprising 3 therapeutic nucleic acids (NA). In one embodiment, the delivery system has a structure selected from formulas (I), (II), (III), (IV), (V), (VI), and embodiments thereof described herein further comprising 4 therapeutic nucleic acids (NA). In one embodiment, the delivery system has a structure selected from formulas (I), (II), (III), (IV), (V), (VI), and embodiments thereof described herein further comprising 5 therapeutic nucleic acids (NA). In one embodiment, the delivery system has a structure selected from formulas (I), (II), (III), (IV), (V), (VI), and embodiments thereof described herein further comprising 6 therapeutic nucleic acids (NA). In one embodiment, the delivery system has a structure selected from formulas (I), (II), (III), (IV), (V), (VI), and embodiments thereof described herein further comprising 7 therapeutic nucleic acids (NA). In one embodiment, the delivery system has a structure selected from formulas (I), (II), (III), (IV), (V), (VI), and embodiments thereof described herein further comprising 8 therapeutic nucleic acids (NA).

In one embodiment, the delivery system has a structure selected from formulas (I), (II), (III), (IV), (V), (VI), further comprising a linker of structure L1 or L2 wherein R is $R^3$ and n is 2. In another embodiment, the delivery system has a structure selected from formulas (I), (II), (III), (IV), (V), (VI), further comprising a linker of structure L1 wherein R is $R^3$ and n is 2. In another embodiment, the delivery system has a structure selected from formulas (I), (II), (III), (IV), (V), (VI), further comprising a linker of structure L2 wherein R is $R^3$ and n is 2.

In an embodiment of the delivery system, the target of delivery is selected from the group consisting of: brain, liver, skin, kidney, spleen, pancreas, colon, fat, lung, muscle, and thymus. In one embodiment, the target of delivery is the brain. In another embodiment, the target of delivery is the striatum of the brain. In another embodiment, the target of delivery is the cortex of the brain. In another embodiment, the target of delivery is the striatum of the brain. In one embodiment, the target of delivery is the liver. In one embodiment, the target of delivery is the skin. In one embodiment, the target of delivery is the kidney. In one embodiment, the target of delivery is the spleen. In one embodiment, the target of delivery is the pancreas. In one embodiment, the target of delivery is the colon. In one embodiment, the target of delivery is the fat. In one embodiment, the target of delivery is the lung. In one embodiment, the target of delivery is the muscle. In one embodiment, the target of delivery is the thymus. In one embodiment, the target of delivery is the spinal cord.

In certain embodiments, compounds of the disclosure are characterized by the following properties: (1) two or more branched oligonucleotides, e.g., wherein there is a non-equal number of 3' and 5' ends; (2) substantially chemically stabilized, e.g., wherein more than 40%, optimally 100%, of oligonucleotides are chemically modified (e.g., no RNA and optionally no DNA); and (3) phoshorothioated single oligonucleotides containing at least 3, phosphorothioated bonds. In certain embodiments, the phoshorothioated single oligonucleotides contain 4-20 phosphorothioated bonds.

It is to be understood that the methods described in this disclosure are not limited to particular methods and experimental conditions disclosed herein; as such methods and conditions may vary. It is also to be understood that the terminology used herein is for the purpose of describing particular embodiments only, and is not intended to be limiting.

Furthermore, the experiments described herein, unless otherwise indicated, use conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY (1987-2008), including all supplements, Molecular Cloning: A Laboratory Manual (Fourth Edition) by MR Green and J. Sambrook and Harlow et al., Antibodies: A Laboratory Manual, Chapter 14, Cold Spring Harbor Laboratory, Cold Spring Harbor (2013, 2nd edition).

Branched oligonucleotides, including synthesis and methods of use, are described in greater detail in WO2017/132669, incorporated herein by reference.

VII. Methods of Introducing Nucleic Acids, Vectors Host Cells, and Branched Oligonucleotide Compounds RNA silencing agents of the disclosure may be directly introduced into the cell (e.g., a neural cell) (i.e., intracellularly); or introduced extracellularly into a cavity, interstitial space, into the circulation of an organism, introduced orally, or may be introduced by bathing a cell or organism in a solution containing the nucleic acid. Vascular or extravascular circulation, the blood or lymph system, and the cerebrospinal fluid are sites where the nucleic acid may be introduced.

The RNA silencing agents of the disclosure can be introduced using nucleic acid delivery methods known in art including injection of a solution containing the nucleic acid, bombardment by particles covered by the nucleic acid, soaking the cell or organism in a solution of the nucleic acid, or electroporation of cell membranes in the presence of the nucleic acid. Other methods known in the art for introducing nucleic acids to cells may be used, such as lipid-mediated carrier transport, chemical-mediated transport, and cationic liposome transfection such as calcium phosphate, and the like. The nucleic acid may be introduced along with other components that perform one or more of the following activities: enhance nucleic acid uptake by the cell or otherwise increase inhibition of the target gene.

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus, the RNA may be introduced along with components that perform one or more of the following activities: enhance RNA uptake by the cell, inhibit annealing of single strands, stabilize the single strands, or other-wise increase inhibition of the target gene.

RNA may be directly introduced into the cell (i.e., intracellularly); or introduced extracellularly into a cavity, interstitial space, into the circulation of an organism, introduced orally, or may be introduced by bathing a cell or organism in a solution containing the RNA. Vascular or extravascular circulation, the blood or lymph system, and the cerebrospinal fluid are sites where the RNA may be introduced.

The cell having the target gene may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

Depending on the particular target gene and the dose of double stranded RNA material delivered, this process may provide partial or complete loss of function for the target gene. A reduction or loss of gene expression in at least 50%, 60%, 70%, 80%, 90%, 95% or 99% or more of targeted cells is exemplary. Inhibition of gene expression refers to the absence (or observable decrease) in the level of protein and/or mRNA product from a target gene. Specificity refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, Enzyme Linked ImmunoSorbent Assay (ELISA), Western blotting, RadioImmunoAssay (RIA), other immunoassays, and Fluorescence Activated Cell Sorting (FACS).

For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentarnycin, hygromycin, kanamycin, lincomycin, methotrexate, phosphinothricin, puromycin, and tetracycline. Depending on the assay, quantitation of the amount of gene expression allows one to determine a degree of inhibition which is greater than 10%, 33%, 50%, 90%, 95% or 99% as compared to a cell not treated according to the present disclosure. Lower doses of injected material and longer times after administration of RNAi agent may result in inhibition in a smaller fraction of cells (e.g., at least 10%, 20%, 50%, 75%, 90%, or 95% of targeted cells). Quantization of gene expression in a cell may show similar amounts of inhibition at the level of accumulation of target mRNA or translation of target protein. As an example, the efficiency of inhibition may be determined by assessing the amount of gene product in the cell; mRNA may be detected with a hybridization probe having a nucleotide sequence outside the region used for the inhibitory double-stranded RNA, or translated polypeptide may be detected with an antibody raised against the polypeptide sequence of that region.

The RNA may be introduced in an amount which allows delivery of at least one copy per cell. Higher doses (e.g., at least 5, 10, 100, 500 or 1000 copies per cell) of material may yield more effective inhibition; lower doses may also be useful for specific applications.

In an exemplary aspect, the efficacy of an RNAi agent of the disclosure (e.g., an siRNA targeting a target sequence of interest) is tested for its ability to specifically degrade mutant mRNA (e.g., target mRNA and/or the production of target protein) in cells, in particular, in neurons (e.g., striatal or cortical neuronal clonal lines and/or primary neurons). Also suitable for cell-based validation assays are other readily transfectable cells, for example, HeLa cells or COS cells. Cells are transfected with human wild type or mutant cDNAs (e.g., human wild type or mutant target cDNA). Standard siRNA, modified siRNA or vectors able to produce siRNA from U-looped mRNA are co-transfected. Selective reduction in target mRNA and/or target protein is measured. Reduction of target mRNA or protein can be compared to levels of target mRNA or protein in the absence of an RNAi agent or in the presence of an RNAi agent that does not target the target mRNA. Exogenously-introduced mRNA or protein (or endogenous mRNA or protein) can be assayed for comparison purposes. When utilizing neuronal cells, which are known to be somewhat resistant to standard transfection techniques, it may be desirable to introduce RNAi agents (e.g., siRNAs) by passive uptake.

VIII. Methods of Treatment

"Treatment," or "treating," as used herein, is defined as the application or administration of a therapeutic agent (e.g., a RNA agent or vector or transgene encoding same) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In one aspect, the disclosure provides a method for preventing in a subject, a disease or disorder as described above, by administering to the subject a therapeutic agent (e.g., an RNAi agent or vector or transgene encoding same). Subjects at risk for the disease can be identified by, for example, any or a combination of diagnostic or prognostic assays as described herein. Administration of a prophylactic agent can occur prior to the manifestation of symptoms characteristic of the disease or disorder, such that the disease or disorder is prevented or, alternatively, delayed in its progression.

Another aspect of the disclosure pertains to methods treating subjects therapeutically, i.e., alter onset of symptoms of the disease or disorder.

With regards to both prophylactic and therapeutic methods of treatment, such treatments may be specifically tailored or modified, based on knowledge obtained from the field of pharmacogenomics. "Pharmacogenomics," as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype," or "drug response genotype"). Thus, another aspect of the disclosure provides methods for tailoring an individual's prophylactic or therapeutic treatment with either the target gene molecules of the present disclosure or target gene modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

Therapeutic agents can be tested in an appropriate animal model. For example, an RNAi agent (or expression vector or transgene encoding same) as described herein can be used in an animal model to determine the efficacy, toxicity, or side effects of treatment with said agent. Alternatively, a therapeutic agent can be used in an animal model to determine the mechanism of action of such an agent. For example, an agent can be used in an animal model to determine the efficacy, toxicity, or side effects of treatment with such an agent. Alternatively, an agent can be used in an animal model to determine the mechanism of action of such an agent.

IX. Pharmaceutical Compositions and Methods of Administration

The disclosure pertains to uses of the above-described agents for prophylactic and/or therapeutic treatments as described infra. Accordingly, the modulators (e.g., RNAi agents) of the present disclosure can be incorporated into pharmaceutical compositions suitable for administration. Such compositions typically comprise the nucleic acid molecule, protein, antibody, or modulatory compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the disclosure is formulated to be compatible with its intended route of administration. Examples of routes of administration include parenteral, e.g., intravenous, intradermal, subcutaneous, intraperitoneal, intramuscular, oral (e.g., inhalation), transdermal (topical), and transmucosal administration. In certain exemplary embodiments, the pharmaceutical composition of the disclosure is administered intravenously and is capable of crossing the blood brain barrier to enter the central nervous system In certain exemplary embodiments, a pharmaceutical composition of the disclosure is delivered to the cerebrospinal fluid (CSF) by a route of administration that includes, but is not limited to, intrastriatal (IS) administration, intracerebroventricular (ICV) administration and intrathecal (IT) administration (e.g., via a pump, an infusion or the like).

The nucleic acid molecules of the disclosure can be inserted into expression constructs, e.g., viral vectors, retroviral vectors, expression cassettes, or plasmid viral vectors, e.g., using methods known in the art, including but not limited to those described in Xia et al., (2002), *Supra*. Expression constructs can be delivered to a subject by, for example, inhalation, orally, intravenous injection, local administration (see U.S. Pat. No. 5,328,470) or by stereotactic injection (see e.g., Chen et al. (1994), Proc. Natl. Acad. Sci. USA, 91, 3054-3057). The pharmaceutical preparation of the delivery vector can include the vector in an acceptable diluent, or can comprise a slow release matrix in which the delivery vehicle is imbedded. Alternatively, where the complete delivery vector can be produced intact from recombinant cells, e.g., retroviral vectors, the pharmaceutical preparation can include one or more cells which produce the gene delivery system.

The nucleic acid molecules of the disclosure can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21 nucleotides. Brummelkamp et al. (2002), Science, 296, 550-553; Lee et al, (2002). *supra*; Miyagishi and Taira (2002), Nature Biotechnol., 20, 497-500; Paddison et al. (2002), *supra*; Paul (2002), *supra*; Sui (2002) *supra*; Yu et al. (2002), *supra*.

The expression constructs may be any construct suitable for use in the appropriate expression system and include, but are not limited to retroviral vectors, linear expression cassettes, plasmids and viral or virally-derived vectors, as known in the art. Such expression constructs may include one or more inducible promoters, RNA Pol III promoter systems such as U6 snRNA promoters or H1 RNA polymerase III promoters, or other promoters known in the art. The constructs can include one or both strands of the siRNA. Expression constructs expressing both strands can also include loop structures linking both strands, or each strand can be separately transcribed from separate promoters within the same construct. Each strand can also be transcribed from a separate expression construct, Tuschl (2002), *Supra*.

In certain embodiments, a composition that includes a compound of the disclosure can be delivered to the nervous system of a subject by a variety of routes. Exemplary routes include intrathecal, parenchymal (e.g., in the brain), nasal, and ocular delivery. The composition can also be delivered systemically, e.g., by intravenous, subcutaneous or intramuscular injection. One route of delivery is directly to the brain, e.g., into the ventricles or the hypothalamus of the brain, or into the lateral or dorsal areas of the brain. The compounds for neural cell delivery can be incorporated into pharmaceutical compositions suitable for administration.

For example, compositions can include one or more species of a compound of the disclosure and a pharmaceutically acceptable carrier. The pharmaceutical compositions of the present disclosure may be administered in a number of ways depending upon whether local or systemic treatment is desired and upon the area to be treated. Administration may be topical (including ophthalmic, intranasal, transdermal), oral or parenteral. Parenteral administration includes intravenous drip, subcutaneous, intraperitoneal or intramuscular injection, intrathecal, or intraventricular (e.g., intracerebroventricular) administration. In certain exemplary embodiments, an RNA silencing agent of the disclosure is delivered across the Blood-Brain-Barrier (BBB) suing a variety of suitable compositions and methods described herein.

The route of delivery can be dependent on the disorder of the patient. In addition to a compound of the disclosure, a patient can be administered a second therapy, e.g., a palliative therapy and/or disease-specific therapy. The secondary therapy can be, for example, symptomatic (e.g., for alleviating symptoms), neuroprotective (e.g., for slowing or halting disease progression), or restorative (e.g., for reversing the disease process). Other therapies can include psychotherapy, physiotherapy, speech therapy, communicative and memory aids, social support services, and dietary advice.

A compound of the disclosure can be delivered to neural cells of the brain. In certain embodiments, the compounds of the disclosure may be delivered to the brain without direct administration to the central nervous system, i.e., the compounds may be delivered intravenously and cross the blood brain barrier to enter the brain. Delivery methods that do not require passage of the composition across the blood-brain barrier can be utilized. For example, a pharmaceutical composition containing a compound of the disclosure can be delivered to the patient by injection directly into the area containing the disease-affected cells. For example, the pharmaceutical composition can be delivered by injection directly into the brain. The injection can be by stereotactic injection into a particular region of the brain (e.g., the substantia nigra, cortex, hippocampus, striatum, or globus pallidus). The compound can be delivered into multiple regions of the central nervous system (e.g., into multiple regions of the brain, and/or into the spinal cord). The compound can be delivered into diffuse regions of the brain (e.g., diffuse delivery to the cortex of the brain).

In one embodiment, the compound can be delivered by way of a cannula or other delivery device having one end implanted in a tissue, e.g., the brain, e.g., the substantia nigra, cortex, hippocampus, striatum or globus pallidus of the brain. The cannula can be connected to a reservoir containing the compound. The flow or delivery can be mediated by a pump, e.g., an osmotic pump or minipump, such as an Alzet pump (Durect, Cupertino, CA). In one embodiment, a pump and reservoir are implanted in an area distant from the tissue, e.g., in the abdomen, and delivery is effected by a conduit leading from the pump or reservoir to the site of release. Devices for delivery to the brain are described, for example, in U.S. Pat. Nos. 6,093,180, and 5,814,014.

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following example, which is included for purposes of illustration only and is not intended to be limiting.

Example 1. Synthesis of a 2'-OMe-exNA Phosphoramidite

Synthesis of Compound 5a

Figure 2:
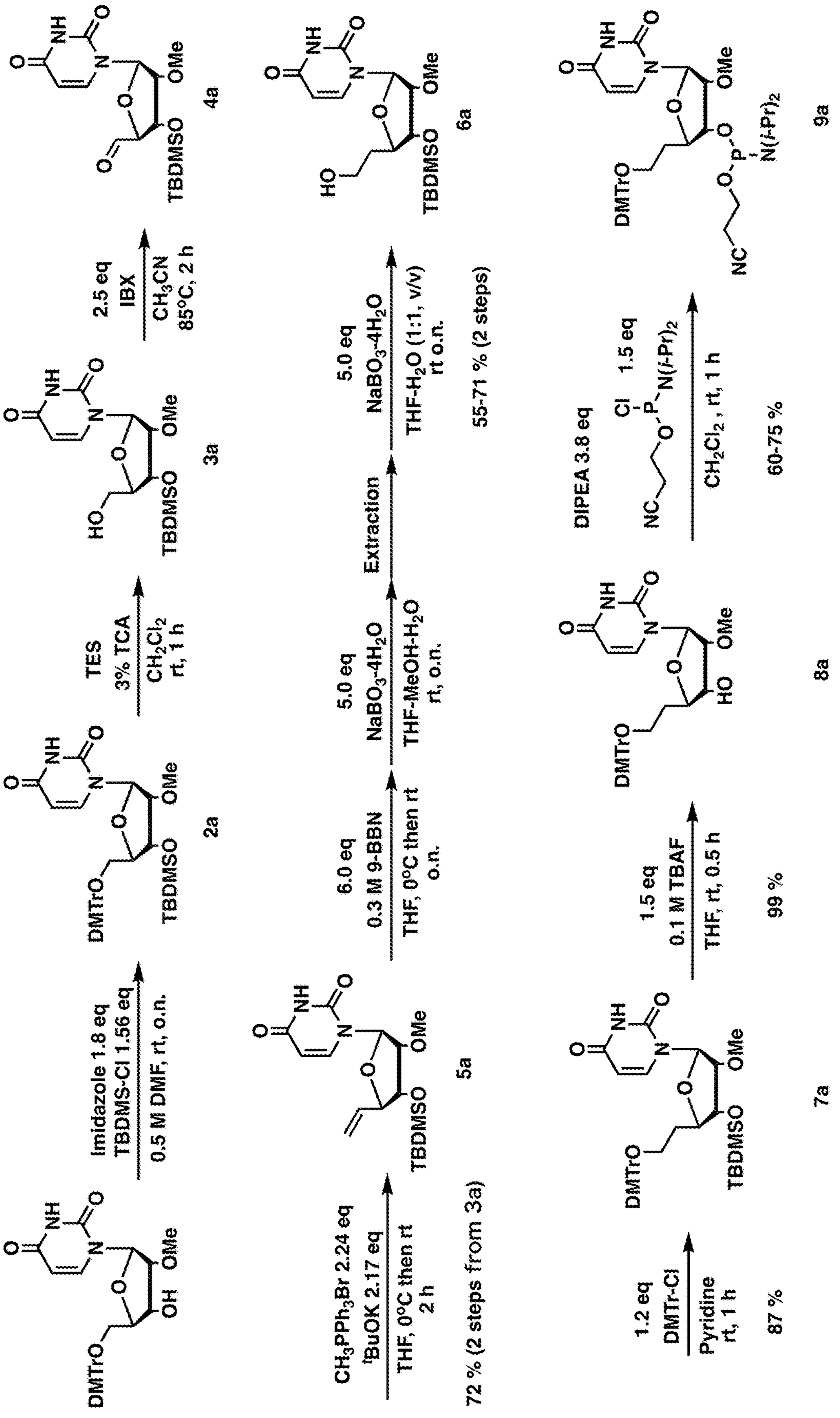

According to FIG. 2, the following synthesis was completed. Anhydrous solution of compound 3a (2.94 g, 7.89 mmol) in $CH_3CN$ (80 mL) was added IBX (5.53 g, 19.7 mmol) and stirred for 2 h at 85° C. After cooling the mixture in an ice bath, the precipitate in the solution was filtered off through celite. Collected eluent was evaporated, co-evaporated with anhydrous $CH_3CN$ three times under argon atmosphere, and obtained compound 4a as a white foam was used without further purification. In a separate flask, anhydrous THF (80 mL) solution containing methyltriphenylphosphonium bromide (8.47 g, 23.7 mmol) was added tert-BuOK (2.57 g, 22.9 mmol) at 0° C. and stirred for 30 min at 0° C. To this solution, anhydrous THF solution (80 mL) of compound 4a was added dropwise (10 min) at 0° C. and stirred for 7 h at rt. After evaporating excess THF, the obtained mixture was dissolved in excess ethyl acetate, washed by aq. sat. $NH_4Cl$, dried over $MgSO_4$, filtered, and evaporated. Obtained material was dissolved into minimum amount of $CH_2Cl_2$ and added dropwise to excess diethyl ether solution under vigorously stirring at 0° C. Precipitate in solution was filtered off through celite and eluents was evaporated. Obtained crude material was purified by silica gel column chromatography (hexane/ethyl acetate, 9:1 to 1:2) yielding compound 5a as a white foam (2.19 g, 75% in 2 steps). $^1H$ NMR (500 MHz, $CDCl_3$) δ 9.55 (br-s, 1H), 7.38 (d, 1H, J=8.2 Hz), 5.89 (ddd, 1H, J=17.1, 10.6, 6.6 Hz), 5.82 (d, 1H, J=2.0 Hz), 5.77 (dd, 1H, J=8.1, 1.5 Hz), 5.44 (dt, 1H, J=17.2, 1.2 Hz), 5.34 (dt, 1H, J=10.5, 1.1 Hz), 4.43-4.40 (m, 1H), 3.90 (dd, 1H, J=7.7, 5.1 Hz), 3.71 (dd, 1H, J=5.0, 2.0 Hz), 3.55 (s, 3H), 0.89 (s, 9H), 0.09 (s, 3H), 0.07 (s, 3H); $^{13}C$ NMR (125 MHz, $CDCl_3$) δ 163.4, 150.0, 139.7, 134.4, 119.2, 102.4, 89.7, 84.0, 83.5, 74.5, 58.7, 25.7, 18.2, −4.6, −4.7; HRMS (ESI) calcd. for $C_{17}H_{29}N_2O_5Si^+$[M+H]$^+$ m/z 369.1840, found m/z 369.1838.

Synthesis of Compound 6a

Anhydrous solution of compound 5a (7.29 g, 19.8 mmol) in THF (158.3 mL) was added 0.5 M 9-BBN/THF solution (237.4 mL, 118.7 mmol) dropwise for 10 min at 0° C. After stirring the mixture at rt 6 h, the solution was iced and added methanol (65.4 mL) and stirred until bubbling cease down. Then under vigorous stirring, $H_2O$ (98.4 mL) was added dropwise for 10 min to avoid precipitation of an intermediate compound. At 0° C., $NaBO_3$-$4H_2O$ (15.7 g, 102.0 mmol) was added in one portion and stirred at rt o.n. After evaporation of excess THF, obtained crude mixture was dissolved into excess ethyl acetate, and washed repeatedly by sat. aq. $NH_4Cl$ solution. After evaporating organic layer, obtained material was dissolved in THF (450 mL) and $H_2O$ (450 mL). To this solution, $NaBO_3$—$4H_2O$ (15.7 g, 102.0 mmol) was added in one portion at rt, then stirred o.n. at rt. After evaporating of excess THF, the mixture was added ethyl acetate, then extracted. Obtained organic layer was repeatedly washed by aq. sat. $NH_4Cl$, dried over $MgSO_4$, filtered, and evaporated. Obtained crude material was purified by silica gel column chromatography (hexane/ethyl acetate, 7:3 to 0:10) yielding compound 6a as a white foam (4.73 g, 62% in 2 steps). $^1H$ NMR (500 MHz, $CDCl_3$) δ 9.21(br-s, 1H), 7.35 (d, 1H, J=8.1 Hz), 5.78-5.76 (m, 2H), 4.14-4.10 (m, 1H), 3.92-3.79 (m, 4H), 3.75 (dd, 1H, J=5.2, 2.3 Hz), 2.06-2.00 (m, 1H), 1.90-1.82 (m, 1H), 0.91 (s, 9H), 0.11 (s, 3H), 0.10 (s, 3H); $^{13}C$ NMR (125 MHz, $CDCl_3$) δ 163.1, 149.9, 140.0, 102.6, 90.1, 83.0, 82.0, 74.5, 60.3, 58.4, 35.5, 25.7, 18.1, −4.6, −4.9; HRMS (ESI) calcd. for $C_{17}H_{31}N_2O_5Si^+$[M+H]$^+$ m/z 387.1946, found m/z 187.1944.

Synthesis of Compound 8a

Anhydrous solution of compound 6a (9.46 g, 24.5 mmol) in pyridine (240 mL) was added DMTrCl (9.95 g, 29.4 mmol) and stirred at rt for 2 h. After quenching the reaction mixture by MeOH (20 mL), excess pyridine was evaporated, then obtained material was dissolved into excess ethyl acetate. The organic solution was washed by aq. sat. $NaHCO_3$, dried over $MgSO_4$, filtered, evaporated, then co-evaporated with toluene to remove pyridine residues. This crude mixture containing compound 7a was dissolved into THF (330 mL), added 1.0 M TBAF-THF solution (36.7 mL, 36.7 mmol), then stirred for 1 h at rt. After evaporation excess THF and co-evaporation with $CH_2Cl_2$, the crude material was purified by silica gel column chromatography yielding compound 8a (13.15 g, 93% in 2 steps). $^1H$ NMR (500 MHz, $CDCl_3$) δ 8.91 (br-s, 1H), 7.43-7.21 (m, 2H), 7.32-7.14 (m, 8H), 6.83-6.82 (m, 1H), 5.80 (d, 1H, J=1.8 Hz), 5.69 (d, 1H, J=8.2 Hz), 4.02-3.98 (m, 1H), 3.85 (dd, 1H, J=6.7, 6.7 Hz), 3.79 (s, 6H), 3.72 (dd, 1H, J=5.5, 1.9 Hz), 3.34-3.25 (m, 2H), 2.91 (br-s, 1H), 2.11-2.04 (m, 1H), 1.95-1.89 (m, 1H); $^{13}C$ NMR (125 MHz, $CDCl_3$) δ 163.2, 163.1, 158.4, 149.9, 114.8, 139.1, 136.1, 136.0, 129.92, 129.90, 128.0, 127.8, 126.8, 113.1, 102.5, 88.1, 86.6, 83.5, 81.3, 73.2, 60.1, 58.8, 55.2, 53.4, 33.4; HRMS (ESI) calcd. for $C_{32}H_{34}N_2O_8Na$ [M+Na]$^+$ m/z 597.2203, found m/z 597.2153.

Synthesis of Compound 9a

Compound 8a (9.57 g, 16.65 mmol) was rendered anhydrous by repeated co-evaporation with anhydrous $CH_3CN$ and then dissolved into anhydrous $CH_2Cl_2$ (150 mL). To this solution N,N-diisopropylethylamine (7.6 mL, 62.4 mmol) and 2-cyanoethyl N,N-diisopropylchlorophosphoramidite (4.85 mL, 25.0 mmol) were added at 0° C. After stirring for 4 h at rt, the reaction mixture was added $CH_2Cl_2$ (200 mL) then aq. sat. $NaHCO_3$ (350 mL). Organic layer was repeatedly washed by aq. sat. $NaHCO_3$, dried over $MgSO_4$, filtered, then evaporated. Obtained crude material was purified by silica gel column chromatography (1% TEA-hexanes-ethyl acetate, from 80:20 to 30:70) yielding compound 9a with an impurity of phosphitylating reagent residues. To remove the impurity, obtained material was dissolved in $Et_2O$-ethylacetate (1:1, v/v, 400 mL), then repeatedly washed by aq. sat. $NaHCO_3$ yielding compound 9a as a white solid (11.12 g, 86%); $^{31}P$ NMR (202 MHz, $CDCl_3$) δ 150.0, 149.9; HRMS (ESI) calcd. for $C_{41}H_{52}N_4O_9P$ $[M+H]^+$ m/z 775.3486, found m/z 775.3414.

Example 2. Synthesis of a 2'-F-exNA phosphoramidite

Synthesis of Compound 5b

Figure 3:
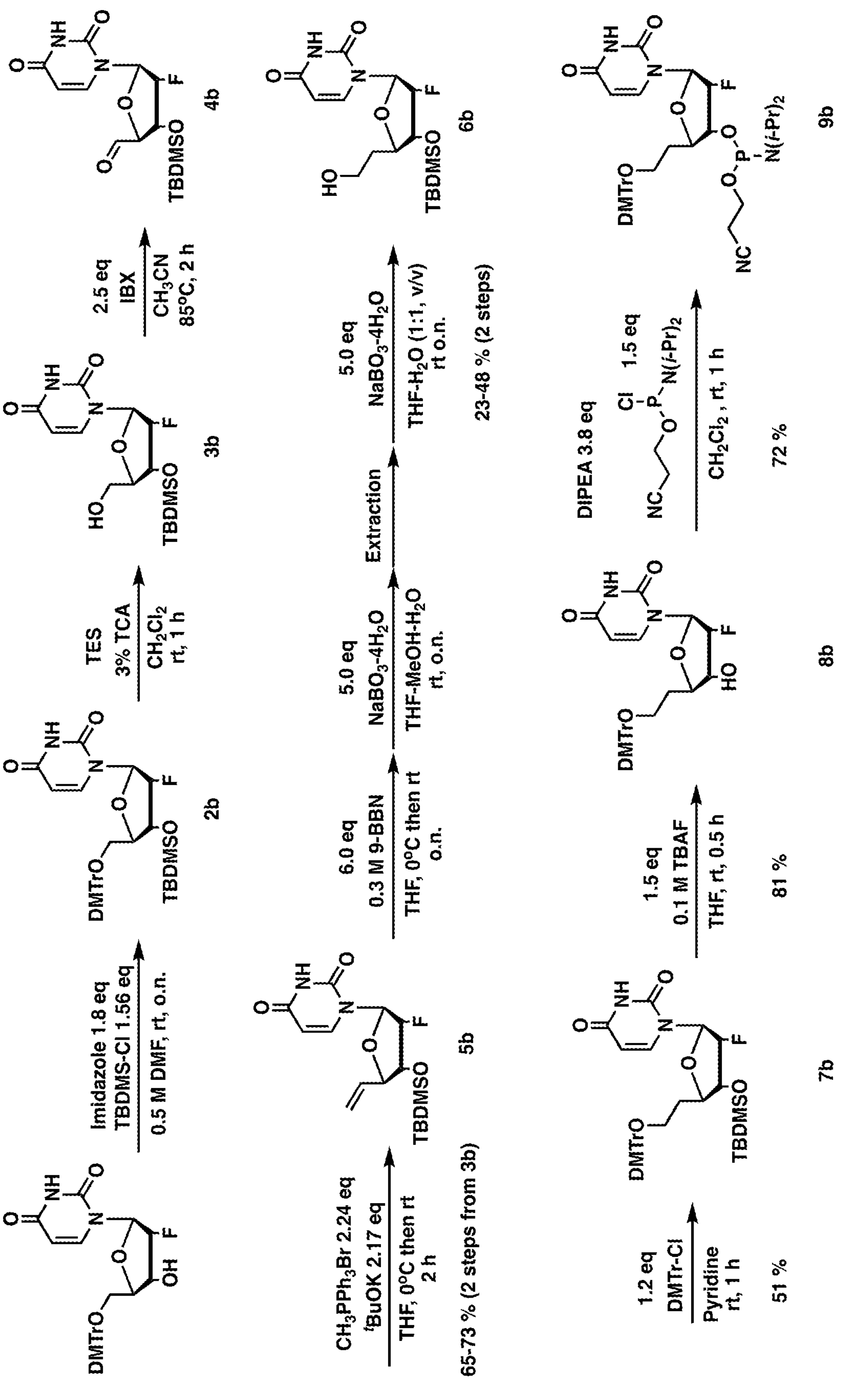
FIG. 3 provides a synthesis of a 2'-F-exNA phosphoramidite 9b.

According to FIG. 3, the following synthesis was completed. Anhydrous solution of compound 3b (10.8 g, 30.0 mmol) in $CH_3CN$ (300 mL) was added IBX (21.0 g, 75.0 mmol) and stirred for 2 h at 85° C. After cooling the mixture in an ice bath, the precipitate in the solution was filtered off through celite. Collected eluent was evaporated, co-evaporated with anhydrous $CH_3CN$ three times under argon atmosphere, and obtained compound 4b as a white foam was used without further purification. In a separate flask, anhydrous THF (250 mL) solution containing tert-BuOK (7.30 g, 65.1 mmol) was added methyltriphenylphosphonium bromide (24.0 g, 68.1 mmol) was added in one portion at 0° C. and stirred for 1 h at 0° C. To this solution, anhydrous THF solution (150 mL) of compound 4b was added dropwise (10 min) at 0° C. and stirred o.n. at rt. After evaporating excess THF, the obtained mixture was dissolved in excess ethyl acetate, washed by aq. sat. $NH_4Cl$, dried over $MgSO_4$, filtered, and evaporated. Obtained material was dissolved into minimum amount of $CH_2Cl_2$ and added dropwise to excess diethyl ether solution under vigorously stirring at 0° C. Precipitate in solution was filtered off through celite and eluents was evaporated. Obtained crude material was purified by silica gel column chromatography (hexane/ethyl acetate, 8:2 to 6:4) yielding compound 5b as a white foam (7.12 g, 67% in 2 steps). $^1H$ NMR (500 MHz, $CDCl_3$) δ 11.4 (br-s, 1H), 7.65 (d, 1H, J=8.1 Hz), 5.93 (ddd, 1H, J=17.5, 10.4, 7.5 Hz), 5.82 (dd, 1H, $J_{HF}$=22.2 Hz, $J_{HH}$=1.3 Hz), 5.65 (d, 1H, J=8.1 Hz), 5.42-5.38 (m, 1H), 5.33-5.31 (m, 1H), 5.15 (ddd, 1H, $J_{HF}$=53.4 Hz, $J_{HH}$=4.6, 1.2 Hz), 4.27 (ddd, 1H, $J_{HF}$=20.6 Hz, $J_{HH}$=8.4, 4.9 Hz), 4.18 (dd, 1H, J=7.7, 7.7 Hz), 0.88 (s, 9H), 0.08 (s, 3H), 0.07 (s, 3H); $^{13}C$ NMR (125 MHz, $CDCl_3$) δ 170.8, 183.7, 150.7, 142.5, 135.3, 120.2, 102.4, 92.9 (d, $J_{CF}$=186.2 Hz), 90.2 (d, $J_{CF}$=36.4 Hz), 83.4, 73.8 (d, $J_{CF}$=15.5 Hz), 60.2, 26.0, 21.2, 18.2, 14.6, −4.4, −4.5; $^{19}F$ NMR (470 MHz, DMSO-d6) δ −198.3 (ddd, J=53.8, 20.8, 20.8 Hz).

Synthesis of Compound 7b

Anhydrous solution of compound 5b (10.15 g, 28.5 mmol) in THF (228 mL) was added 0.5 M 9-BBN/THF solution (342 mL, 171 mmol) dropwise for 20 min at 0° C. After stirring the mixture at rt 4 h, the solution was iced and added methanol (131 mL) and stirred until bubbling cease down. Then under vigorous stirring, $H_2O$ (197 mL) was added dropwise for 15 min to avoid precipitation of an intermediate compound. At 0° C., $NaBO_3$—$4H_2O$ (21.9 g, 142.5 mmol) was added in one portion and stirred at rt o.n. After evaporation of excess THF, obtained crude mixture was dissolved into excess ethyl acetate, and washed repeatedly by sat. aq. $NH_4Cl$ solution. After evaporating organic layer, obtained material was dissolved in THF (450 mL) and $H_2O$ (450 mL). To this solution, $NaBO_3$—$4H_2O$ (21.9 g, 142.5 mmol) was added in one portion at rt, then stirred o.n. at rt. After evaporating of excess THF, the mixture was added ethyl acetate, then extracted. Obtained organic layer was repeatedly washed by aq. sat. $NH_4Cl$, dried over $MgSO_4$, filtered, and evaporated. Obtained crude material was purified by silica gel column chromatography ($CH_2Cl_2$/methanol, 100:0 to 93:7) yielding compound 6b as a syrup (2.44 g with reagent impurity); HRMS (ESI) calcd. for $C_{16}H_{28}FN_2O_5Si^+[M+H]^+$ m/z 375.1746, found m/z 375.1746. This compound 6b with reagent impurity was rendered anhydrous by repeated co-evaporation with anhydrous pyridine under argon atmosphere, then dissolved in anhydrous pyridine (64 mL). To this solution, DMTrCl (2.64 g, 7.79 mmol) was added and stirred at rt for 1 h. After the reaction was quenched by addition of methanol (5 mL), reaction mixture was diluted with ethyl acetate (300 mL) and washed repeated by aq. sat. $NaHCO_3$, dried over $MgSO_4$, filtered, evaporated, then co-evaporated with toluene three times to remove remaining pyridine. Obtained crude material was purified by silica gel chromatography (hexane-ethyl acetate from 2:8 to 4:6) yielding compound 7b as a white solid (2.25 g, 12% in 2 steps). $^1H$ NMR (500 MHz, $CD_3CN$) δ 9.16 (br-s, 1H), 7.43-7.42 (m, 2H), 7.31-7.28 (m, 8H), 6.86-6.85 (m, 4H), 5.75 (dd, 1H, $J_{HF}$=20.0 Hz, $J_{HH}$=1.9 Hz), 5.59 (d, 1H, J=8.1 Hz), 4.96 (ddd, $J_{HF}$=53.3 Hz, $J_{HH}$=4.6, 1.8 Hz), 4.06-3.98 (m, 2H), 3.76 (s, 6H), 3.19 (dd, 2H, J=7.4, 5.6 Hz), 2.09-2.02 (m, 1H), 1.89-1.82 (m, 1H), 0.91 (s, 9H), 0.10 (s, 3H), 0.09 (s, 3H); $^{13}C$ NMR (125 MHz, $CD_3CN$) δ 163.9, 159.6, 151.1, 146.4, 141.9, 137.31, 137.26, 130.92, 130.89, 128.9, 128.8, 127.8, 114.0, 102.9, 93.7 (d, $J_{CF}$=188.0 Hz), 90.6 (d, J=36.4 Hz), 87.0, 80.7, 74.6 (d, J=15.4 Hz), 60.9, 55.9, 33.8, 26.1, 18.7, −4.5, −4.8; $^{19}F$ NMR (470 MHz, $CD_3CN$) δ −201.4 (ddd, J=53.7, 19.1, 19.1 Hz); HRMS (ESI) calcd. for $C_{37}H_{45}FN_2O_7Na$ $[M+Na]^+$ m/z 699.2872, found m/z 699.2866.

Synthesis of Compound 8b

Compound 7a (2.24 g, 3.30 mmol) was dissolved into THF (36.0 mL), then added 1.0 M TBAF-THF solution (4.0 mL, 4.0 mmol), then stirred for 30 min at rt. After evaporation excess THF and co-evaporation with $CH_2Cl_2$, the crude material was purified by silica gel column chromatography [$CH_2Cl_2$(1% TEA)-methanol from 100:0 to 95:5] yielding compound 8b (1.51 g, 81%). $^1H$ NMR (500 MHz, $CDCl_3$) δ 9.20 (br-s, 1H), 7.45-7.43 (m, 2H), 7.32-7.13 (m, 8H), 6.87-6.85 (m, 4H), 5.77 (dd, 1H, $J_{HF}$=20.1 Hz, $J_{HH}$=1.5 Hz), 5.60 (d, 1H, J=8.1 Hz), 4.98 (ddd, $J_{HF}$=51.0 Hz, $J_{HH}$=4.6, 1.6 Hz), 4.04-3.92 (m, 2H), 3.76 (s, 6H), 3.23-3.17 (m, 2H), 2.20 (br-s, 1H), 2.11-2.06 (m, 1H), 1.91-1.87 (m, 1H); $^{13}C$ NMR (125 MHz, $CD_3CN$) δ 164.1, 159.7, 151.2, 146.4 141.7, 139.0, 137.33, 137.29, 131,00, 130.97, 129.3, 129.0, 128.9, 127.8, 126.3, 114.1, 103.0, 94.7 (d, J=184.4 Hz), 90.3 (d, J=35.4 Hz), 87.2, 80.5, 73.9 (d, J=16.4 Hz), 61.0, 56.0, 33.9; $^{19}F$ NMR (470 MHz, $CD_3CN$) δ −201.8 (ddd, J=53.7, 20.8, 20.8 Hz).

Synthesis of Compound 9b

Compound 8b (1.5 g, 2.67 mmol) was rendered anhydrous by repeated co-evaporation with anhydrous $CH_3CN$ and then dissolved into anhydrous $CH_2Cl_2$ (30 mL). To this solution N,N-diisopropylethylamine (1.76 mL, 10.1 mmol) and 2-cyanoethyl N,N-diisopropylchlorophosphoramidite (0.90 mL, 4.01 mmol) were added at 0° C. After stirring for 2 h at rt, the reaction mixture was added $CH_2Cl_2$ (70 mL) then aq. sat. $NaHCO_3$ (100 mL). Organic layer was repeatedly washed by aq. sat. $NaHCO_3$, dried over $MgSO_4$, filtered, then evaporated. Obtained crude material was purified by silica gel column chromatography (1% TEA-hexanes-ethyl acetate, from 80:20 to 20:80) yielding compound 9a with an impurity of phosphitylating reagent residues. To remove the impurity, obtained material was dissolved in $Et_2O$ (100 mL), then repeatedly washed by aq. sat. $NaHCO_3$ yielding compound 9b as a white solid (1.47 g, 64%); $^{31}P$ NMR (202 MHz, $CDCl_3$) δ 150.4 (d, J=9.0 Hz), 149.9 (d, J=10.0 Hz); $^{19}F$ NMR (470 MHz, $CD_3CN$) δ −198.61, −198.63, −198.66, −198.68, −198.70, −198.73, −198.75, −198.77, −198.79, −198.82, −198.84, −199.04, −199.06, −199.08, −199.10, −199.12, −199.14, −199.15, −199.17, −199.20, −199.21, −199.24, −199.26.

Example 3. Synthesis of an exNA-C Phosphoramidite

Figure 4:
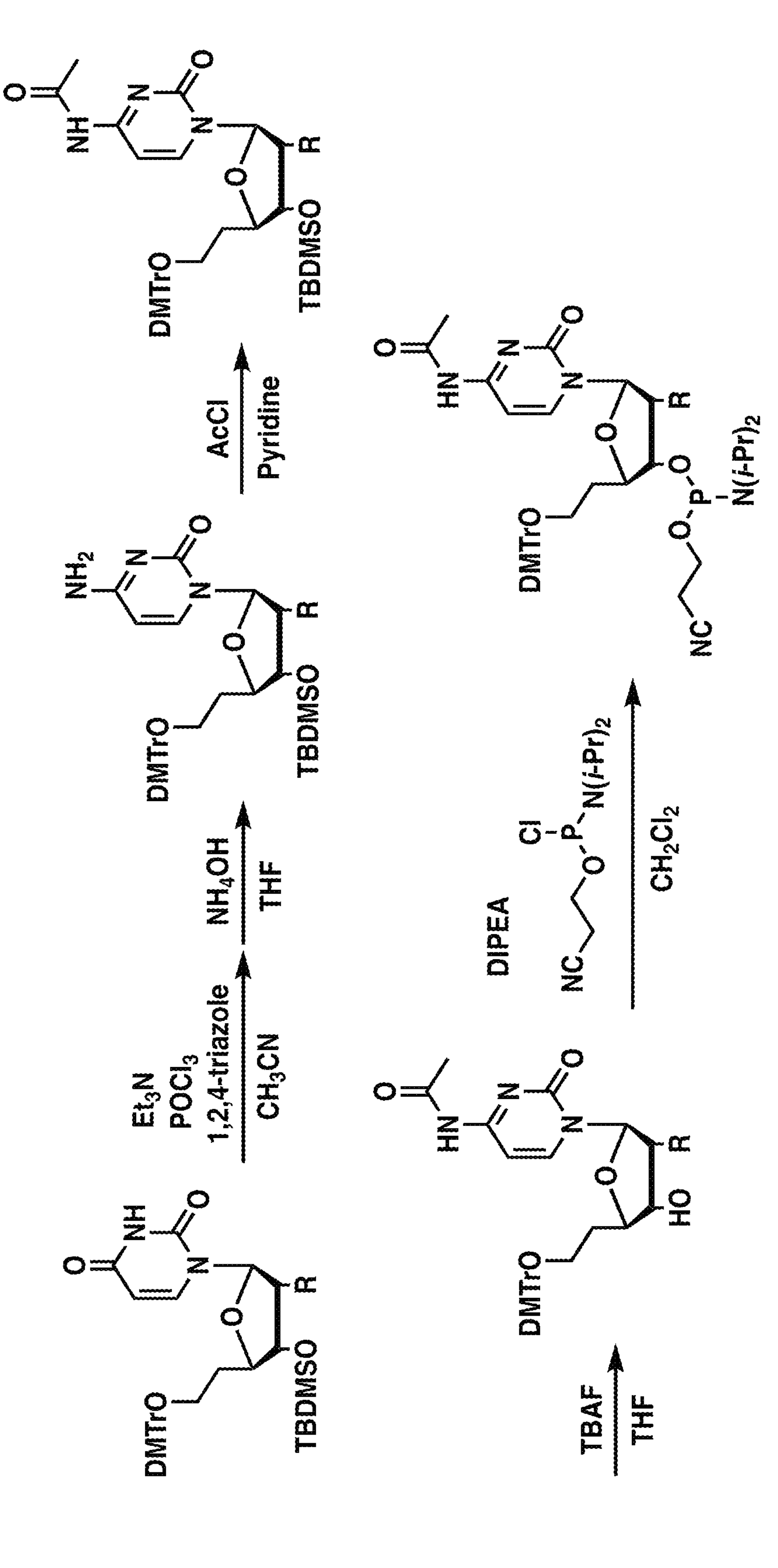
FIG. 4 provides a synthesis of an exNA-C phosphoramidite.

According to FIG. 4, the starting material will be first converted to cytidine derivative (Kaura, M. et al. J Org. Chem. 2014, 79, 6256-6268), and then yielding 4-amino group of cytosine base will be protected by an acyl protecting group such as acetyl. After deprotection of 3'-O-TBDMS, yielding 3'-hydroxyl group will be converted to 3'-O-phosphoramidite. Each step will be first quenched and extracted followed by purification by silica gel column chromatography.

Example 4. Synthesis of an exNA-G and an exNA-A phosphoramidite

Figure 5:
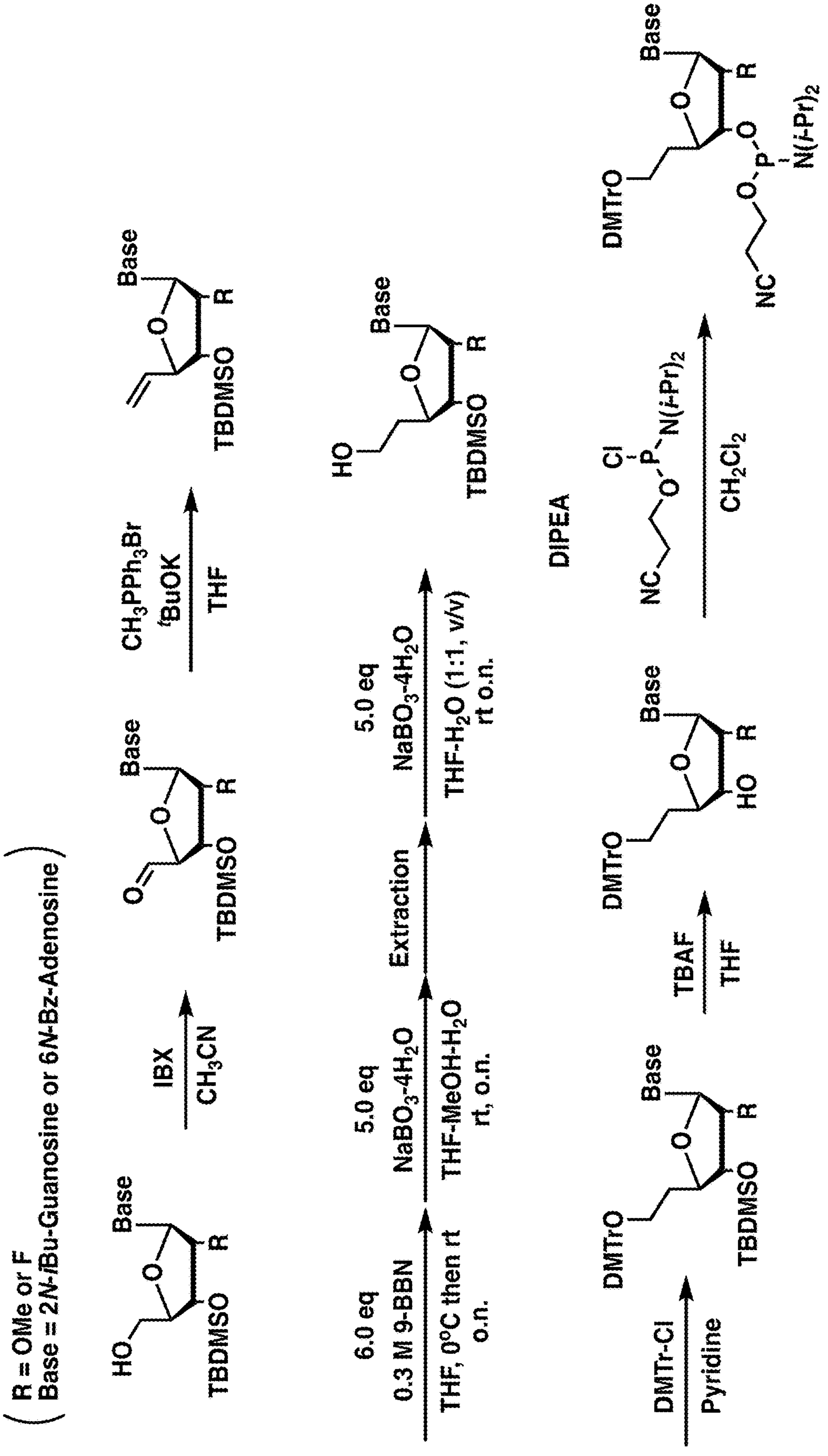
FIG. 5 provides a synthesis of an exNA-G and an exNA-A phosphoramidite.

According to FIG. 5, a 3'-O-TBDMS protected starting material will be first oxidized to aldehyde by using IBX, then applied to Wittig olefination using methyltriphenylphosphonium bromide and tert-BuOK in anhydrous THF solution to yield vinyl substituted nucleoside derivatives. This vinyl group will be reacted with 9-BBN to have boronated intermediate then forwarded to oxidation by sodium perborate yielding exNA structure with 6'-hydroxyl group. This hydroxyl group will be first protected by DMTr group, and without silica gel column purification, followed by deprotection of 3'-O-TBDMS group by 0.1 M TBAF-THF solution. Obtained 6'-O-DMTr nucleoside derivatives will be phosphitylated to yield phosphoramidites. Each step will be first quenched and extracted followed by purification by silica gel column chromatography except for the 6'-O-tritylation step.

Example 5. Synthesis of a 5'-3'-bis-methylene-exNA phosphoramidite

Figure 6:
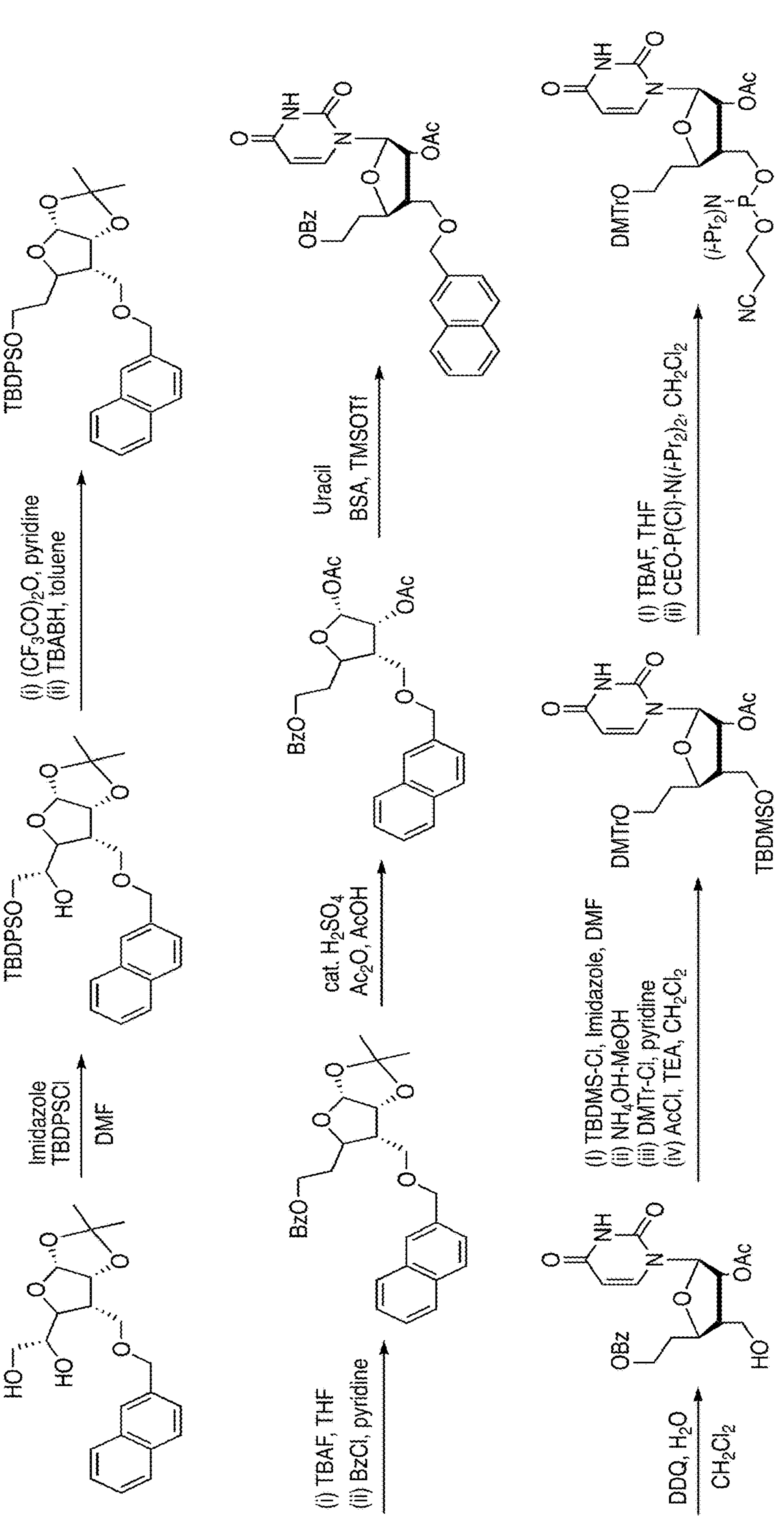
FIG. 6 provides a synthesis of a 5'-3'-bis-methylene-exNA phosphoramidite.

According to FIG. 6, a primary hydroxyl group of a starting material having Nap-protected hydroxymethyl group (Betkekar, V. V. et al. Org. *Lett.* 2012, 14, 1, 198-201) will be first selectively protected by TBDPS group, followed by deoxygenation of secondary alcohol (Prakash, T. P. et al. *Nucleic Acids Res.* 2015, 43,2993-3011). Next, TBDPS group will be switched to benzoyl (Bz) protecting group by deprotection in 0.1M TBAF-THF solution and benzoylation using benzoyl chloride in pyridine. Isopropylidene protecting group of the sugar will next deprotected to yield 1,2-bis-acetylated sugar, then conventional BSA/TMSOTf-mediated glycosylation of uracil will be conducted to have uridine nucleoside derivative. The Nap protecting group at 3'-hydroxymethyl group will be deprotected by DDQ. Obtaining material having 6'-O-Bz-3'-hydroxymethyl group will be converted to 6'-O-DMTr-3'-TBDMS-protected hydroxymethyl compound with 2'-O-acetyl protection. After deprotection of TBDMS group, 3'-hydroxymethyl group will be phosphitylated to yield 5'-3'-bis-exNA-phosphoramidite. Each step will be first quenched and extracted followed by purification by silica gel column chromatography.

Example 6. Synthesis of an exNA-ribo-uridine phosphoramidite

Figure 7:
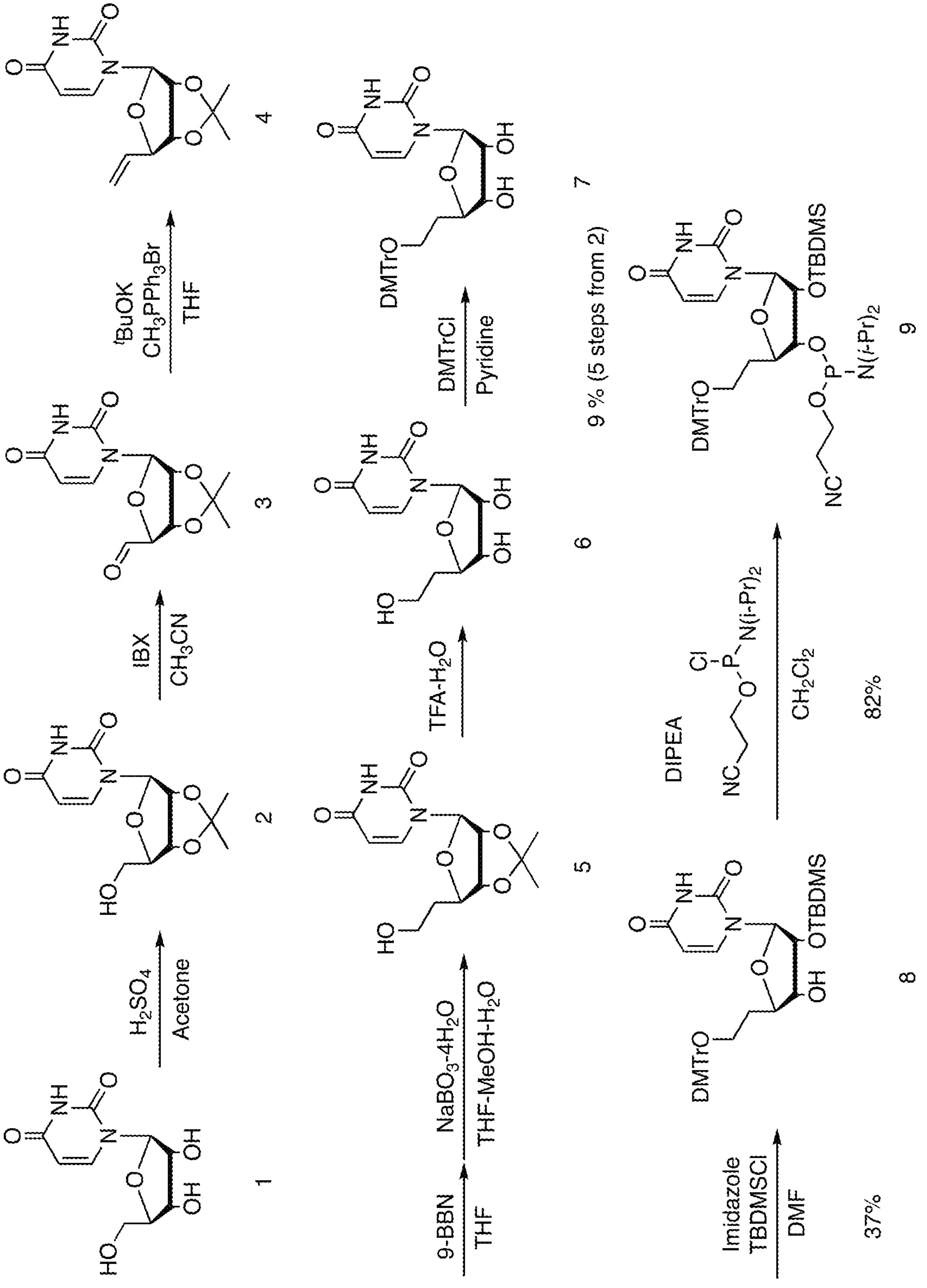
FIG. 7 provides a synthesis of an exNA-ribo-uridine phosphoramidite.
Figure 8:
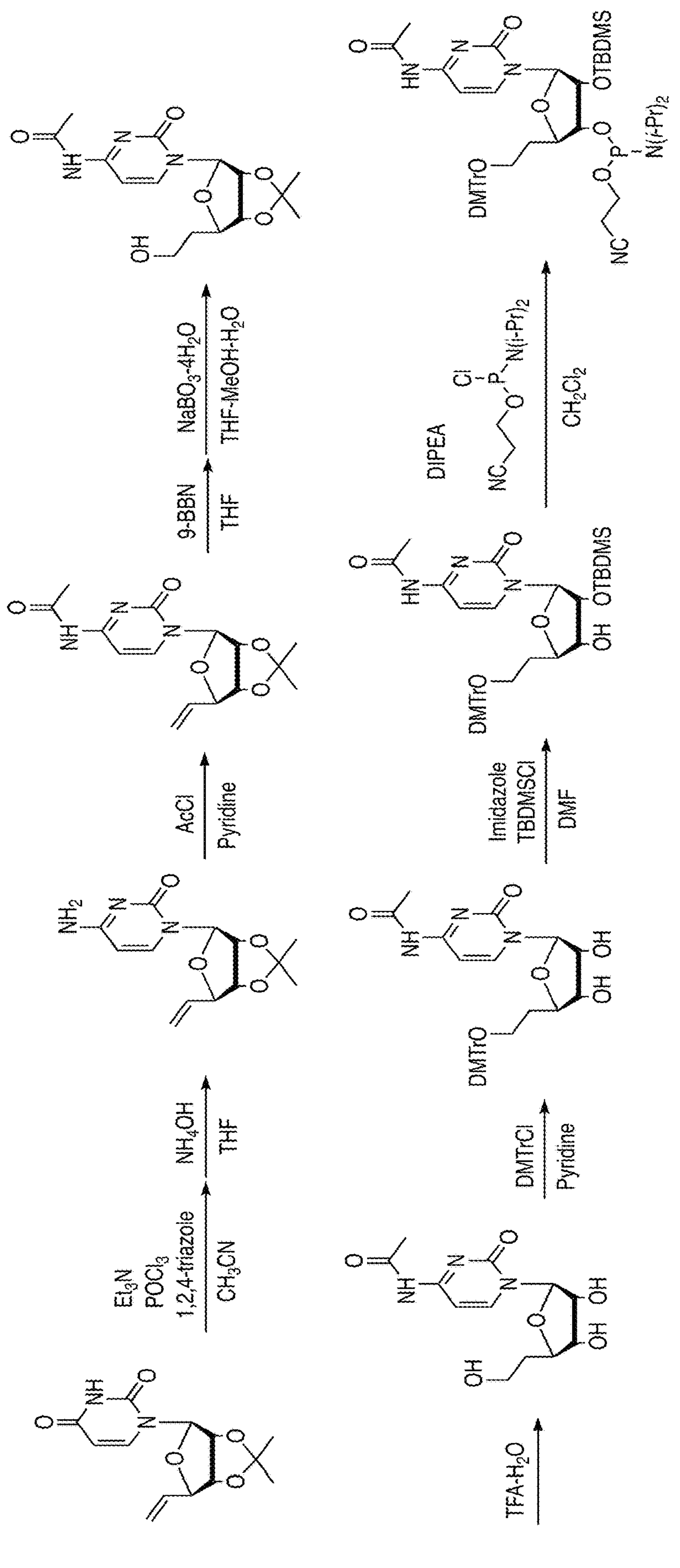
FIG. 8 provides a synthesis of an exNA-ribo-cytosine phosphoramidite.

According to FIG. 7, the following synthesis was completed. Anhydrous solution of compound 2 (15.4 g, 54.1 mmol) in $CH_3CN$ (520 mL) was added IBX (30.3 g, 108.2 mmol) and stirred for 2 h at 85° C. After cooling the mixture in an ice bath, the precipitate in the solution was filtered off through celite. Collected eluent was evaporated, co-evaporated with anhydrous $CH_3CN$ three times under argon atmosphere, and obtained compound 3 as a white foam was used without further purification. In a separate flask, anhydrous THF (500 mL) solution containing tert-BuOK (13.2 g, 117.4 mmol) was added methyltriphenylphosphonium bromide (43.3 g, 121.2 mmol) was added in one portion at 0° C. and stirred for 1 h at 0° C. To this solution, anhydrous THF solution (150 mL) of compound 3 was added dropwise (10 min) at 0° C. and stirred for 4 h. at rt. After evaporating excess THF, the obtained mixture was dissolved in excess ethyl acetate, washed by aq. sat. $NH_4Cl$, dried over $MgSO_4$, filtered, and evaporated. Obtained material was dissolved into minimum amount of $CH_2Cl_2$ and added dropwise to excess diethyl ether solution under vigorously stirring at 0° C. Precipitate in solution was filtered off through celite and eluents was evaporated. Obtained crude material was purified by silica gel column chromatography (hexane/ethyl acetate, 8:2 to 3:7) yielding compound 4 with impurity of triphenylphosphineoxide. ¾ of this crude material was rendered anhydrous by repeated co-evaporation with anhydrous $CH_3CN$, and then dissolved in anhydrous THF (200 mL). To this solution, 0.5 M 9-BBN/THF (300 mL, 150.0 mmol) was added dropwise for 10 min, then stirred at rt o.n. After confirming disappearance of starting material by TLC, the solution was iced, then added methanol (200 mL) dropwise for 10 min. After bubbling is cease down, $H_2O$ (300 mL) was added dropwise then $NaBO_3$—$4H_2O$ (19.2 g, 125.0 mmol) was added in one portion. The solution was stirred o.n. at rt. After evaporation of excess THF, obtained crude mixture was dissolved into excess ethyl acetate, and washed repeatedly by sat. aq. $NH_4Cl$ solution. After evaporating organic layer, obtained material was dissolved in THF (400 mL) and $H_2O$ (400 mL). To this solution, $NaBO_3$—$4H_2O$ (19.2 g, 125.0 mmol) was added in one portion at rt, then stirred o.n. at rt. After evaporating of excess THF, the mixture was added ethyl acetate, then extracted. Obtained organic layer was repeatedly washed by aq. sat. $NH_4Cl$, dried over $MgSO_4$, filtered, and evaporated. Obtained crude material was purified by silica gel column chromatography ($CH_2Cl_2$-methanol, 100:0 to 93:7) yielding compound 5 with impurity of reagent residues. This obtained material was added TFA solution [TFA (85 mL) and $H_2O$ (9.2 mL)] and stirred at 0° C. for 1 h. After evaporation, co-evaporation with toluene four times, crude material was purified by silica gel column chromatography ($CH_2Cl_2$—MeOH from 100:0 to 90:10) yielding compound 6 (760 mg, 12% in 3 steps). $^1H$ NMR (500 MHz, DMSO-d6) δ 11.4 (br-s, 1H), 7.58 (d, 1H, J=5.0 Hz), 5.71 (d, 1H, J=5.0 Hz), 5.64 (dd, 1H, J=8.0, 2.2 Hz), 5.34 (d, 1H, J=5.2 Hz), 5.09 (d, 1H, J=4.7 Hz), 4.51 (br-s, 1H), 4.06, (dd, 1H, J=9.8, 4.9 Hz), 3.80-3.78 (m, 1H), 3.53-3.45 (m, 2H), 1.84-1.70 (m, 2H); $^{13}$C NMR (125 MHz, DMSO-d6) δ 163.5, 151.1, 141.6, 102.5, 89.0, 80.9, 73.5, 73.2, 58.0, 46.2, 36.8, 9.1; HRMS (ESI) calcd. for $C_{10}H_{14}N_2O_6Na$ $[M+Na]^+$ m/z 281.0744, found m/z 281.0730.

Synthesis of Compound 7

The compound 6 (760 mg, 2.94 mmol) was added anhydrous pyridine (30 mL) and then added DMTr-Cl (1.3 g, 3.82 mmol). After stirring for 2 h, reaction mixture was first extracted with $CH_2Cl_2$ an aq. sat. $NaHCO_3$, and organic layer was dried over $MgSO_4$, filtered, evaporated, co-evaporated to remove pyridine. Obtained crude material was purified by silica gel column chromatography ($CH_2Cl_2$-MeOH from 100:0 to 95:5) yielding compound 7 (1.70 g, quant). HRMS (ESI) calcd. for $C_{31}H_{32}N_2O_8Na$ $[M+Na]^+$ m/z 583.2051, found m/z 583.2025.

Synthesis of Compound 8

An anhydrous solution of compound 7 (2.35 g, 4.19 mmol) in pyridine (21 mL) was added imidazole (576.1 mg, 8.46 mmol) and TBDMSCI (1.10 g, 7.33 mmol), and then stirred for 2 h at rt. To this reaction mixture was added $CH_2Cl_2$ (150 mL) then added aq. sat. $NaHCO_3$ (150 mL). The organic layer was repeatedly washed by aq. sat. $NaHCO_3$, dried over $MgSO_4$, filtered, evaporated, then co-evaporated with toluene to remove pyridine residue. Obtained crude material containing compound 8, 3'-O-TBDMS protected compound, 5'-3'-O-bis-TBDMS protected compound was separated by silica gel column chromatography [$CH_2Cl_2$ (1% TEA)-Acetone from 100:0 to 85:15] yielding pure compound 8 (780 mg, 28%). $^1$H NMR (500 MHz, DMSO-d6) δ 11.4 (br-s, 1H), 7.53-7.52 (m, 2H), 7.39-7.22 (m, 8H), 6.89-6.88 (m, 4H), 5.72 (d, 1H, J=5.0 Hz), 5.62 (d, 1H, J=8.1, 2.0 Hz), 5.00 (d, 1H, J=6.0 Hz), 4.19 (dd, 1H, J=5.1, 5.1 Hz), 3.92 (ddd, 1H, J=8.8, 8.8, 4.5 Hz), 3.78-3.73 (m, 7H), 3.07-3.03 (m, 2H), 2.05-1.83 (m, 2H), 0.83 (s, 9H), 0.05 (s, 3H), 0.01 (s, 3H); $^{13}$C NMR (125 MHz, DMSO-$d_6$) δ 162.9, 158.0, 150.5, 145.1, 140.7, 135.8, 130.1, 129.4, 128.7, 128.3, 128.1, 127.1, 125.8, 113.6, 102.5, 88.8, 86.0, 81.5, 74.9, 73.4, 60.6, 55.5, 33.8, 26.1, 25.1, 18.4; HRMS (ESI) calcd. for $C_{37}H_{46}N_2O_8Na$ $[M+Na]^+$ m/z 697.2916, found m/z 697.2867.

Synthesis of Compound 9

Compound 8 (780 g, 1.16 mmol) was rendered anhydrous by repeated co-evaporation with anhydrous $CH_3CN$ and then dissolved into anhydrous $CH_2Cl_2$ (12 mL). To this solution N,N-diisopropylethylamine (0.53 mL, 4.34 mmol) and 2-cyanoethyl N,N-diisopropylchlorophosphoramidite (0.34 mL, 1.73 mmol) were added at 0° C. After stirring for 4 h at rt, the reaction mixture was added $CH_2Cl_2$ (90 mL) then aq. sat. $NaHCO_3$ (100 mL). Organic layer was repeatedly washed by aq. sat. $NaHCO_3$, dried over $MgSO_4$, filtered, then evaporated. Obtained crude material was purified by silica gel column chromatography (1% TEA-hexanes-ethyl acetate, from 80:20 to 50:50) yielding compound 9 (825.9 mg, 82%). $^{31}$P NMR (202 MHz, $CDCl_3$) δ 149.6, 149.1.

Example 7. Synthesis of an exNA-ribo-cytosine phosphoramidite

Starting material bearing vinyl substituted uridine derivative will be first converted to cytidine (Kaura, M. et al. J Org. Chem. 2014, 79, 6256-6268), and then yielding 4-amino group of cytosine base will be protected by an acyl protecting group such as acetyl. After deprotection of 2'-3'-O-isopropylidene, 6'-hydroxyl group will be protected by DMTr followed by TBDMS protection. Silica gel column separated 2'-O-TBDMS protected compound will be phosphitylated to yield 3'-O-phosphoramidite. Each step will be first quenched and extracted followed by purification by silica gel column chromatography.

Figure 9:
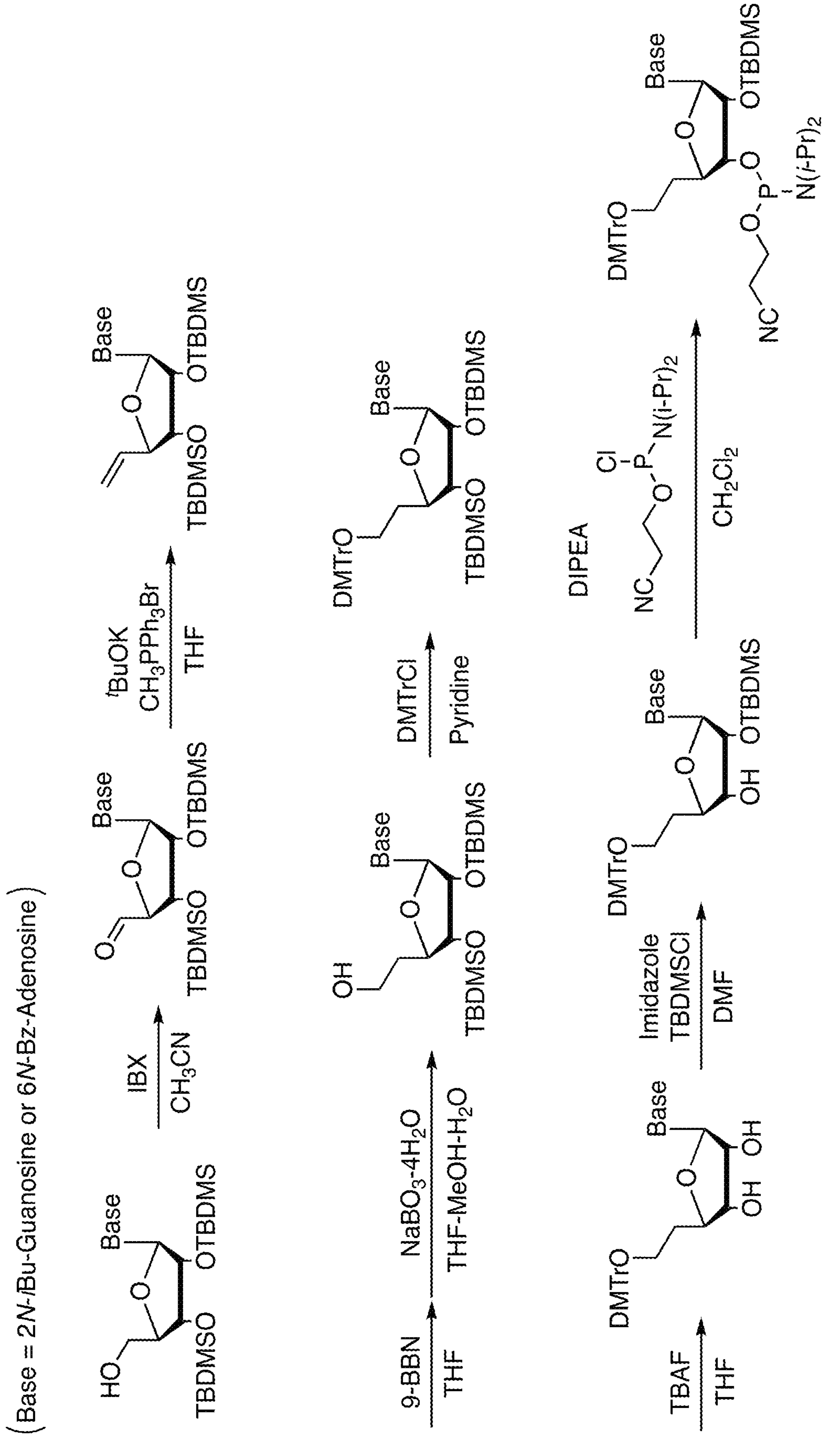
FIG. 9 provides a synthesis of an exNA-ribo-guanosine or exNA-ribo-adenine phosphoramidite.

Example 8. Synthesis of an exNA-ribo-guanosine or exNA-ribo-adenine phosphoramidite According to FIG. 9, 2'-3'-O-bis-TBDMS protected starting material will be first oxidized to aldehyde by using IBX, then applied to Wittig olefination using methyltriphenylphosphonium bromide and tert-BuOK in anhydrous THF solution to yield vinyl substituted nucleoside derivatives. This vinyl group will be reacted with 9-BBN to have boronated intermediate then forwarded to oxidation by sodium perborate yielding exNA structure with 6'-hydroxyl group. This hydroxyl group will be first protected by DMTr group followed by TBDMS protection. Silica gel column separated 2'-O-TBDMS protected compound will be phosphitylated to yield 3'-O-phosphoramidite. Each step will be first quenched and extracted followed by purification by silica gel column chromatography. and without silica gel column purification, followed by deprotection of 3'-O-TBDMS group by 0.1 M TBAF-THF solution. Obtained 6'-O-DMTr nucleoside derivatives will be phosphitylated to yield phosphoramidites. Each step will be first quenched and extracted followed by purification by silica gel column chromatography.

Example 9. Synthesis of an exNA-ribo-uridine phosphoramidite

Figure 10:
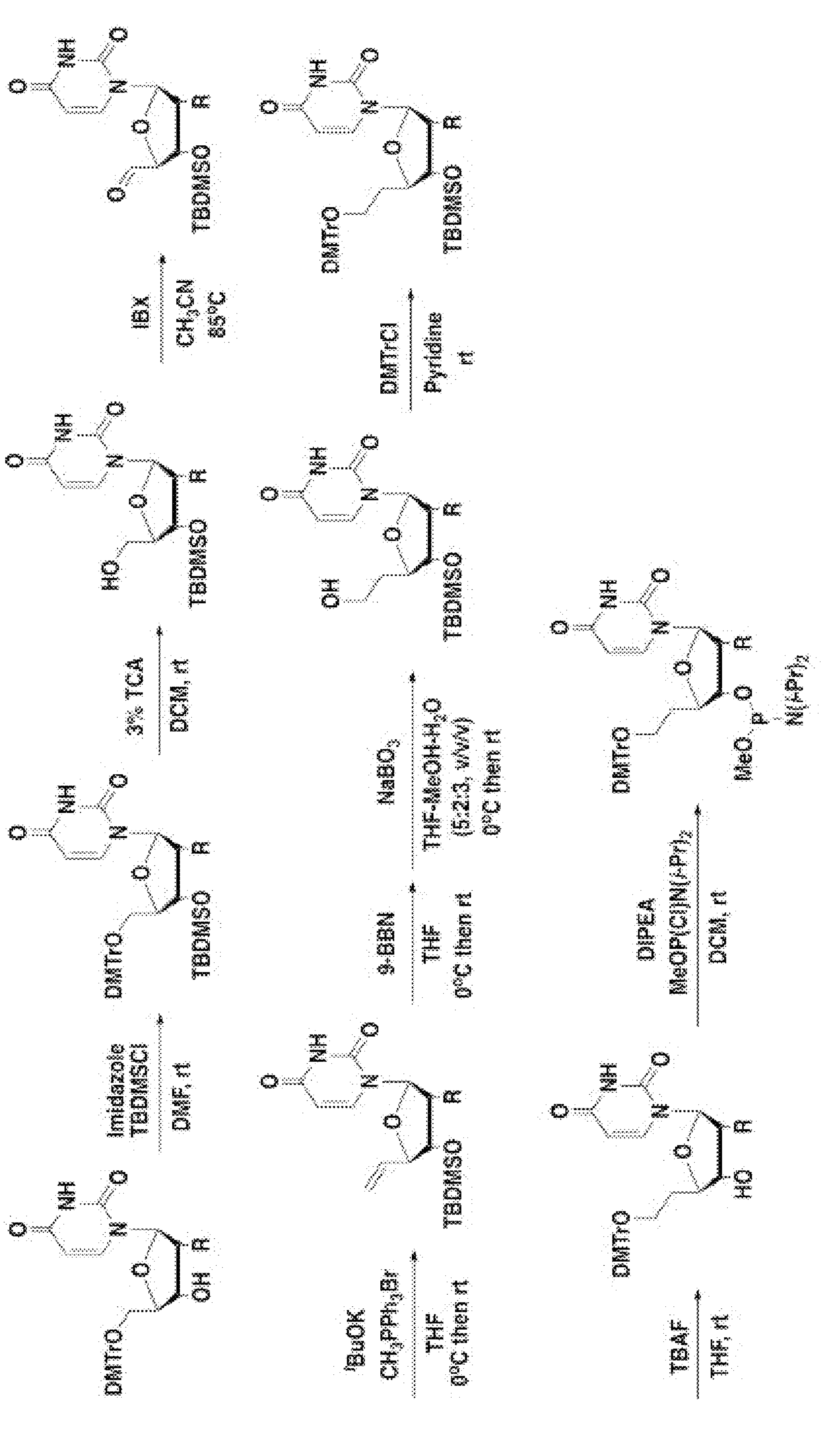
FIG. 10 provides a synthesis of a phosphoramidite monomer.

According to FIG. 10, 5'-O-DMTr protected starting material will be first protected by TBDMS, then followed by 5'-O-detritylation. Obtained compound will be next oxidized to aldehyde by using IBX, then applied to Wittig olefination using methyltriphenylphosphonium bromide and tert-BuOK in anhydrous THF solution to yield vinyl substituted nucleoside derivatives. This vinyl group will be reacted with 9-BBN to have boronated intermediate then forwarded to oxidation by sodium perborate yielding exNA structure with 6'-hydroxyl group. This hydroxyl group will be first protected by DMTr group, and without silica gel column purification, followed by deprotection of 3'-O-TBDMS group by 0.1 M TBAF-THF solution. Obtained 6'-O-DMTr nucleoside derivatives will be phosphitylated to yield methyl protected phosphoramidites. Each step will be first quenched and extracted followed by purification by silica gel column chromatography except for the first 3'-O-TBDMS protection step.

Example 10. Synthesis of oligonucleotides Incorporating exNA backbones

Figure 12:
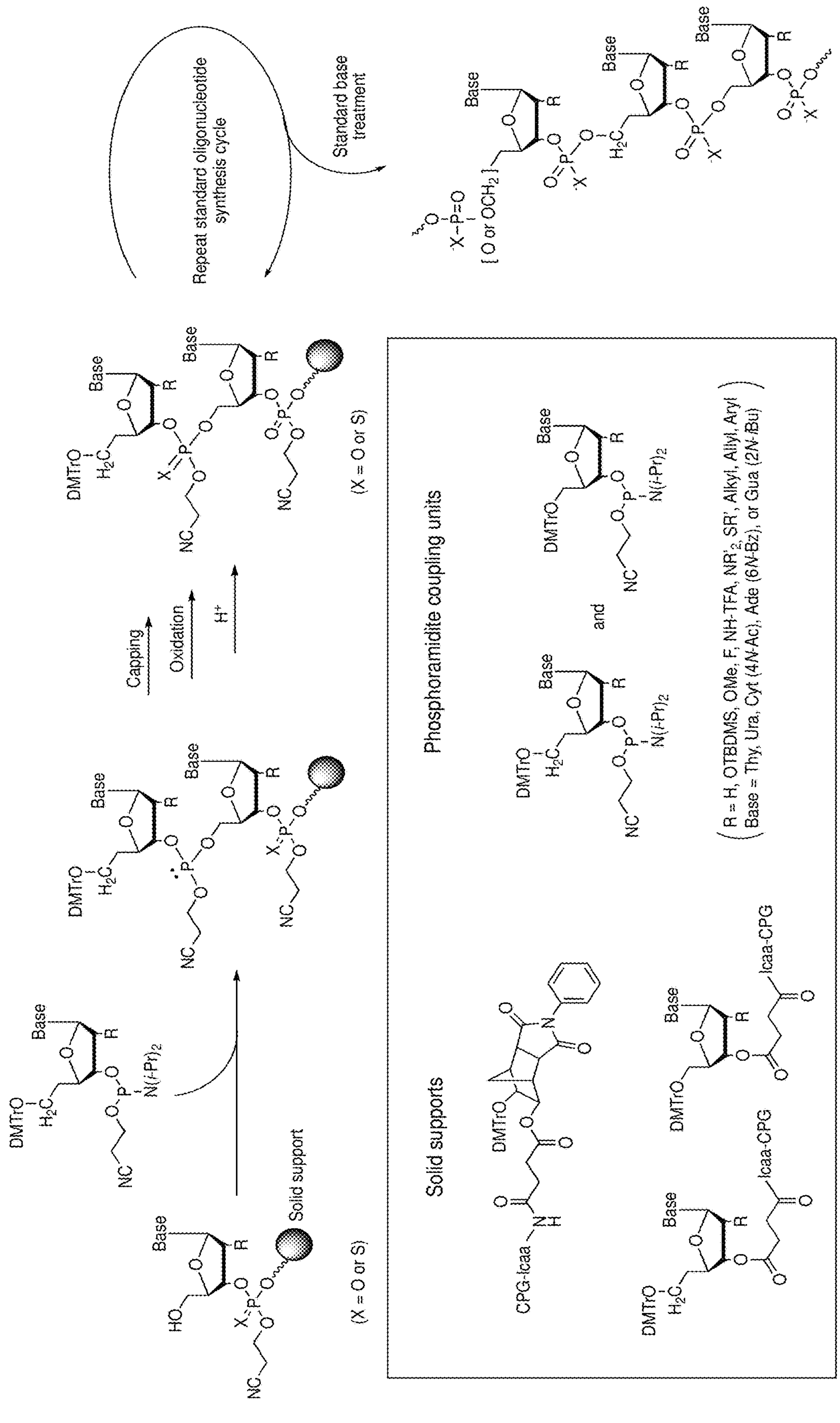
FIG. 12 provides synthesis for oligonucleotides incorporating exNA backbones.

According to FIG. 12, a method for synthesizing a modified oligonucleotide comprising a 5' end, a 3' end and at least one modified intersubunit linkage has been done. The method includes (a) providing a nucleoside having a 5'-protecting group linked to a solid support; (b) removal of the protecting group; (c) combining the deprotected nucleoside with a phosphoramidite derivative of Formula (VII) to form a phosphite triester;

(VII)

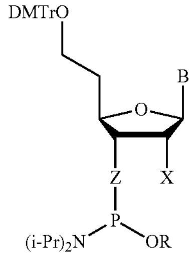

(d) capping the phosphite triester; (e) oxidizing the phosphite triester; (f) repeating steps (b) through (e) using an additional phosphoramidite; and (g) cleaving from the solid support.

Examples of some oligonucleotides synthesized by the above method with one or more exNA-intersubunit linkages is shown in FIG. 13. The exNA-intersubunit linkages are 5'-methylene-exNA-uridine with 2'-OH.

Example 11. In vitro Silencing Efficacy of Target mRNA with siRNA Duplexes Containing exNA Intersubunit Linkages An ex-NA intersubunit linkages was used in an oligonucleotide walk experiment, where each intersubunit linkage in an antisense and sense strand was modified with the ex-NA intersubunit linkage. The ex-NA intersubunit linkage was either (ex_mU): 5'-methylene-exNA-uridine with 2'-OMe or (ex_fU): 5'-methylene-exNA-uridine with 2'-fluoro-ex-uridine. Tables 4-10 below show the antisense and sense strands used in this Example, as well as duplexes formed by different combinations of said antisense and sense strands. A novel synthesis scheme for generating ex-NA containing oligonucleotides was also employed as shown in FIG. 12.

TABLE 4

Antisense strand having ex-NA intersubunit linkages

| Name | Sequence (5' –> 3')[a] |
|---|---|
| ex-1 | 5'- P(ex_mU)#(fU)#(mA)(fA)(mU)(fC)(mU)(fC)(mU)(fU)(mU)(fA)(mC)#(fU)#(mG)#(fA)#(mU)#(fA)#(mU)#(fA) (SEQ ID NO: 1) |
| ex-2 | 5'-P(mU)#(ex_fU)#(mA)(fA)(mU)(fC)(mU)(fC)(mU)(fU)(mU)(fA)(mC)#(fU)#(mG)#(fA)#(mU)#(fA)#(mU)#(fA) (SEQ ID NO: 2) |
| ex-3 | 5'-P(mU)#(fU)#(ex_mU)(fU)(mU)(fA)(mA)(fA)(mU)(fC)(mC)(fU)(mG)#(fA)#(mG)#(fA)#(mA)#(fG)#(mA)#(fA) (SEQ ID NO: 3) |
| ex-4 | 5'-P(mU)#(fU)#(mU)(ex_fU)(mU)(fA)(mA)(fA)(mU)(fC)(mC)(fU)(mG)#(fA)#(mG)#(fA)#(mA)#(fG)#(mA)#(fA) (SEQ ID NO: 4) |
| ex-5 | 5'-P(mU)#(fU)#(mA)(fA)(ex_mU)(fC)(mU)(fC)(mU)(fU)(mU)(fA)(mC)#(fU)#(mG)#(fA)#(mU)#(fA)#(mU)#(fA) (SEQ ID NO: 5) |
| ex-6 | 5'-P(mU)#(fC)#(mC)(fA)(mC)(ex_fU)(mA)(fU)(mG)(fU)(mU)(fU)(mU)#(fC)#(mA)#(fC)#(mA)#(fU)#(mA)#(fU) (SEQ ID NO: 6) |
| ex-7 | 5'-P(mU)#(fU)#(mA)(fA)(mU)(fC)(ex_mU)(fC)(mU)(fU)(mU)(fA)(mC)#(fU)#(mG)#(fA)#(mU)#(fA)#(mU)#(fA) (SEQ ID NO: 7) |
| ex-8 | 5'-P(mU)#(fC)#(mC)(fA)(mC)(fU)(mA)(ex_fU)(mG)(fU)(mU)(fU)(mU)#(fC)#(mA)#(fC)#(mA)#(fU)#(mA)#(fU) (SEQ ID NO: 8) |
| ex-9 | 5'-P(mU)#(fU)#(mA)(fA)(mU)(fC)(mU)(fC)(ex_mU)(fU)(mU)(fA)(mC)#(fU)#(mG)#(fA)#(mU)#(fA)#(mU)#(fA) (SEQ ID NO: 9) |
| ex-10 | 5'-P(mU)#(fU)#(mA)(fA)(mU)(fC)(mU)(fC)(mU)(ex_fU)(mU)(fA)(mC)#(fU)#(mG)#(fA)#(mU)#(fA)#(mU)#(fA) (SEQ ID NO: 10) |
| ex-11 | 5'-P(mU)#(fU)#(mA)(fA)(mU)(fC)(mU)(fC)(mU)(fU)(ex_mU)(fA)(mC)#(fU)#(mG)#(fA)#(mU)#(fA)#(mU)#(fA) (SEQ ID NO: 11) |
| ex-12 | 5'-P(mU)#(fC)#(mC)(fA)(mC)(fU)(mA)(fU)(mG)(fU)(mU)(ex_fU)(mU)#(fC)#(mA)#(fC)#(mA)#(fU)#(mA)#(fU) (SEQ ID NO: 12) |
| ex-13 | 5'-P(mU)#(fC)#(mC)(fA)(mC)(fU)(mA)(fU)(mG)(fU)(mU)(fU)(ex_mU)#(fC)#(mA)#(fC)#(mA)#(fU)#(mA)#(fU) (SEQ ID NO: 13) |
| ex-14 | 5'-P(mU)#(fU)#(mA)(fA)(mU)(fC)(mU)(fC)(mU)(fU)(mU)(fA)(mC)#(ex_fU)#(mG)#(fA)#(mU)#(fA)#(mU)#(fA) (SEQ ID NO: 14) |
| ex-15 | 5'-P(mU)#(fG)#(mC)(fC)(mU)(fA)(mA)(fG)(mA)(fG)(mC)(fA)(mC)#(fA)#(ex_mU)#(fU)#(mU)#(fA)#(mG)#(fU) (SEQ ID NO: 15) |
| ex-16 | 5'-P(mU)#(fG)#(mC)(fC)(mU)(fA)(mA)(fG)(mA)(fG)(mC)(fA)(mC)#(fA)#(mU)#(ex_fU)#(mU)#(fA)#(mG)#(fU) (SEQ ID NO: 16) |
| ex-17 | 5'-P(mU)#(fU)#(mA)(fA)(mU)(fC)(mU)(fC)(mU)(fU)(mU)(fA)(mC)#(fU)#(mG)#(fA)#(ex_mU)#(fA)#(mU)#(fA) (SEQ ID NO: 17) |
| ex-18 | 5'-P(mU)#(fC)#(mC)(fA)(mC)(fU)(mA)(fU)(mG)(fU)(mU)(fU)(mU)#(fC)#(mA)#(fC)#(mA)#(ex_fU)#(mA)#(fU) (SEQ ID NO: 18) |
| ex-19 | 5'-P(mU)#(fU)#(mA)(fA)(mU)(fC)(mU)(fC)(mU)(fU)(mU)(fA)(mC)#(fU)#(mG)#(fA)#(mU)#(fA)#(ex_mU)#(fA) (SEQ ID NO: 19) |
| ex-20 | 5'-P(mU)#(fC)#(mC)(fA)(mC)(fU)(mA)(fU)(mG)(fU)(mU)(fU)(mU)#(fC)#(mA)#(fC)#(mA)#(fU)#(mA)#(ex_fU) (SEQ ID NO: 20) |
| ex-21 | 5'-P(mU)#(fU)#(mA)(fA)(mU)(fC)(mU)(fC)(mU)(fU)(mU)(fA)(mC)#(fU)#(mG)#(fA)#(mU)#(fU)#(mU)#(ex_fU) (SEQ ID NO: 21) |
| ex-22 | 5'-P(mU)#(fU)#(mA)(fA)(mU)(fC)(mU)(fC)(mU)(fU)(mU)(fA)(mC)#(fU)#(mG)#(fA)#(mU)#(fU)#(ex_mU)#(ex_fU) (SEQ ID NO: 22) |
| ex-23 | 5'-P(mU)#(fU)#(mA)(fA)(mU)(fC)(mU)(fC)(mU)(fU)(mU)(fA)(mC)#(fU)#(mG)#(fA)#(mU)#(ex_fU)#(ex_mU)#(ex_fU) (SEQ ID NO: 23) |
| ex-24 | 5'-P(mU)#(fU)#(mA)(fA)(mU)(fC)(mU)(fC)(mU)(fU)(mU)(fA)(mC)#(fU)#(mG)#(fA)#(ex_mU)#(ex_fU)#(ex_mU)#(ex_fU) (SEQ ID NO: 24) |

[a](mN): 2'-OMe, (fN): 2'-Fluoro, (ex_mU): 5'-methylene-exNA-uridine with 2'-OMe: (ex_fU): 5'-methylene-exNA-uridine with 2'-fluoro-ex-uridine, P: Phosphate, #: Phosphorothioate

TABLE 5

| Sense strands having ex-NA intersubunit linkages | |
|---|---|
| Name | Sequence (5' –> 3')[a] |
| ex-SS-1 | 5'-(ex_fU)#(mG)#(fA)(mA)(fA)(mA)(fC)(mA)(fU)(mA)(fG)(mU)(fG)#(mG)#(fA)-TegChol (SEQ ID NO: 25) |
| ex-SS-2 | 5'-(fC)#(ex_mU)#(fC)(mA)(fG)(mG)(fA)(mU)(fU)(mU)(fA)(mA)(fA)#(mA)#(fA)-TegChol (SEQ ID NO: 26) |
| ex-SS-3 | 5'-(fA)#(mA)#(ex_fU)(mG)(fU)(mU)(fG)(mU)(fG)(mA)(fC)(mC)(fG)#(mG)#(fA)-TegChol (SEQ ID NO: 27) |
| ex-SS-4 | 5'-(fC)#(mA)#(fG)(ex_mU)(fA)(mA)(fA)(mG)(fA)(mG)(fA)(mU)(fU)#(mA)#(fA)-TegChol (SEQ ID NO: 28) |
| ex-SS-5 | 5'-(fA)#(mA)#(fU)(mG)(ex_fU)(mU)(fG)(mU)(fG)(mA)(fC)(mC)(fG)#(mG)#(fA)-TegChol (SEQ ID NO: 29) |
| ex-SS-6 | 5'-(fA)#(mA)#(fU)(mG)(fU)(ex_mU)(fG)(mU)(fG)(mA)(fC)(mC)(fG)#(mG)#(fA)-TegChol (SEQ ID NO: 30) |
| ex-SS-7 | 5'-(fA)#(mU)#(fG)(mU)(fG)(mC)(ex_fU)(mC)(fU)(mU)(fA)(mG)(fG)#(mC)#(fA)-TegChol (SEQ ID NO: 31) |
| ex-SS-8 | 5'-(fC)#(mU)#(fC)(mA)(fG)(mG)(fA)(ex_mU)(fU)(mU)(fA)(mA)(fA)#(mA)#(fA)-TegChol (SEQ ID NO: 32) |
| ex-SS-9 | 5'-(fC)#(mU)#(fC)(mA)(fG)(mG)(fA)(mU)(ex_fU)(mU)(fA)(mA)(fA)#(mA)#(fA)-TegChol (SEQ ID NO: 33) |
| ex-SS-10 | 5'-(fC)#(mU)#(fC)(mA)(fG)(mG)(fA)(mU)(fU)(ex_mU)(fA)(mA)(fA)#(mA)#(fA)-TegChol (SEQ ID NO: 34) |
| ex-SS-11 | 5'-(fC)#(mU)#(fG)(mG)(fA)(mA)(fA)(mA)(fG)(mC)(ex_fU)(mG)(fA)#(mU)#(fA)-TegChol (SEQ ID NO: 35) |
| ex-SS-12 | 5'-(fC)#(mA)#(fG)(mU)(fA)(mA)(fA)(mG)(fA)(mG)(fA)(ex_mU)(fU)#(mA)#(fA)-TegChol (SEQ ID NO: 36) |
| ex-SS-13 | 5'-(fC)#(mA)#(fG)(mU)(fA)(mA)(fA)(mG)(fA)(mG)(fA)(mU)(ex_fU)#(mA)#(fA)-TegChol (SEQ ID NO: 37) |
| ex-SS-14 | 5'-(fC)#(mU)#(fG)(mG)(fA)(mA)(fA)(mA)(fG)(mC)(fU)(mG)(fA)#(ex_mU)#(fA)-TegChol (SEQ ID NO: 38) |
| ex-SS-15 | 5'-(fC)#(mA)#(fG)(mU)(fA)(mA)(fA)(mG)(fA)(mG)(fA)(mU)(fU)#(mA)#(ex_fU)-TegChol (SEQ ID NO: 39) |

[a](mN): 2'-OMe, (fN): 2'-Fluoro, (ex_mU): 2'-OMe-ex-uridine, (ex_fU): 2'-fluoro-ex-uridine, P: Phosphate, #: Phosphorothioate, TegChol: Tetraethyleneglycol-linked cholesterol

TABLE 6

| Control antisense strands | |
|---|---|
| Name | Sequence (5' –> 3')[a] |
| AS-0 | 5'-P(mU)(fU)(mA)(fA)(mU)(fC)(mU)(fC)(mU)(fU)(mU)(fA)(mC)(fU)(mG)(fA)(mU)(fU)(mU)(fU) (SEQ ID NO: 40) |
| AS-1 | 5'-P(mU)#(fU)#(mA)(fA)(mU)(fC)(mU)(fC)(mU)(fU)(mU)(fA)(mC)#(fU)#(mG)#(fA)#(mU)#(fA)#(mU)#(fA) (SEQ ID NO: 41) |
| AS-2 | 5'-P(mU)#(fU)#(mA)(fA)(mU)(fC)(mU)(fC)(mU)(fU)(mU)(fA)(mC)#(fU)#(mG)#(fA)#(mU)#(fU)#(mU)#(fU) (SEQ ID NO: 42) |
| AS-3 | 5'-P(mU)#(fU)#(mU)(fU)(mU)(fA)(mA)(fA)(mU)(fC)(mC)(fU)(mG)#(fA)#(mG)#(fA)#(mA)#(fG)#(mA)#(fA) (SEQ ID NO: 43) |
| AS-4 | 5'-P(mU)#(fC)#(mC)(fA)(mC)(fU)(mA)(fU)(mG)(fU)(mU)(fU)(mU)#(fC)#(mA)#(fC)#(mA)#(fU)#(mA)#(fU) (SEQ ID NO: 44) |
| AS-5 | 5'-P(mU)#(fG)#(mC)(fC)(mU)(fA)(mA)(fG)(mA)(fG)(mC)(fA)(mC)#(fA)#(mU)#(fU)#(mU)#(fA)#(mG)#(fU) (SEQ ID NO: 45) |
| AS-6 | 5'-P(mU)#(fA)#(mU)(fC)(mA)(fG)(mC)(fU)(mU)(fU)(mU)(fC)(mC)#(fA)#(mG)#(fG)#(mG)#(fU)#(mC)#(fG) (SEQ ID NO: 46) |
| AS-7 | 5'-P(mU)#(fC)#(mC)(fG)(mG)(fU)(mC)(fA)(mC)(fA)(mA)(fC)(mA)#(fU)#(mU)#(fG)#(mU)#(fG)#(mG)#(fU) (SEQ ID NO: 47) |
| AS-8 | 5'-P(mA)#(fU)#(mA)(fA)(mU)(fC)(mU)(fC)(mU)(fU)(mU)(fA)(mC)#(fU)#(mG)#(fA)#(mU)#(fA)#(mU)#(fA) (SEQ ID NO: 48) |

[a](mN): 2' -OMe, (fN): 2'-Fluoro, P: Phosphate, #: Phosphorothioate

TABLE 7

| Control sense strands | |
|---|---|
| Name | Sequence (5' –> 3')[a] |
| SS-1 | 5'-(fC)#(mA)#(fG)(mU)(fA)(mA)(fA)(mG)(fA)(mG)(fA)(mU)(fU)#(mA)#(fA)-TegChol (SEQ ID NO: 49) |
| SS-2 | 5'-(fC)#(mU)#(fC)(mA)(fG)(mG)(fA)(mU)(fU)(mU)(fA)(mA)(fA)#(mA)#(fA)-TegChol (SEQ ID NO: 50) |
| SS-3 | 5'-(fU)#(mG)#(fA)(mA)(fA)(mA)(fC)(mA)(fU)(mA)(fG)(mU)(fG)#(mG)#(fA)-TegChol (SEQ ID NO: 51) |
| SS-4 | 5'-(fA)#(mU)#(fG)(mU)(fG)(mC)(fU)(mC)(fU)(mU)(fA)(mG)(fG)#(mC)#(fA)-TegChol (SEQ ID NO: 52) |

TABLE 7-continued

| Control sense strands | |
|---|---|
| Name | Sequence (5' -> 3')[a] |
| SS-5 | 5'-(fC)#(mU)#(fG)(mG)(fA)(mA)(fA)(mA)(fG)(mC)(fU)(mG)(fA)#(mU)#(fA)-TegChol (SEQ ID NO: 53) |
| SS-6 | 5'-(fA)#(mA)#(fU)(mG)(fU)(mU)(fG)(mU)(fG)(mA)(fC)(mC)(fG)#(mG)#(fA)-TegChol (SEQ ID NO: 54) |
| SS-7 | 5'-(fC)#(mA)#(fG)(mU)(fA)(mA)(fA)(mG)(fA)(mG)(fA)(mU)(fU)#(mA)#(fU)-TegChol (SEQ ID NO: 55) |

[a](mM): 2'-OMe, (fN): 2'-Fluoro, #: Phosphorothioate, TegChol: Tetraethyleneglycol-linked cholesterol

TABLE 8

| siRNA duplexes (D1-D20) having ex-NA modified antisense strands | | | | |
|---|---|---|---|---|
| | Duplex # | exNA modified Antisense strand | Sense strand | Corresponding control duplex # (See Group 3) |
| Group 1 exNA walk on Antisense strand | D1 | ex-1 | SS-1 | D40 |
| | D2 | ex-2 | SS-1 | D40 |
| | D3 | ex-3 | SS-2 | D42 |
| | D4 | ex-4 | SS-2 | D42 |
| | D5 | ex-5 | SS-1 | D40 |
| | D6 | ex-6 | SS-3 | D43 |
| | D7 | ex-7 | SS-1 | D40 |
| | D8 | ex-8 | SS-3 | D43 |
| | D9 | ex-9 | SS-1 | D40 |
| | D10 | ex-10 | SS-1 | D40 |
| | D11 | ex-11 | SS-1 | D40 |
| | D12 | ex-12 | SS-3 | D43 |
| | D13 | ex-13 | SS-3 | D43 |
| | D14 | ex-14 | SS-1 | D40 |
| | D15 | ex-15 | SS-4 | D44 |
| | D16 | ex-16 | SS-4 | D44 |
| | D17 | ex-17 | SS-1 | D40 |
| | D18 | ex-18 | SS-3 | D43 |
| | D19 | ex-19 | SS-1 | D40 |
| | D20 | ex-20 | SS-3 | D43 |
| | D21 | ex-21 | SS-1 | D41 |
| | D22 | ex-22 | SS-1 | D41 |
| | D23 | ex-23 | SS-1 | D41 |
| | D24 | ex-24 | SS-1 | D41 |

TABLE 9

| siRNA duplexes (D25-D39) having ex-NA modified sense strands | | | | |
|---|---|---|---|---|
| | Duplex # | Antisense strand | exNA modified Sense strand | Corresponding control duplex # (See Group 3) |
| Group 2 exNA walk on Antisense | D25 | AS-3 | ex-SS-1 | D43 |
| | D26 | AS-2 | ex-SS-2 | D42 |
| | D27 | AS-6 | ex-SS-3 | D46 |
| | D28 | AS-1 | ex-SS-4 | D40 |
| | D29 | AS-6 | ex-SS-5 | D46 |
| | D30 | AS-6 | ex-SS-6 | D46 |
| | D31 | AS-4 | ex-SS-7 | D44 |
| | D32 | AS-2 | ex-SS-8 | D42 |
| | D33 | AS-2 | ex-SS-9 | D42 |
| | D34 | AS-2 | ex-SS-10 | D42 |
| | D35 | AS-5 | ex-SS-11 | D45 |

TABLE 9-continued

| siRNA duplexes (D25-D39) having ex-NA modified sense strands | | | |
|---|---|---|---|
| Duplex # | Antisense strand | exNA modified Sense strand | Corresponding control duplex # (See Group 3) |
| D36 | AS-1 | ex-SS-12 | D40 |
| D37 | AS-1 | ex-SS-13 | D40 |
| D38 | AS-5 | ex-SS-14 | D45 |
| D39 | AS-7 | ex-SS-15 | D47 |

TABLE 10

| Control siRNA duplexes | | | | |
|---|---|---|---|---|
| | Duplex # | Antisense strand | Sense strand | Corresponding exNA-duplexes |
| Group 3 exNA walk on Antisense | D40 | AS-1 | SS-1 | D1, D2, D5, D7, D9, D10, D11, D14, D17, D19, D28, D36, D37 |
| | D42 | AS-3 | SS-2 | D3, D4, D26, D32, D33, D34 |
| | D43 | AS-4 | SS-3 | D6, D8, D12, D13, D18, D20, D25 |
| | D44 | AS-5 | SS-4 | D15, D16, D31 |
| | D45 | AS-6 | SS-5 | D35, D38 |
| | D46 | AS-7 | SS-6 | D27, D29, D30 |
| | D47 | AS-8 | SS-7 | D39 |

The siRNA duplexes recited above were used in in vitro mRNA silencing experiments to determine relative silencing efficacy. Experimental details are described below.

In vitro screen.

1.5 μM siRNAs were passively delivered to cells. Cells were plated in Dulbecco's Modified Eagle's Medium containing 6% FBS at 8,000 cells per well in 96-well cell culture plates. siRNAs were diluted to twice the final concentration in OptiMEM (Carlsbad, CA; 31985-088), and 50 μL diluted siRNAs were added to 50 μL of cells, resulting in 3% FBS final. Cells were incubated for 72 hours at 37° C. and 5% $CO_2$.

Quantitative Analysis of Target mRNA.

mRNA was quantified from cells using the QuantiGene 2.0 assay kit (Affymetrix, QS0011). Cells were lysed in 250 μL diluted lysis mixture composed of one part lysis mixture (Affymetrix, 13228), two parts $H_2O$ and 0.167 μg/μL proteinase K (Affymetrix, QS0103) for 30 min at 55° C. Cell lysates were mixed thoroughly, and 40 μL of each lysate was added per well of a capture plate with 40 μL diluted lysis mixture without proteinase K and 20 μL diluted probe set. Probe sets for human HTT and Hypoxanthine Phosphoribosyltransferase (HPRT) (Affymetrix; #SA-50339, SA-10030) were diluted and used according to the manufacturer's recommended protocol. Datasets were normalized to HPRT Cell Treatment: Reporter Assay.

HeLa cells were grown and maintained in Gibco DMEM (ref. #11965-092) with 1% pen/strep and 10% heat inactivated FBS. Three days prior to treatment, two 10 $cm^2$ dishes were plated with $2\times10^6$ HeLa cells. The following day, DMEM was replaced with Gibco OptiMEM (ref. #31985-070) and 6 μg of reporter plasmid was added to cells using Invitrogen Lipofectamine 3000 (ref. #L3000-015), following the manufacturer's protocol. Cells were left in OptiMEM/lipofectamine overnight to allow for maximum reporter plasmid transfection. The following day, siRNA was diluted in Opti-MEM and added to 96-well white wall clear bottom tissue culture plate, in triplicate, for each reporter plasmid. HeLa cells transfected with reporter plasmids the night prior were resuspended in DMEM with 6% heat inactivated FBS (no pen/strep) at $0.15\times10^6$ cells/mL and added to plate containing siRNA.

Cells were lysed after 72 hours of treatment (100% confluency) with 1× Passive Lysis Buffer from Dual-Luciferase Assay System Pack (Promega ref. #E1960). Following lysis, luminescence was read after addition of 50 μl Luciferase Assay Reagent II (Promega ref. #E1960), then read a second time after addition of 50 μL/well of Stop and Glow reagent (Promega ref. #E1960). Absorbances were normalized to untreated controls and graphed on a log scale.

Figure 14:
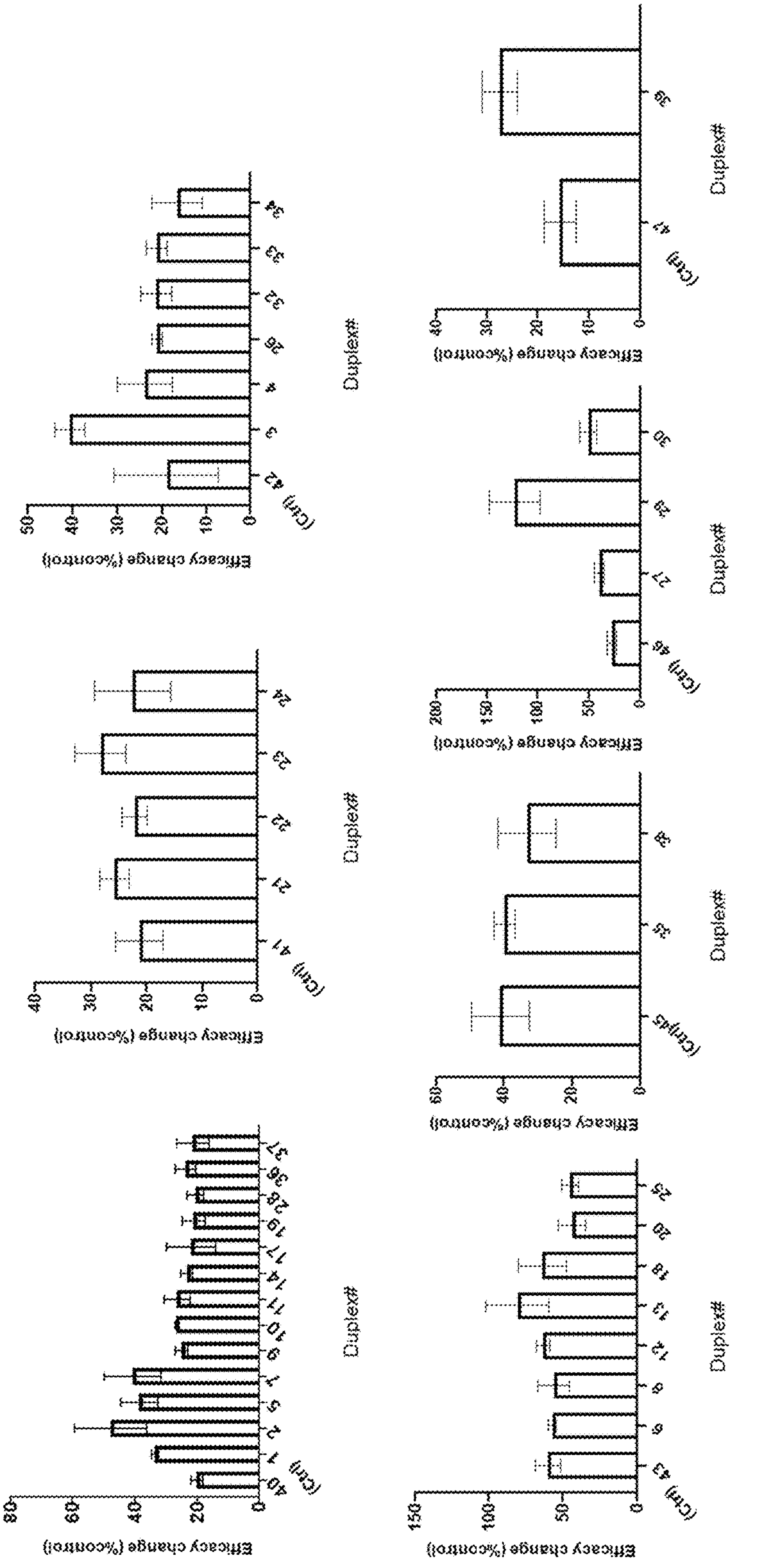
FIG. 14 provides results of in vitro silencing efficacy of target mRNA with siRNA duplexes containing exNA with intersubunit linkages at various positions.

As shown in FIG. 14, all tested siRNA duplexes effectively silenced the target HTT mRNA. Moreover, numerous siRNA duplexes silenced the target mRNA as well as the control duplex siRNA.

Figure 15:
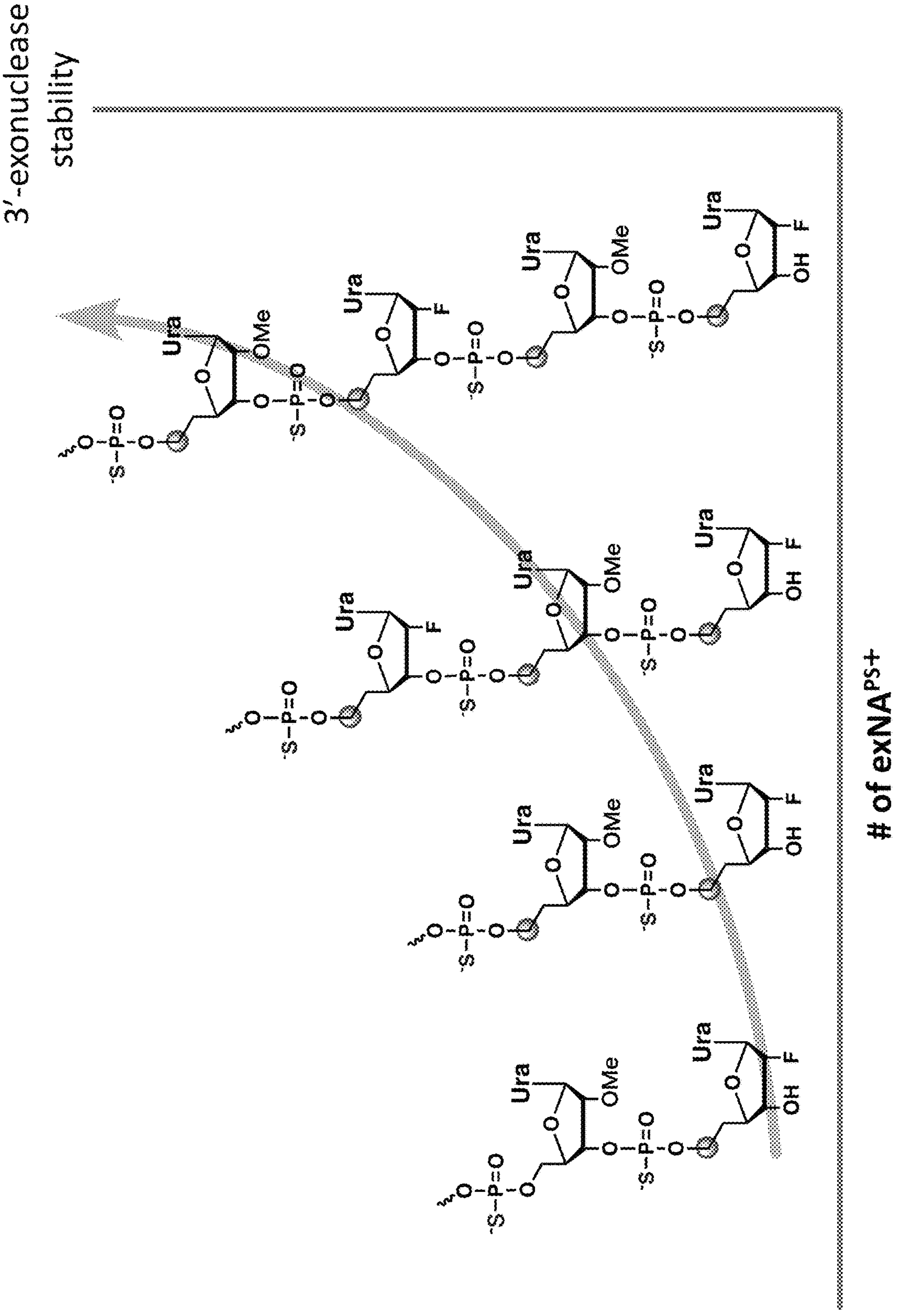
FIG. 15 provides a model depicting an increase in 3' exonuclease stability for oligonucleotides with increasing numbers of exNA and phosphorothioate intersubunit linkages.

Example 12. Nuclease Stability of siRNA Duplexes Containing exNA Intersubunit Linkages It was hypothesized that the ex-NA intersubunit linkage would be useful for increasing the nuclease stability of oligonucleotides. This effect may be observed with ex-NA intersubunit linkages alone or in combination with phosphorothioate intersubunit linkages. Moreover, multiple consecutive ex-NA intersubunit linkages in an oligonucleotide may have a greater impact on stability than a single ex-NA intersubunit linkage. There are two primary ways stability may be increased, 1) the aberrant local backbone structure of ex-NA lowers kinetics of nuclease cleavage, and 2) multiply extended backbones lower binding affinity of nucleases (poly-extension impact on whole structure of 3'-terminal region) (FIG. 15). To demonstrate this effect, several nuclease assays where employed with oligonucleotides containing one or more ex-NA intersubunit linkages.

3' Exonuclease Stability Test.

Figure 16:
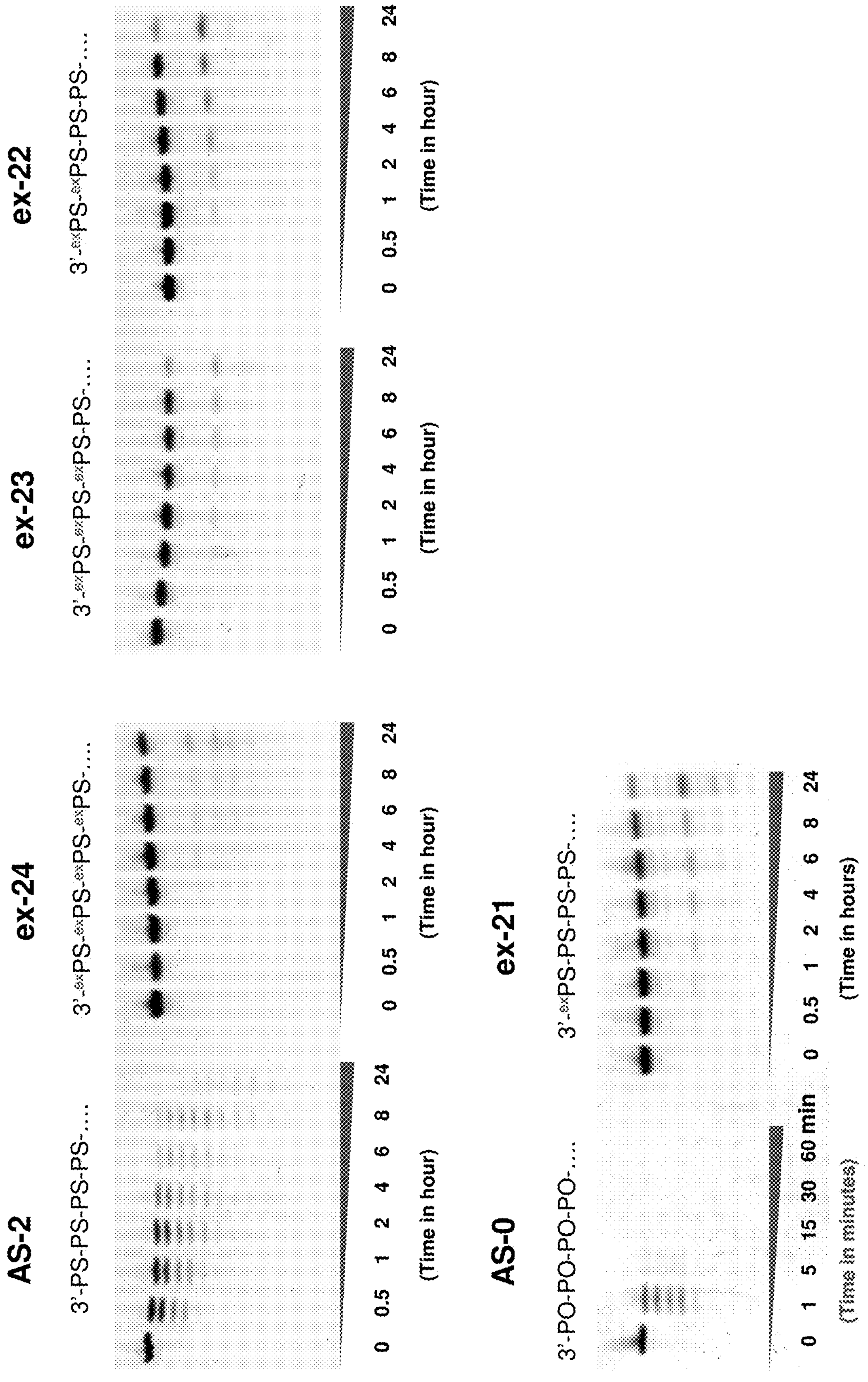
FIG. 16 provides results from a 3'-exonuclease stability test. Each oligonucleotide (17.5 mM) was incubated in a buffer containing 10 mM Tris-HCl (pH 8.0), 2 mM $MgCl_2$, and Snake Venom Phosphodiesterase I (20 mU/mL) at 37° C.

Oligonucleotides with a varying number of ex-NA intersubunit linkages at the 3' end were tested in a 3' exonuclease stability test. Oligonucleotides ex-21, ex-22, ex-23, ex-24, AS-0, and AS-2 (as recited above in Table 4 and Table 6) at a concentration of 17.5 mM were incubated in a buffer containing 10 mM Tris-HCl (pH 8.0), 2 mM $MgCl_2$, and Snake Venom Phosphodiesterase I (20 mU/mL) at 37° C. As shown in FIG. 16, multiple ex-NA intersubunit linkages with phosphorothioate intersubunit linkages (ex-24) drastically improved 3'-exonuclease stability compared to AS-2, which has the same phosphorothioate content found in clinically approved siRNA drugs. Moreover, even a single ex-NA intersubunit linkage at the 3' end dramatically improved stability (ex-21). As 3'-exonucleases are dominant in the serum, the 3' ex-NA intersubunit linkages are useful in therapeutic oligonucleotides.

Figure 17:
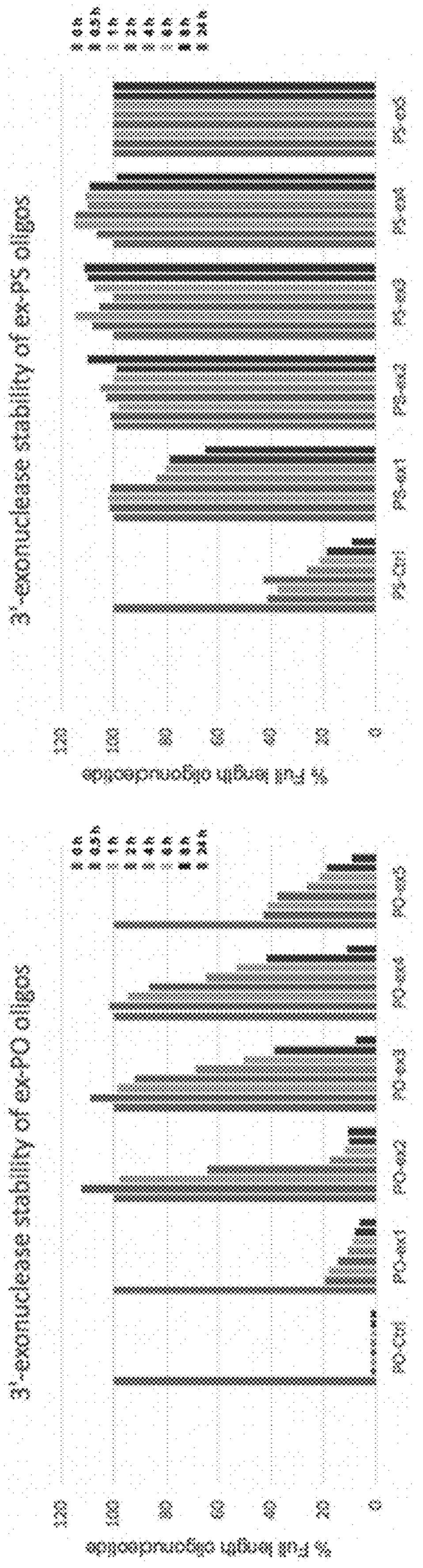
FIG. 17 provides results from a 3'-exonuclease stability test of ex-NA intersubunit linkages in a context of poly-uridyl sequence with phosphodiester (PO) and phosphorothioate (PS) containing oligonucleotides. Oligonucleotides were tested with 1, 2, 3, 4, or 5 ex-NA intersubunit linkages.

An additional 3' exonuclease test was performed with ex-NA intersubunit linkages in a context of poly-uridyl sequence with phosphodiester (PO) and phosphorothioate (PS) containing oligonucleotides. Oligonucleotides were tested with 1, 2, 3, 4, or 5 ex-NA intersubunit linkages. Table 11 below recites the polynucleotides used in this test. As shown in FIG. 17, the presence of even a single ex-NA intersubunit linkage dramatically improved oligonucleotide stability. This was demonstrated in both the PO and PS oligonucleotides. Moreover, the PO-containing oligonucleotide with 5 ex-NA intersubunit linkages achieved similar nuclease stability compared the PS-containing oligonucleotide with no ex-NA intersubunit linkages (PS control). This result indicates that the number of PS-containing intersubunit linkages may be reduced if using ex-NA intersubunit linkages, thereby reducing toxicity associated with PS-containing oligonucleotides.

TABLE 11

Poly-uridyl oligonucleotides for the 3'-exonuclease stability test

| Name | Sequence (5' -> 3') [a] |
|---|---|
| FAM-Ctrl-PO | 5'-FAM-(mU)(mU)(mU)(mU)(mU)(mU)(mU)(mU)(mU)(mU)(mU)(mU)(mU)(mU)(mU)(mU)(mU)(mU)(mU)(mU) (SEQ ID NO: 56) |
| FAM-PO-ex1 | 5'-FAM-(mU)(mU)(mU)(mU)(mU)(mU)(mU)(mU)(mU)(mU)(mU)(mU)(mU)(mU)(mU)(mU)(mU)(mU)(mU)(ex-mU) (SEQ ID NO: 57) |
| FAM-PO-ex2 | 5'-FAM-(mU)(mU)(mU)(mU)(mU)(mU)(mU)(mU)(mU)(mU)(mU)(mU)(mU)(mU)(mU)(mU)(mU)(mU)(ex-mU)(ex-mU) (SEQ ID NO: 58) |
| FAM-PO-ex3 | 5'-FAM-(mU)(mU)(mU)(mU)(mU)(mU)(mU)(mU)(mU)(mU)(mU)(mU)(mU)(mU)(mU)(mU)(mU)(ex-mU)(ex-mU)(ex-mU) (SEQ ID NO: 59) |
| FAM-PO-ex4 | 5'-FAM-(mU)(mU)(mU)(mU)(mU)(mU)(mU)(mU)(mU)(mU)(mU)(mU)(mU)(mU)(mU)(mU)(ex-mU)(ex-mU)(ex-mU)(ex-mU) (SEQ ID NO: 60) |
| FAM-PO-ex5 | 5'-FAM-(mU)(mU)(mU)(mU)(mU)(mU)(mU)(mU)(mU)(mU)(mU)(mU)(mU)(mU)(mU)(ex-mU)(ex-mU)(ex-mU)(ex-mU)(ex-mU) (SEQ ID NO: 61) |
| FAM-Ctrl-PS | 5'-FAM-(mU)(mU)(mU)(mU)(mU)(mU)(mU)(mU)(mU)(mU)(mU)(mU)(mU)(mU)(mU)#(mU)#(mU)#(mU)#(mU)#(mU) (SEQ ID NO: 62) |
| FAM-PS-ex1 | 5'-FAM-(mU)(mU)(mU)(mU)(mU)(mU)(mU)(mU)(mU)(mU)(mU)(mU)(mU)(mU)(mU)#(mU)#(mU)#(mU)#(mU)#(ex-mU) (SEQ ID NO: 63) |
| FAM-PS-ex2 | 5'-FAM-(mU)(mU)(mU)(mU)(mU)(mU)(mU)(mU)(mU)(mU)(mU)(mU)(mU)(mU)(mU)#(mU)#(mU)#(mU)#(ex-mU)#(ex-mU) (SEQ ID NO: 64) |

TABLE 11-continued

| Poly-uridyl oligonucleotides for the 3'-exonuclease stability test | |
|---|---|
| Name | Sequence (5' -> 3') [a] |
| FAM-PS-ex3 | 5'-FAM-(mU)(mU)(mU)(mU)(mU)(mU)(mU)(mU)(mU)(mU)(mU)(mU)(mU)(mU)(mU)#(mU)#(mU)#(ex-mU)#(ex-mU)#(ex-mU) (SEQ ID NO: 65) |
| FAM-PS-ex4 | 5'-FAM-(mU)(mU)(mU)(mU)(mU)(mU)(mU)(mU)(mU)(mU)(mU)(mU)(mU)(mU)(mU)#(mU)#(ex-mU)#(ex-mU)#(ex-mU) #(ex-mU) (SEQ ID NO: 66) |
| FAM-PS-ex5 | 5'-FAM-(mU)(mU)(mU)(mU)(mU)(mU)(mU)(mU)(mU)(mU)(mU)(mU)(mU)(mU)(mU)#(ex-mU)#(ex-mU)#(ex-mU)#(ex-mU) #(ex-mU) (SEQ ID NO: 67) |

[a] (mU): 2'-OMe-uridine, (ex-mU): 2'-OMe-ex-uridine, #: Phosphorothioate, FAM: 6-FAM fluorescein-label The fluorescein-label, "FAM" used on the oligonucleotides has no impact on 3' exonuclease activity and was used to monitor cleavage in the stability test.

5' Exonuclease Stability Test.

Oligonucleotides with an ex-NA intersubunit linkage at the 5' end were tested in two different 5' exonuclease stability tests.

Figure 18:
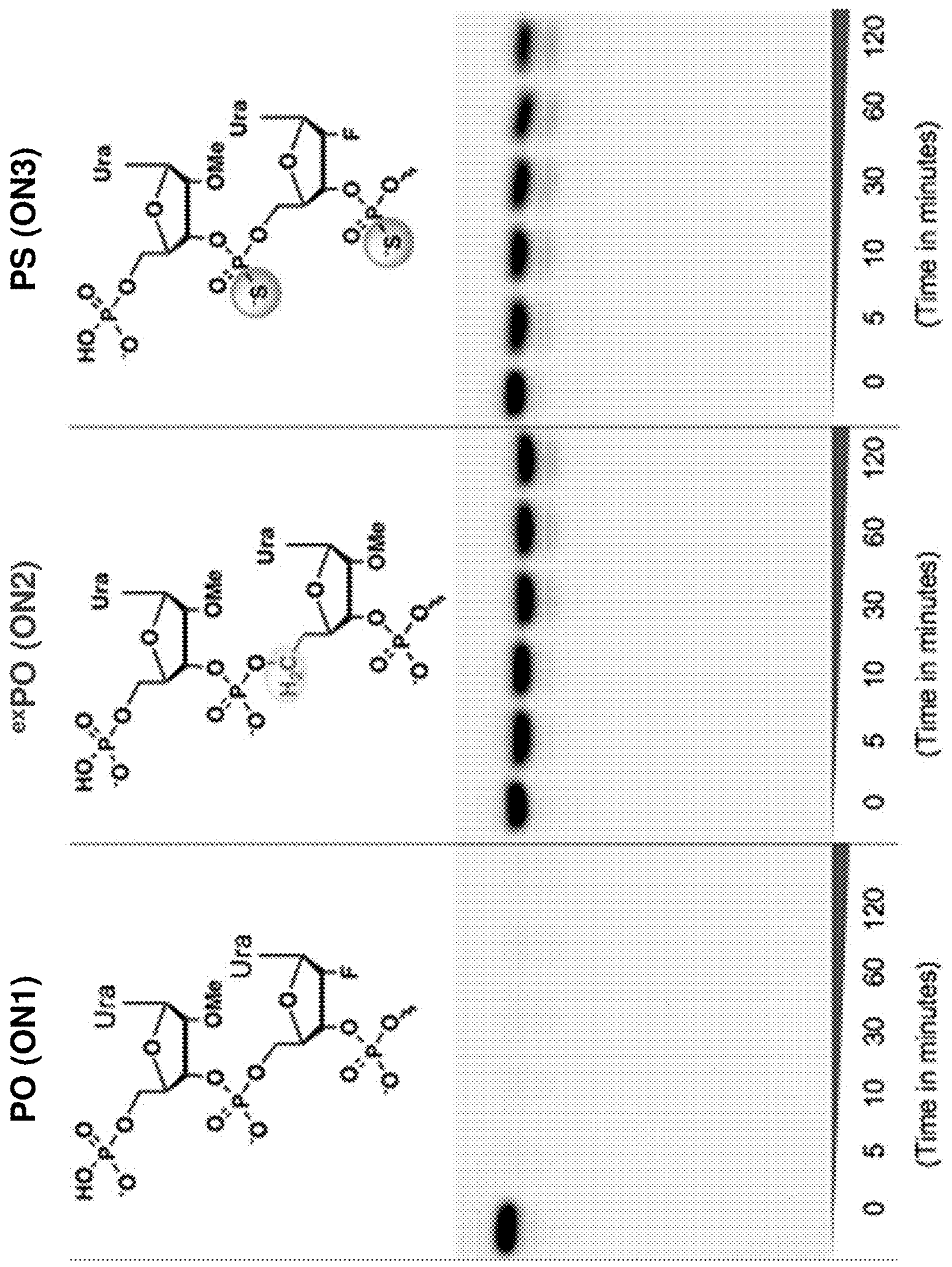
FIG. 18 provides results from a 5'-Phosphate-dependent 5'-exonuclease stability test. 2.5 μM (50 μmol) of each oligonucleotide was incubated in RNase-free water or with 3.3 Units of Terminator™ (EpiCentre) exonuclease at 37° C. in buffer A (EpiCentre, provided with Terminator™ enzyme).

The first test was a 5'-Phosphate-dependent 5'-exonuclease stability test. Oligonucleotides employed in this test are shown below in Table 12. Oligonucleotides were used at 2.5 μM (50 μmol) and were incubated in RNase-free water, or with 3.3 Unit of Terminator™ (EpiCentre) exonuclease at 37° C. in buffer A (EpiCentre, provided with Terminator™ enzyme). As shown in FIG. 18, a single ex-NA intersubunit linkage at the 5' end (ON2) drastically improved 5'-exonuclease stability compared to ON1, which contains a 5' phosphodiester linkage. Importantly, ON2 does not contain a phosphorothioate intersubunit linkage. The data demonstrates that a single ex-NA intersubunit linkage at the 5' end enhances stability to the same extent as multiple phosphorothioate intersubunit linkages at the 5' end (ON3). Excessive phosphorothioate content in therapeutic oligonucleotides can be toxic. The use of a 5' ex-NA intersubunit linkage provides a mechanism to improve oligonucleotide stability while reducing the phosphorothioate content.

Figure 19:
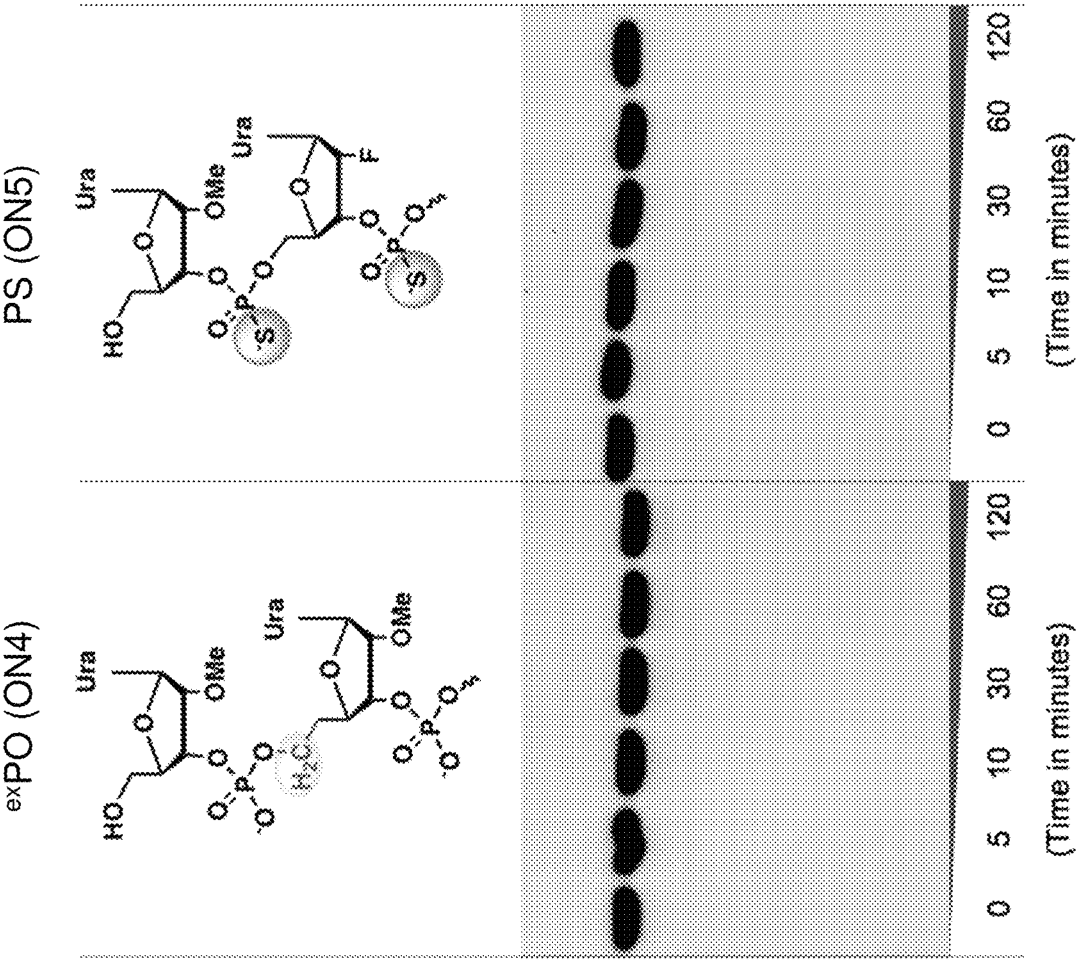
FIG. 19 provides results from a 5'-Phosphate-independent 5'-exonuclease stability test. Each oligonucleotide (10 μM) was incubated in RNase-free water or 30 mM NaOAc (pH 6.0) buffer containing 0.25 U/mL Bovine Spleen Phosphodiesterase II (BSP) at 37° C.

The second 5'-exonuclease stability test was a 5'-Phosphate-independent 5'-exonuclease stability test. Oligonucleotides employed in this test are shown below in Table 13. Oligonucleotides were used at 10 μM and were incubated in RNase-free water or with 30 mM NaOAc (pH 6.0) buffer containing 0.25 U/mL Bovine Spleen Phosphodiesterase II (BSP) at 37° C. As shown in FIG. 19, a single ex-NA intersubunit linkage at the 5' end (ON4) possess similar 5'-exonuclease stability compared to ON5, which contains multiple 5' phosphorothioate linkages. The data demonstrates that a single ex-NA intersubunit linkage at the 5' end enhances stability to the same extent as multiple phosphorothioate intersubunit linkages at the 5' end (ON5). Excessive phosphorothioate content in therapeutic oligonucleotides can be toxic. The use of a 5' ex-NA intersubunit linkage provides a mechanism to improve oligonucleotide stability while reducing the phosphorothioate content.

TABLE 12

| Oligonucleotides for the 5'-Phosphate-dependent 5'-exonuclease stability test | |
|---|---|
| Name | Sequence (5' -> 3') |
| ON1 | 5'-P(mU)(fU)(mA)(fA)(mU)(fC)(mU)(fC)(mU)(fU)(mU)(fA)(mC)(fU)(mG)(fA) (mU)(fU)(mU)(mU) (SEQ ID NO: 68) |
| ON2 | 5'-P (mU)(ex-mU)(mA)(fA)(mU)(fC)(mU)(fC)(mU)(fU)(mU)(fA)(mC)(fU)(mG) (fA)(mU)(fU)(mU)(ex-mU) (SEQ ID NO: 69) |
| ON3 | 5'-P(mu)#(fu)#(mA)(fA)(mU)(fC)(mU)(fC)(mU)(fU)(mU)(fA)(mC)(fU)(mG)(fA) #(mU)#(fU)#(mU)#(mU) (SEQ ID NO: 70) |

TABLE 13

| Oligonucleotides for the 5'-Phosphate-independent 5'-exonuclease stability test | |
|---|---|
| Name | Sequence (5' -> 3') |
| ON4 | 5'-(mU)(ex-mU)(mA)(fA)(mU)(fC)(mU)(fC)(mU)(fU)(mU)(fA)(mC)(fU)(mG)(fA)(mU) (fU)(mU)(ex-mU) (SEQ ID NO: 69) |
| ON5 | 5'-(mU)#(fU)#(mA)(fA)(mU)(fC)(mU)(fC)(mU)(fU)(mU)(fA)(mC)(fU)(mG)(fA)#(mU) #(fU)#(mU)#(mU) (SEQ ID NO: 70) |

Example 13. Universal 3' exNA intersubunit linkage block for enhanced stability and silencing The in vitro silencing data and exonuclease stability data of Examples 11 and 12 above demonstrate the exceptional utility of the ex-NA intersubunit linkage. The 3' exonuclease stability data with multiple 3' ex-NA intersubunit linkages was particularly dramatic. This modification, including the multiple contiguous 3' modifications, can be utilized on any oligonucleotide in the art, including, but not limited to, an siRNA, an antisense oligonucleotide, a miRNA, and an mRNA. It is noted however that the nucleotide sequence at the 3' end of an oligonucleotide can be variable. For example, the antisense strand of an siRNA that targets a particular mRNA (i.e., Htt mRNA), may have a sequence that is perfectly complementary to its target. In order to facilitate the use of the ex-NA intersubunit linkage for 3' end stabilization, a universal block concept was developed. The siRNA antisense strands ex-21, ex-22, ex-23, and ex-24 in Table 4 above each employ a universal "UUUU" sequence. The "UUUU" sequence lacks complementarity to the intended target of each antisense strand, Htt mRNA. None-the-less, as demonstrated from duplexes 21, 22, 23, 24 in FIG. 14, each siRNA duplex retains effective silencing activity against the target mRNA. In addition to retaining silencing activity, the antisense strands display high 3' end stability, as depicted in FIG. 16. The use of four uracil nucleotides as the universal sequence is merely for illustrative purposes. Any universal sequence may be employed, such as "AAAA" or "CCCC". Moreover, the universal sequence need not comprise the same four nucleotides. For example, but in no way limiting, the universal sequence may comprise the nucleotide sequence "AUAU". The working examples employed uracil for the universal sequence because the synthesis of an ex-NA modified uracil is easier and less costly for the starting material. As noted above, the universal 3' end sequence may be applied to any oligonucleotide, such as an siRNA, an ASO, or an mRNA.

Figure 20A:
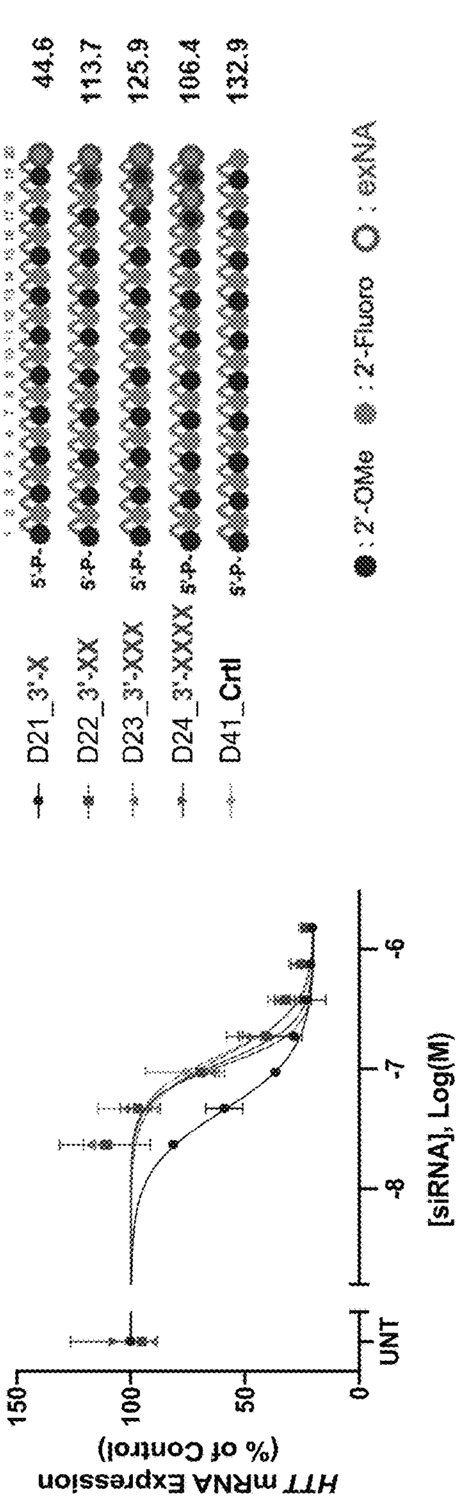
FIG. 20A-FIG. 20B provide results depicting in vitro silencing activity of several siRNA duplexes containing one or more antisense strand 3' end exNA intersubunit linkages. An antisense strand comprising one, two, three, or four 3' end exNA intersubunit linkages was used in a dose response curve (FIG. 20A). The percent potency change relative to an siRNA duplex control that does not contain an exNA intersubunit linkage was also determined (FIG. 20B).
Figure 20B:
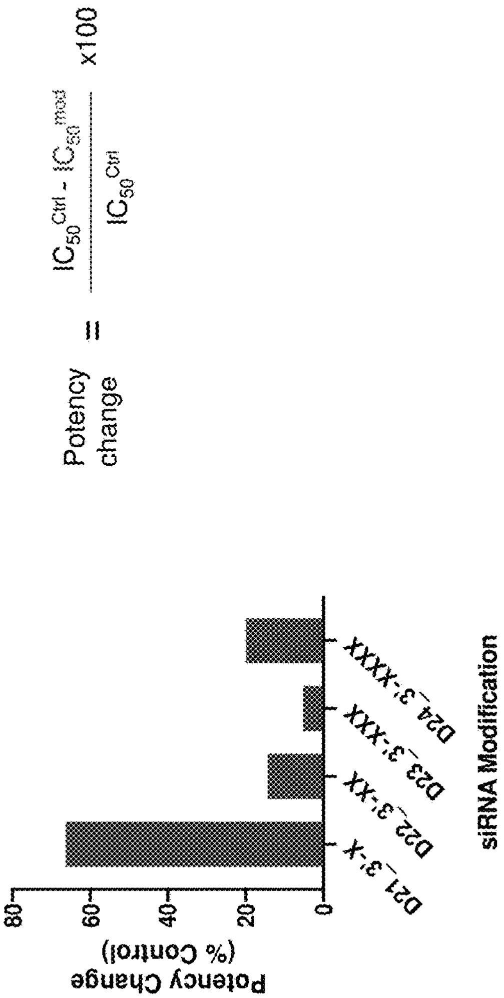
Figure 21B:
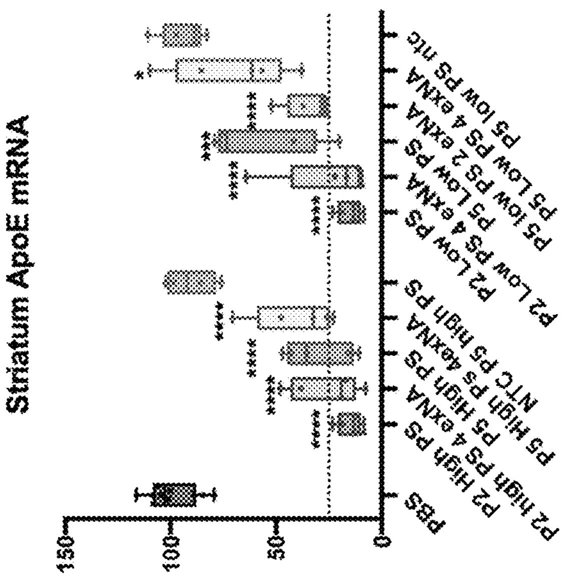
FIG. 21A-FIG. 21E provide results depicting in vivo silencing activity of several siRNA duplexes containing one or more antisense strand 3' end exNA intersubunit linkages. The siRNA duplexes were in the Di-siRNA format targeting ApoE mRNA. Each siRNA duplex was administered at 5 nmol by ICV injection to mice, with ApoE mRNA levels measured 1 month later. ApoE mRNA levels were measured in the following brain regions: medial cortex (FIG. 21A), striatum (FIG. 21B), hippocampus (FIG. 21C), thalamus (FIG. 21D, and cerebellum (FIG. 21E).
Figure 21A:
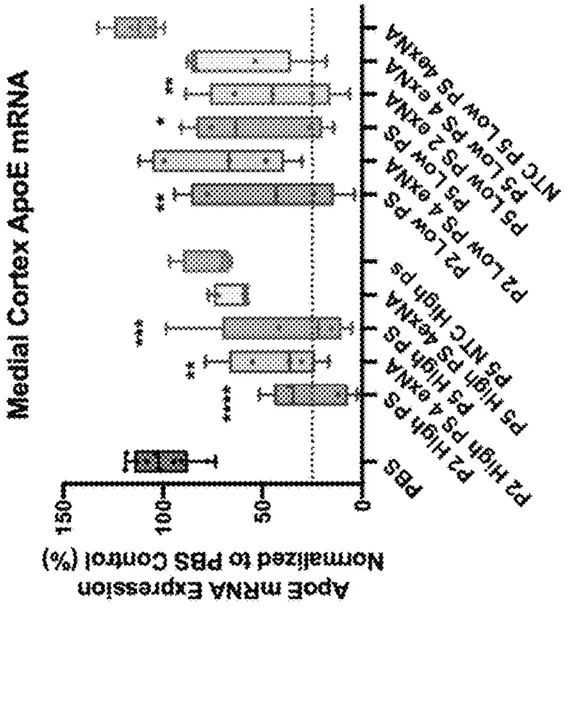
Figure 21C:
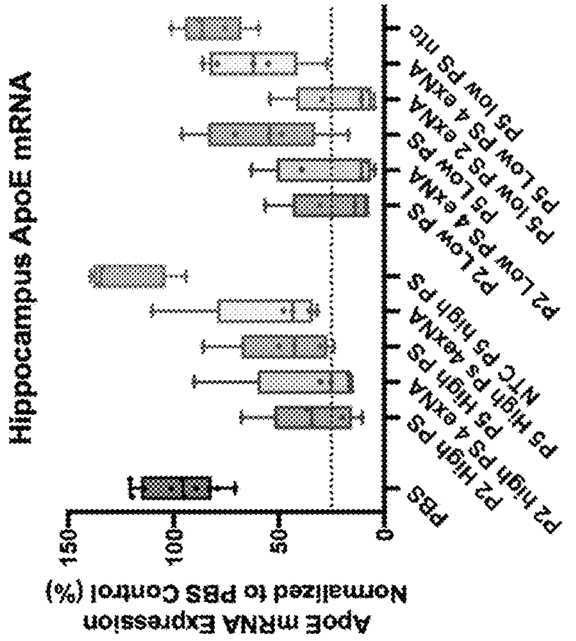
Figure 21E:
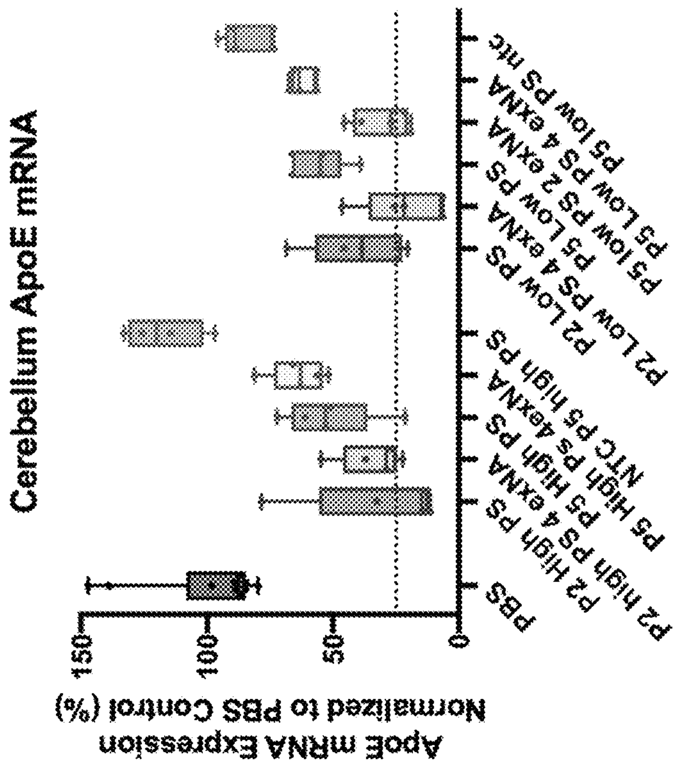
Figure 21D:
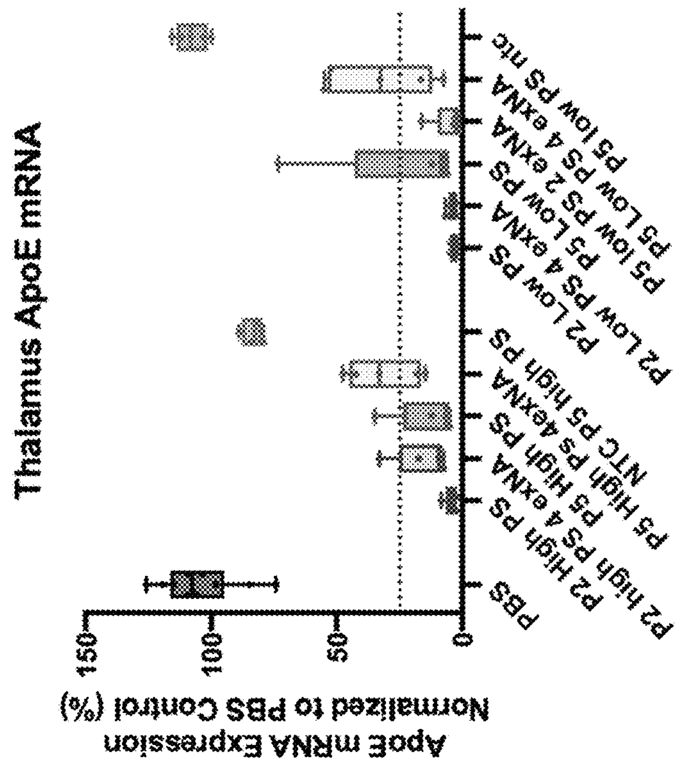
Figures 22A, 22B, 22C, 22D, 22E:
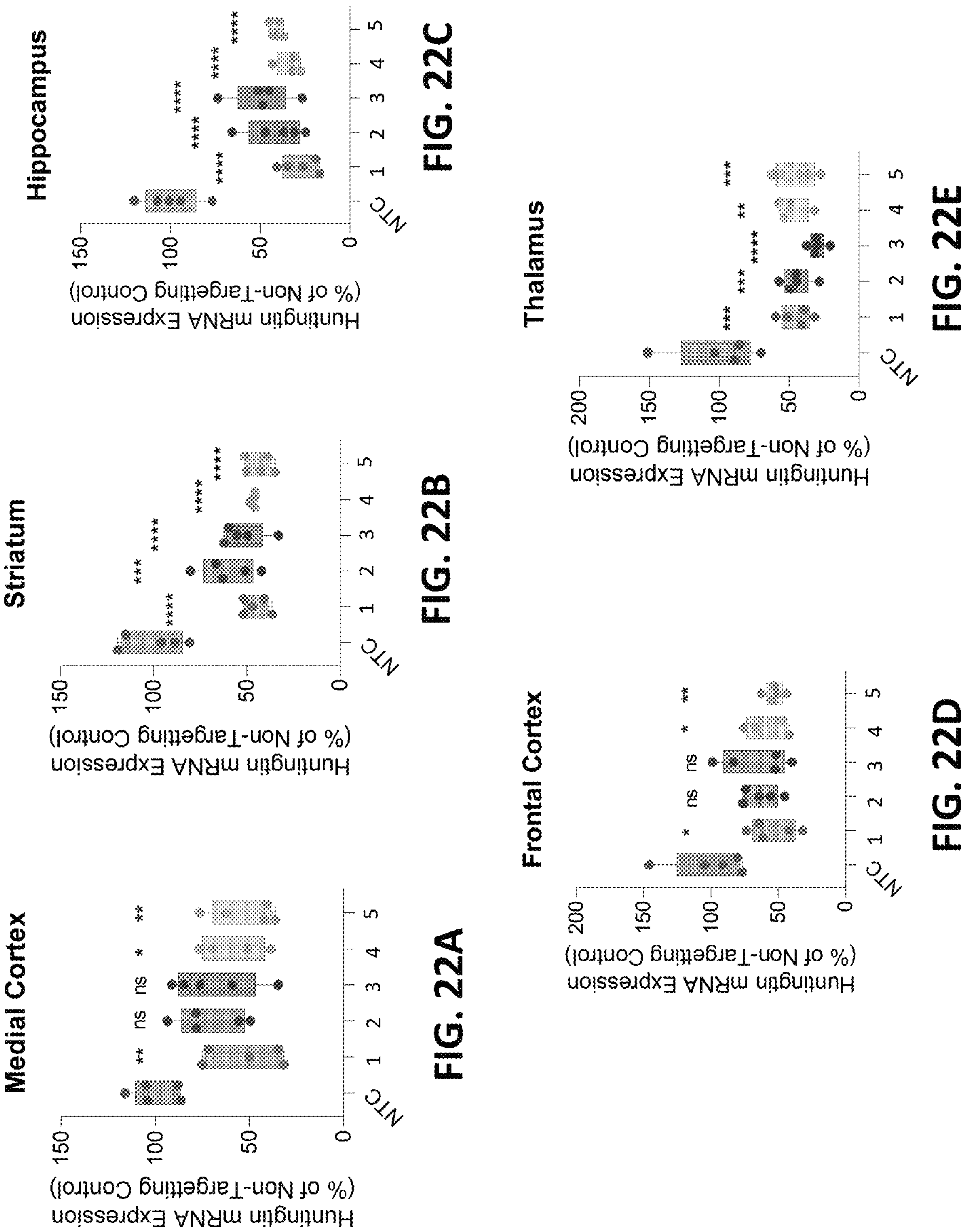
FIG. 22A-FIG. 22E provide results depicting in vivo silencing activity of several siRNA duplexes containing one or more antisense strand 3' end exNA intersubunit linkages. The siRNA duplexes targeted Htt mRNA. Each siRNA duplex was administered at ~60 μg by ICV injection to mice, with Htt mRNA levels measured 2 months later. Htt mRNA levels were measured in the following brain regions: medial cortex (FIG. 22A), striatum (FIG. 22B), hippocampus (FIG. 22C), frontal cortex (FIG. 22D), and thalamus (FIG. 22E). Numbers 1-5 along the X-axis correspond to the correspond to the siRNA chemical modification patterns depicted in Example 15.
Figures 23A, 23B, 23C, 23D, 23E:
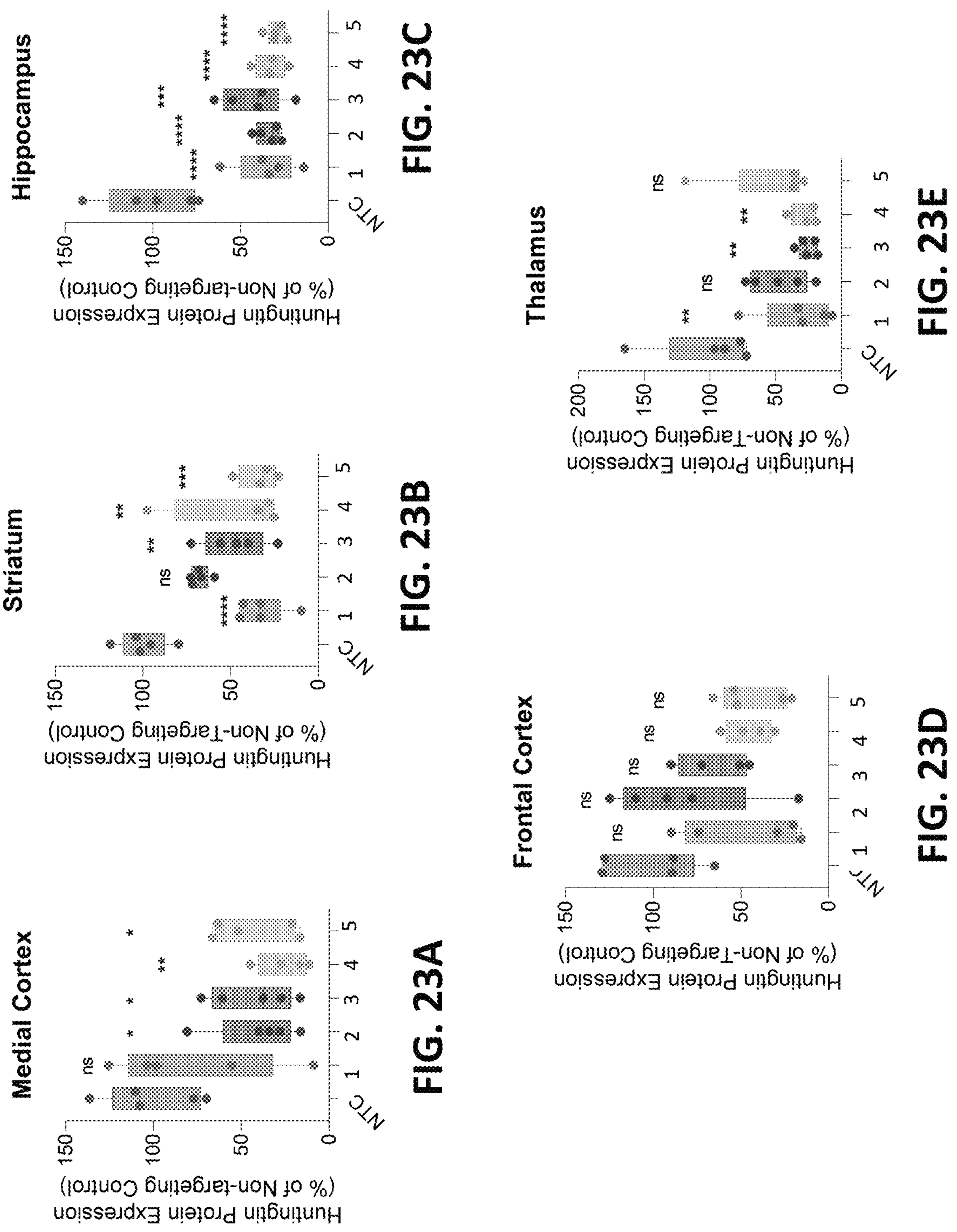
FIG. 23A-FIG. 23E provide results depicting in vivo silencing activity of several siRNA duplexes containing one or more antisense strand 3' end exNA intersubunit linkages. The siRNA duplexes targeted Htt mRNA. Each siRNA duplex was administered at ~60 μg by ICV injection to mice, with Htt protein levels measured 2 months later. Htt protein levels were measured in the following brain regions: medial cortex (FIG. 23A), striatum (FIG. 23B), hippocampus (FIG. 23C), frontal cortex (FIG. 23D), and thalamus (FIG. 23E). Numbers 1-5 along the X-axis correspond to the correspond to the siRNA chemical modification patterns depicted in Example 15.

Example 14. Activity of siRNA Duplexes Containing One or More Antisense Strand 3' End exNA Intersubunit Linkages The in vitro silencing activity of several siRNA duplexes containing one or more antisense strand 3' end exNA intersubunit linkages was tested. An antisense strand comprising one, two, three, or four 3' end exNA intersubunit linkages was used in a dose response curve, as depicted in FIG. 20A. The percent potency change relative to an siRNA duplex control that does not contain an exNA intersubunit linkage was also determined (FIG. 20B). The data demonstrates that siRNA duplexes with antisense strands comprising one, two, three, or four 3' end exNA intersubunit linkages possess greater silencing efficacy than an siRNA duplex with an antisense strand lacking exNA intersubunit linkages.

Example 15. In Vivo Activity of siRNA Duplexes Containing One or More Antisense Strand 3' End exNA Intersubunit Linkages The in vivo silencing activity of several siRNA duplexes containing one or more antisense strand 3' end exNA intersubunit linkages was tested. The siRNA duplexes were in the Di-siRNA format, as described above. The sequences and chemical modification patterns are recited below in Table 14, each siRNA targeting ApoE mRNA. 5 nmol of each Di-siRNA was administered by ICV injection to mice, and ApoE mRNA was quantified 1 month later. As shown in FIG. 21A-FIG. 21E, exNA intersubunit linkage-containing siRNAs were capable of silencing ApoE in several brain regions (medial cortex, striatum, hippocampus, thalamus, and cerebellum). The silencing efficacy of siRNA duplexes containing a low phosphorothioate (PS) content was approximately maintained or improved with the inclusion of exNA intersubunit linkages.

TABLE 14

Anti-ApoE siRNA sequences used in Example 15 and FIG. 21

| TYPE | CHEM | PS Content | Duplex # | Sequence |
|---|---|---|---|---|
| Ctrl | P5_Ctrl | Low | 1 | VP(mU)#(fU)#(mG)(mG)(mA)(fU)(mA)(mU)(mG)(mG)(mA)(mU)(mG)(fU)(mU)(fG)(mU)(mU)(mU)#(mU)#(mU)<br>(SEQ ID NO: 71)<br>(mC)#(mA)#(mA)(mC)(mA)(mU)(mC)(fC)(mA)(fU)(fA)(fU)(mC)(mC)#(mA)#(mA)-Dio<br>(SEQ ID NO: 72) |
| | P2_Ctrl | Low | 2 | VP(mU)#(fU)#(mG)(fG)(mA)(fU)(mA)(fU)(mG)(fG)(mA)(fU)(mG)(fU)(mU)(fG)(mU)(mU)(mU)#(mU)#(mU)<br>(SEQ ID NO: 73)<br>(mC)#(fA)#(mA)(fC)(mA)(fU)(mC)(fC)(mA)(fU)(mA)(fU)(mC)(fC)#(mA)#(mA)-Dio<br>(SEQ ID NO: 74) |
| | P5_Ctrl | High | 3 | VP(mU)#(fU)#(mG)(mG)(mA)(fU)(mA)(mU)(mG)(mG)(mA)(mU)(mG)(fU)#(mU)#(fG)#(mU)#(mU)#(mU)#(mU)#(mU)<br>(SEQ ID NO: 75)<br>(mC)#(mA)#(mA)(mC)(mA)(mU)(mC)(fC)(mA)(fU)(fA)(fU)(mC)(mC)#(mA)#(mA)-Dio<br>(SEQ ID NO: 72) |
| | P2_Ctrl | High | 4 | VP(mU)#(fU)#(mG)(fG)(mA)(fU)(mA)(fU)(mG)(fG)(mA)(fU)(mG)(fU)#(mU)#(fG)#(mU)#(mU)#(mU)#(mU)#(mU)<br>(SEQ ID NO: 76)<br>(mC)#(fA)#(mA)(fC)(mA)(fU)(mC)(fC)(mA)(fU)(mA)(fU)(mC)(fC)#(mA)#(mA)-Dio<br>(SEQ ID NO: 74) |
| exNA | P5_ex | Low | 5 | VP(mU)#(fU)#(mG)(mG)(mA)(fU)(mA)(mU)(mG)(mG)(mA)(mU)(mG)(fU)(mU)(fG)(mU)(ex-mU)(ex-mU)#(ex-mU)#(ex-mU)<br>(SEQ ID NO: 77)<br>(mC)#(mA)#(mA)(mC)(mA)(mU)(mC)(fC)(mA)(fU)(fA)(fU)(mC)(mC)#(mA)#(mA)-Dio<br>(SEQ ID NO: 72) |

TABLE 14-continued

Anti-ApoE siRNA sequences used in Example 15 and FIG. 21

| TYPE | CHEM | PS Content | Duplex # | Sequence |
|---|---|---|---|---|
| | P5_ex | Low | 6 | VP(mU)#(fU)#(mG)(mG)(mA)(fU)(mA)(mU)(mG)(mG)(mA)(mU)(mG)(fU)(mU)(fG)(mU)(mU)(mU)#(ex-mU)#(ex-mU)<br>(SEQ ID NO: 78)<br>(mC)#(mA)#(mA)(mC)(mA)(mU)(mC)(fC)(mA)(fU)(fA)(fU)(mC)(mC)#(mA)#(mA)-Dio<br>(SEQ ID NO: 72) |
| | P2_ex | Low | 7 | VP(mU)#(fU)#(mG)(fG)(mA)(fU)(mA)(fU)(mG)(fG)(mA)(fU)(mG)(fU)(mU)(fG)(mU)(ex-mU)(ex-mU)#(ex-mU)#(ex-mU)<br>(SEQ ID NO: 79)<br>(mC)#(mA)#(mA)(mC)(mA)(mU)(mC)(fC)(mA)(fU)(fA)(fU)(mC)(mC)#(mA)#(mA)-Dio<br>(SEQ ID NO: 72) |
| | P5_ex | High | 8 | VP(mU)#(fU)#(mG)(mG)(mA)(fU)(mA)(mU)(mG)(mG)(mA)(mU)(mG)(fU)#(mU)#(fG)#(mU)#(ex-mU)#(ex-mU)#(ex-mU)#(ex-mU)<br>(SEQ ID NO: 80)<br>(mC)#(mA)#(mA)(mC)(mA)(mU)(mC)(fC)(mA)(fU)(fA)(fU)(mC)(mC)#(mA)#(mA)-Dio<br>(SEQ ID NO: 72) |
| | P2_ex | High | 9 | VP(mU)#(fU)#(mG)(fG)(mA)(fU)(mA)(fU)(mG)(fG)(mA)(fU)(mG)(fU)#(mU)#(fG)#(mU)#(ex-mU)#(ex-mU)#(ex-mU)#(ex-mU)<br>(SEQ ID NO: 81)<br>(mC)#(mA)#(mA)(mC)(mA)(mU)(mC)(fC)(mA)(fU)(fA)(fU)(mC)(mC)#(mA)#(mA)-Dio<br>(SEQ ID NO: 72) |
| NTC | P5_ex | Low | 10 | VP(mU)#(fA)#(mA)(mU)(mC)(fG)(mU)(mA)(mU)(mU)(mU)(mG)(mU)(fC)(mA)(fA)(mU)(ex-mU)(ex-mU)#(ex-mU)#(ex-mU)<br>(SEQ ID NO: 82)<br>(mU)#(mU)#(mG)(mA)(mC)(mA)(mA)(fA)(mU)(fA)(fC)(fG)(mA)(mU)#(mU)#(mA)-Dio<br>(SEQ ID NO: 83) |
| | P5_ex | High | 11 | VP(mU)#(fA)#(mA)(mU)(mC)(fG)(mU)(mA)(mU)(mU)(mU)(mG)(mU)(fC)#(mA)#(fA)#(mU)#(ex-mU)#(ex-mU)#(ex-mU)#(ex-mU)<br>(SEQ ID NO: 84)<br>(mU)#(mU)#(mG)(mA)(mC)(mA)(mA)(fA)(mU)(fA)(fC)(fG)(mA)(mU)#(mU)#(mA)-Dio<br>(SEQ ID NO: 83) |

For Table 14 above, "VP" corresponds to a 5' vinyl phosphonate; "mX" corresponds to any nucleotide (A, U, G, or C) with a 2'-O-methyl modification; "fX" corresponds to any nucleotide (A, U, G, or C) with a 2'-fluoro modification; "#" corresponds to a phosphorothioate modification; "ex-mX" corresponds to any nucleotide (A, U, G, or C) with a 2'-O-methyl modification and exNA internucleotide linkage; "ex-fX" corresponds to any nucleotide (A, U, G, or C) with a 2'-fluoro modification and exNA internucleotide linkage; and "Dio" corresponds to a di-oligonucleotide format (two siRNAs linked together via a linker attached to the 3' end of each sense strand).

An additional in vivo silencing activity experiment was performed, with Di-sRNA duplexes targeting Htt mRNA. The chemical modification patterns employed are recited below. Wild type male mice treated with ~60 μg of siRNA for 2 months, followed by quantification of Htt mRNA and protein levels in several brain regions (medial cortex, striatum, hippocampus, thalamus, and frontal cortex). The siRNA duplexes with antisense strands containing one or two exNA internucleotide linkages displayed equal or greater silencing of Htt mRNA (FIG. 22A-FIG. 22E) and protein (FIG. 23A-FIG. 23E) expression compared to siRNA duplexes lacking exNA intemucleotide linkages. The exNA internucleotide linkage, which confers greater nuclease resistance than the phosphorothioate modification, permits the reduction of toxic phosphorothioate modifications without sacrificing nuclease resistance or silencing efficacy.

Chemical modification patterns used in FIG. 22 and FIG. 23:

1—High PS:

Antisense strand (5' to 3'):

VP(mX)#(fX)#(m(fXf)(fX)(mX)(fX)(mX)(fX)(mX)(fX)(mX)(fX)#(mX)#(fX)#(m X)#(mX)#(mX)#(fX)#(mX)

Sense strand (5' to 3'):

(mX)#(mX)#(mX)(fX)(mX)(fX)(mX)(fX)(mX)(fX)(mX)(mX)(mX)(fX)#(mX)#(mX)

2—Low PS fm:

Antisense strand (5' to 3'):

VP(mX)#(fX)#(mX)(fX)(fX)(fX)(mX)(fX)(mX)(fX)(mX)(fX)(mX)(fX)(mX)(fX)(mX)(mX)(mX)#(fX)#(mX)

Sense strand (5' to 3'):

(mX)#(mX)#(mX)(fX)(mX)(fX)(mX)(fX)(mX)(fX)(mX)(mX)(mX)(fX)#(mX)#(mX)

3—Low PS mf:

Antisense strand (5' to 3'):

VP(mX)#(fX)#(mX)(fX)(fX)(fX)(mX)(fX)(mX)(fX)(mX)(fX)(mX)(fX)(mX)(fX)(mX)(mX)(mX)#(mX)#(fX)

Sense strand (5' to 3'):

(mX)#(mX)#(mX)(fX)(mX)(fX)(mX)(fX)(mX)(fX)(mX)(mX)(mX)(fX)#(mX)#(mX)

4—Low PS mf 2 exNA:

Antisense strand (5' to 3'):

VP(nmX)#(fX)#(mX)(fX)(fX)(fX)(mX)(fX)(mX)(fX)(mX)(fX)(mX)(fX)(mX)(fX)(mX)(mX)(mX)#(ex-mX)#(ex-fX)

Sense strand (5' to 3'):

(mX)#(mX)#(mX)(fX)(mX)(fX)(mX)(fX)(mX)(fX)(mX)(mX)(mX)(fX)#(mX)#(mX)

5—Low PS mf 1 exNA:

Antisense strand (5' to 3'):

VP(mX)#(fX)#(mX)(fX)(fX)(fX)(mX)(fX)(mX)(fX)(mX)(fX)(mX)(fX)(mX)(fX)(mX)(mX)(mX)#(mX)#(ex-fX)

Sense strand (5' to 3'):

(mX)#(mX)#(mX)(fX)(mX)(fX)(mX)(fX)(mX)(fX)(mX)(mX)(mX)(fX)#(mX)#(mX)

For the above recited 5 chemical modification patterns, "VP" corresponds to a 5' vinyl phosphonate; "mX" corresponds to any nucleotide (A, U, G, or C) with a 2'-O-methyl modification; "fX" corresponds to any nucleotide (A, U, G, or C) with a 2'-fluoro modification; "#" corresponds to a phosphorothioate modification; "ex-mX" corresponds to any nucleotide (A, U, G, or C) with a 2'-O-methyl modification and exNA intemucleotide linkage; and "ex-fX" corresponds to any nucleotide (A, U, G, or C) with a 2'-fluoro modification and exNA internucleotide linkage.

INCORPORATION BY REFERENCE

The contents of all cited references (including literature references, patents, patent applications, and websites) that maybe cited throughout this application are hereby expressly incorporated by reference in their entirety for any purpose, as are the references cited therein. The disclosure will employ, unless otherwise indicated, conventional techniques of immunology, molecular biology and cell biology, which are well known in the art.

The present disclosure also incorporates by reference in their entirety techniques well known in the field of molecular biology and drug delivery. These techniques include, but are not limited to, techniques described in the following publications:

Atwell et al. J. Mol. Biol. 1997, 270: 26-35;

Ausubel et al. (eds.), Current Protocols In Molecular Biology, John Wiley & Sons, NY (1993);

Ausubel, F. M. et al. eds., Short Protocols In Molecular Biology (4th Ed. 1999) John Wiley & Sons, NY. (ISBN 0-471-32938-X);

Controlled Drug Bioavailability, Drug Product Design and Performance, Smolen and Ball (eds.), Wiley, New York (1984);

Giege, R. and Ducruix, A. Barrett, Crystallization of Nucleic Acids and Proteins, a Practical Approach, 2nd ea., pp. 20 1-16, Oxford University Press, New York, New York, (1999);

Goodson, in Medical Applications of Controlled Release, vol. 2, pp. 115-138 (1984);

Hammerling, et al., in: Monoclonal Antibodies and T-Cell Hybridomas 563-681 (Elsevier, N.Y., 1981;

Harlow et al., Antibodies: A Laboratory Manual, (Cold Spring Harbor Laboratory Press, 2nd ed. 1988);

Kabat et al., Sequences of Proteins of Immunological Interest (National Institutes of Health, Bethesda, Md. (1987) and (1991);

Kabat, E. A., et al. (1991) Sequences of Proteins of Immunological Interest, Fifth Edition, U.S. Department of Health and Human Services, NIH Publication No. 91-3242;

Kontermann and Dubel eds., Antibody Engineering (2001) Springer-Verlag. New York. 790 pp. (ISBN 3-540-41354-5).

Kriegler, Gene Transfer and Expression, A Laboratory Manual, Stockton Press, NY (1990);

Lu and Weiner eds., Cloning and Expression Vectors for Gene Function Analysis (2001) BioTechniques Press. Westborough, MA. 298 pp. (ISBN 1-881299-21-X).

Medical Applications of Controlled Release, Langer and Wise (eds.), CRC Pres., Boca Raton, Fla. (1974);

Old, R. W. & S. B. Primrose, PRINCIPLES OF GENE MANIPULATION: AN INTRODUCTION TO GENETIC ENGINEERING (3d Ed. 1985) Blackwell Scientific Publications, Boston. Studies in Microbiology; V.2:409 pp. (ISBN 0-632-01318-4).

Sambrook, J. et al. eds., Molecular Cloning: A Laboratory Manual (2d Ed. 1989) Cold Spring Harbor Laboratory Press, NY. Vols. 1-3. (ISBN 0-87969-309-6).

Sustained and Controlled Release Drug Delivery Systems, J. R. Robinson, ed., Marcel Dekker, Inc., New York, 1978

Winnacker, E. L. From Genes To Clones: Introduction To Gene Technology (1987) VCH Publishers, NY (translated by Horst Ibelgaufts). 634 pp. (ISBN 0-89573-614-4).

Equivalents

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

What is claimed:

1. A modified RNA oligonucleotide comprising a 5' end, a 3' end and at least two modified intersubunit linkages of Formula Ia:

(Ia)

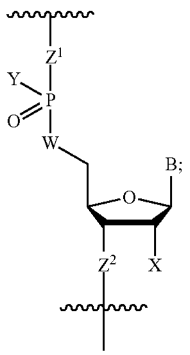

wherein:

B is a base moiety;

W is O or $O(CH_2)n^1$, wherein $n^1$ is an integer between 1 and 10;

X is selected from the group consisting of OH, $OR^1$, $R^1$, F, Cl, Br, I, SH, $SR^1$, $NH_2$, $NHR^1$, $NR^1_2$ and $COOR^1$;

Y is selected from the group consisting of $O^-$, OH, $OR^2$, $NH^-$, $NH_2$, $NR^2_2$, $BH_3$, $S^-$, $R^2$, and SH;

$Z^1$ is O or $O(CH_2)_n{}^2$, wherein $n^2$ is an integer between 1 and 10;

$Z^2$ is O or $O(CH_2)_n{}^3$, wherein $n^3$ is an integer between 1 and 10;

$R^1$ is a substituted or unsubstituted $C_1$-$C_6$ alkyl, alkenyl, alkynyl, aryl, or mixtures thereof; and $R^2$ is a substituted or unsubstituted $C_1$-$C_6$ alkyl, alkenyl, alkynyl, aryl, or mixtures thereof;

wherein at least two of the at least two modified intersubunit linkages are present at one or both of the 5' end and the 3' end of the modified RNA oligonucleotide, and wherein:

$Z^1$ is $O(CH_2)_n{}^2$, $n^2$ is 1, W is O, and Y is $O^-$;

$Z^1$ is O, W is $O(CH_2)_n{}^1$, $n^1$ is 1, and Y is $O^-$;

$Z^1$ is $O(CH_2)_n{}^2$, $n^2$ is 1, W is O, and Y is $S^-$;

$Z^1$ is $O(CH_2)_n{}^2$, $n^2$ is 1, W is $O(CH_2)_n$, and Y is $O^-$; or $Z^1$ is $O(CH_2)_n{}^2$, $n^2$ is 1, W is $O(CH_2)_n$, and Y is $S^-$.

2. The modified RNA oligonucleotide of claim 1, wherein the base moiety B is selected from the group consisting of adenine, guanine, cytosine, and uracil.

3. The modified RNA oligonucleotide of claim 1, wherein between two and ten of the at least two modified intersubunit linkages are present at one or both of the 5' end and the 3' end of the modified RNA oligonucleotide.

4. The modified RNA oligonucleotide of claim 1, wherein the at least two modified intersubunit linkages are consecutive.

5. The modified RNA oligonucleotide of claim 1, wherein the modified RNA oligonucleotide is selected from the group consisting of an siRNA, a miRNA, an antisense oligonucleotide, a ribozyme, and a mRNA.

6. A modified RNA oligonucleotide comprising a 5' end, a 3' end and at least two modified intersubunit linkages of one or more of:

Formula IIa:

(IIa)

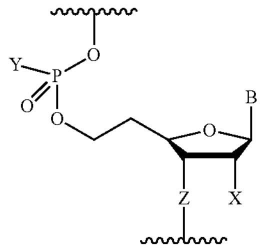

wherein:

B is a base moiety;

X is selected from the group consisting of OH, $OR^1$, $R^1$, F, Cl, Br, I, SH, $SR^1$, $NH_2$, $NHR^1$, $NR^1_2$ and $COOR^1$;

Y is selected from the group consisting of $O^-$, OH, $OR^2$, $NH^-$, $NH_2$, $NR^2_2$, $BH_3$, S, $R^2$, and SH;

Z is O or $O(CH_2)_n$, wherein n is an integer between 1 and 10;

$R^1$ is a substituted or unsubstituted $C_1$-$C_6$ alkyl, alkenyl, alkynyl, aryl, or mixtures thereof; and $R^2$ is a substituted or unsubstituted $C_1$-$C_6$ alkyl, alkenyl, alkynyl, aryl, or mixtures thereof;

Formula IIIa:

(IIIa)

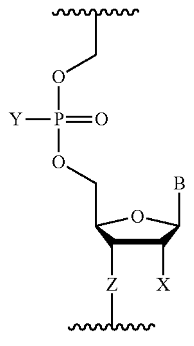

wherein:

B is a base moiety;

X is selected from the group consisting of OH, $OR^1$, $R^1$, F, Cl, Br, I, SH, $SR^1$, $NH_2$, $NHR^1$, $NR^1_2$ and $COOR^1$;

Y is selected from the group consisting of $O^-$, OH, $OR^2$, $NH^-$, $NH_2$, $NR^2_2$, $BH_3$, $S^-$, $R^2$, and SH;

Z is O or $O(CH_2)_n$, wherein n is an integer between 1 and 10;

$R^1$ is a substituted or unsubstituted $C_1$-$C_6$ alkyl, alkenyl, alkynyl, aryl, or mixtures thereof; and $R^2$ is a substituted or unsubstituted $C_1$-$C_6$ alkyl, alkenyl, alkynyl, aryl, or mixtures thereof;

Formula Va:

(Va)

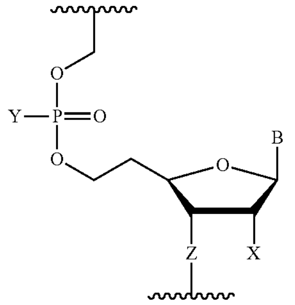

wherein:

B is a base moiety;

X is selected from the group consisting of OH, $OR^1$, $R^1$, F, Cl, Br, I, SH, $SR^1$, $NH_2$, $NHR^1$, $NR^1_2$ and $COOR^1$;

Y is selected from the group consisting of $O^-$, OH, $OR^2$, $NH^-$, $NH_2$, $NR^2_2$, $BH_3$, $S^-$, $R^2$, and SH;

Z is O or $O(CH_2)_n$, wherein n is an integer between 1 and 10;

$R^1$ is a substituted or unsubstituted $C_1$-$C_6$ alkyl, alkenyl, alkynyl, aryl, or mixtures thereof; and $R^2$ is a substituted or unsubstituted $C_1$-$C_6$ alkyl, alkenyl, alkynyl, aryl, or mixtures thereof;

Formula III:

(III)

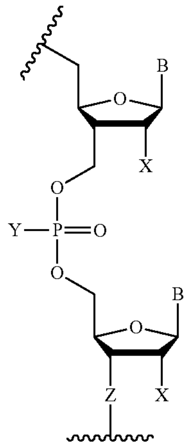

wherein:

B is a base moiety;

X is selected from the group consisting of OH, $OR^1$, $R^1$, F, Cl, Br, I, SH, $SR^1$, $NH_2$, $NHR^1$, $NR^1_2$ and $COOR^1$;

Y is selected from the group consisting of $O^-$, OH, $OR^2$, $NH^-$, $NH_2$, $NR^2_2$, $BH_3$, $S^-$, $R^2$, and SH;

Z is O or $O(CH_2)_n$, wherein n is an integer between 1 and 10;

$R^1$ is a substituted or unsubstituted $C_1$-$C_6$ alkyl, alkenyl, alkynyl, aryl, or mixtures thereof; and $R^2$ is a substituted or unsubstituted $C_1$-$C_6$ alkyl, alkenyl, alkynyl, aryl, or mixtures thereof; and/or Formula V:

(V)

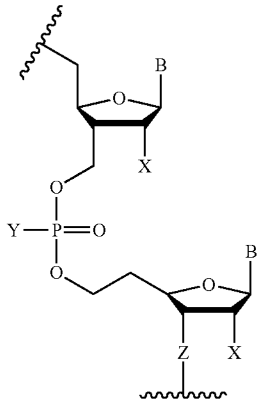

wherein:

B is a base moiety;

X is selected from the group consisting of OH, $OR^1$, $R^1$, F, Cl, Br, I, SH, $SR^1$, $NH_2$, $NHR^1$, $NR^1_2$ and $COOR^1$;

Y is selected from the group consisting of $O^-$, OH, $OR^2$, $NH^-$, $NH_2$, $NR^2_2$, $BH_3$, $S^-$, $R^2$, and SH;

Z is O or $O(CH_2)_n$, wherein n is an integer between 1 and 10;

$R^1$ is a substituted or unsubstituted $C_1$-$C_6$ alkyl, alkenyl, alkynyl, aryl, or mixtures thereof; and $R^2$ is a substituted or unsubstituted $C_1$-$C_6$ alkyl, alkenyl, alkynyl, aryl, or mixtures thereof; and wherein at least two of the at least two modified intersubunit linkages of any one or more of Formula (IIa), (IIIa), (Va), (III), and (V) are present at one or both of the 5' end and the 3' end of the modified RNA oligonucleotide.

7. A modified universal 3' end RNA sequence for stabilization of an RNA oligonucleotide, the RNA sequence comprising at least two modified intersubunit linkages of Formula Ia:

(Ia)

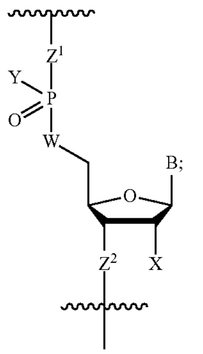

wherein:

B is a base moiety;

W is O or $O(CH_2)n^1$, wherein $n^1$ is an integer between 1 and 10;

X is selected from the group consisting of OH, $OR^1$, $R^1$, F, Cl, Br, I, SH, $SR^1$, $NH_2$, $NHR^1$, $NR^1_2$ and $COOR^1$;

Y is selected from the group consisting of $O^-$, OH, $OR^2$, $NH^-$, $NH_2$, $NR^2_2$, $BH_3$, $S^-$, $R^2$, and SH;

$Z^1$ is O or $O(CH_2)_n^2$, wherein $n^2$ is an integer between 1 and 10;

$Z^2$ is O or $O(CH_2)_n^3$, wherein $n^3$ is an integer between 1 and 10;

$R^1$ is a substituted or unsubstituted $C_1$-$C_6$ alkyl, alkenyl, alkynyl, aryl, or mixtures thereof; and $R^2$ is a substituted or unsubstituted $C_1$-$C_6$ alkyl, alkenyl, alkynyl, aryl, or mixtures thereof, wherein:

$Z^1$ is $O(CH_2)_n^2$, $n^2$ is 1, W is O, and Y is $O^-$;

$Z^1$ is O, W is $O(CH_2)_n^1$, $n^1$ is 1, and Y is $O^-$;

$Z^1$ is $O(CH_2)_n^2$, $n^2$ is 1, W is O, and Y is $S^-$;

$Z^1$ is $O(CH_2)_n^2$, $n^2$ is 1, W is $O(CH_2)_n^1$, and Y is $O^-$; or $Z^1$ is $O(CH_2)_n^2$, $n^2$ is 1, W is $O(CH_2)_n^1$, and Y is $S^-$.

8. The modified universal 3' end RNA sequence of claim 7, wherein the RNA sequence is three to ten consecutive nucleotides in length.

9. The modified universal 3' end RNA sequence of claim 7, wherein:

the RNA sequence comprises at least two consecutive modified intersubunit linkages of Formula Ia;

the RNA sequence comprises four consecutive modified intersubunit linkages of Formula Ia; or the RNA sequence comprises five consecutive modified intersubunit linkages of Formula Ia.

10. The modified universal 3' end RNA sequence of claim 7, wherein the RNA sequence comprises consecutive nucleotides selected from the group consisting of UUUU, AAAA, CCCC, UUUUU, AAAAA, and CCCCC.

11. The modified universal 3' end RNA sequence of claim 7, wherein the base moiety B is selected from the group consisting of adenine, guanine, cytosine, and uracil.

12. A modified universal 3' end RNA sequence for stabilization of an RNA oligonucleotide, the RNA sequence comprising at least two modified intersubunit linkages of Formula X:

(X)

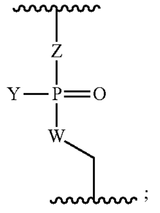

wherein:

W is O or $O(CH_2)n^1$, wherein $n^1$ is an integer between 1 and 10;

Y is selected from the group consisting of $O^-$, OH, $OR^2$, $NH^-$, $NH_2$, $NR^2_2$, $BH_3$, $S^-$, $R^2$, and SH;

Z is O or $O(CH_2)_n^2$, wherein $n^2$ is an integer between 1 and 10; and $R^2$ is a substituted or unsubstituted $C_1$-$C_6$ alkyl, alkenyl, alkynyl, aryl, or mixtures thereof, wherein:

Z is $O(CH_2)_n^2$, $n^2$ is 1, W is O, and Y is $O^-$;

Z is O, W is $O(CH_2)_n^1$, $n^1$ is 1, and Y is $O^-$;

Z is $O(CH_2)_n^2$, $n^2$ is 1, W is O, and Y is $S^-$;

Z is $O(CH_2)_n^2$, $n^2$ is 1, W is $O(CH_2)_n$, and Y is $O^-$; or

Z is $O(CH_2)_n^2$, $n^2$ is 1, W is $O(CH_2)_n$, and Y is $S^-$.

13. The modified RNA oligonucleotide of claim 1, wherein between two and five of the at least two modified intersubunit linkages are present at one or both of the 5' end and the 3' end of the modified RNA oligonucleotide.

14. The modified RNA oligonucleotide of claim 1, wherein three of the at least two modified intersubunit linkages are present at one or both of the 5' end and the 3' end of the modified RNA oligonucleotide.

15. The modified RNA oligonucleotide of claim 1, wherein four of the at least two modified intersubunit linkages are present at one or both of the 5' end and the 3' end of the modified RNA oligonucleotide.

16. The modified RNA oligonucleotide of claim 1, wherein five of the at least two modified intersubunit linkages are present at one or both of the 5' end and the 3' end of the modified RNA oligonucleotide.

17. The modified RNA oligonucleotide of claim 3, wherein the at least two intersubunit linkages are consecutive.

18. The modified RNA oligonucleotide of claim 5, wherein the siRNA comprises an antisense strand and a sense strand, and wherein one or both of the antisense A strand and the sense strand comprise the at least two modified intersubunit linkages.

19. The modified universal 3' end RNA sequence of claim 7, wherein the RNA sequence consists of four consecutive nucleotides in length.

20. The modified universal 3' end RNA sequence of claim 7, wherein the modified universal sequence consists of five consecutive nucleotides in length.

21. The universal 3' end RNA sequence of claim 12, wherein each of the at least two intersubunit linkages of Formula X bridges two ribonucleosides.

* * * * *